(12) United States Patent
Messing et al.

(10) Patent No.: US 9,949,488 B2
(45) Date of Patent: Apr. 24, 2018

(54) MIRNA169 COMPOSITIONS AND METHODS FOR THE REGULATION OF CARBOHYDRATE METABOLISM AND FLOWERING IN PLANTS

(71) Applicant: Rutgers, The State University of New Jersey, New Brunswick, NJ (US)

(72) Inventors: Joachim Messing, Somerset, NJ (US); Martin Calvino, Highland Park, NJ (US)

(73) Assignee: RUTGERS, THE STATE UNIVERSITY OF NEW JERSEY, New Brunswick, NJ (US)

( * ) Notice: Subject to any disclaimer, the term of this patent is extended or adjusted under 35 U.S.C. 154(b) by 0 days.

(21) Appl. No.: 14/728,633

(22) Filed: Jun. 2, 2015

(65) Prior Publication Data
US 2015/0284718 A1 Oct. 8, 2015

Related U.S. Application Data

(63) Continuation-in-part of application No. 13/114,675, filed on May 24, 2011, now Pat. No. 9,044,019, and a continuation-in-part of application No. 14/160,520, filed on Jan. 21, 2014, now abandoned.

(60) Provisional application No. 61/347,741, filed on May 24, 2010, provisional application No. 61/754,745, filed on Jan. 21, 2013.

(51) Int. Cl.
*A01N 25/00* (2006.01)
*A01H 5/00* (2006.01)
*A01N 57/16* (2006.01)
*C12N 15/82* (2006.01)

(52) U.S. Cl.
CPC ........... *A01N 57/16* (2013.01); *C12N 15/827* (2013.01); *C12N 15/8218* (2013.01); *C12N 15/8245* (2013.01); *C12N 15/8271* (2013.01); *C12N 15/8273* (2013.01)

(58) Field of Classification Search
None
See application file for complete search history.

(56) References Cited

U.S. PATENT DOCUMENTS 9,044,019 B2 * 6/2015 Messing ................ A01N 57/16

OTHER PUBLICATIONS

Xu et al, 2014, J. Exp. Botany, 65:89-101.*
Li et al, 2008, The Plant Cell, 20:2238-2251.*
Allen, et al. 2004. Evolution of microRNA genes by inverted duplication of target gene sequences in *Arabidopsis thaliana*. Nature Genetics 36: 1282-1290.
Axtell, et al. 2008. Evolution of plant microRNAs and their targets. Trends in plant science 13: 343-349.
Bennetzen, et al. 2012. Reference genome sequence of the model plant Setaria. Nature biotechnology.
Brown, et al. 2008. Efficient mapping of plant height quantitative trait loci in a sorghum association population with introgressed dwarfing genes. Genetics 180: 629-637.
Calvino, et al. 2011. Characterization of the small RNA component of the transcriptome from grain and sweet sorghum stems. BMC genomics 12: 356.
Calvino, et al. 2008. Screen of Genes Linked to High-Sugar Content in Stems by Comparative Genomics. Rice 1:166-176.
Calvino, et al. 2011. Sweet sorghum as a model system for bioenergy crops. Current opinion in biotechnology 23:1-7.
Calvino, et al. 2009. Molecular Markers for Sweet Sorghum Based on Microarray Expression Data. Rice 2: 129-142.
Dai, et al. 2011. psRNATarget: a plant small RNA target analysis server. Nucleic Acids Research 39: W155-159.
Duchene, et al. 2012. Towards the adaptation of grapevine varieties to climate change: QTLs and candidate genes for developmental stages. Theoretical and Applied Genetics 124: 623-635.
Fahlgen, et al. 2007. High-throughput sequencing of *Arabidopsis* microRNAs: evidence for frequent birth and death of MIRNA genes. PloS one 2: e219.
Fenselau, et al. 2008. Evolution of *Arabidopsis thaliana* microRNAs from random sequences. RNA 14: 2455-2459.
Fernandez, et al. 2009. From dwarves to giants? Plant height manipulation for biomass yield. Trends in plant science 14: 454-461.
Franks, et al. 2007. Rapid evolution of flowering time by an annual plant in response to a climate fluctuation. Proceedings of the National Academy of Sciences of the United States of America 104: 1278-1282.
Fulton, et al. 2002. Identification, analysis, and utilization of conserved ortholog set markers for comparative genomics in higher plants. The Plant cell 14: 1457-1467.
Griffith, et al. 2003. The Evolution of CONSTANS-Like Gene Families in Barley, Rice, and *Arabidopsis*. Plant Physiology 131: 1855-1867.
Hasan, et al. 2008. Association of gene-linked SSR markers to seed glucosinolate content in oilseed rape (*Brassica napus* ssp. *napus*). TAG. Theoretical and applied genetics. Theoretische und angewandte Genetik 116: 1035-1049.
Initiative 2010. Genome sequencing and analysis of the model grass *Brachypodium distachyon*. Nature 463: 763-768.
Jaillon, et al. 2007. The grapevine genome sequence suggests ancestral hexaploidization in major angiosperm phyla. Nature 449: 463-465.
Jiang, et al. 2006. Duplication and expression analysis of multicopy miRNA gene family members in *Arabidopsis* and rice. Cell Research 16: 507-518.
Li, et al. 2008. The *Arabidopsis* NFYA5 Transcription Factor Is Regulated Transcriptionally and Posttranscriptionally to Promote Drought Resistance. The Plant Cell Online 20: 2238-2251.
Ma, et al. 2010. *Arabidopsis lyrata* small RNAs: transient MIRNA and small interfering RNA loci within the *Arabidopsis* genus. The Plant cell 22: 1090-1103.
Maher, et al. 2006. Evolution of *Arabidopsis* microRNA families through duplication events. Genome Research 16:510-519.

(Continued)

*Primary Examiner* — Jason Deveau Rosen
(74) *Attorney, Agent, or Firm* — Kathleen D. Rigaut; Dann, Dorfman, Herrell & Skillman

(57) ABSTRACT

Compositions and methods for modulating flowering, sugar metabolism and stress response in plants are provided.

7 Claims, 97 Drawing Sheets

(56) References Cited

OTHER PUBLICATIONS

Meng, et al. 2011. Construction of microRNA- and microRNA-mediated regulatory networks in plants. RNA Biology 8: 1124-1148.
Messing, et al. 2004. Sequence composition and genome organization of maize. Proceedings of the National Academy of Sciences of the United States of America 101: 14349-14354.
Meyers, et al. 2008. Criteria for annotation of plant MicroRNAs. The Plant cell 20: 3186-3190.
Murat, et al. 2010. Ancestral grass karyotype reconstruction unravels new mechanisms of genome shuffling as a source of plant evolution. Genome Res 20: 1545-1557.
Murray, et al. 2008. Genetic Improvement of Sorghum as a Biofuel Feedstock: I. QTL for Stem Sugar and Grain Nonstructural Carbohydrates. Crop science 48: 2165.
Nozawa, et al. 2012. Origins and evolution of microRNA genes in plant species. Genome biology and evolution 4:230-239.
Paterson, et al. 2009. The Sorghum bicolor genome and the diversification of grasses. Nature 457: 551-556.
Piriyapongsa, et al. 2008. Dual coding of siRNAs and miRNAs by plant transposable elements. RNA 14: 814-821.
Sun, et al. 2012. Characterization and Evolution of microRNA Genes Derived from Repetitive Elements and Duplication Events in Plants. PloS one 7: e34092.
Swingonova, et al. 2004. Close split of sorghum and maize genome progenitors. Genome research 14: 1916-1923.
Tamura, et al. 2011. MEGA5: molecular evolutionary genetics analysis using maximum likelihood, evolutionary distance, and maximum parsimony methods. Molecular biology and evolution 28: 2731-2739.
Tang, et al. 2010. Angiosperm genome comparisons reveal early polyploidy in the monocot lineage. PNAS 107:472-477.
Toledo-Ortiz, et al. 2003. The *Arabidopsis* Basic/Helix-Loop-Helix Transcription Factor Family. The Plant cell 15: 1749-1770.
Valverde, et al. 2011. CONSTANS and the evolutionary origin of photoperiodic timing of flowering. Journal of Experimental Botany 62: 2453-2463.
Wenkel, et al. 2006. CONSTANS and the CCAAT Box Binding Complex Share a Functionally Important Domain and Interact to Regulate Flowering of *Arabidopsis*. The Plant cell 18: 2971-2984.
Wolfe, et al. 1989. Date of the monocot-dicot divergence estimated from chloroplast DNA sequence data. Proceedings of the National Academy of Sciences of the United States of America 86: 6201-6205.
Woodhouse, et al. 2010. Following Tetraploidy in Maize, a Short Deletion Mechanism Removed Genes Preferentially from One of the Two Homeologs. PLoS biology 8: e1000409.
Xu, et al. 2008. Diverged Copies of the Seed Regulatory Opaque-2 Gene by a Segmental Duplication in the Progenitor Genome of Rice, Sorghum, and Maize. Mol Plant 1: 760-769.
Xue, et al. 2009. Characterization and expression profiles of miRNAs in rice seeds. Nucleic Acids Research 37:916-930.
Yang, et al. 2011. Widespread regulatory activity of vertebrate microRNA species. RNA (New York, N.Y.) 17:312-326.
Zentella, et al. 2007. Global Analysis of DELLA Direct Targets in Early Gibberellin Signaling in *Arabidopsis*. The Plant cell 19: 3037-3057.
Zhang, et al. 2012. Genome sequence of foxtail millet (*Setaria italica*) provides insights into grass evolution and biofuel potential. Nature biotechnology 30:549-554.
Zhang, et al. 2009. A genome-wide characterization of microRNA genes in maize. PLoS genetics 5: e1000716.
Goldemberg, et al. 2007. Ethanol for a sustainable energy future. Science 315:808-810.
Grivet, et al. 2002. Sugarcane genomics: depicting the complex genome of an important tropical crop. Curr Opion Plant Biol 5:122-127.
Paterson, et al. 2009. The Sorghum bicolor genome and the diversification of grasses. Nature 457:551-6.
Nobuta, et al. 2008. Distinct size distribution of endogeneous siRNAs in maize: Evidence from deep sequencing in the mopl-1 mutant. PNAS 105:14958-63.
Louro, et al. 2009. Long intronic noncoding RNA transcription: expression noise or expression choice? Genomics 93:291-8.
Okamura, et al. 2007. The mirtron pathway generates microRNA-class regulatory RNAs in *Drosophila*. Cell 130:89-100.
Ruby, et al. 2007. Intronic microRNA precursors that bypass Drosha processing. Nature 448:83-6.
Taft, et al. 2009. Evolution, biogenesis and function of promoter-associated RNAs. Cell Cycle 8:2332-8.
Chuck et al. 2007. The maize tasselseed4 microRNA controls sex determination and meristem cell fate by targeting Tasselseed6/indeterminate spikelet1. Nat Genet 39:1517-21.
Lauter, et al. 2005. microRNA172 down-regulates glossy15 to promote vegetative phase change in maize. PNAS 102:9412-7.
Mathieu, et al. 2009. Repression of flowering by the miR172 target SMZ. PLoS Biol 7:e1000148.
Wu, et al. 2009. The sequential action of miR156 and miR172 regulates developmental timing in *Arabidopsis*. Cell 138:750-9.
Zhu, et al. 2009. Over-expression of miR172 causes loss of spikelet determinacy and floral organ abnormalities in rice (*Oryza sativa*). BMC Plant Biol. 9:149.
Li, et al.2008.The *Arabidopsis* NFYA5 transcription factor is regulated transcriptionally and posttranscriptionally to promote drought resistance. Plant Cell 20:2238-51.
Ghildiyal, et al. 2010. Sorting of *Drosophila* small silencing RNAs partitions microRNA strands into the RNA interference pathway. RNA 16:43-56.
Torney, et al. 2007. Genetic engineering approaches to improve bioethanol production from maize. Curr. Opin Biotechnol. 18:193-9.
Kawashima, et al. 2009. Sulphur starvation induces the expression of microRNA-395 and one of its target genes but in different cell types. Plant J. 57:313-21.
Lomako, et al. 2004. Glycogenin: the primer for mammalian and yeast glycogen synthesis. Biochim Biophys Acta 1673:45-55.
Ogas, et al. 1999. Pickle is a CHD3 chromatin-remodeling factor that regulates the transition from embryonic to vegetative development in *Arabidopsis*. PNAS 96:13839-44.
El-Din, et al. 2003. The role of cryptochrome 2 in flowering in *Arabidopsis*. Plant Physiol. 133:1504-16.
Henderson, et al. 2004. PICKLE acts throughout the plant to repress expression of embryonic traits and may play a role in gibberellin-dependent responses. Plant Physiol. 134:995-1005.
Endo, et al. 2007. CRYPTOCHROME2 in vascular bundles regulates flowering in *Arabidopsis*. Plant Cell 19:84-93.
Jiang, et al. 2008. Repression of Flowering Locus C and Flowering Locus T by the *Arabidopsis Polycomb* repressive complex 2 components. PLoS One 3:e3404.
Kim, et al. 2010. Epigenetic regulation of gene programs by EMF1 and EMF2 in *Arabidopsis*. Plant Physiol. 152:516-28.
Michaels, et al. 2004. FRIGIDA-related genes are required for the winter-annual habit in *Arabidopsis*. PNAS 101:3281-5.
Schlappi, et al. 2006. FRIGIDA LIKE 2 is a functional allele in Landsberg erecta and compensates for a nonsense allele of FRIGIDA LIKE 1. Plant Physiol. 142:1728-38.
Salome, et al. 2006. *Arabidopsis* response regulators ARR3 and ARR4 play cytokinin-independent roles in the control of circadian period. Plant Cell. 18:55-69.
Swaminathan, et al. 2010. Genomic and small RNA sequencing of Miscanthus x giganteus shows the utility of sorghum as a reference genome sequence for Andropogoneae grasses. Genome Biol. 11:R12.

* cited by examiner

Figure 8A

```
sbi-miR169cd --> target score: 6
3'-AUCCGUUCAGUAGGAACCGAU-5'
     |||||||  |  ||||||||
5'-UAGGCAAGGCCUACUUGGCUA-3'
Sb10g002400.1_5'UTR_chromosome --> similar to Glycine-rich protein-like sbi-miR169i --> target score: 6
3'-AUCCGUUCAGUAAGAACCGAU-5'
     |||||||  |  ||||||||
5'-UAGGCAAGGCCUACUUGGCUA-3'
Sb10g002400.1_5'UTR_chromosome --> similar to Glycine-rich protein-like sbi-miR395bacde --> target score: 1.0
3'-CUCAAGGGGGUUUGUGAAGUG-5'
   ||||:|||||||||||||||:
5'-GAGUUUCCCCAAACACUUCAU-3'
Sb01g044100.1_5'UTR_chromosome --> similar to Putative sulfate transporter sbi-miR395f --> target score: 0.5
3'-CUCAAGGGGGUUUGUGAAGUA-5'
   ||||:||||||||||||||||
5'-GAGUUUCCCCAAACACUUCAU-3'
Sb01g044100.1_5'UTR_chromosome --> similar to Putative sulfate transporter chromosome_5_379_mature.BC_04 --> target score: 6
3'-UAGGAGCGUG-GA-GAAGGG-5'
   |||||||||-||-| ||||
5'-AUCCUCGCACGCUCCCUCCC-3'
Sb02g001110.1_5'UTR_chromosome --> similar to Casein kinase II subunit alpha chromosome_5_978_mature.BC_01 --> target score: 4.0
3'-CGUCCGAGAGCCGUUUCUU-5'
   |||  |||||||  |:||||
5'-GCAGUCUCUCGGAAGAGAA-3'
Sb04g023680.2_5'UTR_chromosome --> similar to Cryptochrome 1a chromosome_5_978_mature.BC_01 --> target score: 4.0
3'-CGUCCGAGAGCCGUUUCUU-5'
   |||  |||||||  |:||||
5'-GCAGUCUCUCGGAAGAGAA-3'
Sb04g023680.1_5'UTR_chromosome --> similar to Cryptochrome 1a chromosome_6_201_mature.BC_02 --> target score: 2.5
3'-ACGUACUGUUCCUCUACU-5'
   |:|||||||||  ||||
5'-AGUAUGACAAGGAAAUGA-3'
Sb06g025550.1_5'UTR_chromosome --> similar to INDETERMINATE-related protein 9 chromosome_4_557_mature.BC_02 --> target score: 2
3'-AUUCCCGUGAGUGUUACGU-5'
   |||||||||||||| ||
5'-UAAGGGCACUCACAAUACA-3'
Sb10g006330.3_5'UTR_chromosome --> similar to Sucrose synthase 1 chromosome_9_1189_mature.BC_05 --> target score: 5
```

Figure 8B

```
3'-GGCAGC-GCGGCGGCGGCACGC-5'
      |||||-|||||||||||- ||
5'-CCGUCGCCGCCGCCGCCG-CCG-3'
Sb01g045200.1_5'UTR_chromosome --> similar to Glycosyl transferase, group 1 family protein, expr chromosome_9_1189_mature.BC_05 --> target score: 4
3'-GGCAGC-GCGGCGGCGGCACGC-5'
      || ||-||||||||| ||||
5'-CCGCCGCCGCCGCCGCCCUGCG-3'
Sb01g045200.1_5'UTR_chromosome --> similar to Glycosyl transferase, group 1 family protein, expr chromosome_1_827_mature.BC_01 --> target score: 4.5
3'-GGUGGGGUUGCGUACACCUAAC-5'
     |||| :|||| |||| ||||||
5'-CCACCUCAACACAUGCGGAUUG-3'
Sb03g041890.1_5'UTR_chromosome --> similar to Putative uncharacterized protein chromosome_1_827_mature.BC_01 --> target score: 3
3'-GGUGGGGUUGCGUACACCUAAC-5'
      ||| ||||| ||||||||||
5'-CCACACCAACACAUGUGGAUUG-3'
Sb06g021860.1_5'UTR_chromosome --> weakly similar to OSJNBa0014K14.20 protein chromosome_1_827_mature.BC_01 --> target score: 3.0
3'-GGUGGGGUUGCGUACACCUAAC-5'
      |||::|||| ||||||||||
5'-CCACUUCAACACAUGUGGAUUG-3'
Sb06g033900.1_5'UTR_chromosome --> similar to Os09g0111800 protein chromosome_1_827_mature.BC_01 --> target score: 2.5
3'-GGUGGGGUUGCGUACACCUAAC-5'
      |||:||||| ||||||||||
5'-CCACUCCAACACAUGUGGAUUG-3'
Sb07g021270.2_5'UTR_chromosome --> similar to Lipoate-protein ligase A-like chromosome_2_1473_mature.BC_01 --> target score: 2.5
3'-GGGGUUAGGUGAGGUUGUGUACA-5'
    :||||||||| |||||||||||
5'-CUCCAAUCCACACCAACACAUGU-3'
Sb06g021860.1_5'UTR_chromosome --> weakly similar to OSJNBa0014K14.20 protein chromosome_2_1473_mature.BC_01 --> target score: 1.0
3'-GGGGUUAGGUGAGGUUGUGUACA-5'
    |||||||||||:|||||||||||
5'-CCCCAAUCCACUUCAACACAUGU-3'
Sb06g033900.1_5'UTR_chromosome --> similar to Os09g0111800 protein chromosome_2_1473_mature.BC_01 --> target score: 0
3'-GGGGUUAGGUGAGGUUGUGUACA-5'
    |||||||||||||||||||||||
5'-CCCCAAUCCACUCCAACACAUGU-3'
Sb07g021270.2_5'UTR_chromosome --> similar to Lipoate-protein ligase A-like chromosome_3_189_mature.BC_01 --> target score: 3
3'-GGGGUUAGGUGGA-GUUGUGUACA-5'
    |||||||||-||-|||||||||||
5'-CCCCAAUCCA-CUCCAACACAUGU-3'
```

Figure 8C

```
Sb07g021270.1_5'UTR_chromosome --> similar to Lipoate-protein ligase A-like chromosome_3_189_mature.BC_01 --> target score: 2.0
3'-GGGGUUAGGUGGAGUUGUGUACA-5'
   :||||||:|||||||||||:|||
5'-CUCCAAUCUACCUCAACACGUGU-3'
Sb09g003590.2_5'UTR_chromosome --> similar to Sodium/hydrogen exchanger chromosome_3_1324_mature.BC_01 --> target score: 2.0
3'-AACCUCACCUAAUCCCACCUUAAA-5'
   ||||||  ||||:||||||||||||
5'-UUGGAGUAGAUUGGGGUGGAAUUU-3'
Sb03g046332.1_5'UTR_chromosome --> Predicted protein chromosome_3_1324_mature.BC_01 --> target score: 1.0
3'-AACCUCACCUAAUCCCACCUUAAA-5'
   |||||||||||:||||||||||||
5'-UUGGAGUGGAUUGGGGUGGAAUUU-3'
Sb06g021860.1_5'UTR_chromosome --> weakly similar to OSJNBa0014K14.20 protein chromosome_3_47_mature.BC_01 --> target score: 4.0
3'-UACACACAACCACACCUAACCCUA-5'
   ||||||||||||||:||||  :|
5'-AUGUGUGUUGGUGUGGGUUGGAGU-3'
Sb09g003590.2_5'UTR_chromosome --> similar to Sodium/hydrogen exchanger
```

Figure 9A

```
sbi-miR169cd ---> target score: 4.0
3'-AUC-CGUUCAGUAGGAACCGAU-5'
    ||-|||||||:||||||| ||
5'-UAGAGCAAGUCGUCCUUGGAUA-3'
Sb05g026273.1_chromosome_5_sbi ---> weakly similar to GRAS family transcription factor, putative sbi-miR169b ---> target score: 5
3'-GGCCGUUCAGUAGGAACCGAC-5'
    |||||| ||||| ||||||
5'-CCGGCAACUCAUCAGUGGCUG-3'
Sb06g002960.1_chromosome_6_sbi ---> similar to Putative non-LTR retroelement reverse transcriptas sbi-miR169a ---> target score: 4
3'-A-GCCGUUCAGUAGGAACCGAC-5'
   -|||||| |||||||||||-|
5'-UCCGGCAAAUCAUCCUUGGC-G-3'
Sb09g008100.1_chromosome_9_sbi ---> similar to Putative uncharacterized protein sbi-miR169b ---> target score: 3
3'---GGCCGUUCAGUAGGAACCGAC-5'
     |||||||  |||||||||||-|
5'-UCCGGCAAAUCAUCCUUGGC-G-3'
Sb09g008100.1_chromosome_9_sbi ---> similar to Putative uncharacterized protein sbi-miR169cd* ---> target score: 6
3'-AUCGGUUCCUACUGAACGGAU-5'
    |||||||||-|- |||||
5'-UAGCCAAGGAUG-C-AGCCUA-3'
Sb01g020840.1_chromosome_1_sbi ---> similar to HAT family dimerisation domain, putative sbi-miR169a* ---> target score: 2.5
3'-GUCGG-UUCCUACUGAACGGCU-5'
    |||-:|||||||||||||
5'-CUGCCGGAGGAUGACUUGCCGA-3'
Sb01g032770.1_chromosome_1_sbi ---> weakly similar to OSMYB3 sbi-miR169b* ---> target score: 4
3'-G-UC-GGUUCCUACUGAACGGCC-5'
   -||-||||||||||||| ||||
5'-CUAGUCCAAGGAUGACUUACCGG-3'
Sb01g036110.1_chromosome_1_sbi ---> similar to Insulinase containing protein, expressed sbi-miR169efgh* ---> target score: 5
3'-AUC-GGUUCCUACUGAACGGAC-5'
    ||-||||||||||||| || |
5'-UAGUCCAAGGAUGACUUACCGG-3'
Sb01g036110.1_chromosome_1_sbi ---> similar to Insulinase containing protein, expressed sbi-miR169b* ---> target score: 5
3'-GUCGGUUCCUACUGAACGGCC-5'
    ||-||||||| ||| ||||||
5'-CAG-CAAGGAGGACCUGCCGG-3'
Sb01g041700.1_chromosome_1_sbi ---> similar to Glutamate decarboxylase sbi-miR169i* ---> target score: 4
```

Figure 9B

```
3'-AUCGGUUCUUACUGAACGGAU-5'
   | |||||||||| ||||||
5'-UAACCAAGAAUGAGUUGCCUC-3'
Sb02g004450.1_chromosome_2_sbi --> similar to Putative uncharacterized protein sbi-miR169b* --> target score: 4
3'-GUCGGUUCCUACUGAACGGCC-5'
   ||||- ||||||||-||||||
5'-CAGCC-UGGAUGAC-UGCCGG-3'
Sb02g026670.1_chromosome_2_sbi --> similar to Calmodulin-like protein sbi-miR169a* --> target score: 5
3'-GUCGGUUCCUACUGAACGGCU-5'
   |||-|||||-| ||||||
5'-CAGCC-AGGAU-AGUUGCCGA-3'
Sb03g004580.1_chromosome_3_sbi --> similar to Putative RST1 sbi-miR169b* --> target score: 3.0
3'-GUCGGUUCCUACUGAACGGCC-5'
   -||||| |||||||||:||
5'-C-GCCAAAGAUGACUUGCUGG-3'
Sb03g028620.1_chromosome_3_sbi --> similar to Cytochrome P450 sbi-miR169b* --> target score: 3.0
3'-GUCGGUUCCUACUGAACGGCC-5'
   |-|||| |||||||||:||
5'-CA-CCAAAGAUGACUUGCUGG-3'
Sb03g028670.1_chromosome_3_sbi --> similar to Cytochrome P450 monooxygenase CYP72A26 sbi-miR169cd* --> target score: 6
3'-AUCGGUUCCUACUGAACGGAU-5'
   ||||||||||-|- |||||
5'-UAGCCAAGGAUG-C-AGCCUA-3'
Sb03g029065.1_chromosome_3_sbi --> similar to HAT family dimerisation domain, putative sbi-miR169a* --> target score: 5
3'-GUCGGU-UCCUACUGAACGGCU-5'
   |||||-|||||||| |||-|||
5'-CAGCCACAGGAUGAGUUG-CGA-3'
Sb03g038380.1_chromosome_3_sbi --> similar to Putative uncharacterized protein sbi-miR169a* --> target score: 5
3'-GUCGGUUCCUACUGAACGGCU-5'
   -||||||||-|-||||||||
5'-C-GCCAAGGA-G-CUUGCCGA-3'
Sb04g022590.1_chromosome_4_sbi --> similar to Putative uncharacterized protein sbi-miR169b* --> target score: 5
3'-GUCGGUUCCUACUGAACGGCC-5'
   |||||||||||- |||||
5'-CCGCCAAGGAUGAC-CGCCGG-3'
Sb05g002790.1_chromosome_5_sbi --> similar to Putative MFAP1 protein sbi-miR169b* --> target score: 5
3'-GUCGGUUCCUACUGAACGGCC-5'
   |||||||||||- |||||
5'-CCGCCAAGGAUGAC-CGCCGG-3'
```

Figure 9C

Sb05g002790.2_chromosome_5_sbi --> similar to Putative MFAP1 protein sbi-miR169cd* --> target score: 6
3'-AUCGGUUCCUACUGAACGGAU-5'
   ||||||||||-|-||-|||
5'-UAGCCAAGGAUG-C-UG-CUA-3'
Sb05g024660.1_chromosome_5_sbi --> similar to Putative uncharacterized protein sbi-miR169b* --> target score: 4
3'-GUCGGUUCCUACUGAACGGCC-5'
   ||||||||||-||-||||
5'-AAGCCAAGGAUGA-UU-CCGG-3'
Sb10g008200.1_chromosome_10_sb --> similar to Starch synthase isoform zSTSII-1 sbi-miR172cad --> target score: 1.0
3'-ACGUCGUAGUAGUUCUAAGA-5'
   |||||||||||:||||||
5'-UGCAGCAUCAUCAGGAUUCU-3'
Sb01g003400.1_chromosome_1_sbi --> similar to Indeterminate spikelet 1 sbi-miR172b --> target score: 3.0
3'-ACGUCGUAGUAGUUCUAAG-G-5'
   |||||||||||:|||||-|
5'-UGCAGCAUCAUCAGGAUUCUC-3'
Sb01g003400.1_chromosome_1_sbi --> similar to Indeterminate spikelet 1 sbi-miR172b --> target score: 3.5
3'-ACGUCGUAGUAGUUCUAAGG-5'
   | |||| |||||||||||:
5'-UGGAGCACCAUCAAGAUUCU-3'
Sb01g029120.1_chromosome_1_sbi --> weakly similar to Agenet domain containing protein, expressed sbi-miR172cad --> target score: 3
3'-ACGUCGUAGUAGUUCUAAGA-5'
   | |||| ||||||||||||
5'-UGGAGCACCAUCAAGAUUCU-3'
Sb01g029120.1_chromosome_1_sbi --> weakly similar to Agenet domain containing protein, expressed sbi-miR172cad --> target score: 5
3'-ACGUCGUAGUAGUUC-UAAGA-5'
   -|||||| ||||||-|||||
5'-U-CAGCAUGAUCAAGCAUUCU-3'
Sb01g041110.1_chromosome_1_sbi --> similar to Expressed protein sbi-miR172b --> target score: 3
3'---ACGUCGUAGUAGUUCUAAGG-5'
     ||| |||||||-||||||||
5'-UUGCUGCAUCAU-AAGAUUCC-3'
Sb01g050166.1_chromosome_1_sbi --> similar to Putative uncharacterized protein sbi-miR172b --> target score: 1.0
3'-ACGUCGUAGUAGUUCUAAGG-5'
   |||||||||||:||||||
5'-CGCAGCAUCAUCAGGAUUCC-3'
Sb10g025053.1_chromosome_10_sb --> similar to Glossy15 sbi-miR172cad --> target score: 2.0

Figure 9D

```
3'-ACGUCGUAGUAGUUCUAAGA-5'
   |||||||||||:|||||
5'-CGCAGCAUCAUCAGGAUUCC-3'
Sb10g025053.1_chromosome_10_sb --> similar to Glossy15 sbi-miR172cad --> target score: 4.0
3'-ACG-UCGUAGUAGUUCUAAGA-5'
   ||-||||||||||:|||
5'-UGCAAGCAUCAUCAAGGCUCU-3'
Sb01g050570.1_chromosome_1_sbi --> similar to Phosphoglycerate mutase family protein, expressed sbi-miR172cad --> target score: 5
3'-ACGUCGUAGUAGUUCUAAG-A-5'
   |-|||||||||| ||||-|
5'-UG-AGCAUCAUCAAAAUUCAU-3'
Sb02g003020.1_chromosome_2_sbi --> similar to Putative uncharacterized protein sbi-miR172e --> target score: 4
3'-CACGU-CGUAGUAGUUCUAAGU-5'
   |||-|||||||||||-|||
5'-GCGCAGGCAUCAUCAAGA-UCA-3'
Sb01g044240.1_chromosome_1_sbi --> similar to Expressed protein sbi-miR172e --> target score: 2.0
3'-CACGUCGUAGUAGUUCUAAGU-5'
   |||||||||||||:|||||
5'-CUGCAGCAUCAUCAGGAUUCU-3'
Sb02g007000.1_chromosome_2_sbi --> similar to Putative indeterminate spikelet 1 sbi-miR172e --> target score: 5
3'-CAC-GUCGUAGUAGUUCUAAGU-5'
   ||-||||||-||||  ||||
5'-GUGACAGCAU-AUCAACAUUCA-3'
Sb03g027080.1_chromosome_3_sbi --> similar to Os01g0601700 protein sbi-miR172e --> target score: 4
3'-CACGUCGUAGU-AGUUCUAAGU-5'
   | |||||-||-|||||||||
5'-GUACAGCA-CACUCAAGAUUCA-3'
Sb05g020460.1_chromosome_5_sbi --> similar to Helicase-like protein sbi-miR172e --> target score: 4
3'-C-ACGUCGUAGUAGUUCUAAGU-5'
   -|||||-|||||  |||||||
5'-GCUGCAG-AUCAUGAAGAUUCA-3'
Sb06g015350.1_chromosome_6_sbi --> similar to H0321H01.9 protein sbi-miR172e --> target score: 4
3'-C-ACGUCGUAGUAGUUCUAAGU-5'
   -|||||||||||||  |||||
5'-GCUGCAGCAUCAUCACGAUUCC-3'
Sb06g030670.1_chromosome_6_sbi --> similar to OSJNBa0010D21.13 protein sbi-miR172cad --> target score: 3
3'-ACGUCGUAGUAGUUCUAAGA-5'
   ||||||||||| |||||
5'-UGCAGCAUCAUCACGAUUCC-3'
```

Figure 9E

```
Sb06g030670.1_chromosome_6_sbi --> similar to OSJNBa0010D21.13 protein sbi-miR172b --> target score: 2
3'-ACGUCGUAGUAGUUCUAAGG-5'
   ||||||||||||| ||||||
5'-UGCAGCAUCAUCACGAUUCC-3'
Sb06g030670.1_chromosome_6_sbi --> similar to OSJNBa0010D21.13 protein sbi-miR395bacde --> target score: 2.0
3'-CUCAAGGGGGUUUGUGAAGUG-5'
   ||||||:||||:||||||||:
5'-GAGUUCCUCCAAGCACUUCAU-3'
Sb01g008450.1_chromosome_1_sbi --> similar to ATP sulfurylase sbi-miR395f --> target score: 1.5
3'-CUCAAGGGGGUUUGUGAAGUA-5'
   ||||||:||||:|||||||||
5'-GAGUUCCUCCAAGCACUUCAU-3'
Sb01g008450.1_chromosome_1_sbi --> similar to ATP sulfurylase sbi-miR395bacde* --> target score: 5
3'-CACUUCACAAACCCCCUUGAG-5'
   |||||| |||-|||||| -||
5'-GUGAAGUUUUU-GGGGAA-UC-3'
Sb03g014780.1_chromosome_3_sbi --> similar to Probable chromatin-remodeling complex ATPase chain sbi-miR395bacde* --> target score: 5
3'-CACUUCACAAACCCCCUUGAG-5'
   ||| ||||||-|||||| -||
5'-GUGAUGUGUUU-GGGGAA-UC-3'
Sb03g026410.1_chromosome_3_sbi --> similar to ATP synthase beta subunit/transcription terminatio sbi-miR395f* --> target score: 5
3'-UACUUCACAAACCCCCUUGAG-5'
   ||||-||-||||||||| ||
5'-AUGAA-UG-UUGGGGGAAAUC-3'
Sb09g023793.1_chromosome_9_sbi --> similar to NOT2/NOT3/NOT5 family protein, expressed sbi-miR395f* --> target score: 5.0
3'-UACUUCACAAACCCCCUUGAG-5'
   |||||||||| -||||:|||
5'-AUGAAGUGUUU-GGGAGCUC-3'
Sb10g012270.1_chromosome_10_sb --> similar to Putative uncharacterized protein sbi-miR395f* --> target score: 4
3'-UACUUCACAAACCCCCUUGA-G-5'
   ||||-|-|||||||||||-|
5'-AUGAAG-G-UUGGGGGAACUAC-3'
Sb10g013750.1_chromosome_10_sb --> similar to Cryptochrome 2 chromosome_1_983_mature.BC_04 --> target score: 4.5
3'-AGUAACCUAAGUGUAAUU-5'
   |||||||| |||| ||:
5'-UCAUUGGAUGCACAGUAG-3'
Sb0010s020250.1_super_10_sbic_ --> putative protein chromosome_1_983_mature.BC_04 --> target score: 5.0
```

Figure 9F

```
3'-AGUAACC-UAAGUGUAAUU-5'
   ||||||-||| ||||||*|
5'-UCAUUGGCAUUGACAUUGA-3'
Sb04g037050.1_chromosome_4_sbi ---> similar to Alcohol dehydrogenase class-3 (EC 1.1.1.1) (Alcoho chromosome_1_466_mature.BC_02 ---> target score: 3
3'--UCGAGCCGUGGUGUCUAGA-5'
     ||||||||||-||||||
5'-CUGCUCGGCACCA-AGAUCU-3'
Sb10g000770.1_chromosome_10_sb ---> similar to Integral membrane protein DUF6 containing protein, chromosome_1_398_mature.BC_02 ---> target score: 5
3'-GUGCCGUGAUAGUCCGUGC-5'
   |||||| | ||||||||
5'-CUCGGCACCAGCAGGCACG-3'
Sb10g006910.1_chromosome_10_sb ---> similar to 2-oxoglutarate-dependent oxygenase chromosome_1_345_mature.BC_03 ---> target score: 3.0
3'---AGGGUGAACGUGGGAGUC-5'
      ||||||-||||||*||||
5'-CUCCCAC-UGCACCUUCAG-3'
Sb10g030730.1_chromosome_10_sb ---> weakly similar to Putative uncharacterized protein chromosome_1_970_mature.BC_03 ---> target score: 6
3'-GAAGCACCAAC-AGCGCCUG-5'
   ||||||| ||-||||-|||
5'-CUUCGUGGAUGUUCGC-GAC-3'
Sb10g024490.2_chromosome_10_sb ---> similar to Putative cinnamoyl-CoA reductase chromosome_1_970_mature.BC_03 ---> target score: 5
3'-GAAGCACCAACAGCGCCUG-5'
   |||| |||||||||  |||
5'-CUUCGAGGUUGUCGAUGAC-3'
Sb09g020980.1_chromosome_9_sbi ---> similar to Class III peroxidase 124 precursor chromosome_1_970_mature.BC_03 ---> target score: 5
3'-GAAGCACCAACAGCGCCUG-5'
   |||| |||||||||  |||
5'-CUUCGAGGUUGUCGAUGAC-3'
Sb09g021000.1_chromosome_9_sbi ---> similar to Class III peroxidase 124 precursor chromosome_1_970_mature.BC_03 ---> target score: 4
3'-GAAGCACCAACAGCGCCUG-5'
   ||||| || |||||||||
5'-CUUCGUCGUCGUCGCGGAC-3'
Sb03g035080.1_chromosome_3_sbi ---> similar to Putative Dof zinc finger protein chromosome_1_527_mature.BC_05 ---> target score: 6
3'-UCACUUCAACUCGAAACA-5'
   |||||||||   |||||
5'-AGUGAAGUUGCUAUUUGU-3'
Sb10g031060.1_chromosome_10_sb ---> similar to Chromosome chr1 scaffold_22, whole genome shotgun chromosome_1_527_mature.BC_05 ---> target score: 6
3'-UCACUUCAACUCGAA-ACA-5'
   ||||||| ||||||- ||
5'-AGUGAAGUCGAGCUUGAGU-3'
```

Figure 9G

Sb03g042460.1_chromosome_3_sbi --> similar to Fructokinase-1 chromosome_1_52_mature.BC_04 --> target score: 4
3'-CGAGC-CGCGGUGUCUAGAA-5'
     |||| -|||| -||||||||
5'-GCUCGUUCGCCA-AGAUCUU-3'
Sb10g024900.1_chromosome_10_sb --> similar to Putative uncharacterized protein OSJNBa0019I19.51 chromosome_1_216_mature.BC_05 --> target score: 5
3'-GGGCAGCUUGGUACCCU-UC-5'
   ||| |||| |||||||-||
5'-CCCGACGAAACAUGGGACAG-3'
Sb10g030940.1_chromosome_10_sb --> similar to Calcium-binding EF hand protein-like chromosome_1_450_mature.BC_02 --> target score: 5
3'-ACGAGUGUCA-UUCCCGCCGA-5'
   | |||||||-|||||||| ||
5'-UGAUCACAGUCAAGGGCGCCU-3'
Sb02g006890.1_chromosome_2_sbi --> similar to Putative uncharacterized protein OSJNBa0086N05.106 chromosome_1_754_mature.BC_04 --> target score: 4
3'-GUUAGGUGUACACAACUCC-5'
   |||||| || |||||||||
5'-AAAUCCAAAUCUGUUGAGG-3'
Sb10g022700.1_chromosome_10_sb --> similar to Os06g0574400 protein chromosome_1_1560_mature.BC_03 --> target score: 6
3'-UUGGAUAACGUCAAAG-AGGUUG-5'
   ||||||||| | |||-||||||
5'-AACCUAUUGCUGAUUCAUCCAAC-3'
Sb03g035550.1_chromosome_3_sbi --> similar to Putative uncharacterized protein chromosome_1_245_mature.BC_01 --> target score: 3
3'-CCCCUUACUUCGGACCAGGCU-5'
   ||||||||||||| |||||
5'-UGGGAAUGAAGCCUCGUCCGC-3'
Sb10g009464.1_chromosome_10_sb --> Predicted protein chromosome_1_1391_mature.BC_04 --> target score: 3.5
3'-GUGAGGUU-AGAUGGAGUU-5'
   :||||||-||||||||:||
5'-CGCUCCAACUCUACCUUAA-3'
Sb10g028850.1_chromosome_10_sb --> similar to 4-amino-4-deoxychorismate synthase chromosome_1_1391_mature.BC_04 --> target score: 3.5
3'-G-UGAGGUUAGAUGGAGUU-5'
   -|||||||-|||||||||:
5'-CUACUCCAA-CUACCUCAG-3'
Sb10g009270.1_chromosome_10_sb --> similar to Endoglucanase 17 precursor chromosome_1_882_mature.BC_04 --> target score: 4
3'-CUACGCGUGCGCCUCAGCU-CC-5'
   ||||||||||||||-|||-||
5'-GAUGCGCACGCGGAG-CGACGG-3'
Sb10g003090.1_chromosome_10_sb --> similar to Pectate lyase homolog chromosome_1_686_mature.BC_02 --> target score: 5

Figure 9H

```
3'-AAAAAUGGCCAGGCUAACGU-5'
   || ||||  |||||||||
5'-UUUAUACCACUCCGAUGGCA-3'
Sb01g035310.1_chromosome_1_sbi ---> similar to Zinc finger, C3HC4 type family protein, expressed chromosome_1_862_mature.BC_02 ---> target score: 3
3'-UGGUCCGAUUCCUCCUCGAGGGCG-5'
   |||||||||||||| ||||||
5'-ACCAGGCUAAGGAGGAACUCCCGG-3'
Sb06g030515.1_chromosome_6_sbi ---> similar to Putative gag-pol polyprotein chromosome_1_346_mature.BC_03 ---> target score: 3
3'-GAGGGUGAACGUGGGAGUCC-GCA-5'
   ||||-|||||||||||||||-|||
5'-GUCCC-CUUGCACCCUCAGGCCGU-3'
Sb03g035140.1_chromosome_3_sbi ---> similar to P0460E08.3 protein chromosome_1_1241_mature.BC_03 ---> target score: 5
3'-GGGGC-GGUACU-GGCCGGGUGG-5'
   ||||-||||||-|||||||  ||
5'-CCCCGUCCAUGACCCGGCCCUCC-3'
Sb03g027140.1_chromosome_3_sbi ---> weakly similar to Os07g0517700 protein chromosome_1_651_mature.BC_03 ---> target score: 1.5
3'-AGCGCCGGUACCGCCCGCUGAAGU-5'
   |||||:||||||||||||:|||||
5'-UCGCGGUCAUGGCGGGCGGCUUCA-3'
Sb08g022810.1_chromosome_8_sbi ---> Predicted protein chromosome_2_2234_mature.BC_05 ---> target score: 4.5
3'-CAUGCCGGCUCUGGCGGCAGCGGU-5'
   |||||||||||||||   |||:
5'-GUACGGCCGAGACCGCCGCAGCCG-3'
Sb03g024845.1_chromosome_3_sbi ---> Predicted protein chromosome_2_2159_mature.BC_04 ---> target score: 4
3'-GGGGC-GUGAGUGCGGGAAGCA-5'
   ||||-||-||||||  ||||||
5'-CCCCGACA-UCACGCGCUUCGU-3'
Sb09g023000.1_chromosome_9_sbi ---> weakly similar to Putative uncharacterized protein chromosome_2_902_mature.BC_02 ---> target score: 4.5
3'-CGUGUUGAAGAUUCUCGUU-5'
   ||||:| |||||||||
5'-GCACAGCAACUAAGAGCAA-3'
Sb0012s004900.1_super_12_sbic_ ---> putative protein chromosome_2_1490_mature.BC_04 ---> target score: 4.0
3'-GGUGCAGGG-GGUGGUGCUGC-5'
   ||-|||||-|||:||||||
5'-CCA-GUCCCACCACUACGACG-3'
Sb0013s004020.1_super_13_sbic_ ---> putative protein chromosome_2_1490_mature.BC_04 ---> target score: 4.0
3'-GGUGCAGGGGGUGGUGCUGC-5'
   |||:|||  |||||||
5'-CAACGUCUCCCUCCACGACG-3'
```

Figure 9I

Sb05g019040.1_chromosome_5_sbi --> similar to O-methyltransferase ZRP4, putative, expressed chromosome_2_3135_mature.BC_05 --> target score: 2.5
3'-UGCGGGCGACCACCCUAGACC-5'
    |||||:|||||||||| ||||
5'-ACGCCUGCUGGUGGGACCUGG-3'
Sb0013s004040.1_super_13_sbic_ --> putative protein chromosome_2_45_mature.BC_01 --> target score: 6
3'-UCCCGGACAAAUCUAACC-5'
   |||||||||  | |||
5'-AGGGCCUGUUUCCAAUGG-3'
Sb10g010410.1_chromosome_10_sb --> similar to Putative uncharacterized protein chromosome_2_3135_mature.BC_04 --> target score: 5
3'-GGAUCGAUGUCGAACAUGCC-5'
   ||||| | |||||||| |||
5'-CCUAGCCAGAGCUUGUCCGG-3'
Sb03g004450.1_chromosome_3_sbi --> similar to Putative brassinosteroid insensitive 1-associated chromosome_2_1061_mature.BC_05 --> target score: 2.0
3'--GUGUGUGCUGUUUCCGGU-5'
    |||-||||:|||||||||
5'-GCAC-CACGGCAAAGGCCA-3'
Sb0010s009900.1_super_10_sbic_ --> putative protein chromosome_2_1061_mature.BC_05 --> target score: 4.5
3'-GUGUGU-GCUGUUUCCGGU-5'
   |||:|-|||-|||||||||
5'-CACAUACCGA-AAAGGCCA-3'
Sb01g035890.1_chromosome_1_sbi --> similar to Sucrose synthase 3 chromosome_2_1061_mature.BC_05 --> target score: 4
3'---GUGUGUGCUGUUUCCGGU-5'
     |||||||||||| |-||
5'-UCACACACGACAAAAG-CA-3'
Sb01g048630.1_chromosome_1_sbi --> similar to Putative callose synthase 1 catalytic subunit chromosome_3_1257_mature.BC_01 --> target score: 3.5
3'-AAGCGUAACUCUUCACAC-5'
   |: |||||||| ||||||
5'-GUUACAUUGAGCAGUGUG-3'
Sb10g022220.1_chromosome_10_sb --> similar to T-complex protein 1 subunit epsilon chromosome_3_397_mature.BC_01 --> target score: 5
3'-CACCUAA-UCUCACCUUGAAC-5'
   ||||||-||| |||||-|||
5'-GUGGAUUCAGAAUGGAA-UUG-3'
Sb09g017875.1_chromosome_9_sbi --> Predicted protein chromosome_3_1435_mature.BC_05 --> target score: 3.0
3'-AUGUUAGGCUUGACUUCCACUC-5'
   ||||||| |||||:|||||
5'-UACAAUCCCAACUGGAGGUGAC-3'
Sb02g012863.1_chromosome_2_sbi --> Predicted protein chromosome_3_201_mature.BC_02 --> target score: 3

Figure 9J

```
3'--CGGCGGUCCCCGUAGGGCUCC-5'
      ||||||-|||||| ||||||
5'-CGCCGCC-GGGGCAGCCCGAGG-3'
Sb08g016760.1_chromosome_8_sbi --> similar to Auxin-binding protein 4 precursor chromosome_3_107_mature.BC_03 --> target score: 4
3'-GCGGUGGAGGCCGAGCUUGA-5'
     |||||||||||| |||
5'-CUCCACCUCCGGCUCCAACC-3'
Sb10g029400.1_chromosome_10_sb --> similar to Mitogen-activated protein kinase 12 chromosome_3_1460_mature.BC_01 --> target score: 5
3'-GGGUUAG-GUGAGGUUGUG-5'
    ||-|||-|||| ||||||
5'-CCC-AUCACACUGCAACAC-3'
Sb10g008780.1_chromosome_10_sb --> similar to Chromosome chr3 scaffold_8, whole genome shotgun s chromosome_3_1374_mature.BC_04 --> target score: 5
3'-AGGUGAGGUUAGGUGGAGUU-5'
    ||| |||||||||| | |||
5'-UCCAAUCCAAUCCAACACAA-3'
Sb09g024050.1_chromosome_9_sbi --> weakly similar to Putative uncharacterized protein P0685G12.3 chromosome_3_235_mature.BC_02 --> target score: 5
3'-GG-UACGAACCGCCCCGUUUA-5'
    |-|||||||||-|||||||| |
5'-CCGAUGCUUGG-GGGGCAAUU-3'
Sb08g005330.1_chromosome_8_sbi --> similar to Os05g0239200 protein chromosome_3_133_mature.BC_04 --> target score: 5
3'-GGCUUUGCC-GAGGCUGAAG-5'
    |||| |||-|||||||| |
5'-CCGAACCGGACUCCGACUCC-3'
Sb0014s008210.1_super_14_sbic_ --> putative protein chromosome_3_133_mature.BC_04 --> target score: 4.0
3'-GGCUUUGCCGAGGCUGAAG-5'
    || |||||||:|| ||||
5'-CCGCAACGGCUUCGCCUUC-3'
Sb09g000430.1_chromosome_9_sbi --> similar to Polygalacturonase inhibiting protein 2 precursor chromosome_3_1462_mature.BC_04 --> target score: 4
3'-U-GUGACCGGGCAGGCUCG-5'
    -| |||||||||-|||||
5'-ACCUCUGGCCCGU-CGAGC-3'
Sb10g023150.1_chromosome_10_sb --> similar to Putative uncharacterized protein chromosome_3_1462_mature.BC_04 --> target score: 5.0
3'-UGUGACCGGGCAGGCUCG-5'
    |||||| :| |||||||
5'-ACACUGGGUCCUCCGAGC-3'
Sb04g024040.1_chromosome_4_sbi --> similar to F-box protein GID2 chromosome_3_213_mature.BC_01 --> target score: 4.5
3'-AUCCCCGA-GACGACCUCAA-5'
    :||||||-|||||| ||||
5'-UGGGGGCUGCUGCUGCAGUU-3'
```

Figure 9K

Sb08g021330.1_chromosome_8_sbi --> similar to DNAJ heat shock N-terminal domain-containing prote chromosome_3_213_mature.BC_01 --> target score: 3
3'-AUCCCC-GAGACGACCUCAA-5'
   |||||-||| |||||||||
5'-AAGGGGUCUCCGCUGGAGUU-3'
Sb06g032760.1_chromosome_6_sbi --> similar to Endoglucanase 13 precursor chromosome_3_821_mature.BC_05 --> target score: 5
3'-AUA-CCUUCGAUCGUCGAGUCG-5'
   ||-|||||-||| |||||||||
5'-UAUGGGAAG-UAGGAGCUCAGC-3'
Sb03g006560.1_chromosome_3_sbi --> similar to Chromosome chr8 scaffold_23, whole genome shotgun chromosome_3_514_mature.BC_02 --> target score: 1.0
3'-GCCACACCCACUUCCUCGGCGACC-5'
   |||||||||||||||||:|||||
5'-CGGUGUGGGUGAAGGAGCUGCUGG-3'
Sb02g000340.1_chromosome_2_sbi --> similar to Putative potassium transporter chromosome_3_954_mature.BC_04 --> target score: 4
3'-UCCCGGCGACUGCC-CACGAGGU-5'
   || ||||-||||-|||||||||
5'-AGGUCCGC-GACGGCGUGCUCCA-3'
Sb03g026360.1_chromosome_3_sbi --> similar to Putative uncharacterized protein chromosome_3_1128_mature.BC_01 --> target score: 5
3'-CAACCUCACCUAACCUCACCU-5'
   ||||||||||| | ||||
5'-GGUGGAGUGGAUUGUACUGGA-3'
Sb10g000900.1_chromosome_10_sb --> similar to Proteasome subunit beta type chromosome_3_216_mature.BC_05 --> target score: 5
3'-CUGCAGGGCCGG-CAACAAG-5'
   ||||-|||||||-| |||||
5'-GACGU-CCGGCCGGGUGUUC-3'
Sb0610s002010.1_super_610_sbic --> putative protein chromosome_3_216_mature.BC_05 --> target score: 4
3'-CU-GCAGGGCCGGCAACAAG-5'
   |-|| |||||||||-|||||
5'-GACCGACCCGGCCG-UGUUC-3'
Sb06g000490.1_chromosome_6_sbi --> similar to Class III peroxidase 52 precursor chromosome_4_1911_mature.BC_05 --> target score: 4
3'-UCGCG-GCGGCGACG-AGACCGGCGC-5'
   || |-|||||||||-||||||||||
5'-AGCUCACGCCGCUGCAUCUGGCCGCG-3'
Sb09g025900.1_chromosome_9_sbi --> similar to Heat shock protein 101 chromosome_4_557_mature.BC_02 --> target score: 6
3'-AUUCCCGUGAGUGUUACGU-5'
   |||||| |||||| | |
5'-UAAGGGCAAUCACAAGGAA-3'
Sb10g022233.1_chromosome_10_sb --> weakly similar to Chromosome chr1 scaffold_84, whole genome s chromosome_4_2454_mature.BC_04 --> target score: 4

Figure 9L

```
3'-CACACCUCCUGUCGUC-GCGGAG-5'
   -||| |||||||||||-||||||
5'-G-GUGCAGGACAGCAGCCGCCUC-3'
Sb10g004840.1_chromosome_10_sb --> similar to RRM-containing RNA-binding protein-like chromosome_4_831_mature.BC_04 --> target score: 4
3'-UGUACACAACUUUAACUAA-5'
   ||| || |||||||||||
5'-ACAUUUGAUGAAAUUGAUG-3'
Sb10g027780.1_chromosome_10_sb --> similar to SMC5 protein chromosome_4_712_mature.BC_01 --> target score: 5
3'-GGCGACCUGCCGCCGC-GC-5'
   ||-|||| |||||||-||
5'-CCG-UGGAGGGCGGCGUCG-3'
Sb0067s002130.1_super_67_sbic_ --> putative protein chromosome_4_712_mature.BC_01 --> target score: 3
3'-GGCGACCUGCCGCCGCGC-5'
   |||||||||||||| |
5'-AAGCUGGACGGCGCGGG-3'
Sb01g021990.1_chromosome_1_sbi --> similar to Kaurene synthase A chromosome_4_712_mature.BC_01 --> target score: 5
3'-G-GCGACCUGCCGCCG-CGC-5'
   -||||||||||||| |-|||
5'-CGCGCUGGACGGCGCCAGCG-3'
Sb03g041900.1_chromosome_3_sbi --> similar to Gibberellin 20 oxidase 2 chromosome_4_712_mature.BC_01 --> target score: 5.0
3'-GGCGACCUGCCGCCGC-GC-5'
   ||||||-|||v||||-||
5'-CCGCUGG-CGGUGGCGCCG-3'
Sb03g043030.1_chromosome_3_sbi --> similar to Gibberellin response modulator-like protein chromosome_4_712_mature.BC_01 --> target score: 4
3'-G-GCGACCUGCCGCCGCGC-5'
   -|||||||||-|||||||
5'-CGCGCUGGAC-GCGGCGCU-3'
Sb03g043030.1_chromosome_3_sbi --> similar to Gibberellin response modulator-like protein chromosome_4_712_mature.BC_01 --> target score: 5
3'-GGCGACCUGCCGCCG-CGC-5'
   ||| ||-|||||||-|||
5'-CCGCAGG-CGGCGGCGGCG-3'
Sb03g047330.1_chromosome_3_sbi --> similar to SbPCL1 protein chromosome_4_712_mature.BC_01 --> target score: 5
3'-GGCG-ACCUGCCGCC-GCGC-5'
   |||-|||-||||||-||||
5'-CCGCGUGG-CGGCGGCGUCGCG-3'
Sb05g003660.1_chromosome_5_sbi --> similar to CCT motif family protein, expressed chromosome_4_712_mature.BC_01 --> target score: 4
3'-GGCGACCUGCCGCCG-CGC-5'
   ||||||-|||||||-|||
5'-GCGCUGG-CGGCGGCAGCG-3'
```

Figure 9M

```
Sb06g024630.1_chromosome_6_sbi --> similar to Squamosa promoter-binding-like protein 7 chromosome_4_712_mature.BC_01 --> target score: 4
3'-GGCGACCUGCCGCCG-CGC-5'
    ||| -|||||||||-|||
5'-CCGCC-GACGGCGGCGGCG-3'
Sb05g007310.1_chromosome_5_sbi --> similar to Sucrose-phosphate synthase chromosome_4_712_mature.BC_01 --> target score: 3
3'-GGCGACCUGCCGCCGCGC-5'
   ||||||||||||||| |
5'-UGGCUGGACGGCGGCGGG-3'
Sb06g031910.1_chromosome_6_sbi --> similar to Beta-fructofuranosidase, insoluble isoenzyme 6 pre chromosome_4_712_mature.BC_01 --> target score: 4
3'-GGCGACCUGCCGCCG-CGC-5'
   |||||||-||||||-|||
5'-GCGCUGGA-GGCGGCGGCG-3'
Sb07g001140.1_chromosome_7_sbi --> similar to Putative Bile acid beta-glucosidase chromosome_4_712_mature.BC_01 --> target score: 4
3'-GGCG-ACCUGCCGC-CGCGC-5'
   |||- |||||||||-|||||
5'-CCGCGCGGACGGCGAGCGCG-3'
Sb03g042460.1_chromosome_3_sbi --> similar to Fructokinase-1 chromosome_4_712_mature.BC_01 --> target score: 5
3'-GGCGAC-CUGCCGCCGCGC-5'
   ||| |-|||||||||-|
5'-CCGCGGAGACGGCGGCG-G-3'
Sb03g010640.1_chromosome_3_sbi --> similar to Alpha-glucosidase-like chromosome_4_712_mature.BC_01 --> target score: 4
3'-GGCGACCUGCCGCCGCGC-5'
   | ||||||||||  |||
5'-CCCAUGGACGGCGGAGCG-3'
Sb09g019480.1_chromosome_9_sbi --> similar to Isoamylase-type starch debranching enzyme ISO2 chromosome_4_712_mature.BC_01 --> target score: 4
3'-GGCGAC-CUGCCGCCG-CGC-5'
   ||| |-|||||||||-|||
5'-CCGCCGAGACGGCGGCGGCG-3'
Sb10g009270.1_chromosome_10_sb --> similar to Endoglucanase 17 precursor chromosome_4_712_mature.BC_01 --> target score: 5
3'-GGCGAC-CUGCCGCCGCGC-5'
   ||| |-|||||||||-|
5'-CCGCGGAGACGGCGGCG-G-3'
Sb10g030140.1_chromosome_10_sb --> similar to Endoglucanase 18 chromosome_4_712_mature.BC_01 --> target score: 6
3'-GGCGACCUGC-CGCCGCGC-5'
   ||||||| |-|||||-||
5'-CCGCUGGAGGUGCGGC-CG-3'
Sb04g036140.1_chromosome_4_sbi --> similar to Putative monosaccharide transporter 6 chromosome_4_712_mature.BC_01 --> target score: 4
```

Figure 9N

```
3'-G-GCGACCUGCCGCCGCGC-5'
   -||||||-|||||||||
5'-CGCGCUGG-CGGCGGCGCU-3'
Sb07g024870.1_chromosome_7_sbi --> similar to Beta-galactosidase 11 precursor chromosome_4_712_mature.BC_01 --> target score: 5
3'-GG-CGACCUGCCGCCG-CGC-5'
   |-||||||-|||||||-|||
5'-CCUGCUGG-CGGCGGCGGCG-3'
Sb10g022620.1_chromosome_10_sb --> similar to Beta-galactosidase 9 precursor chromosome_4_712_mature.BC_01 --> target score: 3
3'-GGCGACCUGCCGCCGCGC-5'
   || |||||||||| ||||
5'-GCGAUGGACGGCGCCGCG-3'
Sb10g024490.1_chromosome_10_sb --> similar to Putative cinnamoyl-CoA reductase chromosome_4_712_mature.BC_01 --> target score: 2
3'-GGCGACCUGCCGCCGCGC-5'
   |||||||||||| ||||
5'-GCGCUGGACGGCGCCGCG-3'
Sb10g024500.1_chromosome_10_sb --> similar to Putative cinnamoyl-CoA reductase chromosome_4_712_mature.BC_01 --> target score: 4
3'-G-GCGACCUGCCGCCGCG-C-5'
   -|||-|||||||||||||-|
5'-CACGC-GGACGGCGGCGCUG-3'
Sb04g010000.1_chromosome_4_sbi --> similar to Expansin-A24 precursor chromosome_4_712_mature.BC_01 --> target score: 3
3'-GGCGACCUGCCGCCGCG-C-5'
   |||-|||||||||||||-|
5'-ACGC-GGACGGCGGCGCUG-3'
Sb04g010160.1_chromosome_4_sbi --> similar to Expansin-A23 precursor chromosome_4_712_mature.BC_01 --> target score: 4
3'-G-GCGACCUGCCGCCGCG-C-5'
   -|||-|||||||||||||-|
5'-CACGC-GGACGGCGGCGCUG-3'
Sb04g010170.1_chromosome_4_sbi --> similar to Expansin-A23 precursor chromosome_4_712_mature.BC_01 --> target score: 4.0
3'-GGCGA-CCUGCCGCCGCGC-5'
   ||||-|||-||:|||||||
5'-CCGCUCGGA-GGUGGCGCG-3'
Sb04g028090.1_chromosome_4_sbi --> similar to Expansin-A5 precursor chromosome_4_712_mature.BC_01 --> target score: 4
3'-GGCGAC-CUGCCGCCGCGC-5'
   || |-|||||||||||
5'-CGGCAGUGACGGCGGCGCG-3'
Sb04g032830.1_chromosome_4_sbi --> similar to Expansin-B11 precursor chromosome_4_712_mature.BC_01 --> target score: 4
3'-GGCGAC-CUGCCGCCGCGC-5'
   || |-||||||||||||
5'-CGGCAGCGACGGCGGCGCG-3'
```

Figure 90

Sb06g023380.1_chromosome_6_sbi --> similar to Expansin-B17 precursor chromosome_4_712_mature.BC_01 --> target score: 4
3'-GGCGACCUGCCGCCGCGC-5'
   |||||||  ||||  ||||
5'-GCGCUGGAGGGCGUCGCG-3'
Sb02g041050.1_chromosome_2_sbi --> similar to Putative esterase chromosome_4_712_mature.BC_01 --> target score: 4.0
3'-GGCGACCUGCCGCCG-CGC-5'
   |||-||:|||||||-|||
5'-CCGC-GGGCGGCGGCGGCG-3'
Sb03g001870.1_chromosome_3_sbi --> similar to Putative esterase chromosome_4_712_mature.BC_01 --> target score: 5
3'-GGCGACCUGCCGCCGC-GC-5'
   |||  ||-|||||||-||
5'-CCGCAGG-CGGCGGCGUCG-3'
Sb02g037310.1_chromosome_2_sbi --> similar to Putative fasciclin-like arabinogalactan-protein chromosome_4_712_mature.BC_01 --> target score: 3
3'---GGCGACCUGCCGCCGCGC-5'
     ||||-||||||||||| |
5'-GCCGC-GGACGGCGGCGAG-3'
Sb05g026710.1_chromosome_5_sbi --> similar to O-methyltransferase family protein chromosome_4_712_mature.BC_01 --> target score: 3
3'---GGCGACCUGCCGCCGCGC-5'
     ||||-||||||||||| |
5'-GCCGC-GGACGGCGGCGAG-3'
Sb05g026730.1_chromosome_5_sbi --> similar to O-methyltransferase family protein chromosome_4_712_mature.BC_01 --> target score: 6
3'-GGCGAC-CUGCCGCCGCGC-5'
   |||||- |||||||||-||
5'-CCGCUGCCACGGCGGC-CG-3'
Sb03g013070.1_chromosome_3_sbi --> similar to Putative pectinacetylesterase chromosome_4_712_mature.BC_01 --> target score: 5
3'-G-GCGACCUGCCGCCGCGC-5'
   -|||||| |||||| ||
5'-CGCGCUGGCCGGCGGCCCG-3'
Sb02g001130.1_chromosome_2_sbi --> similar to Putative peroxidase chromosome_4_712_mature.BC_01 --> target score: 5
3'-GGCGACCUGCCGCCGC-GC-5'
   |||  |||||  |||||-||
5'-CCGCGGGACGACGGCGACG-3'
Sb10g010040.1_chromosome_10_sb --> similar to Putative Peroxidase 49 chromosome_4_712_mature.BC_01 --> target score: 5
3'-GGCGACCUGCCGCCG-CGC-5'
   |||-| |||||||||-|||
5'-CCGC-GUACGGCGGCGGCG-3'
Sb10g005820.1_chromosome_10_sb --> similar to Glutathione peroxidase chromosome_4_712_mature.BC_01 --> target score: 5

Figure 9P

```
3'-G-GCGACCUGCCGCCGCGC-5'
   -|||||| |||||| |||
5'-CGCGCUGGCCGGCGGGGCG-3'
Sb01g028610.1_chromosome_1_sbi ---> similar to Class III peroxidase 120 precursor chromosome_4_712_mature.BC_01 ---> target score: 3
3'-GGCGACCUGCCGCCGCGC-5'
   ||| ||||| |||||||
5'-CCGCCGGACGUCGGCGCG-3'
Sb02g029340.1_chromosome_2_sbi ---> similar to Class III peroxidase 123 precursor chromosome_4_712_mature.BC_01 ---> target score: 6
3'-GGCGACCUGCCGCCGCGC-5'
   ||||| || | |||||||
5'-CCGCUGAACUGGGGCGCG-3'
Sb04g026510.1_chromosome_4_sbi ---> similar to Phenylalanine ammonia-lyase chromosome_4_712_mature.BC_01 ---> target score: 2.0
3'---GGCGACCUGCCGCCGCGC-5'
     |||-||||||||+|||||||
5'-UCCG-UGGACGGUGGCGCG-3'
Sb02g022220.1_chromosome_2_sbi ---> similar to Polygalacturonase isoenzyme 1 beta subunit-like chromosome_4_712_mature.BC_01 ---> target score: 5
3'-GGCGACCUGCCGCCGCGC-5'
   ||| || || |||||||
5'-CCGCAGGCCGCCGGCGCG-3'
Sb03g013310.1_chromosome_3_sbi ---> similar to Putative polygalacturonase PG2 chromosome_4_712_mature.BC_01 ---> target score: 5
3'-GG-CGACCUGCCGC-CGCGC-5'
   |-|||||-|||||-|||||
5'-CCUGCUGG-CGGCGCGCGCG-3'
Sb07g025220.1_chromosome_7_sbi ---> similar to Sorbitol dehydrogenase chromosome_4_1912_mature.BC_05 ---> target score: 4
3'-UCGCG-GCGGCGACG-AGACCGGCGC-5'
   || |-|||||||||-||||||||||
5'-AGCUCACGCCGCUGCAUCUGGCCGCG-3'
Sb09g025900.1_chromosome_9_sbi ---> similar to Heat shock protein 101 chromosome_4_174_mature.BC_05 ---> target score: 2
3'-UGGAGCGGGACGCGGGCCCGGCG-5'
   ||||||||||||||| |||||
5'-ACCUCGCCCUGCGCCCCGCGCCGC-3'
Sb02g009005.1_chromosome_2_sbi ---> weakly similar to PREDICTED: hypothetical protein chromosome_4_608_mature.BC_02 ---> target score: 5
3'-CGUAACCGGCACCUCCGCC-5'
   || |||||| || |||||
5'-GCACUGGCCGCGGCGGCGG-3'
Sb10g027990.1_chromosome_10_sb ---> weakly similar to Cysteine protease Mir1 chromosome_4_608_mature.BC_02 ---> target score: 5
3'-CGUAACCGGCACCUCCGCC-5'
   || || || |||||||||
5'-GCACUGCCCAUGGAGGCGG-3'
```

Figure 9Q

Sb06g029476.1_chromosome_6_sbi --> similar to OSJNBa0089N06.14 protein chromosome_4_608_mature.BC_02 --> target score: 5
3'-CGUAACCGGCACCUCCGCC-5'
   ||  ||||| ||||||  ||
5'-GCAGUGGCCUUGGAGGAGG-3'
Sb09g019110.1_chromosome_9_sbi --> similar to Os05g0387700 protein chromosome_4_608_mature.BC_02 --> target score: 6
3'-CGUAACCGGCACCUCCGC-C-5'
   ||||||||  |||  ||||-|
5'-GCAUUGGCCUUGGCGGCGUG-3'
Sb09g022270.1_chromosome_9_sbi --> similar to Putative homeodomain protein chromosome_4_1677_mature.BC_05 --> target score: 5
3'-CGCCGGCGGCACCUACCU-5'
   |  ||||  |||||  ||||
5'-GCAGCCGGCGUGGCUGGA-3'
Sb0013s010110.1_super_13_sbic_ --> putative protein chromosome_4_1677_mature.BC_05 --> target score: 5
3'-CGCCGGCGGCACCUACCU-5'
   ||||  ||||||||  ||
5'-GCGGCGGCCGUGGAGGGC-3'
Sb06g023760.1_chromosome_6_sbi --> similar to Beta-fructofuranosidase 1 precursor chromosome_4_1677_mature.BC_05 --> target score: 4.0
3'-CGCCGGCGGCACCUACCU-5'
   |||  |||:|||| ||||
5'-GCGGGCGCUGUGGCUGGA-3'
Sb06g031910.1_chromosome_6_sbi --> similar to Beta-fructofuranosidase, insoluble isoenzyme 6 pre chromosome_4_1677_mature.BC_05 --> target score: 2.0
3'-CGCCGGCGGCACCUACCU-5'
   ||  ||||||||:|||||
5'-GCGCCCGCCGUGGGUGGA-3'
Sb01g016730.1_chromosome_1_sbi --> similar to Monosaccharide transporter 2 chromosome_4_1677_mature.BC_05 --> target score: 5
3'-CGCCGGCG-GCACCUACCU-5'
   ||||  ||-||||||  |||
5'-GCGGCGGCGCGUGGAAGGA-3'
Sb08g016530.1_chromosome_8_sbi --> similar to Sugar transporter family protein, expressed chromosome_4_1677_mature.BC_05 --> target score: 5.0
3'-CGCCGGCGGCACCUACCU-5'
   |||||||:|  ||||||
5'-GCGGCCGCUGGAGAUGGA-3'
Sb02g039600.1_chromosome_2_sbi --> similar to Putative alcohol dehydrogenase chromosome_4_1677_mature.BC_05 --> target score: 6
3'-CGCCGGCGGCACCUACCU-5'
   |||||||  |  || ||||
5'-GCGGCCGCAGGGCUGGA-3'
Sb03g029770.1_chromosome_3_sbi --> similar to Glycosyl transferase family 1 protein-like chromosome_4_1677_mature.BC_05 --> target score: 5

Figure 9R

```
3'-CG-CCGGCGGCACCUACCU-5'
   |-|||||||| |||-|||
5'-GCGGGCCGCCGAGGA-GGA-3'
Sb02g001045.1_chromosome_2_sbi --> weakly similar to Putative 4-coumarate--CoA ligase 1 chromosome_4_1677_mature.BC_05 --> target score: 5
3'-CGC-CGGCGGCACCUACCU-5'
   ||-|||||||| |||-|||
5'-GCGCGCCGCCGAGGA-GGA-3'
Sb02g001050.1_chromosome_2_sbi --> weakly similar to Putative 4-coumarate--CoA ligase 1 chromosome_4_1677_mature.BC_05 --> target score: 3
3'---CGCCGGCGGCACCUACCU-5'
      || |||||||||||-|||
5'-GGCUGCCGCCGUGGA-GGA-3'
Sb07g007810.1_chromosome_7_sbi --> similar to 4-coumarate--CoA ligase 1 chromosome_4_1677_mature.BC_05 --> target score: 5
3'-CGCCGGCGGCACCUACCU-5'
   ||| ||||||||| |||
5'-GGGGCGGCCGUGGAAGGA-3'
Sb01g037900.1_chromosome_1_sbi --> similar to Pectinesterase family protein, expressed chromosome_4_1677_mature.BC_05 --> target score: 6
3'-CGCCGGCGGCACCU-ACC-U-5'
   |||||||||||||- ||-|
5'-GCGGCCGCCGUGGAGCGGCA-3'
Sb02g042780.1_chromosome_2_sbi --> similar to Putative pectinesterase chromosome_4_1677_mature.BC_05 --> target score: 5
3'-CG-CCGGCGGCACCUACCU-5'
   |-||||| |-||||||||
5'-GCAGGCCGGC-UGGAUGGA-3'
Sb03g016510.1_chromosome_3_sbi --> similar to Peroxidase family protein, expressed chromosome_4_1677_mature.BC_05 --> target score: 5
3'-C-GCCGGCGGCACCUACCU-5'
   -||||||| |||||-||||
5'-GCCGGCCGGCGUGG-UGGA-3'
Sb07g026520.1_chromosome_7_sbi --> similar to UDP-glucuronic acid 4-epimerase isoform 3 chromosome_4_1677_mature.BC_05 --> target score: 3.5
3'-CGCCGGCGGCACCUACCU-5'
   | |:|||||||||| |||
5'-GCUGUCGCCGUGGACGGA-3'
Sb01g020070.1_chromosome_1_sbi --> similar to Xyloglucan galactosyltransferase KATAMARI 1, putat chromosome_4_571_mature.BC_03 --> target score: 2
3'-CCGUUGCGGCUUCGGGCCC-A-5'
   |||||||||||||||||||-|
5'-GGCAACGCCGAAGCCCGGGCU-3'
Sb0139s002040.1_super_139_sbic --> putative protein chromosome_5_737_mature.BC_03 --> target score: 5
3'-CGCCCGUGAGCUGUU-UCC-5'
   || |||-||||||||-|||
5'-GCGCGCA-UCGACAACAGG-3'
```

Figure 9S

Sb10g027155.1_chromosome_10_sb --> weakly similar to Putative uncharacterized protein chromosome_5_737_mature.BC_03 --> target score: 5
3'-CGCC-CGUGAGCUGUUUCC-5'
    |||-|||||-||||||  ||
5'-GCGGUGCAC-CGACAACGG-3'
Sb06g026010.1_chromosome_6_sbi --> similar to Putative xyloglucan galactosyltransferase chromosome_5_456_mature.BC_02 --> target score: 4.0
3'-GAUG-GGAGCUCGCUGGCUCAGG-5'
    |||-|||||-||||||||||:|
5'-CUACGCCUCG-GCGACCGAGUUC-3'
Sb07g027680.1_chromosome_7_sbi --> similar to DNA-binding protein family-like chromosome_5_148_mature.BC_03 --> target score: 4
3'-CACACAUUUGU-GUGUAGAG-5'
   |||-|||||-||||||||
5'-GGGUG-AAACACCACAUCUC-3'
Sb10g004810.1_chromosome_10_sb --> similar to Putative uncharacterized protein chromosome_5_70_mature.BC_01 --> target score: 5
3'-ACGACUGC-ACCGA-CUGUGCAC-5'
   |||||||-|||||-||||||-|
5'-UGCUGACGUUGGCUGGACACG-G-3'
Sb10g006310.1_chromosome_10_sb --> similar to Os11g0622800 protein chromosome_5_509_mature.BC_03 --> target score: 1
3'-CCGUGAACUUGUACCCAUUCGGCU-5'
   ||||||| ||||||||||||||||
5'-GGCACUUGCACAUGGGUAAGCCGA-3'
Sb1994s002010.1_super_1994_sbi --> putative protein chromosome_5_978_mature.BC_01 --> target score: 4
3'-CGUCCGAGAG-CCGUUUCUU-5'
   || |||||-||||||||
5'-GAAGCCUCUCUGGCAAAGAA-3'
Sb10g025390.1_chromosome_10_sb --> similar to Transcription initiation factor TFIID subunit 1 chromosome_5_181_mature.BC_05 --> target score: 4
3'-GUUAGAUAUAC-ACAACCC-5'
   || |||||||-||||||
5'-CAAGCUAUAUGCUGUUGGC-3'
Sb10g025390.1_chromosome_10_sb --> similar to Transcription initiation factor TFIID subunit 1 chromosome_5_181_mature.BC_05 --> target score: 5
3'-GUUAGAUAU-ACACAACCC-5'
   ||-|||||-|| ||||||
5'-CAA-CUAUACUGAGUUGGG-3'
Sb06g033440.1_chromosome_6_sbi --> similar to Glutathione peroxidase-like protein GPX15Hv chromosome_5_139_mature.BC_05 --> target score: 5
3'-GCGUACGUCCACC-CCUGGAG-5'
   |||-||||| ||-|||||||
5'-CGCA-GCAGGAGGAGGACCUC-3'
Sb09g027200.1_chromosome_9_sbi --> similar to Os01g0702700 protein chromosome_5_612_mature.BC_02 --> target score: 4

Figure 9T

```
3'-GCCGAGGUAGUAUAGA-GUUCGUU-5'
   ||||||||||||||-|||-|||
5'-UGGCUCCAUCAUAUCUACAA-CAA-3'
Sb03g043320.1_chromosome_3_sbi --> similar to P0497A05.20 protein chromosome_5_379_mature.BC_04 --> target score: 3
3'-UAGGAGCGUGGAGAAGGG-5'
   || |||| |||||||||
5'-CUCGUCGCCCCUCUUCCC-3'
Sb0013s011230.1_super_13_sbic_ --> putative protein chromosome_5_379_mature.BC_04 --> target score: 6
3'-UAGGAGC-G-UGGAGAAGGG-5'
   ||||||-|-| |||||||||
5'-AUCCUCGCCAAGCUCUUCCC-3'
Sb07g021680.1_chromosome_7_sbi --> similar to Cinnamoyl CoA reductase chromosome_5_379_mature.BC_04 --> target score: 3.0
3'-UAGGAGCGUGGAGAAGGG-5'
   ||||||||||||||:  |
5'-GUCCUCGCACCUCUUUGC-3'
Sb02g010110.2_chromosome_2_sbi --> similar to Cellulose synthase-7 chromosome_5_379_mature.BC_04 --> target score: 4
3'---UAGGAGCGUGGAGAAGGG-5'
     ||||||-||||||| |||
5'-GAUCCUC-CACCUCUACCC-3'
Sb03g004320.1_chromosome_3_sbi --> similar to Cellulose synthase-1 chromosome_5_379_mature.BC_04 --> target score: 6
3'-UAGGAGCGUGGAG-AAGGG-5'
   |||||||-||||-|| ||
5'-AUCCUCGC-CCUCGUUACC-3'
Sb04g008640.1_chromosome_4_sbi --> weakly similar to Cationic peroxidase 1 precursor chromosome_5_379_mature.BC_04 --> target score: 4
3'-UAGGAGCGUGGAGAAGGG-5'
   ||||| | |||||||||
5'-CUCCUCCCUCCUCUUCCC-3'
Sb01g049890.1_chromosome_1_sbi --> similar to LysM domain containing protein, expressed chromosome_6_200_mature.BC_05 --> target score: 3.0
3'-GGUGGAAUUGUGUACACCUA-5'
   ||||||:||| |||||||||
5'-UCACCUUGACAGAUGUGGAU-3'
Sb01g038920.1_chromosome_1_sbi --> similar to Putative uncharacterized protein chromosome_6_337_mature.BC_03 --> target score: 5
3'-GUCCUCGCGGCGGCCGAGGU-GGU-5'
   || |||||||||||-|||-|||
5'-CAGCAGCGCCGCCGGC-CCAGCCA-3'
Sb09g016440.1_chromosome_9_sbi --> similar to Putative uncharacterized protein chromosome_6_202_mature.BC_05 --> target score: 3.5
3'-CG-UGCCGGGUUCAGGGUCGA-5'
   |-||||:||||| ||||||
5'-GCGACGGUCCAAGUACCAGCU-3'
```

Figure 9U

Sb09g029260.1_chromosome_9_sbi --> similar to Putative uncharacterized protein chromosome_6_1475_mature.BC_04 --> target score: 4
3'-UGGAAGUUCUGGCCGUGACCGGAGA-5'
   |||||||||||||| ||||| |
5'-ACCUUCAAGACCGGCACCGGCCUGU-3'
Sb10g010410.1_chromosome_10_sb --> similar to Putative uncharacterized protein chromosome_6_801_mature.BC_01 --> target score: 1.5
3'-UACUCACUAUAACCAAGCCGAGU-5'
   |:|||||||||||||||||||
5'-CCGGGUGAUAUUGGUUCGGCUCA-3'
Sb01g040270.1_chromosome_1_sbi --> similar to Putative uncharacterized protein chromosome_6_67_mature.BC_04 --> target score: 5
3'-GCUUAGAGGAGAAGGAACCGGA-5'
   | |||||||| |||| |||||
5'-CGCAUCUCCUCCUCCUCGGCCU-3'
Sb03g032710.1_chromosome_3_sbi --> similar to Methyltransferase-like chromosome_6_313_mature.BC_03 --> target score: 4
3'-GACCCACCGGUCUCCUCGGUCG-5'
   | | ||||||||||||| |||
5'-CUCGAUGGCCAGAGGAGCGAGC-3'
Sb05g017920.1_chromosome_5_sbi --> similar to Putative uncharacterized protein chromosome_6_657_mature.BC_01 --> target score: 4.0
3'-GAGGGUAG-GUAAUCUAAGCG-5'
   ||| |||-||||:|||||||
5'-CUCCAAUCUCAUUGGAUUCGC-3'
Sb01g002140.1_chromosome_1_sbi --> similar to Putative lysyl-tRNA synthetase chromosome_6_201_mature.BC_02 --> target score: 3
3'-ACGUACUGUUC-CUCUACU-5'
   |||| |||||-|||||||
5'-AGCAUUACAAGAGAGAUGA-3'
Sb0017s004030.1_super_17_sbic_ --> putative protein chromosome_6_201_mature.BC_02 --> target score: 5
3'-ACGU-ACUGUUCCUCUA-CU-5'
   |||-|||||||||| ||-||
5'-UGCAUUGACAAGGAAAUCGA-3'
Sb01g021990.1_chromosome_1_sbi --> similar to Kaurene synthase A chromosome_6_201_mature.BC_02 --> target score: 4
3'-A-CGUACUGUUCCUCUACU-5'
   - |||||||||||-||||
5'-UCACAUGACAAGGA-AUGA-3'
Sb04g003660.1_chromosome_4_sbi --> similar to Putative adagio-like protein 2 chromosome_6_201_mature.BC_02 --> target score: 4
3'-ACGUACUGUUCCUCUACU-5'
   | | || |||||||||
5'-UGAAGGAGAAGGAGAUGA-3'
Sb01g049020.1_chromosome_1_sbi --> similar to MADS box protein 1 chromosome_6_201_mature.BC_02 --> target score: 5

Figure 9V

```
3'-ACGUACUGUUCCUCUACU-5'
     |||||||||||||  |
5'-UCCAUGACAAGGAGAGCA-3'
Sb01g033060.1_chromosome_1_sbi --> similar to Sucrose synthase 2 chromosome_6_201_mature.BC_02 --> target score: 5
3'-ACGUAC-UGUUCCUCUACU-5'
   | |||-||||| ||||||
5'-UGGAUGUACAAGCAGAUGA-3'
Sb03g008810.1_chromosome_3_sbi --> similar to Putative ribokinase chromosome_6_201_mature.BC_02 --> target score: 4
3'-ACGU-ACUGUUCCUCUACU-5'
   | |-|||-|||||||||
5'-UGAAGUGA-AAGGAGAUGA-3'
Sb05g002900.1_chromosome_5_sbi --> similar to Pyruvate kinase chromosome_6_555_mature.BC_02 --> target score: 4
3'-UCGUGC-CGUUAAACCGGGCC-5'
   |||||-||||||||||| |
5'-AGCACGAGCAAUUUGGCCAGC-3'
Sb01g024773.1_chromosome_1_sbi --> weakly similar to Os09g0101100 protein chromosome_6_166_mature.BC_02 --> target score: 5
3'-UCGU-CACCAACCUGUGGCCCU-5'
   |||-||||||||||  ||||
5'-AGCAUGUGGUUGGACAGGGGA-3'
Sb04g036810.1_chromosome_4_sbi --> Predicted protein chromosome_6_166_mature.BC_01 --> target score: 5
3'-GAGGCAGUAGAAGUUGAC-UAG-5'
   |-||||||||||||| |-|||
5'-CU-CGUCAUCUUCAACCGCAUC-3'
Sb09g025120.1_chromosome_9_sbi --> similar to Putative uncharacterized protein chromosome_6_351_mature.BC_05 --> target score: 3.5
3'-CGG-CUCACGGCCUACGAAACGG-5'
   ||-||||||||-|||||||||:
5'-GCCGGAGUGCC-GAUGCUUUGCU-3'
Sb02g036220.1_chromosome_2_sbi --> similar to Putative uncharacterized protein chromosome_6_336_mature.BC_03 --> target score: 4.5
3'-GGCACGAGAGGGAGCUG-GGCAG-5'
   ||||||:|||||||||-||| |
5'-CCGUGCUUUCCCUCGACACCGAC-3'
Sb09g027430.1_chromosome_9_sbi --> similar to Os01g0693800 protein chromosome_7_516_mature.BC_03 --> target score: 5
3'-GU-GGCCAGCCCCUCCCGG-5'
   |-|||| || ||||||||
5'-CAGCCGGCCGAGGAGGGCC-3'
Sb0019s003290.1_super_19_sbic_ --> putative protein chromosome_7_516_mature.BC_03 --> target score: 6
3'-GUGGCCA-GCCCUC-CCGG-5'
   ||||||-| |||||-||||
5'-CACCGGUGCUGGGAGCGGCC-3'
```

Figure 9W

```
Sb06g017600.1_chromosome_6_sbi --> similar to Endoglucanase 11 precursor chromosome_7_516_mature.BC_03 --> target score: 5
3'-GU-GGCCAGCCCCUCCCGG-5'
    |-|||| || ||||||||
5'-CAGCCGGCCGUGGAGGGCC-3'
Sb10g031000.1_chromosome_10_sb --> similar to Hexose transporter, putative, expressed chromosome_7_627_mature.BC_05 --> target score: 5
3'-GGUGCCGCCAGCGCGAAGGGG-5'
   | |||||||| |||| |||||
5'-CCUCGGCGGUGGCGCCUCCCC-3'
Sb10g024440.1_chromosome_10_sb --> similar to Putative uncharacterized protein chromosome_7_627_mature.BC_05 --> target score: 5.0
3'-GGUGCCGCCAGCGC-GAAGGGG-5'
   ||||||||| |||-||||:||
5'-CCACGGCGGUGGCGCCUUCUCC-3'
Sb03g013170.1_chromosome_3_sbi --> similar to S-adenosylmethionine synthetase 1 chromosome_7_1887_mature.BC_05 --> target score: 4
3'-GCAGGCGUAGCCCUGGAG-5'
   | | ||| |||||||||
5'-CGCCAGCACCGGGACCUC-3'
Sb10g028600.1_chromosome_10_sb --> similar to AAA-type ATPase-like chromosome_7_1887_mature.BC_05 --> target score: 4
3'-GCAGGCGUAGC-CCUGGAG-5'
   |-|| ||||| -||||||
5'-CG-CCCCAUCGCGGACCUC-3'
Sb01g019850.1_chromosome_1_sbi --> similar to Beta-amylase chromosome_7_1887_mature.BC_05 --> target score: 6
3'-GCAGGCGUAGC-CCUGGAG-5'
   |||||||||- ||| ||
5'-CGUCCGCAUCGCCGACGUC-3'
Sb02g033070.1_chromosome_2_sbi --> similar to Expansin-like A3 precursor chromosome_7_1887_mature.BC_05 --> target score: 4
3'-GCA-GGC-GUAGC-CCUGGAG-5'
   ||-|||-|||||-|||||||
5'-CGUCCGUCAUCGUGGACCUC-3'
Sb02g035070.1_chromosome_2_sbi --> similar to Brittle stalk-2-like protein 5 chromosome_7_366_mature.BC_03 --> target score: 6
3'-GGUCCAUAUGGCACACGG-5'
   |||| || |||||| ||
5'-CCAGGGAUUCCGUGUUCC-3'
Sb10g028460.1_chromosome_10_sb --> similar to Class III peroxidase 93 precursor chromosome_7_366_mature.BC_03 --> target score: 5
3'-GGUCCAUAU-GGCACACGG-5'
   ||-||| |-|||||||||
5'-CCA-GUACACCGUGUGCC-3'
Sb06g024650.1_chromosome_6_sbi --> similar to Expansin-B15 precursor chromosome_7_1053_mature.BC_04 --> target score: 3
```

Figure 9X

```
3'-CCGCUUAGCGCUCGCCGACGCGCG-5'
   | ||| | |||||||||||||||
5'-GGAGAACCCCGAGCGGCUGCGCGC-3'
Sb02g038550.1_chromosome_2_sbi --> similar to HDA1 chromosome_7_483_mature.BC_04 --> target score: 3
3'-CCAGGGCCGUUUCUU-UGCG-5'
   |-|||||||||||||-||||
5'-UG-CCCGGCAAAGAACACGC-3'
Sb10g027830.1_chromosome_10_sb --> weakly similar to Chromosome chr18 scaffold_59, whole genome chromosome_7_454_mature.BC_03 --> target score: 4
3'--GCGGCGGCGGCAACACGUGGGUCG-5'
    |||||||||||| ||-|||||||||
5'-GCGCCGCCGCCGCUG-GCACCCAGC-3'
Sb05g019000.1_chromosome_5_sbi --> similar to Putative uncharacterized protein chromosome_7_287_mature.BC_03 --> target score: 4
3'-C-UCGCGCGGUCGGUCGGAGGAC-5'
   -|| ||||| |||||||||||
5'-GAAGGGCGCCUGCCAGCCUCCUG-3'
Sb09g018380.1_chromosome_9_sbi --> similar to Os07g0685900 protein chromosome_7_287_mature.BC_01 --> target score: 5
3'-AAGGGCUCGGCCACGACGG-GAA-5'
   ||||| |||||||||||||-| |
5'-UUCCCGCGCCGGUGCUGCCGCGU-3'
Sb03g035860.1_chromosome_3_sbi --> similar to Putative uncharacterized protein chromosome_7_22_mature.BC_03 --> target score: 5.0
3'-UGUACCGGACGUCGCGCGCG-5'
    |||||||| |*||||||| |
5'-ACAUGGCCUCCGGCGCGCCC-3'
Sb10g006690.1_chromosome_10_sb --> similar to Putative growth-regulating factor 1 chromosome_7_22_mature.BC_03 --> target score: 3.0
3'-UGUACCG-GACGUCGCGCGCG-5'
   | ||||-||||||*|||||||
5'-ACCUGGCGCUGCAGUGCGCGC-3'
Sb06g017230.1_chromosome_6_sbi --> similar to H0315A08.5 protein chromosome_7_22_mature.BC_03 --> target score: 5
3'-UGUACC-GGACGUCGCGCGCG-5'
   ||||||-| |||||||||||-|
5'-ACAUGGUCGUGCAGCGCGC-C-3'
Sb09g027310.1_chromosome_9_sbi --> similar to Putative uncharacterized protein chromosome_7_22_mature.BC_03 --> target score: 4
3'-UGUACCGGACGUCGCGCGCG-5'
   || || ||||||||| ||
5'-ACAAGGACUGCAGCGCGAGC-3'
Sb03g028190.1_chromosome_3_sbi --> similar to Arbutin synthase-like chromosome_7_22_mature.BC_03 --> target score: 6
3'-UGUACCGGACGUCG-C-GCGCG-5'
   |||||||||| |-|-|||||
5'-ACAUGGCCUGCAACAGCCGCGC-3'
```

Figure 9Y

Sb03g047220.1_chromosome_3_sbi ---> Predicted protein chromosome_7_22_mature.BC_03 ---> target score: 6
3'-UGUACCGGACGUCG-CGCGCG-5'
     |||||||  ||  ||-||||||
5'-ACAUGGCCGGCUGCGGCGCGC-3'
Sb09g018400.1_chromosome_9_sbi ---> similar to Putative esterase chromosome_7_22_mature.BC_03 ---> target score: 6
3'-UGUACCGGACGUCG-CGCGCG-5'
     |||||||  ||  ||-||||||
5'-ACAUGGCCGGCUGCGGCGCGC-3'
Sb09g018440.1_chromosome_9_sbi ---> similar to Putative esterase chromosome_7_243_mature.BC_01 ---> target score: 4
3'-ACACAAC-CCCACCUAACCUCAC-5'
    ||| ||-|||||||| ||||||
5'-UGUGCUGUGGGUGGAUAGGAGUG-3'
Sb10g022527.1_chromosome_10_sb ---> weakly similar to Os06g0484800 protein chromosome_8_297_mature.BC_05 ---> target score: 4
3'-ACA-GUAACCACCUGAAGGU-5'
    ||-||-|||||||||||| |
5'-UGUCCA-UGGUGGACUUCAA-3'
Sb10g029360.1_chromosome_10_sb ---> similar to Os06g0707000 protein chromosome_8_297_mature.BC_05 ---> target score: 4
3'---ACAGUAACCACCUGAAGGU-5'
     |||||||||||| |-||
5'-UUGUCAUUGGUGGACCU-CA-3'
Sb03g011930.1_chromosome_3_sbi ---> similar to S-adenosylmethionine synthetase 1 chromosome_8_497_mature.BC_04 ---> target score: 4
3'-UGAGCCGACUAUUUGAGUUCG-5'
    | |||||| ||||||||||
5'-AGUAGGCUGACAAACUCAAGC-3'
Sb09g004060.1_chromosome_9_sbi ---> similar to Os07g0438500 protein chromosome_8_468_mature.BC_05 ---> target score: 5
3'-UGU-GAGCGAAGAGACGCGGC-5'
    ||-||||  |||-||||||||
5'-ACAGCUCGGUUC-CUGCGCCG-3'
Sb07g004840.1_chromosome_7_sbi ---> similar to Ribosomal protein-like chromosome_8_401_mature.BC_01 ---> target score: 4.0
3'-GCUGAUGAUGGUUCUCCG-5'
    ||| ||||| |:||||
5'-CGACGACUACGAGGAGGC-3'
Sb1558s002010.1_super_1558_sbi ---> putative protein chromosome_8_401_mature.BC_01 ---> target score: 4
3'-GCUG-A-UGAUGGUUCUCCG-5'
    |||-|-|||||||||-|||
5'-CGACUUCACUACCAAG-GGC-3'
Sb07g023020.1_chromosome_7_sbi ---> similar to Alpha-amylase isozyme 3D precursor chromosome_8_618_mature.BC_05 ---> target score: 6

Figure 9Z

```
3'-GGUGGUGGUGGUACCAGCC-5'
   ||||||  ||||  |  ||||
5'-CCACCACGACCACGUUCGG-3'
Sb0024s002110.1_super_24_sbic_ --> putative protein chromosome_8_618_mature.BC_05 --> target score: 6
3'-GGUGGUGGUGGUACCAGCC-5'
   |||||||||||  |  |  |
5'-CCACCACCACCAUCGGCAG-3'
Sb07g024550.1_chromosome_7_sbi --> similar to INDETERMINATE-related protein 1 chromosome_8_618_mature.BC_05 --> target score: 5
3'-GGU-GGUGGUGGUACCAGCC-5'
   ||-|||||| |||||-|||
5'-CCAUCCACCAGCAUGG-CGG-3'
Sb09g025540.1_chromosome_9_sbi --> similar to O-methyltransferase ZRP4, putative, expressed chromosome_8_618_mature.BC_05 --> target score: 5
3'-GGU-GGUGGUGGUACCAGCC-5'
   ||-|||||| |||||-|||
5'-CCAUCCACCAGCAUGG-CGG-3'
Sb09g025560.1_chromosome_9_sbi --> similar to O-methyltransferase ZRP4, putative, expressed chromosome_8_618_mature.BC_05 --> target score: 6
3'-GGUGGUGGUGGUACCA-GCC-5'
   |||||||||||-| |-|||
5'-CCACCACCACCA-GCUCCGG-3'
Sb05g025950.1_chromosome_5_sbi --> similar to Extensin-like protein precursor chromosome_8_533_mature.BC_03 --> target score: 3.5
3'-AUGUGGUCGAAGCUCAGCUG-5'
   |:||||||||||| ||||
5'-UUCGCCAGCUUCGAGACGAC-3'
Sb04g032020.1_chromosome_4_sbi --> similar to Putative uncharacterized protein chromosome_8_765_mature.BC_01 --> target score: 6
3'-UUCAAGGUGAGGUUAGGU-G-5'
   ||||||||||- ||||-|
5'-AAGUUCCACUCC-UUCCAUC-3'
Sb0012s002210.1_super_12_sbic_ --> putative protein chromosome_8_751_mature.BC_01 --> target score: 5.0
3'-CUGGGAAAUUGUGGCCAA-5'
   ||||||| *||||  |||
5'-GACCCUUUUGCACCAGUU-3'
Sb08g014065.1_chromosome_8_sbi --> weakly similar to OSJNBa0035O13.10 protein chromosome_8_751_mature.BC_01 --> target score: 4
3'-CUGGGAAAUUGU-GGCCAA-5'
   || |-||||||-||||||
5'-GACGC-UUAACAGCCGGUU-3'
Sb01g016630.1_chromosome_1_sbi --> weakly similar to Putative 4-coumarate--CoA ligase 1 chromosome_8_298_mature.BC_05 --> target score: 5
3'-UCGG-GUGGUUACUGUUGAA-5'
   |||-|| || ||||||||||
5'-AGCCACAACACUGACAACUU-3'
```

Figure 9AA

Sb07g028620.1_chromosome_7_sbi ---> similar to Alkaline alpha galactosidase 3 chromosome_8_216_mature.BC_04 ---> target score: 4.5
3'-UUGUGAACACCUAACUACG-5'
  :|||||||| ||| ||||
5'-AGCACUUGUGCAUUCAUGC-3'
Sb10g009460.1_chromosome_10_sb ---> similar to Os02g0731900 protein chromosome_8_216_mature.BC_03 ---> target score: 4
3'-UU-UAUCGCGAGCCGUUUAU-5'
  |-||| || |||||||||||
5'-AAGAUAUCGAUCGGCAAAUA-3'
Sb09g028730.1_chromosome_9_sbi ---> similar to Putative uncharacterized protein OJ1781_H11.10 chromosome_9_544_mature.BC_02 ---> target score: 4
3'-CGUGCUGGGUUCCCUCGUCCG-5'
  | |||| |||||| ||||||
5'-GCUCGACGCAAGGGUGCAGGC-3'
Sb03g036680.1_chromosome_3_sbi ---> similar to Probable indole-3-acetic acid-amido synthetase GH chromosome_9_1189_mature.BC_05 ---> target score: 5
3'-GGC-AGCGCGGCGGCGGCACGC-5'
  ||-||||||||||||| | |
5'-CCGCUCGCGCCGCCGCCGCGGG-3'
Sb0011s007590.1_super_11_sbic_ ---> putative protein chromosome_9_1189_mature.BC_05 ---> target score: 6
3'-GGCAGCGCGGCGGCGGC-AC-GC-5'
  |||||||||||||| |-||-||
5'-CCGUCGCGCCGCCGCAGAUGUCG-3'
Sb07g024550.1_chromosome_7_sbi ---> similar to INDETERMINATE-related protein 1 chromosome_9_1189_mature.BC_05 ---> target score: 4
3'-G-GCAGCGCG-GCGGCGGCACGC-5'
  -|| |||||-|||||||||||
5'-CACGACGCGCGCGCCGCCGUGCG-3'
Sb06g017600.1_chromosome_6_sbi ---> similar to Endoglucanase 11 precursor chromosome_9_1189_mature.BC_05 ---> target score: 5
3'-GGCA-GCGCGGCGGCGGCACGC-5'
  |||-||||||||-||||| |||
5'-CCGUCCGCGCCG-CGCCGCGCG-3'
Sb10g008060.1_chromosome_10_sb ---> similar to Glycosyl transferase protein A-like chromosome_9_1189_mature.BC_05 ---> target score: 4
3'-GGCAGC-GCGGCGGCGGCACGC-5'
  |||||-| |||||||||-|||
5'-CCGUCGUCUCCGCCGCCG-GCG-3'
Sb10g006230.1_chromosome_10_sb ---> similar to Putative pectin methylesterase chromosome_9_1189_mature.BC_05 ---> target score: 4
3'-GGCAGCGCGGCGGCGGCA-CGC-5'
  || |||-||||||||||-|||
5'-CCGCCGC-CCGCCGCCGUCGCG-3'
Sb10g028480.1_chromosome_10_sb ---> similar to Putative peroxidase ATP8a chromosome_9_554_mature.BC_02 ---> target score: 5

Figure 98B

```
3'-CACUGGACUGAUGUUUCG-GG-5'
      ||-|||||  ||||||||-||
5'-GUG-CCUGAGUACAAAGCUCC-3'
Sb02g032720.1_chromosome_2_sbi ---> similar to Ribosomal protein S15-like chromosome_10_93_mature.BC_01 ---> target score: 4
3'-UACACACAACCACACCUAACCC-5'
      |||||  |||||||||||| ||
5'-AAGUGUGCUGGUGUGGAUUCGG-3'
Sb06g001305.1_chromosome_8_sbi ---> similar to Putative uncharacterized protein chromosome_10_77_mature.BC_03 ---> target score: 4.0
3'-AGCCUCUUUCGAAAGGG-CUC-5'
   ||||||||*|||||||-|||
5'-UGGGAGAAAGUUUUCCCUGAG-3'
Sb03g034510.1_chromosome_3_sbi ---> similar to Box2a protein chromosome_10_962_mature.BC_01 ---> target score: 5
3'-GAGUUAGG-UGUACACAAC-5'
   ||||  ||-||-|||||||
5'-CUCAAGCCUAC-UGUGUUG-3'
Sb10g025070.2_chromosome_10_sb ---> similar to Protein kinase-like chromosome_10_962_mature.BC_01 ---> target score: 5
3'-GAGUUAGGUGUACAC-AAC-5'
   |||||||-|||||-|||
5'-CCCAAUCCA-AUGUGCUUG-3'
Sb10g006330.2_chromosome_10_sb ---> similar to Sucrose synthase 1 chromosome_10_962_mature.BC_01 ---> target score: 6
3'-GAGUUAGGU-GUACACAAC-5'
   ||||||||-||| || ||
5'-CUCAAUCCAGCAUAUGAUG-3'
Sb03g047440.1_chromosome_3_sbi ---> similar to Putative pectinacetylesterase chromosome_10_792_mature.BC_03 ---> target score: 4.0
3'-ACGUUGUACUAGA-CCGCU-5'
   |||  ||||||||-||*||
5'-UGCACCAUGAUCUCGGUGA-3'
Sb10g026740.1_chromosome_10_sb ---> similar to Putative uncharacterized protein chromosome_10_792_mature.BC_03 ---> target score: 3
3'-ACGUUGUACUAG-ACCGCU-5'
   |||  ||||||||-||||||
5'-UGCACCAUGAUCAUGGCGA-3'
Sb02g000470.1_chromosome_2_sbi ---> similar to Class III peroxidase 97 precursor chromosome_10_283_mature.BC_05 ---> target score: 4.0
3'-GCAGCAGUAGGGGUCGCUUGC-5'
   |||||||||||||*|||* ||
5'-CGUCGUCAUCCCCGGCGGCCG-3'
Sb05g022900.1_chromosome_5_sbi ---> similar to Intracellular protease, PfpI family protein, expre chromosome_10_73_mature.BC_03 ---> target score: 5
3'-UCCA-GAGACGUACAG-CAGGCUCGU-5'
   |||-||||||||||||-||||-||||
5'-AGGUGCUCUGCAUGUCGGUCC-AGCA-3'
```

Figure 9CC

Sb01g006100.1_chromosome_1_sbi --> similar to Ferredoxin--NADP reductase, root isozyme, chloropl

Figure 10A

```
sbi-miR169a ---> target score: 3.0
3'-AGCCGUUCAGUAGGAACCGAC-5'
       |||||  ||||:||||||||
5'-UAGGCAAAUCAUUCUUGGCUG-3'
Sb08g021910.1_3'UTR ---> similar to CCAAT-binding transcription factor subunit B family protein, sbi-miR169b ---> target score: 2.5
3'-GGCCGUUCAGUAGGAACCGAC-5'
    :|||||  |||||||||||||
5'-CUGGCAACUCAUCCUUGGCUU-3'
Sb01g045500.1_3'UTR ---> similar to RAPB protein sbi-miR169efgh ---> target score: 3.0
3'-GUCCGUUCAGUAGGAACCGAU-5'
   ||||||  ||||:||||||||
5'-CAGGCAAUUCAUUCUUGGCUU-3'
Sb01g011220.1_3'UTR ---> similar to CCAAT-binding transcription factor subunit B family protein, sbi-miR169efgh ---> target score: 4
3'-GUCCGUUCAGUAGGAACCG-AU-5'
    |||||  |||||||||||-||
5'-CUGGCAACUCAUCCUUGGCUUA-3'
Sb01g045500.1_3'UTR ---> similar to RAPB protein sbi-miR169cd ---> target score: 4
3'-AUCCGUUCAGUAGGAACCG-AU-5'
   -|||||  |||||||||||-||
5'-U-GGCAACUCAUCCUUGGCUUA-3'
Sb01g045500.1_3'UTR ---> similar to RAPB protein sbi-miR169cd ---> target score: 4.0
3'-AUCCGUUCAGUAGGAACCGA-U-5'
   ||||||  ||||:||||||||-|
5'-UAGGCAAAUCAUUCUUGGCUGA-3'
Sb08g021910.1_3'UTR ---> similar to CCAAT-binding transcription factor subunit B family protein, sbi-miR169i ---> target score: 3
3'-A-UCCGUUCAGUAAGAACCGAU-5'
   -||||||  ||||||||||||
5'-UCAGGCAAUUCAUUCUUGGCUU-3'
Sb01g011220.1_3'UTR ---> similar to CCAAT-binding transcription factor subunit B family protein, sbi-miR169i ---> target score: 3
3'-AUCCGUUCAGUAAGAACCGAU-5'
   ||  |||||||  |||||||||
5'-GAGUCAAGUCACUCUUGGCUA-3'
Sb02g003070.1_3'UTR ---> similar to Os07g0152000 protein sbi-miR172e ---> target score: 3.0
3'-C-ACGUCGUAGUAGUUCUAAGU-5'
   -|||||||||||||:|||||
5'-GCUGCAGCAUCAUCAGGAUUCU-3'
Sb09g002080.1_3'UTR ---> similar to AP2 domain transcription factor sbi-miR172e ---> target score: 3.0
```

Figure 10B

```
3'-C-ACGUCGUAGUAGUUCUAAGU-5'
   -|||||-|||||||:|||||
5'-GAUGCAG-AUCAUCAGGAUUCA-3'
Sb04g038320.1_3'UTR --> similar to Type A response regulator 3 sbi-miR172b --> target score: 5
3'-ACGUCGUAGUAGUUCU-AAGG-5'
   ||| ||| ||||||||-||||
5'-UGCAACAUAAUCAAGACUUCC-3'
Sb10g009462.1_3'UTR_chromosome --> similar to Putative very-long-chain fatty acid condensing sbi-miR172b --> target score: 3.0
3'-ACGUCGUAGUAGUUCUAAG-G-5'
   |||||||||||||:|||||-|
5'-UGCAGCAUCAUCAGGAUUCUC-3'
Sb09g002080.1_3'UTR_chromosome --> similar to AP2 domain transcription factor sbi-miR172cad --> target score: 1.0
3'-ACGUCGUAGUAGUUCUAAGA-5'
   ||||||||||||:||||||
5'-UGCAGCAUCAUCAGGAUUCU-3'
Sb09g002080.1_3'UTR_chromosome --> similar to AP2 domain transcription factor chromosome_1_983_mature.BC_04 --> target score: 3.5
3'-AGUAACCUAAGUGUAAUU-5'
   ||||| ||||:|||||:
5'-UCAUUGAAUUCGCAUUAG-3'
Sb10g024780.1_3'UTR_chromosome --> similar to Putative uncharacterized protein chromosome_1_466_mature.BC_02 --> target score: 2.0
3'-UCGAGCCGUGGUGUCUAGA-5'
   || |||||||||||||:|
5'-AGCCCGGCACCACAGAUUU-3'
Sb01g047670.1_3'UTR_chromosome --> similar to Expressed protein chromosome_1_970_mature.BC_03 --> target score: 4
3'-GAAGCACCAACAGCG-CCUG-5'
   ||| |-|||||||||-||||
5'-CUUCUU-GUUGUCGCUGGAC-3'
Sb01g018940.1_3'UTR_chromosome --> similar to Expressed protein chromosome_1_398_mature.BC_02 --> target score: 6
3'-GUGCCGUGAUA-GUCCGUGC-5'
   |||||||  ||-|| |||||
5'-CACGGCACCAUGCACGCACG-3'
Sb09g021890.1_3'UTR_chromosome --> similar to Putative uncharacterized protein chromosome_1_827_mature.BC_01 --> target score: 5
3'-GGUGGGGUUGCGUACACCUA-AC-5'
   ||-||||||| |||||||||-||
5'-CCA-CCCAACACAUGUGGAUGUG-3'
Sb10g001370.1_3'UTR_chromosome --> similar to High-affinity nickel-transport protein-like chromosome_1_216_mature.BC_05 --> target score: 3.0
3'-GGGCAGCUUGGUACCCUUC-5'
   |:||: |||||||||||||
5'-CCUGUUCAACCAUGGGAAG-3'
```

Figure 10C

Sb10g000450.1_3'UTR_chromosome ---> similar to Putative uncharacterized protein chromosome_1_754_mature.BC_04 ---> target score: 1.5
3'-GUUAGGUGUACACAACUCC-5'
   |||:|||||||||||:||
5'-CAAUUCACAUGUGUUGGGG-3'
Sb09g024990.1_3'UTR_chromosome ---> similar to Putative uncharacterized protein chromosome_1_1391_mature.BC_04 ---> target score: 3
3'-G-UGAGGUUAGAUGGAGUU-5'
   ~||||||||| |||||||
5'-CUACUCCAAUCCACCUCAA-3'
Sb09g026510.1_3'UTR_chromosome ---> similar to Os05g0531400 protein chromosome_1_527_mature.BC_05 ---> target score: 5
3'-UCACUUCAACUCG-AAACA-5'
   ||||| |||||~|||||
5'-AUUGAAGGUGAGCAUUUGU-3'
Sb08g004620.1_3'UTR_chromosome ---> similar to Os12g0172500 protein chromosome_2_902_mature.BC_02 ---> target score: 6
3'-CGUGUUGAAGAUUCUCGU-U-5'
   |||||||| |||||~||~|
5'-GCACAACUUAUAAGA-CAUA-3'
Sb09g004320.1_3'UTR_chromosome ---> similar to Importin subunit alpha-1b chromosome_2_1473_mature.BC_01 ---> target score: 4
3'-G-GGG-UUAGGUGAGGUUGUGUACA-5'
   ~|||~|||||||~|||||||||||
5'-CACCCUAAUCCAC-CCAACACAUGU-3'
Sb10g001370.1_3'UTR_chromosome ---> similar to High-affinity nickel-transport protein-like chromosome_2_573_mature.BC_04 ---> target score: 2
3'-UAACUUAAACGAAACUCUUCACACG-5'
   ||| ||| ||||||||||||||||
5'-AUUGUAUUCGCUUUGAGAAGUGUGC-3'
Sb05g000930.1_3'UTR_chromosome ---> similar to BTB/POZ domain containing protein, expressed chromosome_2_45_mature.BC_01 ---> target score: 3.0
3'-UCCCGGACAAAUCUAACC-5'
   ||||||||||:|||||
5'-AAGGCCUGUUUGGAUGU-3'
Sb10g005250.1_3'UTR_chromosome ---> similar to Pyrophosphate-energized vacuolar membrane proton p chromosome_2_45_mature.BC_01 ---> target score: 4.0
3'-UCCCGGACAAAUCUAACC-5'
   ||||||||||:||| |
5'-AGGGCCUGUUUGGAUCGU-3'
Sb01g027960.1_3'UTR_chromosome ---> similar to Xyloglucan endotransglucosylase/hydrolase protein chromosome_2_1061_mature.BC_05 ---> target score: 5
3'-GU-GUGUGCUGUUUCCGGU-5'
   |~|||||||~|| |||||
5'-CACCACACGA-AAUGGCCA-3'
Sb02g034380.1_3'UTR_chromosome ---> similar to Methionine aminopeptidase chromosome_3_397_mature.BC_01 ---> target score: 3

Figure 10D

```
3'-CACCUAAUC-UCACCUUGAAC-5'
   ||||||-|-||||||||||
5'-GUGGAUU-GAAGUGGAACUUG-3'
Sb03g023980.1_3'UTR_chromosome --> similar to Putative uncharacterized protein chromosome_3_1222_mature.BC_01 --> target score: 4
3'-GG-UUAGAUGGGGUUGUGUACA-5'
   |-|||| |-|||||||||||
5'-CCUAAUCCA-CCCAACACAUGU-3'
Sb10g001370.1_3'UTR --> similar to High-affinity nickel-transport protein-like chromosome_3_1257_mature.BC_01 --> target score: 5
3'-AAGCGUAACU-CUUCACAC-5'
   |||-|||||-||| ||||
5'-UUCG-AUUGAGGAAUUGUG-3'
Sb10g027000.1_3'UTR_chromosome --> similar to SEC14 cytosolic factor-like chromosome_3_1460_mature.BC_01 --> target score: 3
3'-GGG-UUAGGUGAGGUUGUG-5'
   ||-|||||||-|||||||
5'-CCCUAAUCCAC-CCAACAC-3'
Sb10g001370.1_3'UTR_chromosome --> similar to High-affinity nickel-transport protein-like chromosome_3_1374_mature.BC_04 --> target score: 0.5
3'-AGGUGAGGUUAGGUGGAGUU-5'
   |:||||||||||||||||
5'-UCUACUCCAAUCCACCUCAA-3'
Sb09g026510.1_3'UTR_chromosome --> similar to Os05g0531400 protein chromosome_3_1324_mature.BC_01 --> target score: 6
3'-AACCUCACCUAAUCCCACCUUAAA-5'
   |||||||||| ||| |||
5'-UUGGAGUGGAUUAAGGUAGAAAUU-3'
Sb10g004900.1_3'UTR_chromosome --> similar to Putative GAMYB-binding protein chromosome_3_47_mature.BC_01 --> target score: 4.0
3'-UACACACAACCACACCUAACCCUA-5'
   | ||||||| ||||||||:|
5'-AUAUGUGUUGGAGUGGAUUGGGGU-3'
Sb01g022490.1_3'UTR_chromosome --> similar to Os10g0403700 protein chromosome_3_213_mature.BC_01 --> target score: 5
3'-AUCCCCGAGACGACCUCAA-5'
   || ||| ||||||||| |
5'-UAGAGGCACUGCUGGAGCU-3'
Sb08g000350.1_3'UTR_chromosome --> similar to Mitochondrial substrate carrier family protein.

chromosome_3_1223_mature.BC_05 --> target score: 4.0
3'-UUGGCUCCGCCCGUAGGAUU-5'
   |||| |||||||||: |||
5'-AACCGUGGCGGGCAUUGUAA-3'
Sb06g029940.1_3'UTR_chromosome --> similar to Putative uncharacterized protein chromosome_3_1128_mature.BC_01 --> target score: 2.0
3'-CAACCUCACCUAACCUCACCU-5'
   |||| ||||:|||||||||
5'-AUUGGUGUGGGUUGGAGUGGA-3'
```

Figure 10E

Sb09g026510.1_3'UTR ---> similar to Os05g0531400 protein chromosome_4_557_mature.BC_02 ---> target score: 1
3'-AUUCCCGUGAGUGUUACGU-5'
   |||||||||||||||||||
5'-UUAGGGCACUCACAAUGCA-3'
Sb09g019570.1_3'UTR_chromosome ---> similar to Os05g0397700 protein chromosome_4_2454_mature.BC_04 ---> target score: 4.0
3'-CACACCUCCUGUCGUCGCGGAG-5'
   || |||||:|||||||||| |
5'-GUGCGGAGGGCAGCAGCGCCAC-3'
Sb01g018940.1_3'UTR_chromosome ---> similar to Expressed protein chromosome_4_831_mature.BC_04 ---> target score: 4.0
3'-UGUACACAACUUUAACUAA-5'
   |||||||||:|:| ||||
5'-ACAUGUGUUGGAGUGGAUU-3'
Sb08g021620.1_3'UTR_chromosome ---> similar to At1g30300 chromosome_4_712_mature.BC_01 ---> target score: 6
3'-GGCGACCUGCC-GCCGCGC-5'
   ||||| | ||-||||||||
5'-CCGCUGCAAGGCCGGCGCG-3'
Sb06g030760.1_3'UTR_chromosome ---> similar to OSJNBb0059K02.4 protein chromosome_4_712_mature.BC_01 ---> target score: 5
3'-GGCGACCU-GCCGCCGCGC-5'
   |||| ||-|||-||||||
5'-CCGCUCGAUCGG-GGCGCG-3'
Sb03g039060.1_3'UTR_chromosome ---> similar to Zinc finger CONSTANS-like protein chromosome_4_134_mature.BC_02 ---> target score: 5.0
3'-UUAGACGAUCGAUAAGUUGUAACA-5'
   ||||||||||| |||:|||| |||
5'-AAUCUGCUAGCCAUUUAACAGUGU-3'
Sb09g026080.1_3'UTR_chromosome ---> similar to Hexokinase chromosome_4_522_mature.BC_01 ---> target score: 4.0
3'-CCUAAGUGGAGUUAGGUGUACACA-5'
   |||||||| ||||||:|||| |||
5'-GGAUUCACAUCAAUCUACAUAUGU-3'
Sb10g001370.1_3'UTR_chromosome ---> similar to High-affinity nickel-transport protein-like chromosome_4_608_mature.BC_02 ---> target score: 5
3'-CGUAACCGGCACCUCCGCC-5'
   ||| ||||||| |||| |
5'-GCAUAGGCCGUGUAGGCAG-3'
Sb08g004570.1_3'UTR_chromosome ---> similar to TRNA-nucleotidyltransferase, putative, expressed chromosome_4_1028_mature.BC_01 ---> target score: 5
3'-GG-UUAGGUGAGGUUAUGUACA-5'
   |-||||||||-|||| ||||||
5'-CCUAAUCCAC-CCAACACAUGU-3'
Sb10g001370.1_3'UTR ---> similar to High-affinity nickel-transport protein-like chromosome_4_1677_mature.BC_05 ---> target score: 5.0

Figure 10F

```
3'-CGCCGGCGGCACCUACCU-5'
   ||||  ||||||||||
5'-GCGGCGAUCGUGGAUGGA-3'
Sb08g002310.1_3'UTR_chromosome --> similar to Putative uncharacterized protein 5 chromosome_4_1677_mature.BC_05 --> target score: 5
3'-CGCCGGCG-GCACCUACCU-5'
   ||||||||-|||||-|||
5'-GCGGCCGCGCGUGG-UGGU-3'
Sb03g045360.1_3'UTR_chromosome --> similar to Hydroxyproline-rich glycoprotein-like chromosome_5_737_mature.BC_01 --> target score: 5
3'-GGGAAAUGUGGCCAACC-5'
   | |||||||  || ||||
5'-CCAUUUAACAGCGUUGG-3'
Sb03g011270.1_3'UTR_chromosome --> similar to Magnesium-protoporphyrin IX monomethyl ester chromosome_5_737_mature.BC_03 --> target score: 3.0
3'-CGCCCGUGAGCUGUUC-C-5'
   |||||||||||||||-|
5'-UCGGGCACUCGGCAAAGAG-3'
Sb10g020140.1_3'UTR_chromosome --> weakly similar to Putative uncharacterized protein chromosome_5_148_mature.BC_03 --> target score: 1
3'-CACACAUUUGUGUGUAGAG-5'
   ||||  |||||||||||||
5'-GUGUGCAAACACACAUCUC-3'
Sb05g000930.1_3'UTR_chromosome --> similar to BTB/POZ domain containing protein, expressed chromosome_5_509_mature.BC_03 --> target score: 1
3'-CCGUGAACUUGUACCCAUUCGGCU-5'
   |||||||  |||||||||||||||
5'-GGCACUUGCACAUGGGUAAGCCGA-3'
Sb0221s002050.1_3'UTR_super_22 --> putative protein chromosome_5_181_mature.BC_05 --> target score: 4
3'-GUUAGAUAUACACAACCC-5'
   ||||||  ||  |||||||
5'-CAAUCUACAUAUGUUGGG-3'
Sb10g001370.1_3'UTR_chromosome --> similar to High-affinity nickel-transport protein-like chromosome_5_181_mature.BC_05 --> target score: 5
3'-GUUAGAUAUACACAAC-CC-5'
   ||||||||  |||||-||
5'-CUAUCUAUAUCUGUUGAGG-3'
Sb08g000990.1_3'UTR_chromosome --> similar to Class III peroxidase 135 precursor chromosome_5_1020_mature.BC_01 --> target score: 5
3'-UACACACAACAACACCUAACCC-5'
   | |||||||  ||||||||||||
5'-AUAUGUGUUGGAGUGGAUUGGG-3'
Sb01g022490.1_3'UTR_chromosome --> similar to Os10g0403700 protein chromosome_5_379_mature.BC_04 --> target score: 4
3'-UAGGAGCGU-GGAGAAGGG-5'
   |||-|||-|||||||||||
5'-AGCCU-GCAUCCUCUUCCC-3'
```

Figure 10G

Sb01g023950.2_3'UTR_chromosome ---> similar to Major facilitator superfamily protein chromosome_6_200_mature.BC_05 ---> target score: 2
3'---GGUGGAAUUGUGUACACCUA-5'
         |||||- |||||||||||||||
5'-UCCACC-CAACACAUGUGGAU-3'
Sb10g001370.1_3'UTR_chromosome ---> similar to High-affinity nickel-transport protein-like chromosome_6_657_mature.BC_01 ---> target score: 5
3'-GA-GGGUAGGUAAUCUAAGCG-5'
      |-|||||||| ||||||||
5'-CUGCCCAUCCAACAGAUUCGC-3'
Sb01g033840.1_3'UTR_chromosome ---> similar to Chromosome chr18 scaffold_1, whole genome shotgun chromosome_6_201_mature.BC_02 ---> target score: 5
3'-ACGUACUGUUCC-UCUACU-5'
     ||-|||||||||-||| ||
5'-UGC-UGACAAGGAAGAGGA-3'
Sb10g000830.1_3'UTR_chromosome ---> similar to Putative MtN21 chromosome_6_323_mature.BC_01 ---> target score: 4.0
3'-UACACACAACCACACCUAACCCUA-5'
     | ||||||||| |||||||||||:|
5'-AUAUGUGUUGGAGUGGAUUGGGGU-3'
Sb01g022490.1_3'UTR_chromosome ---> similar to Os10g0403700 protein chromosome_6_351_mature.BC_05 ---> target score: 4.5
3'-CGGCUCACGGCCUACGAAACGG-5'
    |||||||:| ||||||||||
5'-GCCGAGUGUCAUAUGCUUUGCC-3'
Sb10g020140.1_3'UTR_chromosome ---> weakly similar to Putative uncharacterized protein chromosome_7_516_mature.BC_03 ---> target score: 3.5
3'-GUG-GCC-AGCCCCUCCCGG-5'
    :|-|||-||||||||||||
5'-CGCUCGGAUCGGGGAGGGCC-3'
Sb02g029640.1_3'UTR_chromosome ---> similar to Os09g0511600 protein chromosome_7_1887_mature.BC_05 ---> target score: 4
3'-GCAGGCGUAGCCCUGGAG-5'
    || ||||| |||||||
5'-CUUCAGCAUCCGGACCUC-3'
Sb01g048800.1_3'UTR_chromosome ---> similar to CBS domain-containing protein, putative, expressed chromosome_7_366_mature.BC_03 ---> target score: 4
3'-GGUCCAUAUGG-CACACGG-5'
    |||||||||-||||| |
5'-ACAGGUAUACCGGUGUGAC-3'
Sb08g001580.1_3'UTR_chromosome ---> similar to Transporter, putative, expressed chromosome_7_62_mature.BC_01 ---> target score: 3
3'-CAUAAGUGAAGUUAGGUACACACAA-5'
     |||||||||||||||||||||| ||
5'-AGAUUCACUUCAAUCCAUGUGUAUU-3'
Sb09g026510.1_3'UTR_chromosome ---> similar to Os05g0531400 protein chromosome_7_287_mature.BC_03 ---> target score: 3

Figure 10H

```
3'-CUCGCGCGGUCGGUCGGA-GGAC-5'
   |-||||||||||||||-||||
5'-CA-CGCGCCAGCCAGCCUGCCUG-3'
Sb07g025170.1_3'UTR_chromosome --> similar to Os08g0546100 protein chromosome_7_49_mature.BC_01 --> target score: 1.5
3'-UUCAAGGUGAGGUUAGGUGGGGUU-5'
   ||||:|||||||||||||:|||
5'-AAGUUCUACUCCAAUCCACCUCAA-3'
Sb09g026510.1_3'UTR_chromosome --> similar to Os05g0531400 protein chromosome_7_294_mature.BC_01 --> target score: 3.5
3'-AACCUCACCUAACCCCACCUUAAA-5'
   ||| ||||:|||| |||||||||
5'-UUGGUGUGGGUUGGAGUGGAAUUU-3'
Sb09g026510.1_3'UTR_chromosome --> similar to Os05g0531400 protein chromosome_7_243_mature.BC_01 --> target score: 3.0
3'-ACACAACCCCACCUAACCUCAC-5'
   ||  |||| ||||:||||||||
5'-UGUAUUGGUGUGGGUUGGAGUG-3'
Sb09g026510.1_3'UTR_chromosome --> similar to Os05g0531400 protein chromosome_8_297_mature.BC_05 --> target score: 6
3'-ACAGUAACCACCUGAAGGU-5'
   |||||| |||| |||||
5'-UGUCAUUGUGGUGUUCCA-3'
Sb03g023980.1_3'UTR_chromosome --> similar to Putative uncharacterized protein chromosome_8_497_mature.BC_04 --> target score: 2.5
3'-UGAGCCGACUAUUUGAGUUCG-5'
   :||| ||||||||:|||||||
5'-AUUCGCCUGAUAAGCUCAAGC-3'
Sb09g019080.1_3'UTR --> similar to Putative uncharacterized protein chromosome_8_401_mature.BC_01 --> target score: 5
3'-GCUGAUGAUGGUU-CUCCG-5'
   |||||||||||-|| ||
5'-CUACUACUACCAAGGAAGC-3'
Sb07g023710.1_3'UTR_chromosome --> similar to Putative uncharacterized protein P0705A05.122 chromosome_8_618_mature.BC_05 --> target score: 5.0
3'-GGUGGUGGUGGUACCAG-CC-5'
   ||||||:|||-|||||-||
5'-CCACCACUACC-UGGUCUGG-3'
Sb01g037180.1_3'UTR_chromosome --> similar to Putative uncharacterized protein chromosome_8_765_mature.BC_01 --> target score: 1.0
3'-UUCAAGGUGAGGUUAGGUG-5'
   |||||:|||||||||||||
5'-AAGUUCUACUCCAAUCCAC-3'
Sb09g026510.1_3'UTR_chromosome --> similar to Os05g0531400 protein chromosome_8_298_mature.BC_05 --> target score: 4
3'-UCGGGUGGUUACUGUUGAA-5'
   ||||||||| |||| |||
5'-AGCCCACCACUGACUACUU-3'
```

Figure 10l

Sb04g021710.1_3'UTR_chromosome --> similar to Os02g0533000 protein chromosome_8_216_mature.BC_04 --> target score: 2.0
3'-UUGUGAACACCUAACUACG-5'
   |||: |||||||||||:
5'-AACAUAUGUGGAUUGAUGU-3'
Sb09g026510.1_3'UTR_chromosome --> similar to Os05g0531400 protein chromosome_8_216_mature.BC_03 --> target score: 6
3'-UUUAUCG-CGAGCCGUUUAU-5'
   ||||||-||| -|||||||
5'-AAAUAGCUGCUA-GCAAAUA-3'
Sb01g027760.1_3'UTR_chromosome --> similar to 50S ribosomal protein L35 chromosome_9_1189_mature.BC_05 --> target score: 4
3'-GGCAGC-GCGGCGGC-GGCACGC-5'
   || ||-|||||||||-|||||||
5'-CCGCCGCCGCCGCCGCCCGUGCG-3'
Sb09g023990.1_3'UTR --> weakly similar to Putative uncharacterized protein chromosome_9_1132_mature.BC_05 --> target score: 3.0
3'-GGCCAACCAGAGUGGUUGGCCC-5'
   |||||||||||: |||||||
5'-CCGGUUGGUCUCAUGAACCGGG-3'
Sb03g013700.1_3'UTR_chromosome --> similar to Putative uncharacterized protein B1045F02.28 chromosome_10_880_mature.BC_05 --> target score: 4.5
3'-CACGGCACUCUGCGACUCGUCA-5'
   |||:||||||  ||||| ||||
5'-GUGCUGUGAGAGGCUGAACAGU-3'
Sb01g015870.1_3'UTR_chromosome --> similar to Putative GDSL-like lipase/acylhydrolase chromosome_10_93_mature.BC_01 --> target score: 4.0
3'-UACACACAACCACACCUAACC-C-5'
   ||||| |||||||||:||||-|
5'-AUGUGUAUUGGUGUGGGUUGGAG-3'
Sb09g026510.1_3'UTR_chromosome --> similar to Os05g0531400 protein chromosome_10_293_mature.BC_01 --> target score: 4.0
3'-CAGCCUAAGCGUAGUUAGGUGUACA-5'
   |||||||| ||||||||:|||| |
5'-GUCGGAUUCACAUCAAUCUACAUAU-3'
Sb10g001370.1_3'UTR_chromosome --> similar to High-affinity nickel-transport protein-like chromosome_10_962_mature.BC_01 --> target score: 4.0
3'-G-AGUUAGGUGUACACAAC-5'
   -|||||:|||| |||||
5'-CAUCAAUCUACAUAUGUUG-3'
Sb10g001370.1_3'UTR_chromosome --> similar to High-affinity nickel-transport protein-like chromosome_10_792_mature.BC_03 --> target score: 5
3'-A-CGUUGUACUA-GACCGCU-5'
   -|||||||||-||||| |
5'-UGGCAACAUGAUGCUGGCAA-3'
Sb06g027260.1_3'UTR_chromosome --> similar to Putative uncharacterized protein

Fig. 22A

Experimental Validation of newly predicted MIR169 stem-loop precursors in sorghum and maize (A) Sorghum stem-derived small RNA reads mapped to predicted sorghum MIR169 stem-loop precursors >sbi-MIR169t
TAGCCAAGGATGATTTGCCTGtgctagcaacctctgagcgctcctgctgccatggcatggcagtcaggggcgcgtagtgggtgcttctccGGGCAAATCATCTGGGCTAG

| | | | | |
|---|---|---|---|---|
| AGCCAAGGATGATTTGC | bc01,4 | | GGGCAAATCATCTGGGC | bc01,2 |
| GCCAAGGATGATTTGCC | bc01,3 | | GGGCAAATCATCTGGGCT | bc01,6 |
| AGCCAAGGATGATTTGCCTG | bc01,4 | | GGGCAAATCATCTGGGCTA | bc01,8 |
| GCCAAGGATGATTTGCC | bc02,2 | | GGGCAAATCATCTGGGCTAG | bc01,6 |
| AGCCAAGGATGATTTGC | bc04,6 | | GGGCAAATCATCTGGGCTA | bc02,4 |
| AGCCAAGGATGATTTGC | bc02,1 | | GGGCAAATCATCTGGGCTA | bc02,4 |
| AGCCAAGGATGATTTGCC | bc02,2 | | GGGCAAATCATCTGGGCT | bc04,10 |
| AGCCAAGGATGATTTGCCTG | bc02,2 | | GGCAAATCATCTGGGCTA | bc04,2 |
| TAGCCAAGGATGATTTGCCT | bc02,2 | | GGGCAAATCATCTGGGC | bc04,16 |
| GCCAAGGATGATTTGCC | bc04,4 | | GGGCAAATCATCTGGGCTA | bc04,32 |
| AGCCAAGGATGATTTGCC | bc04,2 | | GGGCAAATCATCTGGGCTAG | bc04,52 |
| AGCCAAGGATGATTTGCCT | bc04,4 | | CCGGGCAAATCATCTGG | bc05,2 |
| TAGCCAAGGATGATTTGCCT | bc04,2 | | GGGCAAATCATCTGGGC | bc05,1 |
| AGCCAAGGATGATTTGCCTG | bc04,2 | | GGGCAAATCATCTGGGCT | bc05,4 |
| AGCCAAGGATGATTTGCCTGT | bc04,2 | | GCAAATCATCTGGGCTAG | bc05,2 |
| TAGCCAAGGATGATTTGCCTG | bc04,2 | | GGGCAAATCATCTGGGCTA | bc05,18 |
| TAGCCAAGGATGATTTGCCTGT | bc04,8 | | GGGCAAATCATCTGGGCTAG | bc05,8 |
| TAGCCAAGGATGATTTGCCTGTA | bc04,2 | | | |
| TAGCCAAGGATGATTTGCCTGTAGC | bc04,4 | | | |
| TAGCCAAGGATGATTTGCCTGT | bc05,2 | | | |

| | |
|---|---|
| AGCTAGCAACCTCTGAGCG | bc01,1 |
| AGCAACCTCTGAGCGCTCCTGC | bc01,1 |
| AGCTAGCAACCTCTGAGCGCTCC | bc02,1 |
| AGCTAGCAACCTCTGAG | bc04,1 |
| AGCTAGCAACCTCTGAGC | bc04,2 |
| AGCTAGCAACCTCTGAGCGCT | bc04,1 |
| AGCTAGCAACCTCTGAGCGCTCC | bc04,3 |
| AGCTAGCAACCTCTGAGC | bc05,1 |
| AGCTAGCAACCTCTGAGCGC | bc05,1 |

>sbi-MIR169u
aagaggcatctttgaTAGCCAGGGATGATTTGCCCTGtagcaccatgcatgcatgcaacctctcgcgttagctcctgctgactgcatgctgccatgacaagttccacggGCAAATCATTCCTGGCTAATCtgagtgcctctt

| | | | | |
|---|---|---|---|---|
| TAGCCAGGGATGATTTGCCC | bc01,2 | | CAAATCATTCCTGGCTA | bc01,1 |
| TAGCCAGGGATGATTTG | bc04,2 | | GCAAATCATTCCTGGCT | bc01,1 |
| TAGCCAGGGATGATTTGC | bc04,1 | | GCAAATCATTCCTGGCTA | bc01,4 |
| TAGCCAGGGATGATTTGCCC | bc04,20 | | GCAAATCATTCCTGGCTAA | bc01,8 |
| TAGCCAGGGATGATTTG | bc05,1 | | GCAAATCATTCCTGGCTAA | bc02,1 |
| TAGCCAGGGATGATTTGC | bc05,2 | | GCAAATCATTCCTGGCTAATC | bc02,1 |
| TAGCCAGGGATGATTTGCCC | bc05,7 | | GCAAATCATTCCTGGCT | bc03,1 |
| | | | GCAAATCATTCCTGGCT | bc04,26 |
| | | | CAAATCATTCCTGGCTA | bc04,3 |
| | | | GCAAATCATTCCTGGCTA | bc04,27 |
| | | | CAAATCATTCCTGGCTAA | bc04,11 |
| | | | GCAAATCATTCCTGGCTAA | bc04,80 |
| | | | CAAATCATTCCTGGCTAAT | bc04,2 |
| | | | GCAAATCATTCCTGGCTAAT | bc04,4 |
| | | | AAATCATTCCTGGCTAATCT | bc04,1 |
| | | | GCAAATCATTCCTGGCTAATC | bc04,11 |
| | | ACGGGCAAATCATTCCTGGCTA | | bc04,1 |
| | | | CAAATCATTCCTGGCTAATCTG | bc04,1 |
| | | | GCAAATCATTCCTGGCT | bc05,2 |
| | | | CAAATCATTCCTGGCTA | bc05,1 |
| | | | GCAAATCATTCCTGGCTA | bc05,5 |
| | | | CAAATCATTCCTGGCTAA | bc05,4 |
| | | | GCAAATCATTCCTGGCTAA | bc05,10 |
| | | | CAAATCATTCCTGGCTAATC | bc05,1 |
| | | | CAAATCATTCCTGGCTAATCTG | bc05,1 |

Fig. 22B

>sbi-MIR169v
gcgatggaagctctgctttggTAGCCAAGGATGAGCTGCCTGtggcctccagctgcagaggctagctaggctacacattgcgtggccaagctcctccgctgcgcgtggtctcgcaGGCAGCCTCCTTGGCTAGTctgagtggcttccatc

| | | | | |
|---|---|---|---|---|
| TAGCCAAGGATGAGCTG | bc01,3 | | TGGCCAAGCTCCTCCGCT | bc02,1 |
| TAGCCAAGGATGAGCTG | bc02,1 | | GGCCAAGCTCCTCCGCT | bc04,1 |
| TAGCCAAGGATGAGCTG | bc04,8 | | CCTCCGCTGCGCGTGGTC | bc05,1 |
| TAGCCAAGGATGAGCTGCCTG | bc04,5 | | | |
| TAGCCAAGGATGAGCTG | bc05,9 | | | |
| TAGCCAAGGATGAGCTGCC | bc05,2 | | | |
| TAGCCAAGGATGAGCTGCCTG | bc05,1 | | | |
| TGGAAGCTCTGCTTTGGTAGCCAA | bc04,1 | | | |
| TCTGCTTTGGTAGCCAA | bc05,1 | | | |

CTAGCTAGGCTACACAT bc05,1

(B) Maize endosperm-derived small RNAs mapped to predicted maize stem-loop precursor >zma-MIR169s
gcgatggaagctctgctttggTAGCCAAGGATGAGCTGCCTGtggcctcctgctgcgacgttgcgtggcccgcctccaccgcgtgcggtccccgcaGGCAGCCTCCTTGGCTAGTctgagcggcttccatc

| | | | | |
|---|---|---|---|---|
| GTAGCCAAGGATGAGCTGCCTGTG | B73, 2 | | ACGTTGCGTGGCCCCGCCTCCACCG | B73, 1 |
| TAGCCAAGGATGAGCTGCCTGTGG | B73xMo17, 1 | | GCCTCCACCGCGTGCGGTCCCCGC | B73xMo17, 1 |
| TAGCCAAGGATGAGCTGCC | Mo17xB73, 1 | | | |
| GTAGCCAAGGATGAGCTGCCTGTG | Mo17xB73, 1 | | | |
| ATGGAAGCTCTGCTTCGGTAGCCAA | B73xMo17, 1 | | | |

```
>Expectation: 1.5
miR169r*              20 UCGGUUCCUACUGAACGGAU 1
                         :::::::: ::::.::::::::
Sb08g021910.1 3'UTR   716 AGCCAAGAAUGAUUUGCCUA 735
CCAAT-binding transcription factor subunit B family protein >Expectation: 2.5
miR169r*              20 UCGGUUCCUACUGAACGGAU 1
                         :::::::: :::: :::::::.
Sb01g011220.1 3'UTR  1259 AGCCAAGAAUGAAUUGCCUG 1278
CCAAT-binding transcription factor (CBF-B/NF-YA) subunit B >Expectation: 3.5
miR169r*              20 UCGGUUCCUACUGAACGGAU 1
                         :::::::::. :::::::..::
Sb01g035610.1 3'UTR  1128 AGCCAAGGGAUACUUGUUUA 1147
ATP-dependent Clp protease proteolytic subunit >Expectation: 3.5
miR169r*              21 AUCGGUUCCUACUGAACGGAU 1
                         :. ::::: :::.::::::::.
Sb02g026600.1 7th exon  1648 UGCCCAAGCAUGGCUUGCCUG 1668
similar to Abscisic acid 8'-hydroxylase 3

>Expectation: 3.0
miR169r*              19 AUCGGUUCCUACUGAACGG 1
                         :. ::::: :::.:::::::
Sb02g026600.1 7th exon  1648 UGCCCAAGCAUGGCUUGCC 1666
similar to Abscisic acid 8'-hydroxylase 3

>Expectation: 3.5
miR169r*              21 AUCGGUUCCUACUGAACGGAU 1
                         : : .:::::::.::::::::.
Sb01g047950.1 3rd exon   980 UUGAUAAGGAUGGCUUGCCUG 1000
similar to Ankyrin repeat protein, chloroplast, putative, expressed >Expectation: 3.5
miR169r*              20 UCGGUUCCUACUGAACGGAU 1
                         :::::::::  :::::::..::
Sb06g001950.1 6th exon  582 AGCCAAGGAGAACUUGUCUU 601
Phosphoglycerate mutase >Expectation: 2.0
miR169r*              18 UCGGUUCCUACUGAACGG 1
                         .::::: :::::::::::
Sb01g043590.1  2076 GGCCAAUGAUGAUUUGCC 2093
similar to CUE domain containing protein, expressed >Expectation: 2.5
miR169r*              18 UCGGUUCCUACUGAACGG 1
                         ::: :::::::::::.::::
Sb01g043450.1 3rd exon  582 AGCAAAGGAUGAUUUGCA 599
```

Figure 24A

Pfam: Syntaxin 6, N-terminal

>Expectation: 2.5
miR169r*                    18 UCGGUUCCUACUGAACGG 1
                               :::::.: :::::.::::.
Sb06g024340.1 4th exon     834 AGCCGAUGAUGAUUUGCU 851
similar to DNAJ heat shock N-terminal domain-containing protein-like >Expectation: 2.5
miR169r*                    18 UCGGUUCCUACUGAACGG 1
                               ::::: ::::::::::.
Sb03g028620.1 3rd exon     949 CGCCAAAGAUGACUUGCU 966
similar to Cytochrome P450

>Expectation: 3.0
miR169r*                    18 UCGGUUCCUACUGAACGG 1
                                ::::: ::::::::::
Sb08g004540.1 2nd exon     669 UGCCAAUGAUGACUUGCA 686
similar to 4-alpha-L-fucosyltransferase >Expectation: 3.0
miR169r*                    19 AUCGGUUCCUACUGAACGG 1
                               ::::::::: ::.::: :
Sb01g035620.1 25th exon   3062 UAGCCAAGGAAGAUUUGGC 3080
similar to AAA-type ATPase family protein, putative, expressed >Expectation: 3.0
 miR169r*                   19 AUCGGUUCCUACUGAACGG 1
                               :. : .:::::::::::::
Sb01g032770.1 3rd exon     680 UGCCGGAGGAUGACUUGCC 698
weakly similar to OSMYB3

>Expectation: 3.0
miR169r*                    19 AUCGGUUCCUACUGAACGG 1
                               :.:::::::::::::.:: .:
Sb03g001440.1 6th exon    3634 UGGCCAAGGAUGAUUUCUC 3652
similar to Ethylene insensitive 2

>Expectation: 3.5
miR169r*                    19 AUCGGUUCCUACUGAACGG 1
                               :::: :.:::::::.::: ::
Sb01g038240.1               32 UAGCCAGGGAUGGCUUCCC 50
Mitochondrial import inner membrane translocase, subunit TIM22

>Expectation: 1.5
miR169r*                    18 UCGGUUCCUACUGAACGG 1
                               :::::::: ::::.:::::
Sorghum EST: TC130929      391 AGCCAAGAAUGAUUUGCC 408 EST mapped to a segment of Sb01g013430.1
CCAAT-binding transcription factor (CBF-B/NF-YA) subunit B >Expectation: 3.5
miR169r*                    18 UCGGUUCCUACUGAACGG 1
                               ::::::::::::::: ::
Sb01g036110.1 17th exon   2618 GUCCAAGGAUGACUUACC 2635 similar to Insulinase containing protein, expressed

Figure 24B

```
>Expectation: 3.0
miR169s              20 UCCGUUCAGUAGGAACCGAU 1
                        :::::  :::::::::::::
Sb01g045500.1 3'UTR  935 UGGCAACUCAUCCUUGGCUU 954
CCAAT-binding transcription factor (CBF-B/NF-YA) subunit B >Expectation: 3.5
miR169s              20 UCCGUUCAGUAGGAACCGAU 1
                        :::::. :..: :::::::::
Sb01g027540.1 3'UTR  1668 AGGCAGCUUGUACUUGGCUA 1687
similar to Serine carboxypeptidase family protein, expressed >Expectation: 4
miR169s              21 AUCCGUUCAGUAGGAACCGAU 1
                        ::  :::  :::.:::::::.
Sb10g005870.1 10th exon 1508 UAAUCAAAUCAUUCUUGGCUG 1528
similar to Serine carboxypeptidase II-2 precursor (EC 3.4.16.6) (CP-MII.2)

>Expectation: 2.0
miR169s              21 AUCCGUUCAGUAGGAACCGAU 1
                        :::::::  ::::.:::::::.
Sb08g021910.1 3'UTR  716 UAGGCAAAUCAUUCUUGGCUG 736
CCAAT-binding transcription factor subunit B family protein, expressed >Expectation: 2.5
miR169s              20 UCCGUUCAGUAGGAACCGAU 1
                        :::::: ::::.:::::::
Sb01g011220.1 3'UTR  1260 AGGCAAUUCAUUCUUGGCUU 1279
CCAAT-binding transcription factor (CBF-B/NF-YA) subunit B
```

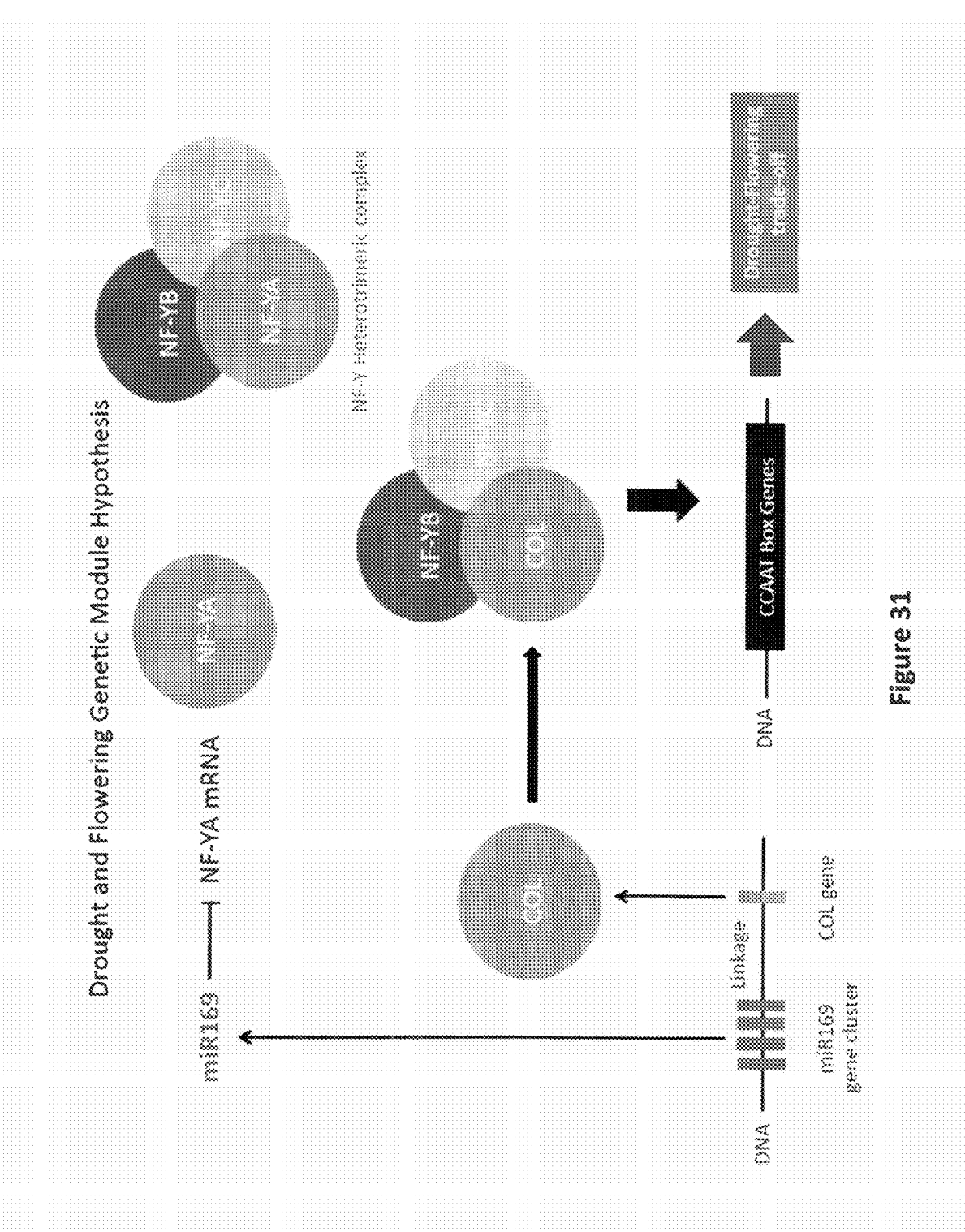

MIRNA169 COMPOSITIONS AND METHODS FOR THE REGULATION OF CARBOHYDRATE METABOLISM AND FLOWERING IN PLANTS

This Continuation-in-Part application is a Continuation-in-Part of U.S. patent application Ser. No. 13/114,675 filed May 24, 2011, now U.S. Pat. No. 9,044,019, which in turn claims priority to U.S. Provisional Application No. 61/347,741 filed May 24, 2010. This application is also a Continuation-in-Part of U.S. application Ser. No. 14/160,520, filed Jan. 21, 2014 which claims priority to U.S. Provisional Application No. 61/754,745 filed Jan. 21, 2013. The entire contents of each of the foregoing applications being incorporated herein by reference as though set forth in full.

FIELD OF THE INVENTION

This invention relates to the fields of plant metabolism and molecular biology. More specifically, the invention provides compositions and methods for modulating expression of target nucleic acids encoding proteins involved in a variety of important biochemical pathways, including those controlling sugar metabolism, flowering and biofuel production.

BACKGROUND OF THE INVENTION

Several publications and patent documents are cited throughout the specification in order to describe the state of the art to which this invention pertains. Each of these citations is incorporated herein by reference as though set forth in full.

Accumulation of soluble sugars is a characteristic trait in two closely related plant species, sorghum [*Sorghum bicolor* (L.) Moench] and sugarcane (*Saccharum* spp.) (1, 2). In both species, sucrose is the main type of sugar and accumulates in the parenchyma tissue of juicy stems. Sorghum belongs to the tribe of the *Andropogoneae* that includes potential biofuel crops like switchgrass, Miscanthus and successful biofuel crops like corn and sugarcane.

However, from a genomics point of view sorghum contains a simpler genome because it lacks the additional rounds of whole genome duplication events present in other species. Therefore, it has become possible to generate a high-quality genome sequence. Furthermore, cultivars exists that rival sugarcane in levels of stem sugar so that a genetic approach can be used to investigate which genes are differentially expressed to achieve high levels of stem sugar.

Small RNAs (18-25 nt) regulate many developmental and physiological processes in plants through the regulation of gene expression at either the transcriptional or post-transcriptional level (Chuck G, et al., (2009) *Current Opinion in Plant Biology*, 12:81-86; Vaucheret H. (2006) *Genes Dev* 2006, 20:759-771; Zamore P D, Haley B. (2005) *Science*, 309:1519-1524). They can be subdivided into short-interfering RNAs (siRNAs) and microRNAs (miRNAs) (Bartel D P. (2004) *Cel*, 116:281-297; Vazquez F. (2006) *Trends in Plant Science*, 11:460-468).

MicroRNAs are derived from capped and polyadenylated primary (pri)-miRNA transcripts that are transcribed by RNA polymerase II and can form a hairpin-loop structure by intramolecular pairing. Two sequential cleavages mediated by DICER LIKE 1 (DCL1) are required to produce a mature miRNA. In the first cleavage, DCL1 cleaves near the base of the hairpin-loop stem of the pri-miRNA to produce a miRNA precursor (pre-miRNA). The second cleavage takes place near the loop of the pre-miRNA to produce a miRNA/miRNA* duplex. The mature miRNA is then loaded into the RNA-induced silencing complex (RISC) and can guide the sequence-specific cleavage or translational inhibition of target mRNAs, as well as gene silencing through DNA methylation, whereas the non-incorporated miRNA* strand is usually degraded.

Through the use of next-generation sequencing, the small RNA component of the *Arabidopsis* and rice transcriptomes has been well characterized, more than in any other plant species (11). This is reflected in the miRBase database on the world wide web at .mirbase.org, release 16: September 2010), where 213 miRNAs are described for *Arabidopsis* whereas 462 miRNAs are described for rice. Besides rice, the identification of miRNAs through deep sequencing in other grasses including maize, wheat, and *Brachypodium* have been described (Wang et al., (2009) *Plant Cell*, 21:1053-1069; Wei B. et al., (2009) *Funct Integr Genomics* 9:499-511). The identification of rice, maize and wheat miRNAs from different tissues, developmental stages and stress-treatments, provides an opportunity to understand how miRNAs regulate the expression of genes influencing traits of agronomic importance.

High sucrose content is a highly desirable trait because sugar can be fermented to produce bioethanol as a source of renewable energy (3). Although sugarcane has been extensively used as a source of biofuel, its use as a model system to understand the genetics of carbohydrate metabolism is hampered by its complex genome, with several cultivars differing greatly in their ploidy levels (4). Sorghum instead, provides a better system to study the genetic basis of sugar accumulation.

SUMMARY OF THE INVENTION

In accordance with the present invention, compositions comprising at least one miRNA provided in Table 2 or Table 3 or a vector encoding said at least one of said miRNA in a biologically compatible carrier for modulating expression of a plant target gene is provided. In a preferred embodiment, the target gene encodes a protein which regulates a biological parameter selected from the group consisting of flowering, and sugar metabolism.

Also provided is a method for modulating a biological parameter selected from the group consisting of flowering and sugar metabolism in a plant or plant cell comprising contacting said plant or plant cell with an effective amount of the miRNA containing compositions (e.g., miRNA expressing vectors) of the invention. The compositions and methods described herein are effective for increasing production of biofuels from plants so treated.

In another embodiment, compositions comprising at least one miRNA provided in the figures or a vector encoding said at least one of said miRNA in a biologically compatible carrier for modulating expression of a plant target gene is provided. In a preferred embodiment, the target gene encodes a protein which regulates a biological parameter selected from the group consisting of flowering, stress or drought resistance, plant height, and sugar metabolism.

Also provided is a method for modulating a biological parameter selected from the group consisting of flowering, drought resistance, plant height and sugar metabolism in a plant or plant cell comprising contacting said plant or plant cell with an effective amount of the miRNA containing compositions (e.g., miRNA expressing vectors) of the invention. The compositions and methods described herein are effective for increasing production of biofuels from plants so treated. In particularly preferred embodiments, the miRNAs are from the miRNA169 cluster.

BRIEF DESCRIPTION OF THE DRAWINGS

(FIG. 1A) Grain sorghum BTx623 with low Brix and early flowering phenotype, was crossed with sweet sorghum Rio with high Brix and late flowering phenotype. The resulting F1 plants were self-crossed and the obtained F2 seeds were planted on the field together with the BTx623 and Rio parents. A total of 553 F2 plants were phenotyped for flowering time (measured as the total number of leaves at flowering) and Brix degree. Using a bulked segregant analysis (BSA) approach, we selected an equal number of F2 plants with low Brix and early flowering (LB/EF) and with high Brix and late flowering (HB/LF) phenotype, respectively. (FIG. 1B) A flow chart describing the procedure for small RNA library construction and sequencing. (FIG. 1C) Histograms displaying the Brix degree and flowering time data obtained from plants grown in the field. We selected 11 LB/EF F2s displaying Brix degree ≤5 and number of leaves ≤9, whereas the 11 HB/LF F2s selected displayed a Brix degree ≥13 and number of leaves ≥14.

(FIG. 2A) Mapping of small RNAs (18-25 nt) with perfect match to different elements of the BTx623 reference genome with the term "other" representing intergenic regions. (FIG. 2B) Frequency and size distribution of small RNAs reads. (FIG. 2C) Size distribution of intron-associated small RNAs. (FIG. 2D) Size distribution of exon-associated small RNAs. (FIG. 2E) Promoter associated small RNAs (PASRs) in sorghum. The percentage of small RNA reads mapping to the promoter region relative to the total number of reads in each library is shown. (FIGS. 2F and 2G) Graphs showing the frequency and distribution of 25 nt small RNAs (FIG. 2F), and the 18 nt small RNAs (FIG. 2G), along the promoter region. The region considered extends from 500 bp upstream from the beginning of the 5' UTR to 500 bp downstream of it. Each vertical line on the graph represents 100 bp interval. The abundance of the small RNA reads is shown on the y-axis.

(FIG. 3A) The abundance of miR172 was the highest in the BTx623 library, comprising almost 6% of the total reads. (FIG. 3B) The rest of the known miRNAs were expressed at very low abundance (less that 0.5% of the total reads in the library) in stem tissue. (FIG. 3C) The abundance of 7 new predicted miRNAs are shown whose allelic variation in expression between BTx623 and Rio were inherited in the F2 progeny. Notice the very low abundance at which these miRNAs are expressed.

(FIG. 4A) The expression of miR169 and miR172 was at least twice as high in BTx623 relative to that in Rio and this difference was inherited in the F2. The opposite was true for miR395 expression. (FIGS. 4B-4D) Quantification of miRNA expression through Taqman Assay in pools of F2 plants with similar flowering time (10-11 leaves) but different sugar content (Brix 3-5 vs Brix 13-16). (FIG. 4B) High expression of miR169d in BTx623 relative to Rio correlates with low Brix in the F2 independently of flowering time. (FIG. 4C-4D) F2 plants with similar flowering time display no differences in miR395f and miR172a expression regardless Brix degree. (FIG. 4E) The allelic variation in the expression of seven new miRNAs between BTx623 and Rio was inherited in the F2 plants selected. (FIG. 4F) The frequency count of small RNAs for each new miRNA was used to calculate its abundance. (FIG. 4G) The miRNA abundances were used to calculate their relative fold change in expression between BTx623 and Rio, and between the LB/EF F2s and HB/LF F2s libraries, respectively. Positive values in the y-axis of the graph denote fold changes in miRNA expression that are higher in BTx623 relative to Rio and higher in LB/EF F2s relative to HB/LF F2s libraries, respectively; the opposite is true for negative values. The miRNA "chromosome_4_684.BC_01" was not included in the graph because it was not detected in the Rio library.

(FIG. 5A) Validation of cleavage for target genes mediated by known miRNAs. (FIG. 5B) Validation of cleavage for target genes mediated by newly predicted miRNAs.

FIGS. 8A-8C. List of miRNAs that target genes at the 5'UTR. The mature sequences of the miRNAs are depicted together with their predicted cleavage sites at the 5' UTR region of target genes. Sequences provided are SEQ ID NOs: 46-91, from top to bottom.

FIGS. 9A-9CC. List of miRNAs that target genes at exons. The mature sequences of the miRNAs are depicted together with their predicted cleavage sites at the exonic region of target genes. Sequences provided are SEQ ID NOs: 92-623, from top to bottom.

FIGS. 10A-10I. List of miRNAs that target genes at the 3'UTR. The mature sequences of the miRNAs are depicted together with their predicted cleavage sites at the 3' UTR region of target genes. Sequences provided are SEQ ID NOs: 624-793, from top to bottom.

(FIG. 11A) Co-localization of miRNAs and their target genes with SSRs markers near Brix QTLs. (FIG. 11B) Co-localization of miRNAs and their targets genes with SSRs markers near flowering time QTLs.

(FIG. 21A) Phylogenetic distribution of MIR169 gene copies in ancestral and current species with gain and losses of MIR169 copy number during grass evolution. Numbers in squares represent the number of MIR169 gene copies for a given cluster in each species. Numbers along each line represent gains (+) and losses (−) of MIR169 gene copies. The estimated divergence time for each species is given at each node in the tree according to (Bennetzen, et al. 2012; Initiative 2010; Paterson, et al. 2009; Zhang, et al. 2012). The gain in MIR169 copy number of sorghum relative to Brachypodium is depicted. WGD:

whole genome duplication; mya: million years ago. Note: WGD in maize is used as a term to represent the allotetraiplody event that took place. (FIGS. 21B-21D) Neighbor Joining (NJ) phylogenetic trees with boostrap support are shown depicting the relationships of MIR169 stem-loop sequences from the grass species shown in FIG. 17A. (FIG. 21B) NJ phylogenetic tree with Brachypodium (bdi) and rice (osa) MIR169 stem-loop sequences orthologous to sorghum MIR169 copies on chromosome 7. (FIG. 21C) NJ phylogenetic tree with rice (osa) and foxtail millet (sit) MIR169 stem-loop sequences (top) and rice, foxtail millet, sorghum (sbi) and maize (zma) MIR169 stem loop sequences (bottom) orthologous to MIR169 copies on sorghum chromosome 2. (FIG. 21D) NJ phylogenetic tree depicting the relationship of foxtail millet and maize MIR169 copies orthologous to sorghum MIR169 copies on chromosome 1 (top), and Brachypodium, rice, foxtail millet and maize MIR169 copies orthologous to sorghum MIR169 copies on chromosome 1 (bottom).

FIGS. 22A-22B. Experimental validation of predicted MIR169 stem-loop precursors in sorghum and maize. (FIG. 22A) Sorghum stem-derived small RNAs were mapped to sbi-MIR169t (SEQ ID NO: 19), sbi-MIR169u (SEQ ID NO: 20), and sbi-MIR169v (SEQ ID NO: 21) stem-loop sequences. Only sequences with perfect match to the BTx623 genome are shown. Predicted mature and star miR169 sequence is highlighted in capital letters on the stem-loop sequence. To the left side of each small RNA sequence a label is shown with information about the small RNA library from which it was sequenced (bc01: Mix library; bc02: BTx623 library; bc03: Rio library; bc04: low Brix and early flowering F2 library; bc05: high Brix and late flowering F2 library), together with the abundance of the small RNA read indicated by a number. For sbi-MIR169t, left column, the sequences are positions 2-18; 3-19; 2-21; 3-19; 2-18; 2-18; 2-19; 2-21; 1-20; 3-19; 2-19; 2-20; 1-20; 2-21; 2-22; 1-21; 1-22; 1-23; 1-25; 1-22; 23-41; 27-48; 23-45; 23-39; 23-40; 23-43; 23-45; 23-43; and 23-42 of SEQ ID NO: 19, from top to bottom. For sbi-MIR169t, right column, the sequences are 92-108; 92-109; 92-110; 92-111; 92-110; 92-111; 92-109; 93-110; 92-108; 92-110; 92-111; 90-106; 92-108; 92-109; 94-111; 92-110; and 92-111 of SEQ ID NO: 19, from top to bottom. For sbi-MIR169u, left column, the sequences are positions 16-35; 16-32; 16-33; 16-35; 16-32; 16-33; and 16-35 of SEQ ID NO: 20, from top to bottom. For sbi-MIR169u, right column, the sequences are positions 111-127; 110-126; 110-127; 110-128; 110-128; 110-130; 110-126; 110-126; 111-127; 110-127; 111-128; 110-128; 111-129; 110-129; 112-131; 110-130; 106-127; 111-132; 110-126; 111-127; 110-127; 111-128; 110-128; 111-130; and 111-132 of SEQ ID NO: 20, from top to bottom. For sbi-MIR169v, left column, the sequences are positions 22-38; 22-38; 22-38; 22-42; 22-38; 22-40; 22-42; 5-28; and 12-28 of SEQ ID NO: 21, from top to bottom. For sbi-MIR169v, right column, the sequences are positions 83-100; 84-100; 93-110; and 62-78 of SEQ ID NO: 21, from top to bottom. (FIG. 22B) Maize endosperm-derived small RNAs were mapped to predicted stem-loop precursor zma-MIR169s (SEQ ID NO: 22). For the left column, the sequences are positions 21-44; 22-45; 22-40; 21-44; and 4-28 of SEQ ID NO: 22, from top to bottom. For the right column, the sequences are positions 59-83 and 74-97 of SEQ ID NO: 22, from top to bottom.

FIGS. 23A-23B. Antisense MIR169r/s gene pair generates small RNAs. Although sequencing of stem-derived small RNAs from grain and sweet sorghum were previously described [10], we mapped small RNAs from our sequenced libraries to the newly annotated sbi-MIR169r and sbi-MIR169s hairpin structures. (FIG. 23A) The most abundant small RNA reads mapped to sbi-MIR169r (SEQ ID NO: 23) corresponded to the miR169r* sequence, whereas the most abundant small RNA reads mapped to sbi-MIR169s (SEQ ID NO: 24) corresponded to miR169s, respectively. For sbi-MIR169r, left column, the sequences are positions 18-37; 19-37; 19-37; 19-37; and 20-37 of SEQ ID NO: 23, from top to bottom. For sbi-MIR169r, right column, the sequences are positions 87-107; 88-106; 88-107; 88-107; 88-105; 89-107; 89-107; 89-107; 89-107; and 90-107 of SEQ ID NO: 23, from top to bottom. For sbi-MIR169s, left column, the sequences are positions 20-40; 21-38; 21-40; 22-39; and 23-40 of SEQ ID NO: 24, from top to bottom. For sbi-MIR169s, right column, the sequences are positions 90-107; 90-107; and 90-109 of SEQ ID NO: 24, from top to bottom. (FIG. 23B) Nucleotide polymorphism between miR169r* (SEQ ID NO: 25) and miR169s (SEQ ID NO: 26).

FIGS. 24A-24B. List of predicted targets of sbi-miR169r*. The psRNATarget program was used to predict mRNAs targeted by sbi-miR169r*. The miR169r*-target alignment is shown together with the expectation level of the prediction with 1 as high confident and 3.5 less confident. The annotation for each predicted gene is shown in conjunction with the region where the miR169r* recognition sequence is located (exon or 3'UTR). Sequences in FIG. 24A are, from top to bottom: SEQ ID NO: 27; SEQ ID NO: 31; SEQ ID NO: 27; SEQ ID NO: 32; SEQ ID NO: 27; SEQ ID NO: 33; SEQ ID NO: 28; SEQ ID NO: 34; SEQ ID NO: 29; SEQ ID NO: 35; SEQ ID NO: 28; SEQ ID NO: 36; SEQ ID NO: 27; SEQ ID NO: 37; SEQ ID NO: 30; SEQ ID NO: 38; SEQ ID NO: 30; and SEQ ID NO: 39. Sequences in FIG. 24B are, from top to bottom: SEQ ID NO: 30; SEQ ID NO: 40; SEQ ID NO: 30; SEQ ID NO: 41; SEQ ID NO: 30; SEQ ID NO: 42; SEQ ID NO: 29; SEQ ID NO: 43; SEQ ID NO: 29; SEQ ID NO: 44; SEQ ID NO: 29; SEQ ID NO: 45; SEQ ID NO: 29; SEQ ID NO: 46; SEQ ID NO: 30; SEQ ID NO: 47; SEQ ID NO: 30; and SEQ ID NO: 48.

FIG. 25. List of predicted targets of sbi-miR169s. The psRNATarget program was used to predict mRNAs targeted by sbi-miR169s. The miR169s-target alignment is shown together with the expectation level of the prediction with 1 as high confident and 3.5 less confident. The annotation for each predicted gene is shown in conjunction with the region where the miR169s recognition sequence is located (exon or 3'UTR). Sequences are, from top to bottom: SEQ ID NO: 49; SEQ ID NO: 49; SEQ ID NO: 51; SEQ ID NO: 49; SEQ ID NO: 52; SEQ ID NO: 50; SEQ ID NO: 53; SEQ ID NO: 50; SEQ ID NO: 54; SEQ ID NO: 49; and SEQ ID NO: 55.

(FIG. 29A) Left: Neighbor Joining (NJ) phylogenetic tree of orthologous bHLH proteins with the *Arabidopsis* bHLH137 protein as reference. Middle: a representation of the gene structure in exons (boxes) and introns (lines) (5' and 3' UTRs not included). Right: graphic representation of the linear protein with the bHLH domain represented as an orange box and the HLH domain as a yellow box with orange border. (FIG. 29B) Protein alignment highlighting the bHLH motif with AtbHLH137 protein as reference. The *Brachypodium* protein encoded by the gene Bradi4g34870 lost most of the basic domain, becoming a HLH protein instead. Sequences are, from top to bottom, SEQ ID NOs: 56-72. (FIG. 29C) Graph depicting the average synonymous and non-synonymous substitution rate of the bHLH Bradi3g41510 orthologous gene pairs compared to HLH Bradi4g34870 orthologous gene pairs.

FIGS. 30A-30B. Evolution of the Zinc finger, B-box and CCT domain protein. (FIG. 30A) Left: Neighbor Joining (NJ) phylogenetic tree of B-box and CCT motif orthologous proteins with *Arabidopsis* COL14 protein as reference. Center: graphic representation of the B-box and CCT motif gene structure for each species with exons as boxes and introns as lines (5' and 3' UTRs not shown). Right: linear representation of the B-box and CCT motif protein for each species with the Zinc finger, B-box domain shown as a blue box where the CCT domain is shown as a red box. (FIG. 30B) Protein alignment highlighting the Zinc finger, B-box domain in blue boxes (*Arabidopsis* COL14 has two) and the CCT domain in a red box. Sequences are, from top to bottom, SEQ ID NOs: 73-80.

FIG. 31. The "Drought and Flowering Genetic Module Hypothesis". Here we suggest that trade-offs between drought stress and flowering time could be explained in part by genetic linkage of MIR169 and COL genes. In this model, a given COL gene genetically linked to a MIR169 gene will be positively selected over any other COL gene located somewhere else in the genome. This is so because COL proteins can replace the NF-YA (HAP2) subunit from the NF-YA, NF-YB (HAP3) and NF-YC (HAPS) heterotrimeric transcription factor complex [26], with NF-YA mRNA targeted by miR169 [38]. Thus, depending on water availability, plants can adjust their flowering time according to the severity of drought during the growing season by modulating the expression of miR169 and COL genes. Under this scenario, high miR169 expression lower NF-YA mRNA levels, consequently decreasing NF-YA protein levels, which may increase the frequency of COL protein to interact with NF-YB and NF-YC subunits and thus guide the transcription complex toward the expression of CCAAT box genes involved in flowering. The current model establishes a genetic framework to explain the observation that plants flower early under drought compared to well watered environments [39].

DETAILED DESCRIPTION OF THE INVENTION

Figure 1A:
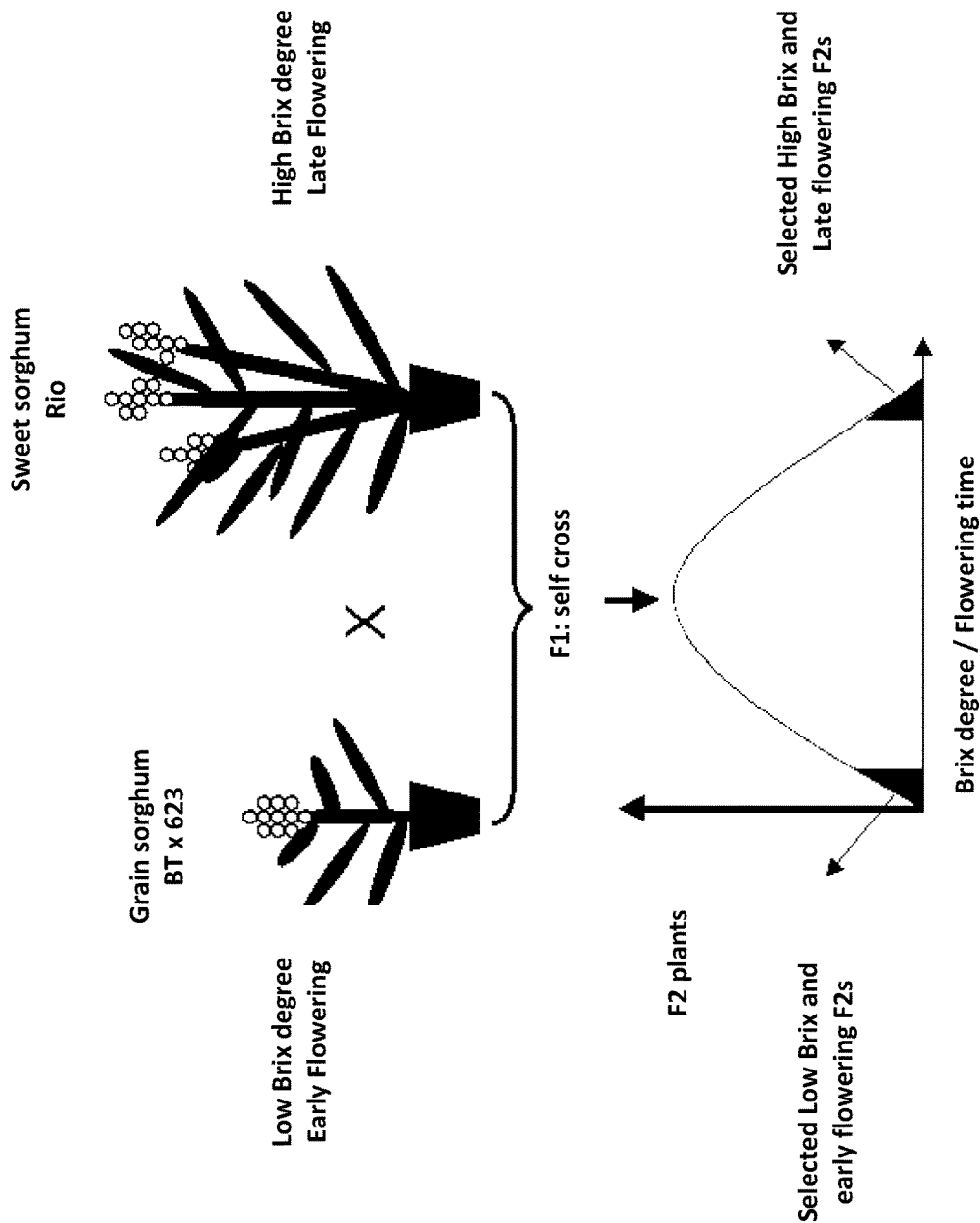
FIGS. 1A-1C. Selection of sorghum plants and construction of small RNA libraries for deep sequencing.

In sorghum, sugar accumulation is under quantitative inheritance (7), and the gene repertoire involved in sugar metabolism has not been well defined yet. Adding to this task is that a correlation between flowering time and sugar content has been suggested (7, 8). Indeed, we previously observed that sugar accumulation (measured as Brix degree and referred herein as Brix) in the stem of grain sorghum BTx623 and sweet sorghum Rio cultivars differed at the time of flowering. Interestingly, 80% of the differentially expressed genes in stem tissue between the two cultivars had orthologous counterparts in syntenic positions in rice (9). This suggested that the ability of sorghum to accumulate soluble sugars relative to rice would probably be due to gene regulation at either the transcriptional or post-transcriptional level rather than differences in gene content.

To address the latter possibility, we investigated the microRNA-mediated posttranscriptional regulation of genes involved in sugar accumulation and flowering time by characterizing the small RNA portion of transcriptomes derived from stem tissues of grain and sweet sorghum at flowering. Using the SOLiD next generation sequencing system, we sequenced with an unprecedented depth small RNAs libraries from BTx623 and Rio, and from a pool of selected F2 plants derived from their cross that differed in sugar content and flowering time. This allowed us to detect the expression of 110 conserved miRNAs and to discover 223 new miRNA candidates, and to correlate allelic variation of miRNA levels with sugar and flowering phenotypes. We also could find that the size distribution of small RNAs in sorghum stems was quite heterogeneous, with the 22 nt small RNAs highly enriched in introns. Furthermore, a new class of small RNAs with a distinct size of at least 25 nt long was found and named "piccolo RNAs" (from the Italian word small). Interestingly, the piccolo RNAs preferentially mapped to the promoter regions of sorghum genes.

Thus, we have characterized the small RNA component of the transcriptome from grain and sweet sorghum stems, and from F2 plants derived from their cross that segregated for sugar content and flowering time. In addition, completely new roles for miR169 in sugar metabolism and miR395 in flowering, respectively, were identified because their respective miRNA/miRNAs* can regulate different target genes. Finally, newly discovered microRNAs co-localized with previously described QTLs for biofuel traits.

I. Definitions

The following definitions are provided to facilitate an understanding of the present invention. Unless defined otherwise, all technical and scientific terms used herein have the same meaning as commonly understood by one of ordinary skill in the art to which this invention belongs. Generally, conventional methods of molecular biology, microbiology, recombinant DNA techniques, cell biology, and virology within the skill of the art are employed in the present invention. Such techniques are explained fully in the literature, see, e.g., Maniatis, Fritsch & Sambrook, Molecular Cloning: A Laboratory Manual (1982); DNA Cloning: A Practical Approach, Volumes I and II (D. N. Glover, ed. 1985); Oligonucleotide Synthesis (M. J. Gait, ed. 1984); Nucleic Acid Hybridization (B. D. Hames & S. J. Higgins, eds. (1984)); Animal Cell Culture (R. I. Freshney, ed. 1986); and RNA Viruses: A Practical Approach, (Alan, J. Cann, Ed., Oxford University Press, 2000).

For purposes of the invention, "Nucleic acid", "nucleotide sequence" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Alternatively, this term may refer to a DNA that has been sufficiently separated from (e.g., substantially free of) other cellular components with which it would naturally be associated. "Isolated" is not meant to exclude artificial or synthetic mixtures with other compounds or materials, or the presence of impurities that do not interfere with the fundamental activity, and that may be present, for example, due to incomplete purification. When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An isolated nucleic acid (either DNA or RNA) may further represent a molecule produced directly by biological or synthetic means and separated from other components present during its production.

According to the present invention, an isolated or biologically pure molecule or cell is a compound that has been removed from its natural milieu. As such, "isolated" and "biologically pure" do not necessarily reflect the extent to which the compound has been purified. An isolated compound of the present invention can be obtained from its natural source, can be produced using laboratory synthetic techniques or can be produced by any such chemical synthetic route. The term "promoter" or "promoter region" generally refers to the transcriptional regulatory regions of a gene. The "promoter region" may be found at the 5' or 3' side of the coding region, or within the coding region, or within introns. Typically, the "promoter region" is a nucleic acid sequence which is usually found upstream (5') to a coding sequence and which directs transcription of the nucleic acid sequence into mRNA. The "promoter region" typically provides a recognition site for RNA polymerase and the other factors necessary for proper initiation of transcription.

Promoters useful in some embodiments of the present invention may be tissue-specific or cell-specific. The term "tissue-specific" as it applies to a promoter refers to a promoter that is capable of directing selective expression of a nucleotide sequence of interest to a specific type of tissue in the relative absence of expression of the same nucleotide sequence of interest in a different type of tissue (e.g., flower vs. root). The term "cell-specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell-specific" when applied to a promoter also means a promoter capable of promoting selective expression of a nucleotide sequence of interest in a region within a single tissue. Alternatively, promoters may be constitutive or regulatable. Additionally, promoters may be modified so as to possess different specificities.

The term "vector" relates to a single or double stranded circular nucleic acid molecule that can be infected, transfected or transformed into cells and replicate independently or within the host cell genome. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. An "expression vector" is a specialized vector that contains a gene or nucleic acid sequence with the necessary regulatory regions needed for expression in a host cell.

DNA constructs or vectors of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al., Embo J. 3:2717-2722 (1984). Electroporation techniques are described in Fromm et al., Proc. Natl. Acad. Sci. USA 82:5824 (1985). Ballistic transformation techniques are described in Klein et al., Nature 327:70-73 (1987).

*Agrobacterium tumefaciens*-mediated transformation techniques, including disarming and use of binary vectors, are well described in the scientific literature. See, for example, Horsch et al., Science 233:496-498 (1984), and Fraley et al., Proc. Natl. Acad. Sci. USA 80:4803 (1983).

Transformed plant cells that are derived by any of the above transformation techniques can be cultured to regenerate a whole plant that possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al., Ann. Rev. of Plant Phys. 38:467-486 (1987).

One of skill will recognize that after the expression cassette or vector is stably incorporated in transgenic plants and confirmed to be operable, it can be introduced into other plants by sexual crossing. Any of a number of standard breeding techniques can be used, depending upon the species to be crossed.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The terms "miRNA" and "microRNA" refer to about 10-35 nt, preferably about 15-30 nt, and more preferably about 19-26 nt, non-coding RNAs derived from endogenous genes encoded in the genomes of plants and animals. They are processed from longer hairpin-like precursors termed pre-miRNAs that are often hundreds of nucleotides in length. MicroRNAs assemble in complexes termed miRNPs and recognize their targets by antisense complementarity. These highly conserved, endogenously expressed RNAs are believed to regulate the expression of genes by binding to the 3'-untranslated regions (3'-UTR) of specific mRNAs as well as other regions on targeted mRNAs. Without being bound by theory, a possible mechanism of action assumes that if the microRNAs match 100% their target, i.e. the complementarity is complete, the target mRNA is cleaved, and the miRNA acts like a siRNA. However, if the match is incomplete, i.e. the complementarity is partial, then the translation of the target mRNA is blocked. The manner by which a miRNA base-pairs with its mRNA target correlates with its function: if the complementarity between a mRNA and its target is extensive, the RNA target is cleaved; if the complementarity is partial, the stability of the target mRNA in not affected but its translation is repressed.

The term "RNA interference" or "RNAi" refers generally to a process or system in which a RNA molecule changes the expression of a nucleic acid sequence with which RNA molecule shares substantial or total homology. The term "RNAi agent" refers to an RNA sequence that elicits RNAi.

An "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting HCV may be between 15-35 nucleotides in length.

"Pri-miRNAs" are several hundred to thousands of base pairs in size. Pri-miRNA contains at least 1, and up to 6, nucleotide hairpin loop structures when transcribed from polycistronic units. They can be composed of multiple miRNAs, and in a particular arrangement of the invention five miRNAs are processed from one nucleic acid sequence. These sequences can also contain siRNA nucleic acids that repress gene transcription once processed in the RNAi system.

As used herein, "agricultural formulations" include formulations for use in the field. The phrase "agriculturally acceptable formulation" as used herein refers to a composition or formulation that allows for the effective distribution of the nucleic acid molecules of the instant invention in the physical location most suitable for their desired activity.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween 80, Polysorbate 80), emulsifier, buffer (e.g., Tris HCl, acetate, phosphate), bulking substance (e.g., lactose, mannitol), excipient, auxiliary agent or vehicle with which an active agent of the present invention is administered. Agriculturally acceptable carriers can be sterile liquids, such as water and oils, including those of petroleum, animal, vegetable or synthetic origin. Water or aqueous saline solutions and aqueous dextrose and glycerol solutions are preferably employed as carriers.

With respect to single-stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (see Sambrook et al. (2001) *Molecular Cloning. A Laboratory Manual*, Cold Spring Harbor, N.Y.: Cold Spring Harbor Laboratory Press):

$$T_m = 81.5°\text{ C.} + 16.6 \text{ Log } [Na+] + 0.41 (\% \; G+C) - 0.63 (\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. Depending upon the specific sequence involved, the $T_m$ of a DNA duplex decreases by 0.5-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high-stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

"Corresponding" means identical to or complementary to the designated sequence. The sequence may be generated in any manner, including chemical synthesis, DNA replication, reverse transcription or a combination thereof. Being "Complementary" means that a nucleic acid, such as DNA and RNA, encodes the only corresponding base pair that non-covalently connects sequences by two or three hydrogen bonds. There is only one complementary base for any of the bases found in DNA and in RNA, and skilled artisans can reconstruct a complementary strand for any single stranded nucleic acid.

The present invention also includes active portions, fragments, derivatives and functional or non-functional mimetics of the miRNAs of the invention. A "fragment" or "portion" of a sequence means a stretch of residues of at least about five to seven contiguous residues, often at least about seven to nine contiguous residues, typically at least about nine to fifteen contiguous residues and, most preferably, at least about fourteen or more contiguous residues.

For purposes of the present invention, "a" or "an" entity refers to one or more of that entity; for example, "a cDNA" refers to one or more cDNA or at least one cDNA. As such, the terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

A "derivative" of a polypeptide, polynucleotide or fragments thereof means a sequence modified by varying the sequence of the construct, e.g. by manipulation of the nucleic acid encoding the protein or by altering the protein itself. "Derivatives" of a gene or nucleotide sequence refers to any isolated nucleic acid molecule that contains significant sequence similarity to the gene or nucleotide sequence or a part thereof. In addition, "derivatives" include such isolated nucleic acids containing modified nucleotides or mimetics of naturally-occurring nucleotides.

The term "functional" as used herein implies that the nucleic or amino acid sequence is functional for the recited assay or purpose.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide can depend on various factors and on the particular application and use of the oligonucleotide.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein. The term "gene" refers to a nucleic acid comprising an open reading frame encoding a polypeptide, including both exon and (optionally) intron sequences. The nucleic acid may also optionally include non coding sequences such as promoter or enhancer sequences. The term "intron" refers to a DNA sequence present in a given gene that is not translated into protein and is generally found between exons.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, depending on the complexity of the target sequence, the oligonucleotide probe typically contains about 10-50 or more nucleotides, more preferably, about 15-25 nucleotides.

The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The terms "percent similarity", "percent identity" and "percent homology" when referring to a particular sequence are used as set forth in the University of Wisconsin GCG software program.

The term "delivery" as used herein refers to the introduction of foreign molecule (i.e., miRNA containing nanoparticle) into cells. The term "administration" as used herein means the introduction of a foreign molecule into a cell. The term is intended to be synonymous with the term "delivery".

The term "kit" refers to a combination of reagents and other materials.

II. Uses of Mirna Constructs

The present invention is based, at least in part, on the identification of new miRNAs in sorghum. The nucleic acids of the invention can be used to control gene expression in plants. In some embodiments, the expression cassettes encoding the miRNAs of the invention are prepared and introduced into plants. The encoded miRNAs then control expression of the endogenous target genes. Alternatively, one can modify the target gene so as to render it miRNA-resistant by modifying the sequence to decrease or inhibit pairing with the miRNA. The modifications will typically be selected such that the sequence of the encoded protein is not altered. The modified target gene can be incorporated into an expression cassette and introduced into a plant. Alternatively, an endogenous target gene can be modified using known techniques (e.g., homologous recombination).

Nucleic acid molecules encoding the miRNAs of the invention may be prepared by using recombinant DNA technology methods. The availability of nucleotide sequence information enables preparation of nucleic acid-based molecules of the invention by a variety of means. The RNAs may be used for a variety of purposes in accordance with the present invention. In a preferred embodiment of the invention, a nucleic acid delivery vehicle (i.e., an expression vector) for modulating target gene expression is provided wherein the expression vector comprises a nucleic acid sequence coding at least one miRNA, or a functional fragments thereof as described herein. Administration of miRNA or derivatives thereof encoding expression vectors to a plant results in the modulation of target gene expression, particularly genes involved in sugar metabolism and flowering.

For some applications, an expression construct may further comprise regulatory elements which serve to drive expression in a particular cell or tissue type. Such regulatory elements are known to those of skill in the art and discussed in depth in Sambrook et al. (1989) and Ausubel et al. (1992). The incorporation of tissue specific regulatory elements in the expression constructs of the present invention provides for at least partial tissue tropism for the expression of miRNA(s). For example, the miRNA constructs can be subcloned into a vector downstream of a tissue specific promoter/enhancer to target gene expression in a particular region of the plant (e.g., root, vs. leaves).

III. Agricultural Compositions

The expression vectors of the present invention may be incorporated into agricultural compositions that may be delivered to a plant. In a particular embodiment of the present invention, compositions comprising isolated nucleic acids which enable the recipient to produce biologically effective miRNAs that modulate target gene expression in the recipient plant are provided. Herein we describe a broad spectrum of the small RNA component of the sorghum transcriptome and provide new insights into how complex processes like carbohydrate metabolism and flowering time are regulated at the post-transcriptional level. Elucidation of this regulatory process provides an opportunity to improve biofuel production, for example, by increasing stem sugar rather than cellulose and increasing biomass because of delayed flowering (38). The compositions may be administered alone or in combination with at least one other agent, such as a stabilizing compound, which may be administered in any sterile, biocompatible carrier, including, but not limited to, saline, buffered saline, dextrose, and water. In preferred embodiments, the pharmaceutical compositions also contain a agriculturally acceptable excipient. Acceptable excipients include, but are not limited to, liquids such as water, saline, glycerol, sugars and ethanol.

After agricultural compositions have been prepared, they may be placed in an appropriate container or kit and labeled for use. For administration of miRNA-containing vectors, such labeling would include amount, frequency, and method of delivery.

IV. Kits and Articles of Manufacture

Any of the aforementioned compositions or methods can be incorporated into a kit which may contain at least one miRNA sequence or a polycistronic transcript of multiple miRNAs. If the agricultural composition in liquid form is under risk of being subjected to conditions which will compromise the stability of the miRNAs or vectors encoding the same, it may be preferred to produce the finished product containing the miRNAs in a solid form, e.g. as a freeze dried material, and store the product is such solid form. The product may then be reconstituted (e.g. dissolved or suspended) in a saline or in a buffered saline ready for use prior to administration.

Hence, the present invention provides a kit comprising (a) a first component containing miRNAs as defined hereinabove, optionally in solid form, and (b) a second component containing saline or a buffer solution (e.g. buffered saline) adapted for reconstitution (e.g. dissolution or suspension) or delivery of said miRNAs or a vector encoding the same. Preferably said saline or buffered saline has a pH in the range of 4.0-8.5, and a molarity of 20-2000 mM. In a preferred embodiment the saline or buffered saline has a pH of 6.0-8.0 and a molarity of 100-500 mM. In a most preferred embodiment the saline or buffered saline has a pH of 7.0-8.0 and a molarity of 120-250 mM.

VI. Agricultural Applications

As mentioned previously, a preferred embodiment of the invention comprises delivery of at least one vector encoding an miRNA or a polycistronic miRNA transcript to a plant to control flowering and/or sugar metabolism. Alternatively, inhibitors of the miRNAs which interfere with the functions of the miRNAs disclosed herein may be delivered to target plants of interest. Field trials can be designed to assess the safety, tolerability, pharmacokinetics, and pharmacodynamics of the miRNA constructs of the invention.

The following materials and methods are provided to facilitate practice of the present invention.

Plant Material

The grain (BTx623) and sweet (Rio) sorghum cultivars together with F2 plants derived from their cross were grown in the field of the Waksman Institute during the summer of 2008. The juice from three internodes of the main stem was harvested at the time of flowering and the Brix degree measured as previously described (M. Calviño, R. Bruggmann, J. Messing, *Rice* 1, 166 (2008).). The average Brix degree from three internodes per plant was used. Flowering time was measured as the number of leaves in the main stem at the time of anthesis.

In total, 15 plants for each parent and 553 F2 plants were scored for Brix degree and flowering time. The F2 plants selected for sequencing had either low Brix (Brix≤5)/early flowering (N0 leaves≤9) or high Brix (Brix≥13)/late flowering (N0 leaves≥14).

Construction of Small RNA Libraries

Total RNA from internode tissue was extracted at the time of flowering with the mirVana miRNA isolation kit (Ambion). RNA extraction was performed in 5 independent plants for each BTx623 and Rio, and 11 independent plants for each low Brix/early flowering and high Brix/late flowering F2 plants respectively. The total RNA (1 µg per sample) was pooled and then fractionated with the flashPage fractionator (Ambion) to isolate RNAs smaller that 40 nt in length. The isolated small RNAs were used to construct small RNA cDNA libraries with the SOLiD small RNA library construction kit (Ambion). The sequencing was carried out at the Waksman genomics laboratory on the world wide web at .solid.rutgers.edu.

Bioinformatic Analysis

We mapped the 25 nt long reads to the sorghum genome using the SHRiMP program (S. M. Rumble et al., *PLoS Comput Biol* 5, e1000386 (2009), with default parameter settings except the number of matches was limited to 10. SHRiMP allowed us to perform the alignment in SOLiD's colorspace. We used only alignments that matched perfectly to the genome starting from the first position in the read up to the sequencing primer. These reads were then clustered with Vmatch on the world wide web at .vmatch.de to reduce the number of identical reads. We required 100% identity among the sequences of a cluster. We have further filtered the clustered reads against the repetitive elements of sorghum and used the remaining sequences for de novo prediction of miRNA.

Quantification of miRNA Expression

The TaqMan MicroRNA Assays (Applied Biosystems) was used to quantify the expression of miR172a, and the Custom TaqMan Small RNA Assays (Applied Biosystems) was used to quantify the expression of miR169d and miR395f respectively. The qRT-PCR reaction was done using the MyiQ Real-Time PCR Detection System (BIO-RAD Laboratories, Inc.). A relative quantification normalized against unit mass (10 ng total RNA) was performed as previously described (M. Calviño, R. Bruggmann, J. Messing, *Rice* 1, 166 (2008).

De Novo Discovery of Sorghum miRNAs

For de novo prediction of potential miRNAs, we have used the miRDeep package (M. R. Friedländer et al., *Nat Biotechnol* 26, 407 (2008). As miRDeep does not take colorspace alignment as input, we had to reshap the output to miRDeep's blastparse format. Moreover, the SHRiMP alignment scores and the score used in the blastparse format of miRDeep had to be recalculated. We used the same formula and method as described by Goff et al. At this point, we also had to translate the color space two base encoding sequences into standard nucleotide base space sequences. As we considered only perfectly matching reads after the initial alignment to the genome, we could easily translate from color space to base space sequence. The subsequent de novo calling of miRNAs was carried out as described in Goff et al. (L. A. Goff et al., *PLoS ONE* 4, e7192 (2009).

Finally, the coordinates of de novo miRNAs predicted on the minus strand were corrected as miRDeep refers the coordinates to the 5' end of the minus strand. Though, conventionally the coordinates refer always to the 5' end of the plus strand.

Target Prediction and Validation

We have used the novel miRNAs for a target prediction. Firstly, we compared the sequences to the unspliced transcripts of sorghum (A. H. Paterson et al., *Nature* 457, 551 (2009).), with BLASTN using these parameters: –F F –W 7 –e 1 –q –2 –G –1. We scored each base of the alignment according to these criteria: match as 0; GU pairs as 0.5; gaps as 2; all other pairs were scored as 1. We doubled the score within the first 13 bases of the miRNA/alignment. We considered the gene as a potential target if the total score of the alignment was smaller than 7. In addition, we have classified the target according to the position of the hit within the unspliced transcript, i.e. 5'UTR, exon, intron and 3'UTR. Furthermore, the web resource known as MicroPC (W. Mhuantong, D. Wichadakul, *BMC Genomics* 10, 366 (2009), (www3a.biotec.or.th/micropc) was used to identify the glycogenin gene as predicted target of miR169i* and PICKLE as predicted target of miR395f*, respectively.

The miRNA-mediated cleavage of mRNAs was performed through a modified procedure of the RLM-RACE protocol from Invitrogen. The sequence of the primers used in the modified RACE are provided below. The validation of predicted targets was performed in BTx623 or Rio cultivars only.

List of Primer Sequences Used in the Modified RLM-RACE Experiment Gene ID Sequence of Reverse Primer

```
Sb01g049020
                                    (SEQ ID NO: 1)
5' TGCAGCCTTGTCTTTGTTTG 3'

Sb01g033060
                                    (SEQ ID NO: 2)
5' CCTGGAACCTGTGGTGAAAT 3'

Sb01g044240
                                    (SEQ ID NO: 3)
5' GCCCATATGGACGGAAGATA 3'

Sb02g007000
                                    (SEQ ID NO: 4)
5' CTGGTAGCCGGAGAACAACT 3'

Sb03g042460
                                    (SEQ ID NO: 5)
5' TTGACAATGTCTGCCTGGTC 3'
```

-continued

Sb03g041660
(SEQ ID NO: 6)
5' CGCTGGTCAGCAATCTGATA 3'

Sb04g003660
(SEQ ID NO: 7)
5' GCACTCAAGTCCAGCACAAA 3'

Sb06g030670
(SEQ ID NO: 8)
5' TTTCATCAGTGCTTGCCAAT 3'

Sb10g005630
(SEQ ID NO: 9)
5' TGGCTGGATCTACCACTTCC 3'

Annotation of the miRNA gene targets into functional categories was based on the Phytozome database on the world wide web at .phytozome.net), the SALAD database (available on the world wide web at salad.dna.affrc.go.jp/salad.en) (7), the Kyoto Encyclopedia of Genes and Genomes (KEGG; available on the worldwide web at www.genome.jp/kegg) and the cell wall genomics database (available on the world wide web at cellwall.genomics.purdue.edu).

DNA Sequences

Rice sequences were downloaded from the Rice Annotation Project Database (RAP-DB) website (available on the world wide web at rapdb.dna.affrc.go.jp), whereas Brachypodium, foxtail millet, sorghum, maize, grapevine, soybean and cassava sequences were downloaded from the Join Genome Institute (JGI) website (www.phytozome.net). MicroRNA sequences were downloaded from the miRBase database on the world wide web at .mirbase.org.

MIR169 Gene Prediction and Annotation

Stem-loop precursors/hairpin structures from previously annotated MIR169 genes were used in reciprocal Blastn analysis during the process of creating synteny graphs. Previously known MIR169 stem-loop precursors were used as query sequences with Blastn. When the corresponding target sequences identified matched a genomic region where there was no any previous annotation of a MIR169 gene copy, we took a 100-300 bp segment and fed it into an RNA folding program (RNAfold web server: rna.tbi.univie.ac.at/cgi-bin/RNAfold.cgi) to look for signatures of hairpin-like structures typical of microRNAs. Guidelines in microRNA gene prediction were followed as suggested by Meyers et al. 2008 (Meyers, et al. 2008).

Experimental Validation of Predicted MIR169 Genes

We took advantage of our previously sequenced small RNA libraries from sorghum stems (Calvino, et al. 2011) and mapped small RNAs to the newly predicted MIR169r/s/t/u/v hairpin sequences. To validate the newly predicted MIR169s in maize, we used the SOLiD platform to sequence small RNAs derived from endosperm tissue from B73 and Mo17 inbred lines as well as endosperm tissue derived from their reciprocal crosses. Small RNA reads were then mapped to zma-MIR169s stem loop precursor.

Prediction of miR169 Targets

Target prediction was conducted in sorghum for the newly discovered miR169r* and miR169s microRNAs using the Small RNA Target Analysis Server psRNATarget (Dai and Zhao 2011) available on the world wide web at plantgrn-.noble.org/psRNATarget/. In addition to the sorghum genome sequence incorporated into psRNATarget (Sorghum DCFI Gene Index SBGI Release 9) as preloaded transcripts, we also uploaded a FASTA file from phytozome on the world wide web at phytozome.net/dataUsagePolicy.php?org=Org_Sbicolor, with all sorghum genes coding sequences and used this data set for target prediction as well. Target prediction was conducted for the annotated 21nt miR169 as well as for the most abundant small RNA reads different from 21nt in size that matched the predicted miR169 sequence (miR169 variants).

Estimation of MIR169 Gene Number in Ancestral Species

In order to estimate the numbers of MIR169 genes in ancestral species of the grass family together with gains and losses of MIR169 copies during grass evolution, we took the parsimony approach as described previously by Nozawa and colleagues (Nozawa, et al. 2012).

Estimation of Substitution Rates in MIR169 Genes and Ancient Duplication Time

To study the rate of nucleotide substitution in MIR169 genes, we aligned MIR169 stemloop sequences using MUSCLE, available with the MEGA5 software package (Tamura, et al. 2011). When we analyzed the gained MIR169 gene copy that gave rise to sit-MIR169h, sbi-MIR169v and zma-MIR169s copies (FIG. 6A: region miR169 cluster on sorghum chr2), we first computed the average (Jukes and Cantor) distance (Da) between zma-MIR169s/sbi-MIR169v and zma-MIR169s/sit-MIR169h gene pairs. The substitution rate (R) was subsequently calculated with the formula R=Da/2T where T is the divergence time (in this case 26 mya), when the ancestor of maize and sorghum diverged from foxtail millet. We then calculated the ancient duplication time at which sit-MIR169h arose by using the formula t=da/2R, where t is the divergence time of two sequences and da is the average distance between sequences in the miR169 cluster (the average of pairwise distances between sit-MIR169h/sit-MIR169g and sit-MIR169h/sit-MIR169f, respectively). A similar rationale was applied for the calculation of the ancient duplication time of sbi-MIR169t in the sorghum miR169 cluster 1 (FIG. 10A).

Rate of Synonymous and Non-Synonymous Substitutions of the bHLH Orthologous Gene Pairs We used gene exon sequences to estimate synonymous and non-synonymous substitutions using the MEGA5 program (Tamura, et al. 2011). The synonymous and non-synonymous substitution rate was calculated for a given bHLH orthologous gene pair (*Brachypodium*-rice; *Brachypodium*-foxtail millet; *Brachypodium*-sorghum and *Brachypodium*-maize), where *Brachypodium* bHLH gene Bradi3g41510 was compared to the HLH gene Bradi4g34870.

Phylogenetic Analysis

Phylogenetic analysis were performed by creating multiple alignments of nucleotide or amino acid sequences using MUSCLE and Clustal_W, respectively, and phylograms were drawn with the MEGA5 program using the NJ (Neighbor Joining) method (Tamura, et al. 2011). Multiple alignments of microRNA 169 stem-loop sequences were improved by removing the unreliable regions from the alignment using the web-based program GUIDANCE (available on the world wide web at guidance.tau.ac.il), and NJ phylogenetic trees were created with 2000 bootstrap replications and the model/method used was the Maximum Composite Likelihood.

The following examples illustrate certain embodiments of the invention. They are not intended to limit the scope of the invention in any way.

Example I

Deep-Sequencing of Small RNAs from Grain and Sweet Sorghum Stems

Figure 1B:
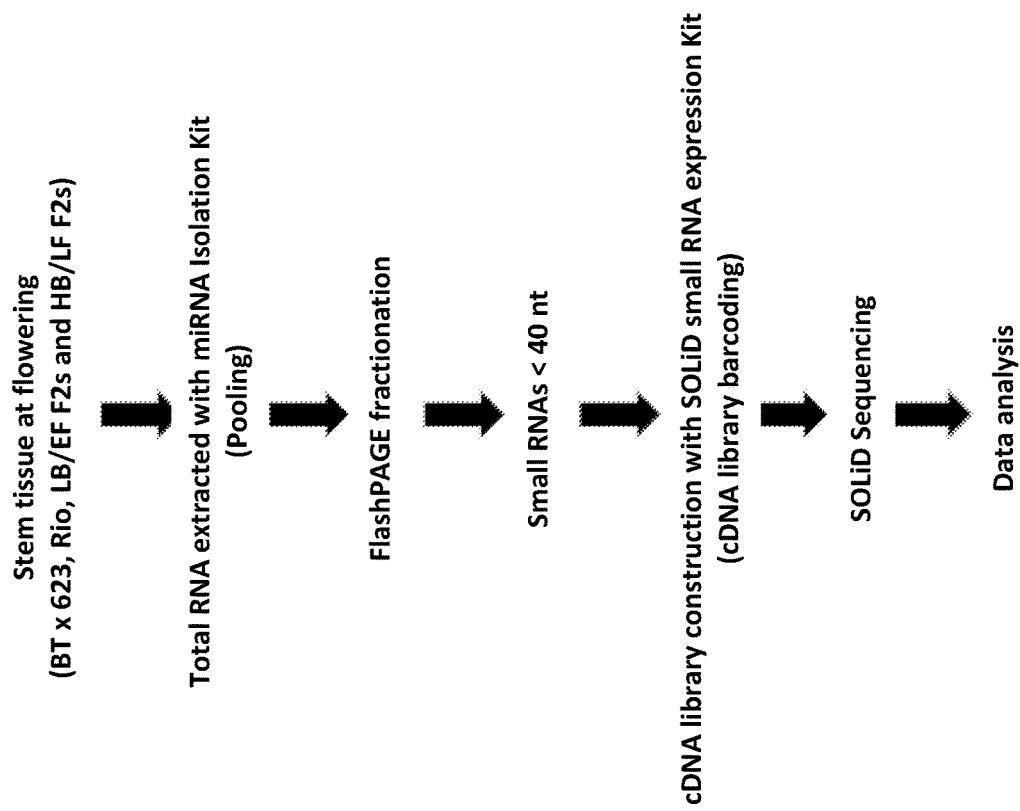
Figure 1C:
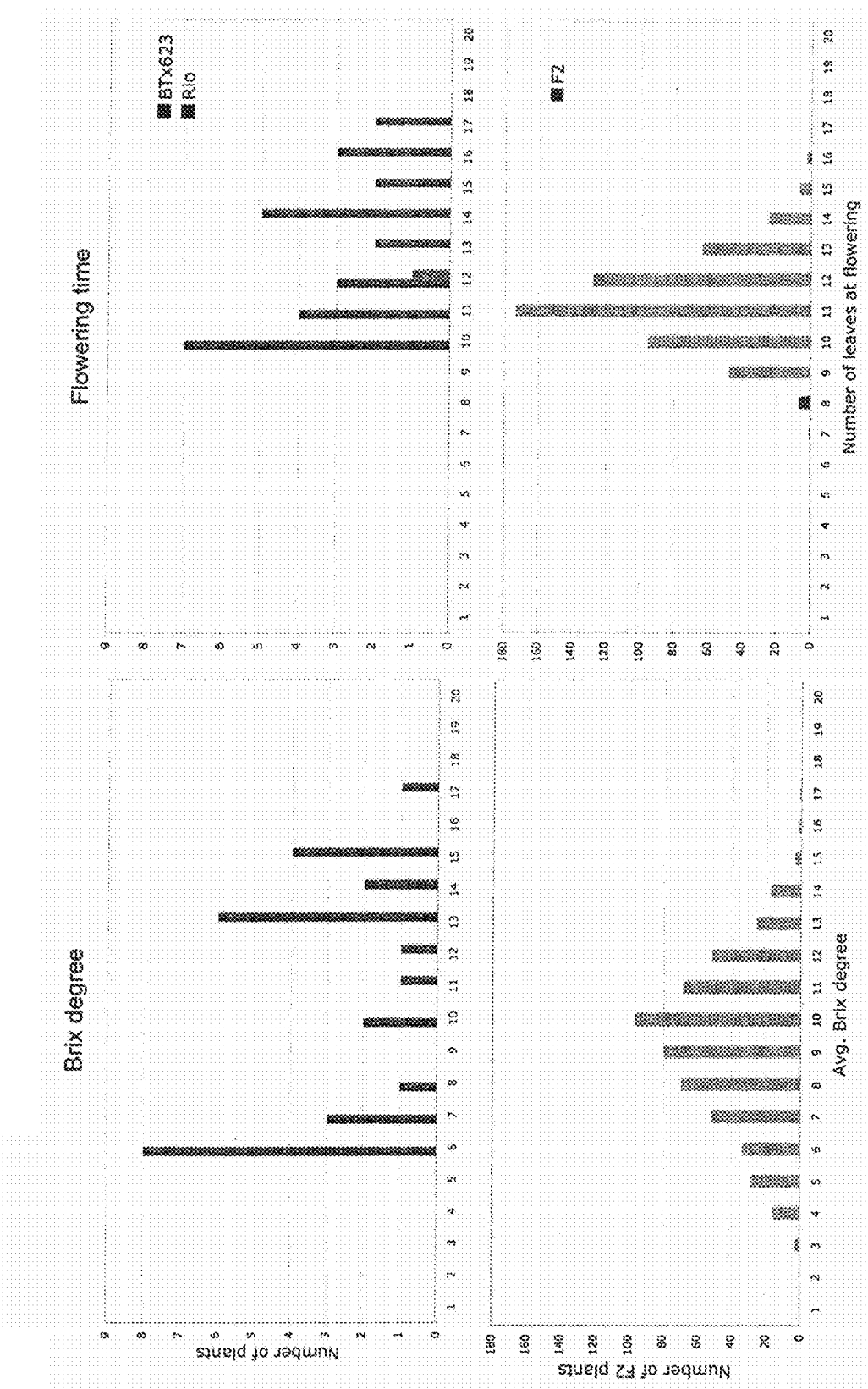

We constructed five small RNAs libraries from sorghum stem tissue at the time of flowering and sequenced them using the SOLiD platform (10). The libraries comprised samples from BTx623, Rio, low Brix and early flowering F2 plants (LB/EF F2s), high Brix and late flowering F2 plants (HB/LF F2s), and a "mixed library" (Mix), where small RNAs from the previous four libraries were mixed in equal proportions (FIGS. 1A, 1B and 1C).

Figure 2A:
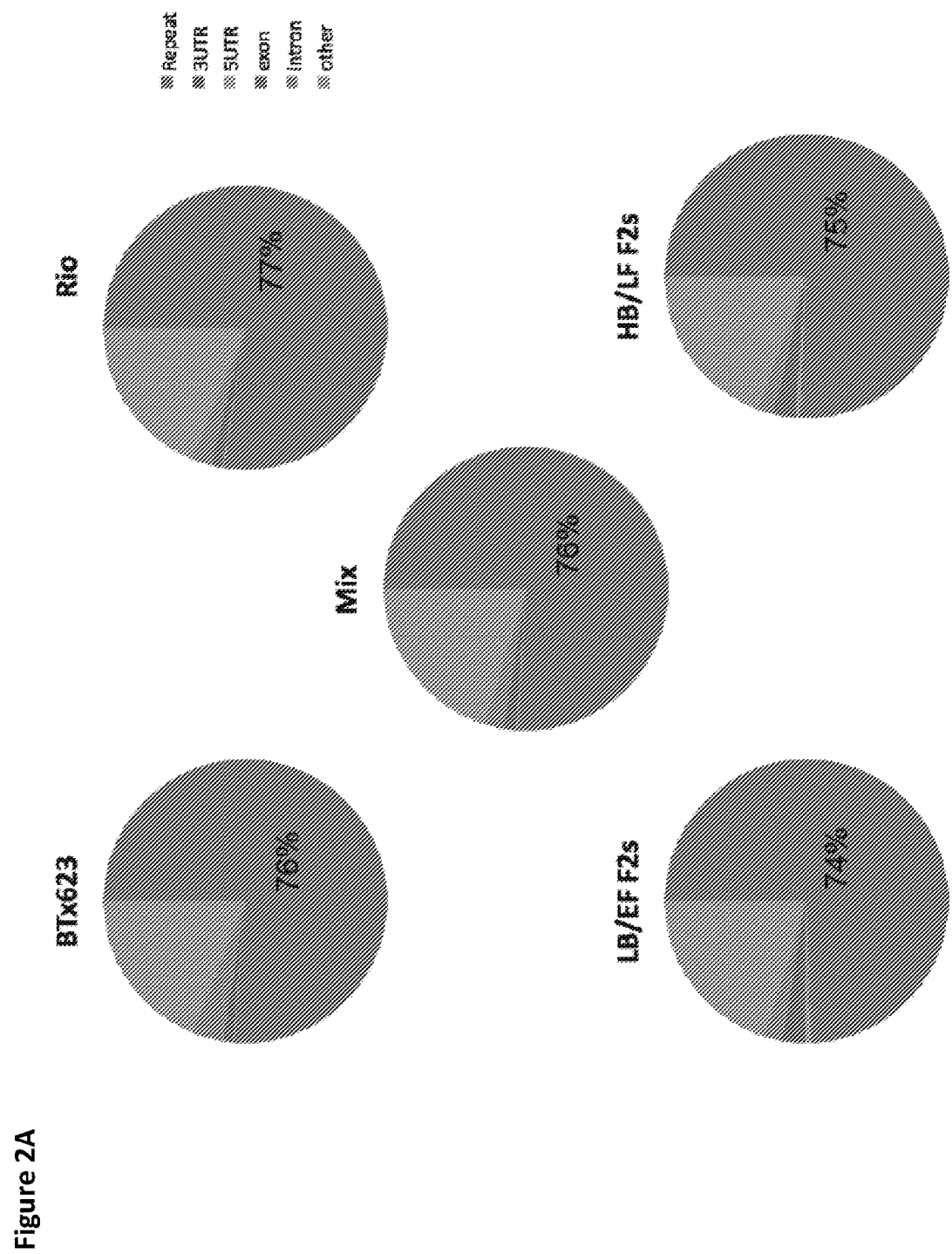
FIGS. 2A-2G. Diversity in the small RNA content of sorghum stem.

We sequenced 38,336,769 reads in total, from which 23,008,945 reads (60%) matched perfectly to the BTx623 reference genome (Table 1). The reads with perfect matches that derived from repeats constituted 74 to 77% of the total reads depending on the library (FIG. 2A). The non-redundant set of sequences comprised 2,539,403 reads in total, and the reads that were sequenced only once (termed here "singlets") comprised 2,167,946 sequences, corresponding only to 9% of the perfect matches (Table 1), suggesting that our sequencing reached a high level of saturation. If we define a cluster as two or more reads with identical sequences, the number of clusters found ranged from 20,056 in the BTx623 library to 164,623 in the HB/LF F2s library (Table 1).

the 22 nt class of small RNAs are specific to maize (11). However, we have shown here that a 22 nt peak is also present in sorghum stem tissue. Furthermore, we found that the 22 nt small RNAs were highly enriched in intronic sequences relative to other small RNAs (FIG. 2C). This was most evident in the BTx623 library, where 68% of all reads that mapped to introns were 22 nt in length. This was in sharp contrast to the distribution of small RNAs that mapped to exons (FIG. 2D). A possible explanation for the origin of the intron-associated 22 nt small RNAs would be that they arise from transcription of intronic noncoding RNAs as has been described for animals (12-14).

Figure 2B:
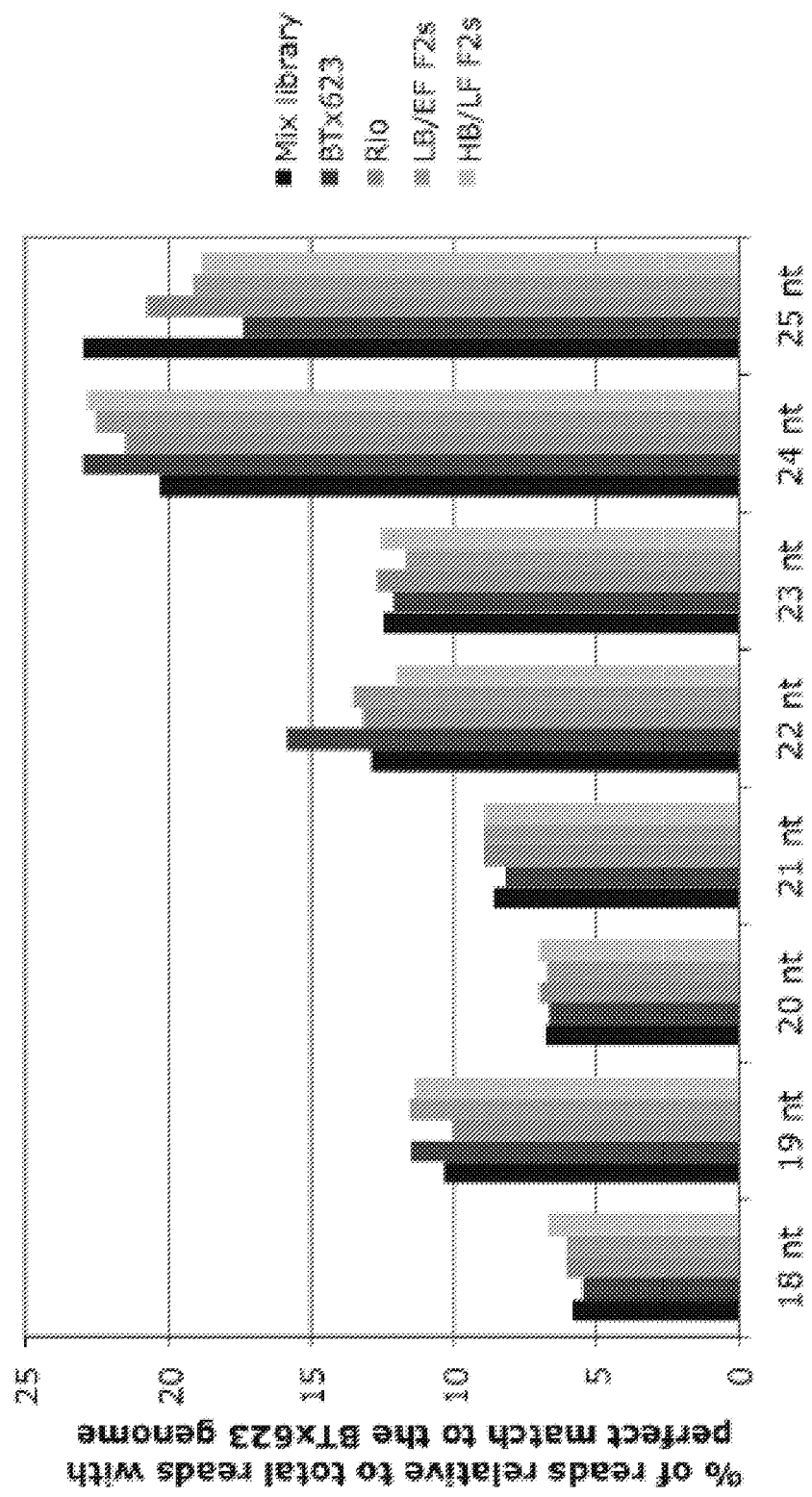
Figure 2C:
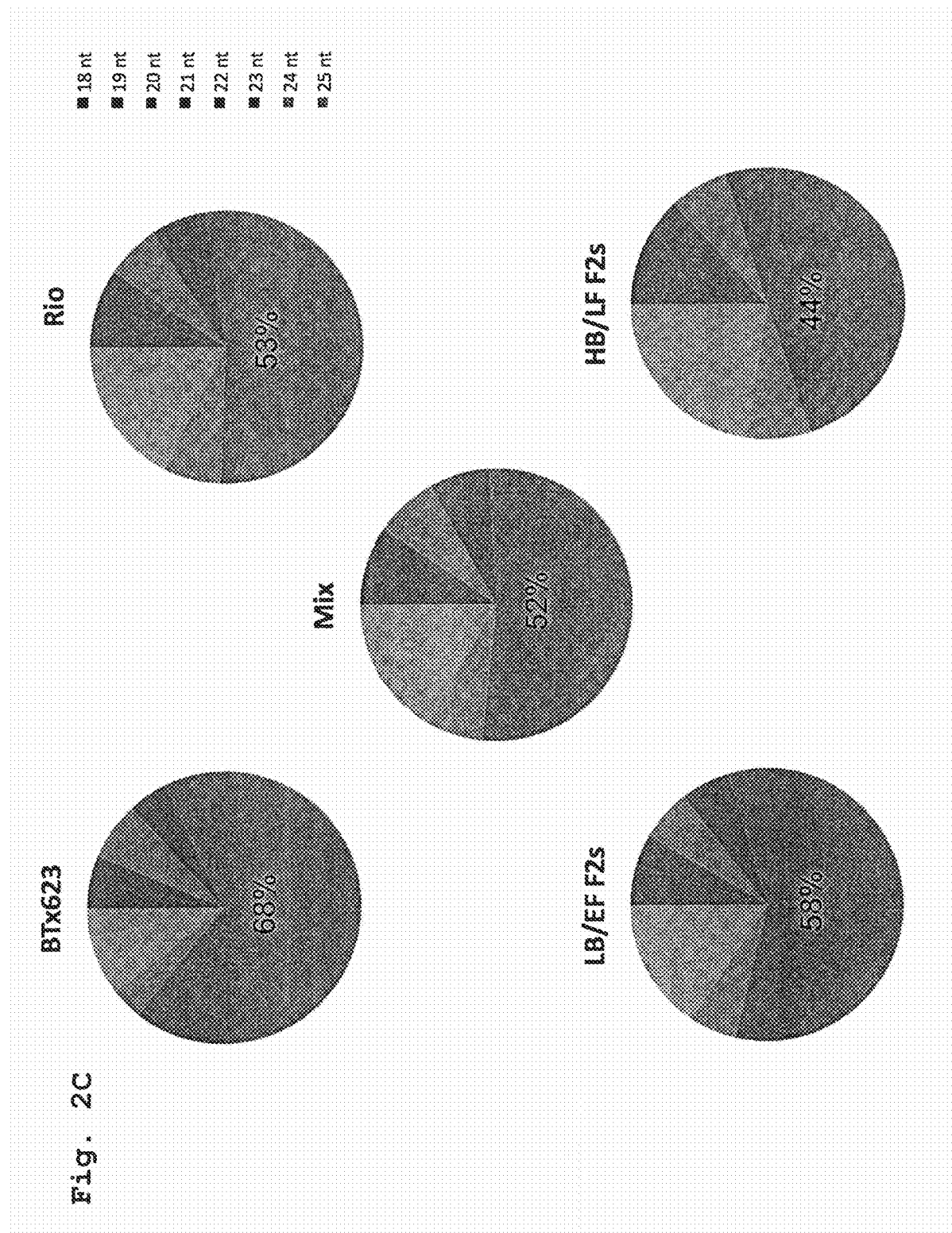
Figure 2D:
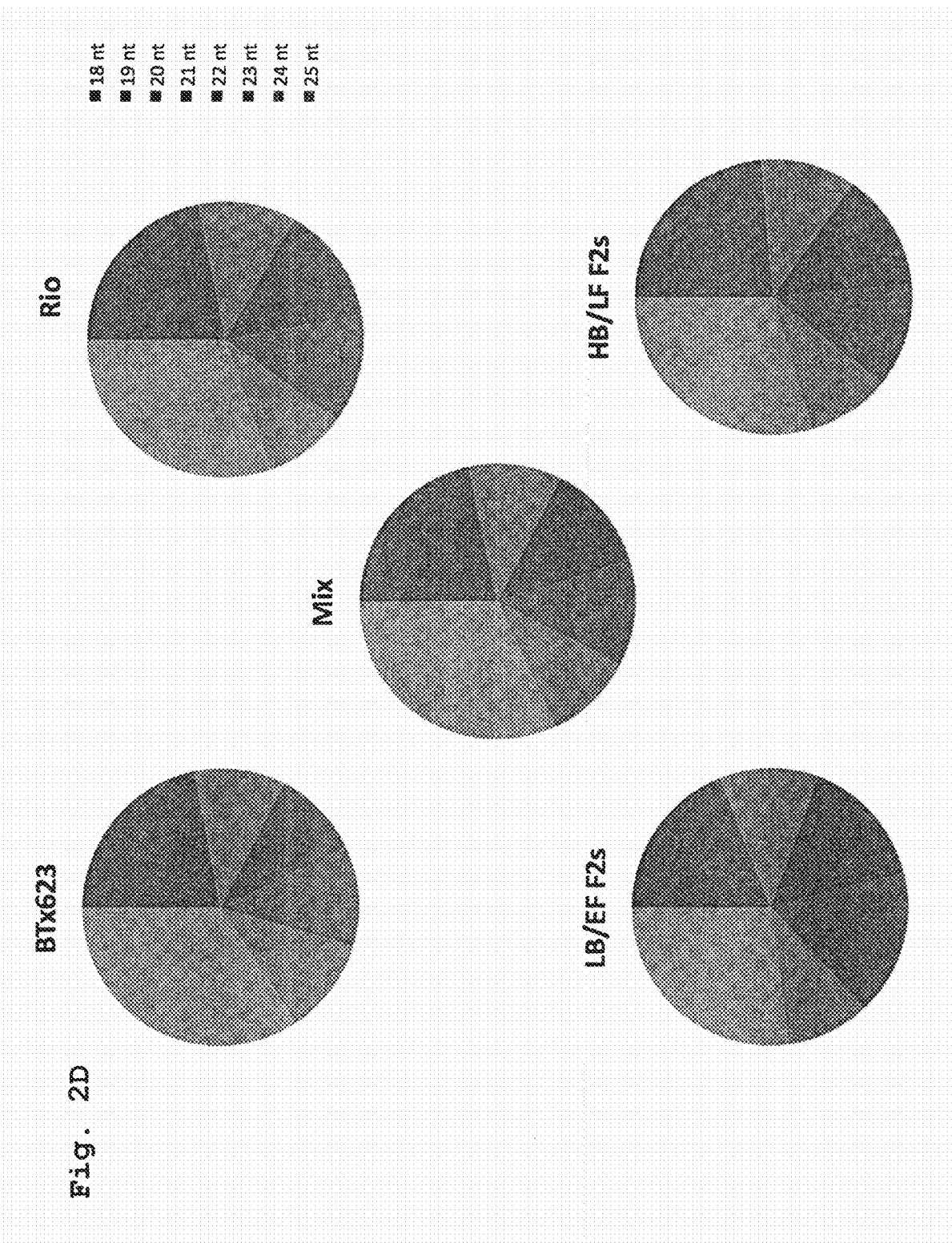
Figure 2E:
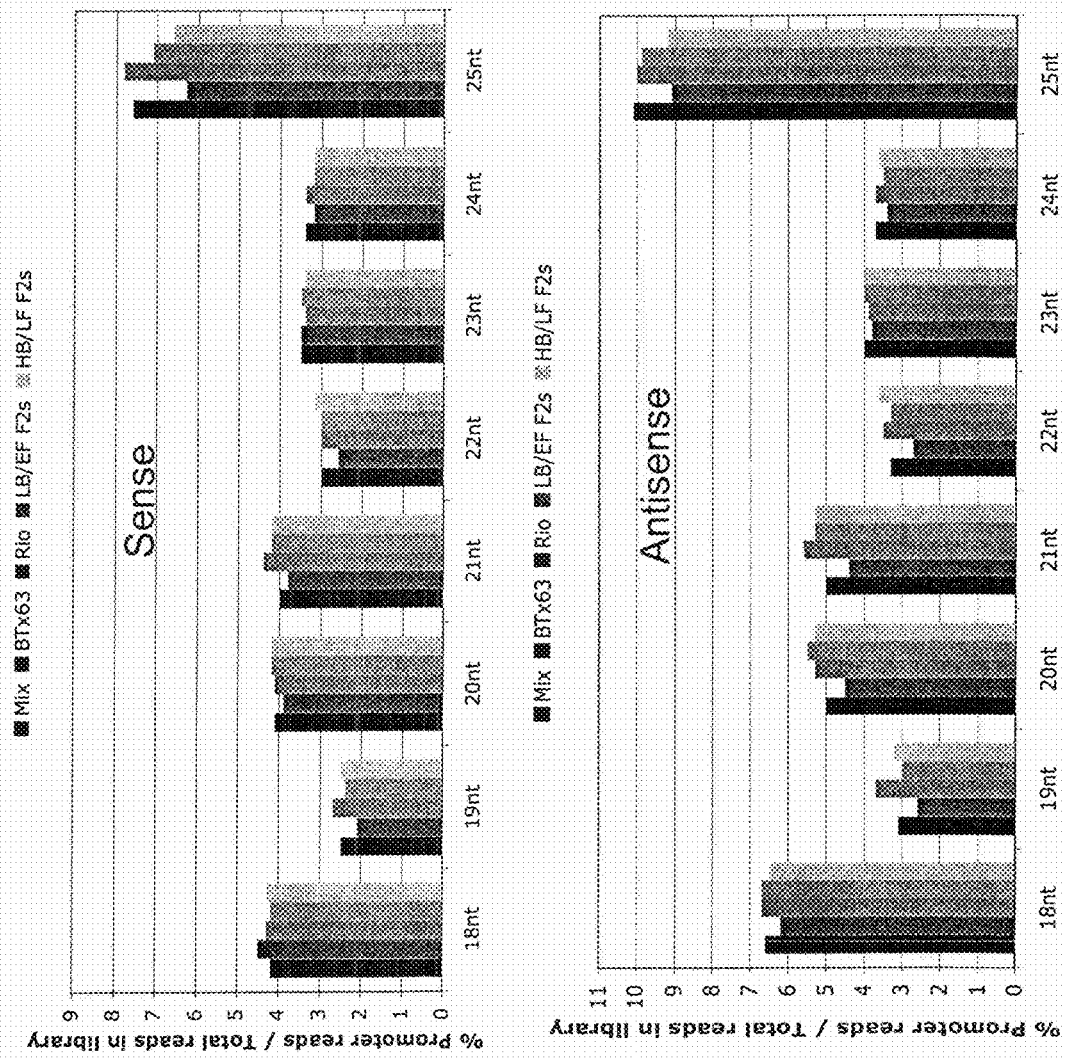
Figure 2F:
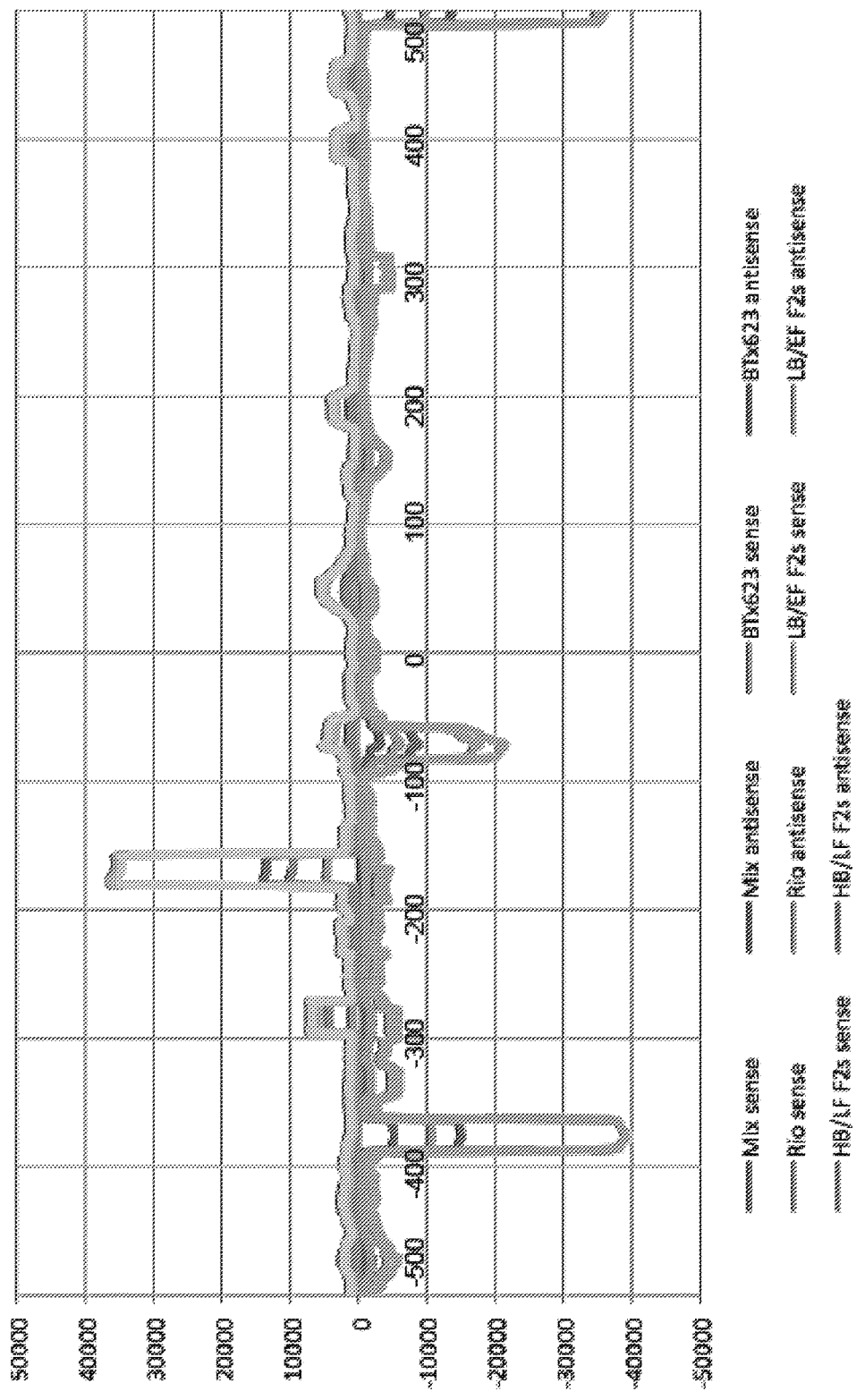
Figure 2G:
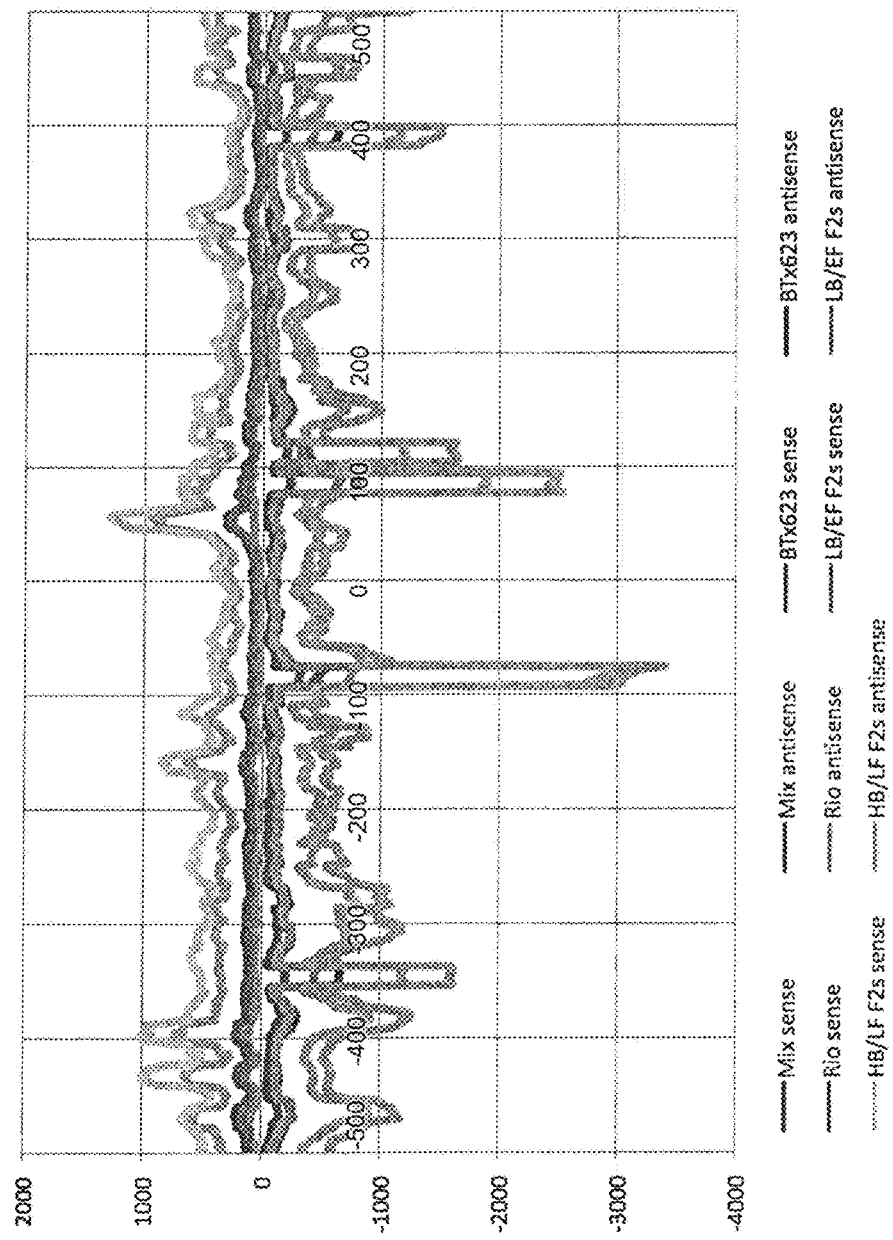

An interesting pattern was also observed for the 25 nt small RNA class, being preferentially enriched at the promoter regions of sorghum genes (FIG. 2E). We named these 25 nt small RNAs as "piccolo RNAs", to distinguish them from the previously described small RNAs in plants. The distribution of piccolo RNAs within the promoter region displayed very discrete peaks of high abundance in both sense and antisense strands (FIG. 2F). This distribution pattern contrasted greatly with the one displayed by the 18 nt class of small RNAs (FIG. 2G), recently shown to be the characteristic type of small RNAs associated with transcription start sites (TSS) in human, chicken and *Drosophila* (15, 16).

Interestingly, TSS-associated small RNAs were not found in *Arabidopsis*, and this led to the hypothesis that they

TABLE 1

Deep sequencing statistics of stem-derived small RNAs

| Library | # raw sequences | # perfect matches | % | # singlets | % | # clusters | Non-redundant set | % |
|---|---|---|---|---|---|---|---|---|
| Mix | 4,023,513 | 2,547,108 | 63 | 276,044 | 11 | 35,083 | 311,127 | 8 |
| BTx623 | 2,115,266 | 1,348,361 | 64 | 169,063 | 12 | 20,056 | 189,119 | 9 |
| Rio | 3,173,601 | 2,180,988 | 69 | 234,276 | 11 | 31,563 | 265,839 | 8 |
| LB/EF F2s | 11,974,953 | 7,472,940 | 62 | 653,279 | 9 | 120,132 | 773,411 | 6 |
| HB/LF F2s | 17,049,436 | 9,459,548 | 55 | 835,284 | 9 | 164,623 | 999,907 | 6 |
| Total | 38,336,769 | 23,008,945 | 60 | 2,167,946 | 9 | 371,457 | 2,539,403 | 8 |

Diversity in the Small RNA Content of Sorghum Stems

The frequency and size distribution of small RNAs from sorghum stems revealed two interesting aspects: a peak of 25 nt small RNAs with similar abundance as the 24 nt class, and a second peak of small RNAs with 22 nt that were more abundant than the 20 and 21 nt classes, respectively (FIG. 2B). This finding contrasted with the size distribution of small RNAs described for several monocot species (including small RNAs from sorghum inflorescence), in which the most abundant small RNAs were 21 and 24 nt in length, with maize being the exception, showing a larger 22 nt peak relative to the 21 nt peak (11). This led to the hypothesis that probably do not exist in plants (16). To our knowledge, this is the first report describing the existence of promoter associated RNAs of 25 nt in length in plant species. Because sequencing cycles were set to 25 nt at the time of our study, the size of piccolo RNAs could be longer.

In summary, we showed that the small RNA component from the stem transcriptome of sorghum is characterized by small RNAs of 22 nt in length that are associated with introns, and by a new class of small RNAs with at least 25 nt in length that are highly enriched in promoter regions. See Table A.

TABLE A 25 nt Hotspots in the *Sorghum* Genome

| Position | Length (bp) | No of 25 nt reads | Annotation (Phytozome) | BLAST nucleuotide collection (n/r n/t) hit | E-value | Identity |
|---|---|---|---|---|---|---|
| Library: Mix | | | | | | |
| Ch3: 72749347 ... 72749911 | 35 | 9381 | Intergenic | *Sorghum bicolor* strain b2 internal transcribed spacer 1 5.8S rRNA | 5E−10 | 100% |
| Ch1: 31857437 ... 31857496 | 60 | 5652 | Intergenic | *Sorghum bicolor* strain b2 internal transcribed spacer 1 5.8S rRNA | 2E−22 | 100% |
| Ch5: 36051996 ... 36052067 | 72 | 4689 | Intergenic | *Sorghum bicolor* strain b2 internal transcribed spacer 1 5.8S rRNA | 7E−29 | 100% |
| Ch10: 657846 ... 657883 | 38 | 3106 | Intergenic | *Arabidopsis thaliana* At5g59055 tRNA | 2E−09 | 97% |

TABLE A-continued 25 nt Hotspots in the *Sorghum* Genome

| Position | Length (bp) | No of 25 nt reads | Annotation (Phytozome) | BLAST nucleuotide collection (n/r n/t) hit | E-value | Identity |
|---|---|---|---|---|---|---|
| Ch5: 35985593 . . . 35985714 | 122 | 2882 | Intergenic | *Sorghum bicolor* strain b2 internal transcribed spacer 1 5.8S rRNA | 4E−61 | 100% |
| Ch5: 35931714 . . . 35931863 | 150 | 2369 | Intergenic | *Sorghum bicolor* strain b2 internal transcribed spacer 1 5.8S rRNA | 1E−77 | 100% |
| Ch3: 59743725 . . . 59743785 | 61 | 1956 | Intergenic | *Arabidopsis thaliana* At5g40545 tRNA | 1E−15 | 93% |
| Ch5: 35976201 . . . 35976253 | 53 | 1691 | Intergenic | *Setaria italica* genes for 25S rRNA, IGS and 17S rRNA | 5E−18 | 98% |
| Ch8: 47608635 . . . 47608659 | 25 | 1352 | Intergenic | *Arabidopsis thaliana* At4g34975 rRNA | 2E−04 | 100% |
| Library: BTx623 | | | | | | |
| Ch3: 72749848 . . . 72749881 | 34 | 3321 | Intergenic | *Sorghum bicolor* strain b2 internal transcribed spacer 1 5.8S rRNA | 2E−09 | 100% |
| Ch5: 36052031 . . . 36052067 | 37 | 3111 | Intergenic | *Sorghum bicolor* strain b2 internal transcribed spacer 1 5.8S rRNA | 4E−11 | 100% |
| Ch5: 35931716 . . . 35931758 | 43 | 2709 | Intergenic | *Sorghum bicolor* strain b2 internal transcribed spacer 1 5.8S rRNA | 1E−14 | 100% |
| Ch5: 35985655 . . . 35985705 | 51 | 2287 | Intergenic | *Sorghum bicolor* strain b2 internal transcribed spacer 1 5.8S rRNA | 2E−17 | 100% |
| Ch1: 31863286 . . . 31863315 | 30 | 1231 | Intergenic | *Oryza brachyantha* 26S-18S rRNA intergenic spacer | 3E−07 | 100% |
| Ch5: 35997943 . . . 35997972 | 30 | 1227 | Intergenic | *Oryza brachyantha* 26S-18S rRNA intergenic spacer | 3E−07 | 100% |
| Ch5: 35976205 . . . 35976252 | 44 | 1117 | Intergenic | *Avena sativa* rDNA spacer | 7E−07 | 100% |
| Library: Rio | | | | | | |
| Ch3: 72749847 . . . 72749881 | 35 | 6727 | Intergenic | *Sorghum bicolor* strain b2 internal transcribed spacer 1 5.8S rRNA | 5E−10 | 100% |
| Ch5: 36052031 . . . 36052067 | 37 | 6467 | Intergenic | *Sorghum bicolor* strain b2 internal transcribed spacer 1 5.8S rRNA | 4E−11 | 100% |
| Ch5: 35931716 . . . 35931758 | 43 | 5622 | Intergenic | *Sorghum bicolor* strain b2 internal transcribed spacer 1 5.8S rRNA | 1E−14 | 100% |
| Ch5: 35985655 . . . 35985713 | 59 | 4104 | Intergenic | *Sorghum bicolor* strain b2 internal transcribed spacer 1 5.8S rRNA | 8E−22 | 100% |
| Ch5: 35976203 . . . 35976252 | 50 | 1583 | Intergenic | *Avena sativa* rDNA spacer | 7E−17 | 100% |
| Ch4: 50861835 . . . 50861859 | 25 | 1362 | Intergenic | *Arabidopsis thaliana* At5g46595 tRNA | 2E−04 | 100% |
| Ch5: 35981272 . . . 35981333 | 62 | 1282 | Intergenic | *Setaria italica* genes for 25S rRNA, IGS and 17S rRNA | 9E−22 | 98% |
| Library: LB/EF F2s | | | | | | |
| Ch3: 72749845 . . . 72749881 | 37 | 23470 | Intergenic | *Sorghum bicolor* strain b2 internal transcribed spacer 1 5.8S rRNA | 4E−11 | 100% |
| Ch1: 31857435 . . . 31857497 | 63 | 14104 | Intergenic | *Sorghum bicolor* strain b2 internal transcribed spacer 1 5.8S rRNA | 5E−24 | 100% |
| Ch5: 36051996 . . . 36052068 | 73 | 12057 | Intergenic | *Sorghum bicolor* strain b2 internal transcribed spacer 1 5.8S rRNA | 2E−29 | 100% |
| Ch5: 35985593 . . . 35985716 | 124 | 7413 | Intergenic | *Sorghum bicolor* strain b2 internal transcribed spacer 1 5.8S rRNA | 2E−57 | 100% |
| Ch4: 50861834 . . . 50861859 | 26 | 6443 | Intergenic | *Arabidopsis thaliana* At5g46595 tRNA | 6E−05 | 100% |
| Ch5: 35931708 . . . 35931865 | 158 | 5861 | Intergenic | *Sorghum bicolor* strain b2 internal transcribed spacer 1 5.8S rRNA | 4E−75 | 100% |
| Ch3: 47608634 . . . 47608659 | 26 | 3034 | Intergenic | *Arabidopsis thaliana* At4g34975 tRNA | 6E−05 | 100% |
| Ch5: 35937803 . . . 35937851 | 49 | 3007 | Intergenic | *Avena sativa* rDNA spacer | 4E−18 | 100% |
| Ch3: 59743724 . . . 59743785 | 62 | 2116 | Intergenic | *Arabidopsis thaliana* At5g40545 tRNA | 3E−17 | 93% |
| Library: HB/EF F2s | | | | | | |
| Ch3: 72749845 . . . 72749881 | 37 | 22694 | Intergenic | *Sorghum bicolor* strain b2 internal transcribed spacer 1 5.8S rRNA | 4E−11 | 100% |
| Ch1: 31857433 . . . 31857497 | 65 | 13314 | Intergenic | *Sorghum bicolor* strain b2 internal transcribed spacer 1 5.8S rRNA | 4E−25 | 100% |
| Ch3: 36051996 . . . 36052068 | 73 | 11712 | Intergenic | *Sorghum bicolor* strain b2 internal transcribed spacer 1 5.8S rRNA | 2E−29 | 100% |
| Ch4: 50861834 . . . 50861859 | 26 | 8290 | Intergenic | *Arabidopsis thaliana* At5g46595 tRNA | 6E−05 | 100% |
| Ch5: 35985593 . . . 35985718 | 126 | 7099 | Intergenic | *Sorghum bicolor* strain b2 internal transcribed spacer 1 5.8S rRNA | 1E−58 | 100% |
| Ch5: 35931708 . . . 35931863 | 156 | 5796 | Intergenic | *Sorghum bicolor* strain b2 internal transcribed spacer 1 5.8S rRNA | 4E−75 | 100% |
| Ch5: 47608634 . . . 47608659 | 26 | 3415 | Intergenic | *Arabidopsis thaliana* At4g34975 tRNA | 6E−05 | 100% |
| Ch5: 35976201 . . . 35976260 | 60 | 2976 | Intergenic | *Setaria italica* genes for 25S rRNA, IGS and 17S rRNA | 5E−20 | 100% |
| Ch3: 59743724 . . . 59743785 | 62 | 2372 | Intergenic | *Arabidopsis thaliana* At5g40545 tRNA | 3E−17 | 93% |

Allelic Variation in the Expression of Known miRNAs Between Grain and Sweet Sorghum Correlated with Sugar Content and Flowering Time The sequencing consortium of the sorghum genome identified 149 predicted miRNAs (5), and we could detect the expression of 110 of them based on the following criteria: a miRNA was considered expressed only if its sequencing reads were detected in at least three libraries and with a frequency of 10 reads or more for the sum of the five libraries. A list with the reads count for each known miRNA is provided in Table B.

Figure 3A:
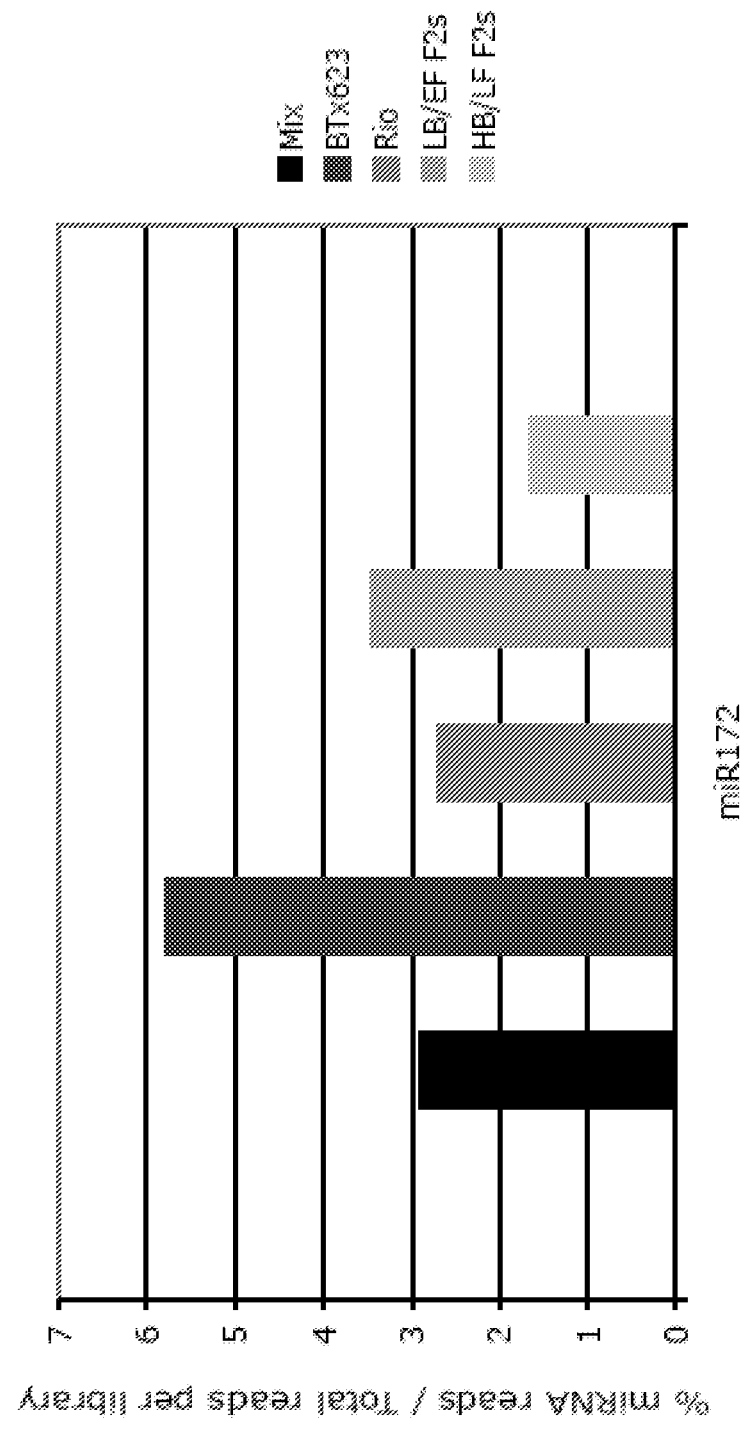
FIGS. 3A-3C. The miR172 is the most abundantly expressed miRNA in sorghum stems.
Figure 3B:
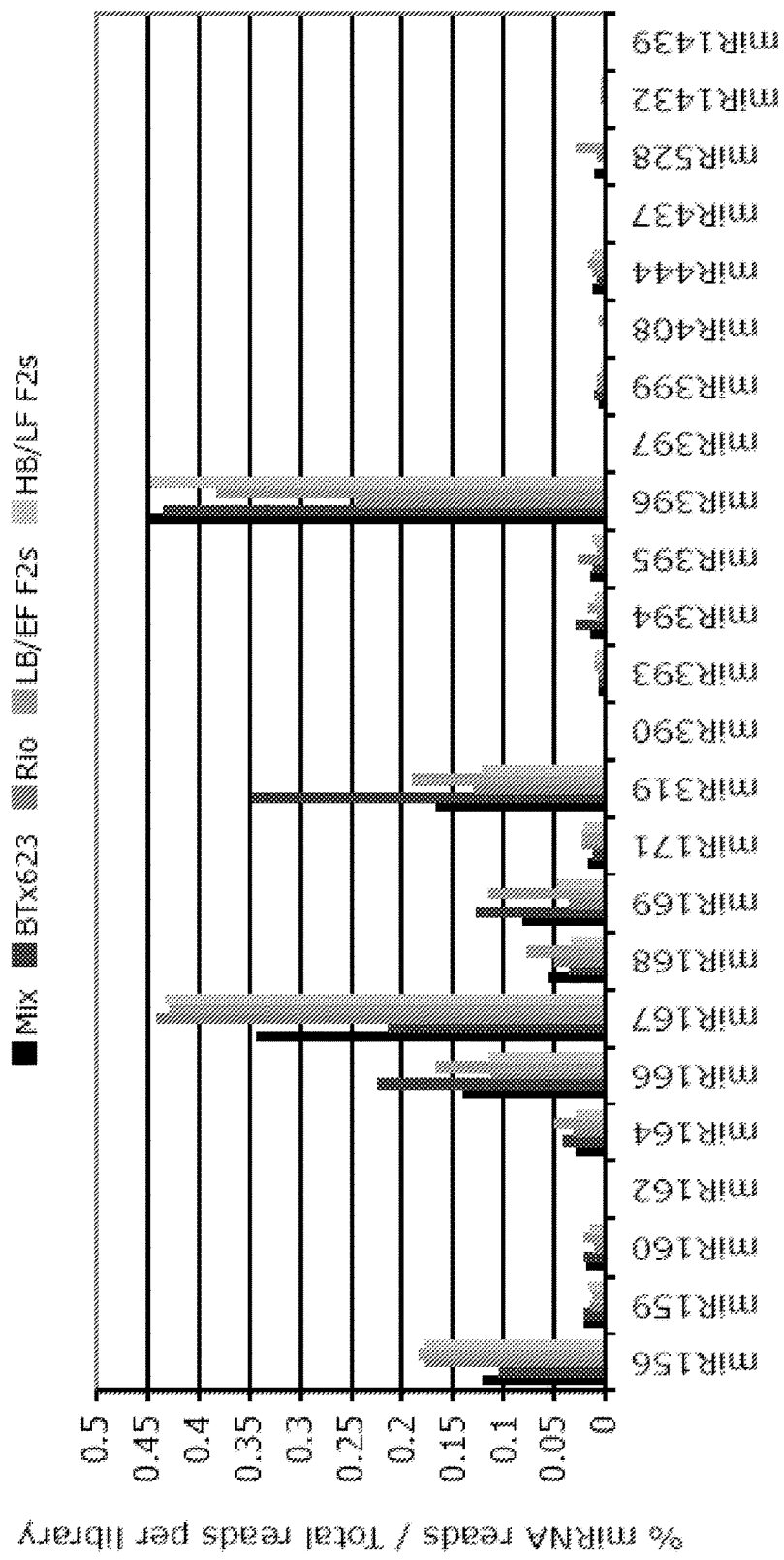
Figure 3C:
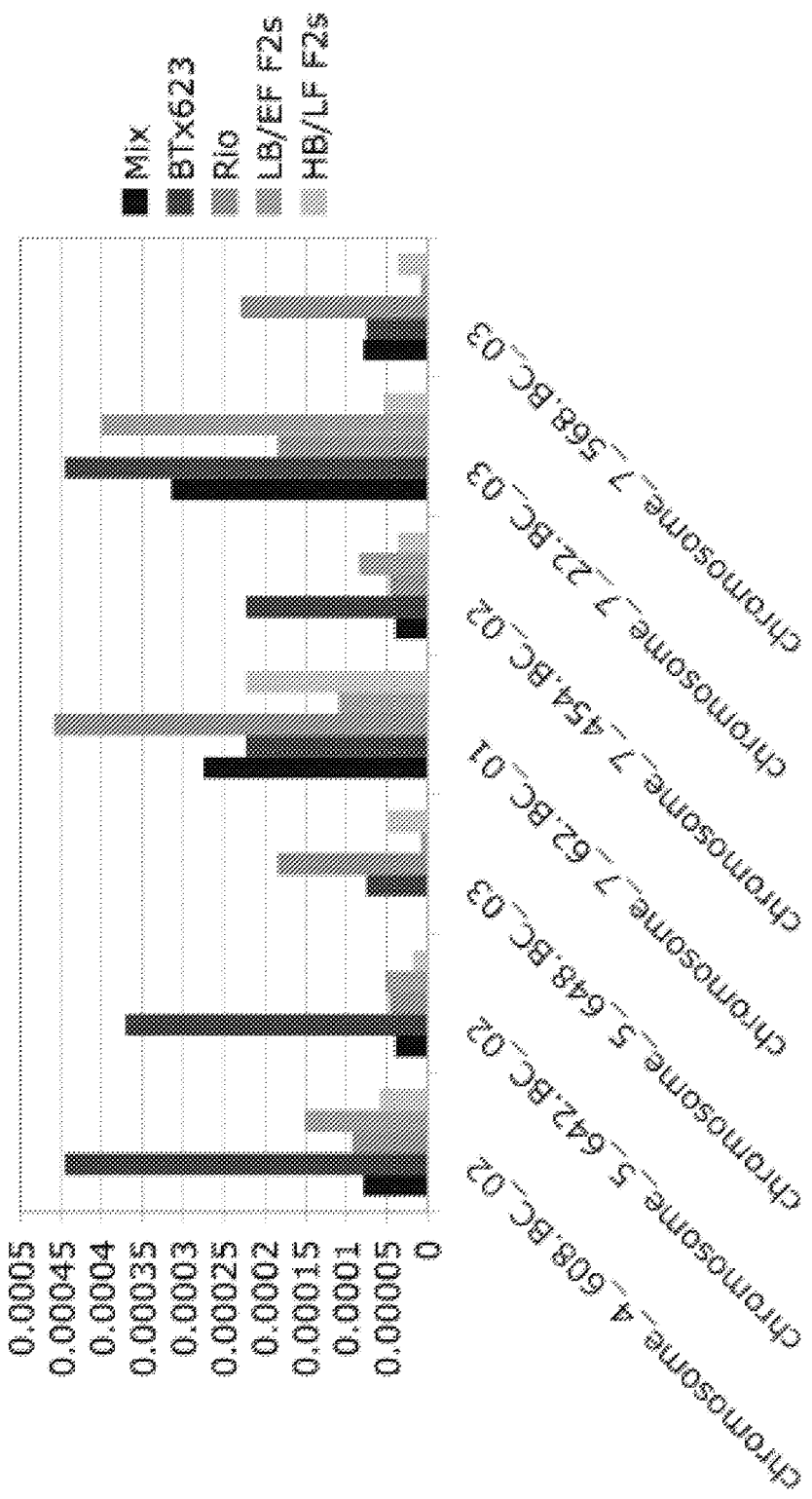
Figure 4A:
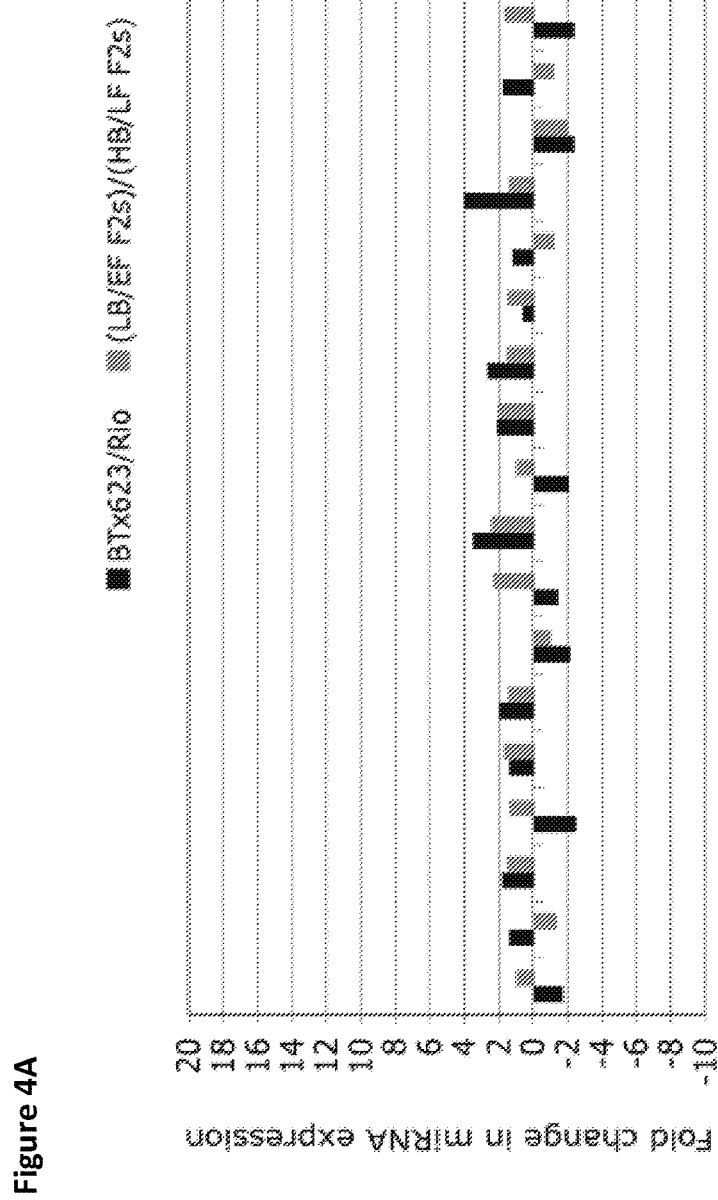
FIGS. 4A-4G. Allelic variation in miRNA expression. The miRNA abundances were used to calculate their relative fold change in expression between BTx623 and Rio, and between the LB/EF F2s and HB/LF F2s libraries, respectively. Positive values in the y-axis of the graph denote fold changes in miRNA expression that are higher in BTx623 relative to Rio and higher in LB/EF F2s relative to HB/LF F2s libraries, respectively; the opposite is true for negative values.

The most abundantly expressed miRNA family was miR172 (FIG. 3A), comprising almost 6% of the total reads with perfect match to the BTx623 genome. The rest of the known miRNAs had abundances below 0.5% (FIGS. 3B and 3C). When the ratio of miRNA abundances between the BTx623 and Rio libraries was compared to the ratio between the LB/EF F2s and HB/LF F2s libraries, we could identify miRNA families whose expression differences between the parents were inherited in the F2 plants (FIG. 4A). Considering a cutoff level of two-fold change in miRNA expression, we found that miR169 and miR172 were expressed higher in BTx623 relative to Rio, and higher in LB/EF F2s compared to HB/LF F2s. This means that high expression of these miRNAs in BTx623 correlated with low Brix and early flowering in the F2 plants selected, and the opposite was true for miR395 (FIG. 4A).

Figure 4B:
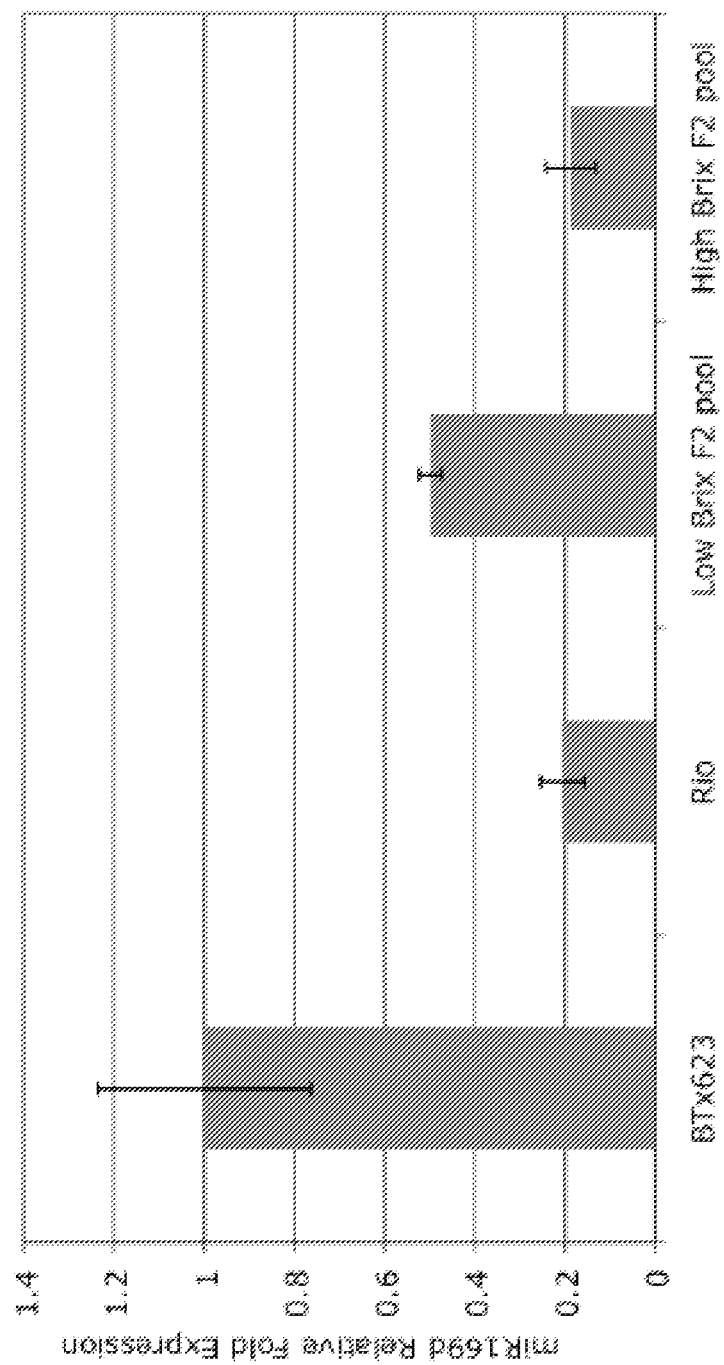
Figure 4C:
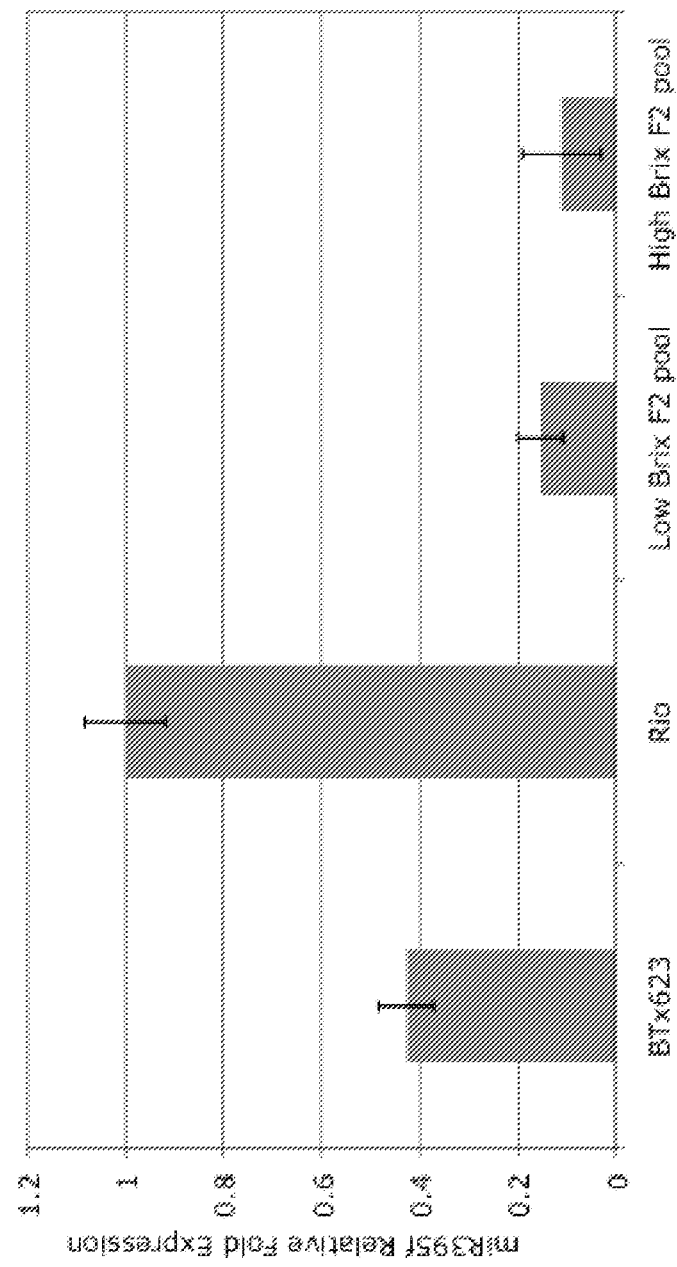
Figure 4D:
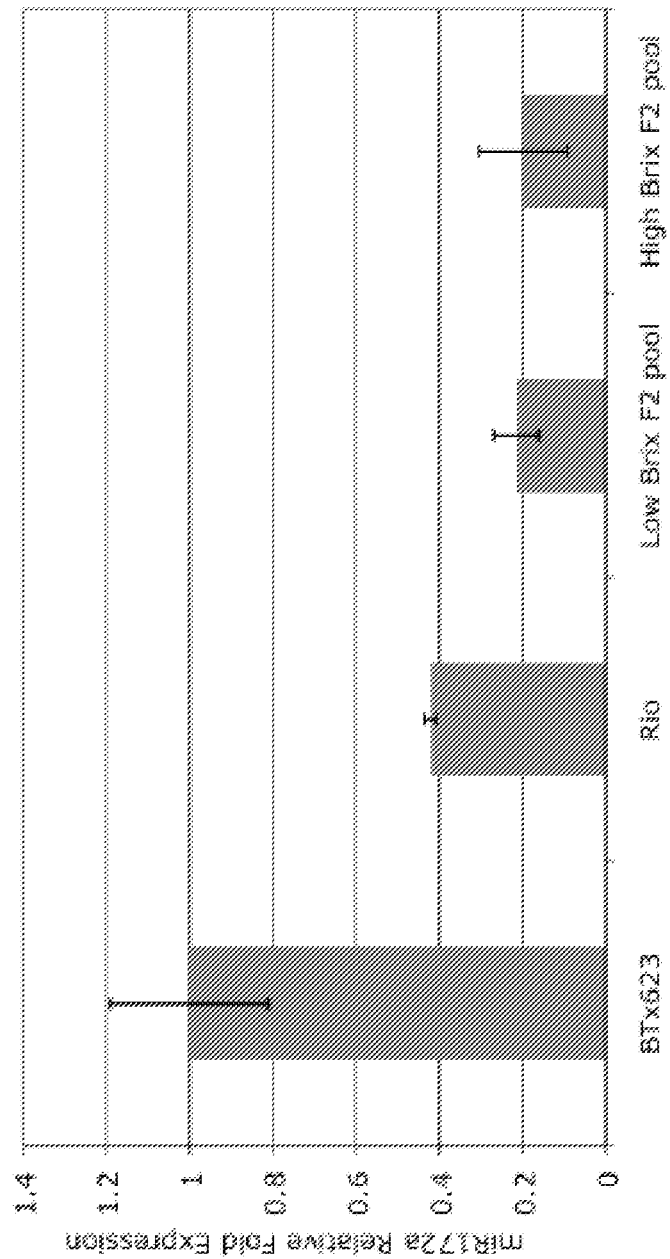

The observation that high expression of miR172 correlated with early flowering is consistent with the reported role of this miRNA in the promotion of flowering (17-21). Although miR169 and miR395 have known roles in drought stress and sulphur starvation, respectively (22, 23), our data suggested a novel function for these miRNAs in sugar accumulation and flowering time. Since the pool of F2 plants used for library construction were selected based on both phenotypes, it was not possible to assign the expression inheritance pattern of both miRNAs to either sugar accumulation or flowering time alone. For this reason, additional plants from the same F2 population differing in sugar content but with similar flowering time were selected and the expression of a representative member from each miRNA family, miR169d and miR395f respectively, was quantified using the TaqMan assay. We found that high expression of miR169d in BTx623 correlated with low Brix (FIG. 4B). This suggested that high expression levels of miR169 might lead to a reduction in stem sugar content regardless of flowering time. Surprisingly, high expression of miR395f in Rio relative to that in BTx623 did not correlate with sugar content in F2 plants (FIG. 4C). This indicates that high expression of miR395 would be required for flowering regardless of sugar content in the stem. Consistent with the role of miR172 in flowering, we did not observe any difference in the expression of miR172a in F2 plants with the same flowering time but different Brix (FIG. 4D).

In summary, high expression of miR172 in BTx623 correlated with early flowering in the F2, whereas the opposite was true for miR395, high expression of this miRNA in Rio correlated with late flowering in the F2 plants selected. Regarding sugar content in the stem, high expression of miR169 in BTx623 correlated with low Brix in the F2 plants selected.

Figure 5A:
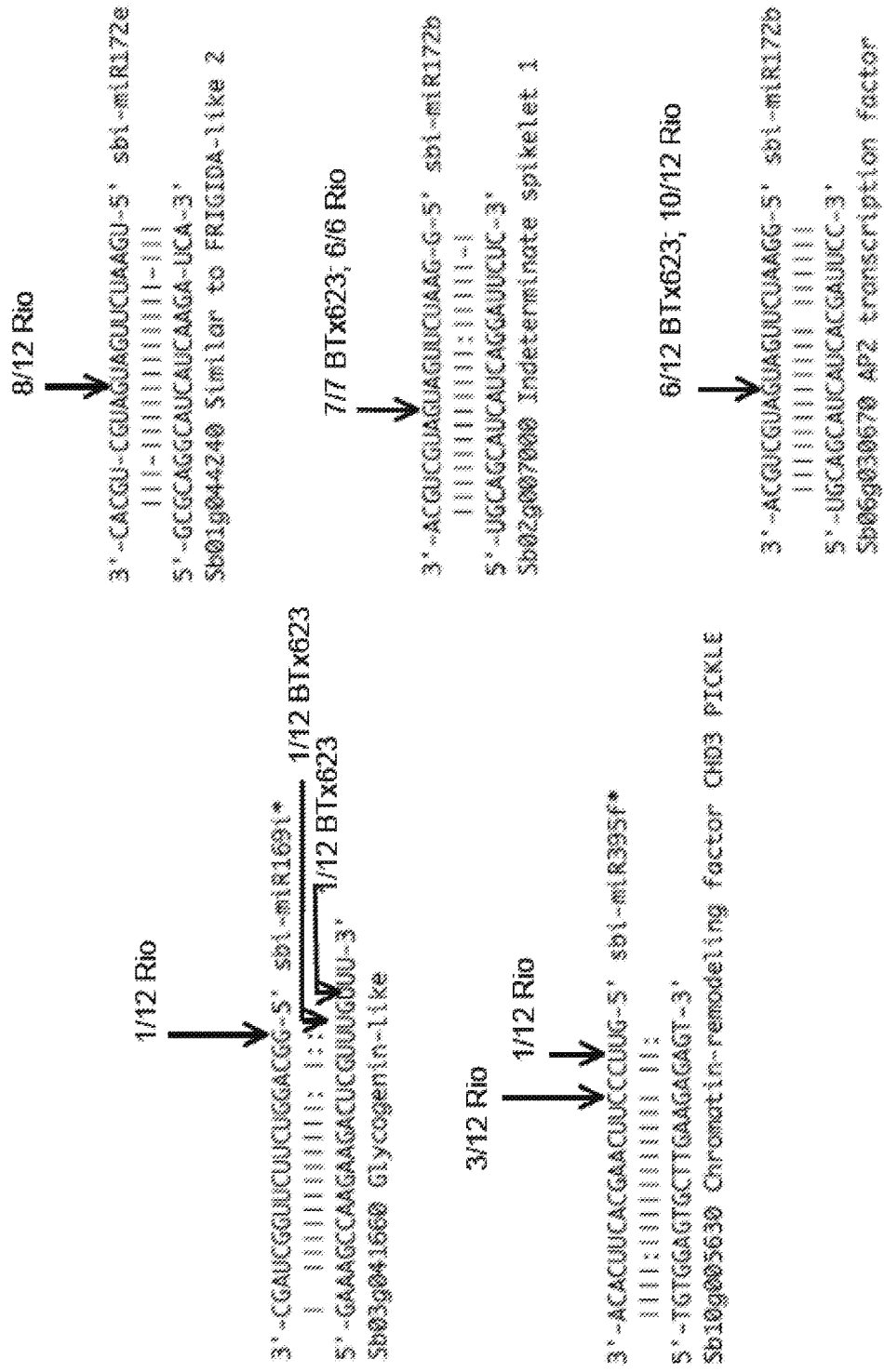
FIGS. 5A-5B. Mapping of miRNA-guided cleavage sites in predicted target genes. The locations of the miRNA-cleavage sites are indicated with downward arrows and the frequency of the cleavages are indicated as the number of clones for each RACE product with respect to the total clones sequenced.

Genes Related to Sugar Metabolism and Flowering Time were Targets of miR169* and miR395*, Respectively The expression of miR169* was detected for all MIR169 gene copies except MIR169e and MIR169j (see our genome browser at muesli.rutgers.edu/cgi-bin/gbrowse/sbicTest/). To our surprise, genes such as STARCH SYNTHASE isoform and GLYCOGENIN-like were identified as novel targets of miR169b* and miR169i* respectively (Table 2). In fact, the predicted miR169i*-mediated cleavage of the GLYCOGENIN-like mRNA was experimentally validated (FIG. 5). In animals, bacteria and yeast, carbon is stored as glycogen, and the priming molecules for glycogen biosynthesis are called glycogenins (24). Glycogen is the analogous form of starch in plants (25) but whether glycogenin-like proteins in plants are involved in starch biosynthesis is not clear (25). Our data provided the first evidence linking the MIR169 gene with carbohydrate metabolism.

We detected the expression of the miRNA* for all MIR395 gene copies. In addition, miR395* was expressed at higher levels relative to miR395 (see genome browser at muesli.rutgers.edu/cgi-bin/gbrowse/sbicTest/). Although miR395 has already a known role in sulfur starvation (23), the genes EMBRYONIC FLOWER 2 (EMF2), PICKLE (PKL) and CRYPTOCHROME 2 (CRY2) were identified as predicted targets of miR395f* and the cleavage product was confirmed for PKL (Table 2 and FIG. 5). All three genes have a role in the regulation of flowering time (26-31), but in addition EMF2 and PKL were also implicated in the repression of embryonic traits in *Arabidopsis* (26, 28, 30, 31). Thus, our data suggested for the first time a possible role of the MIR395 gene in the regulation of flowering time.

Figure 6:
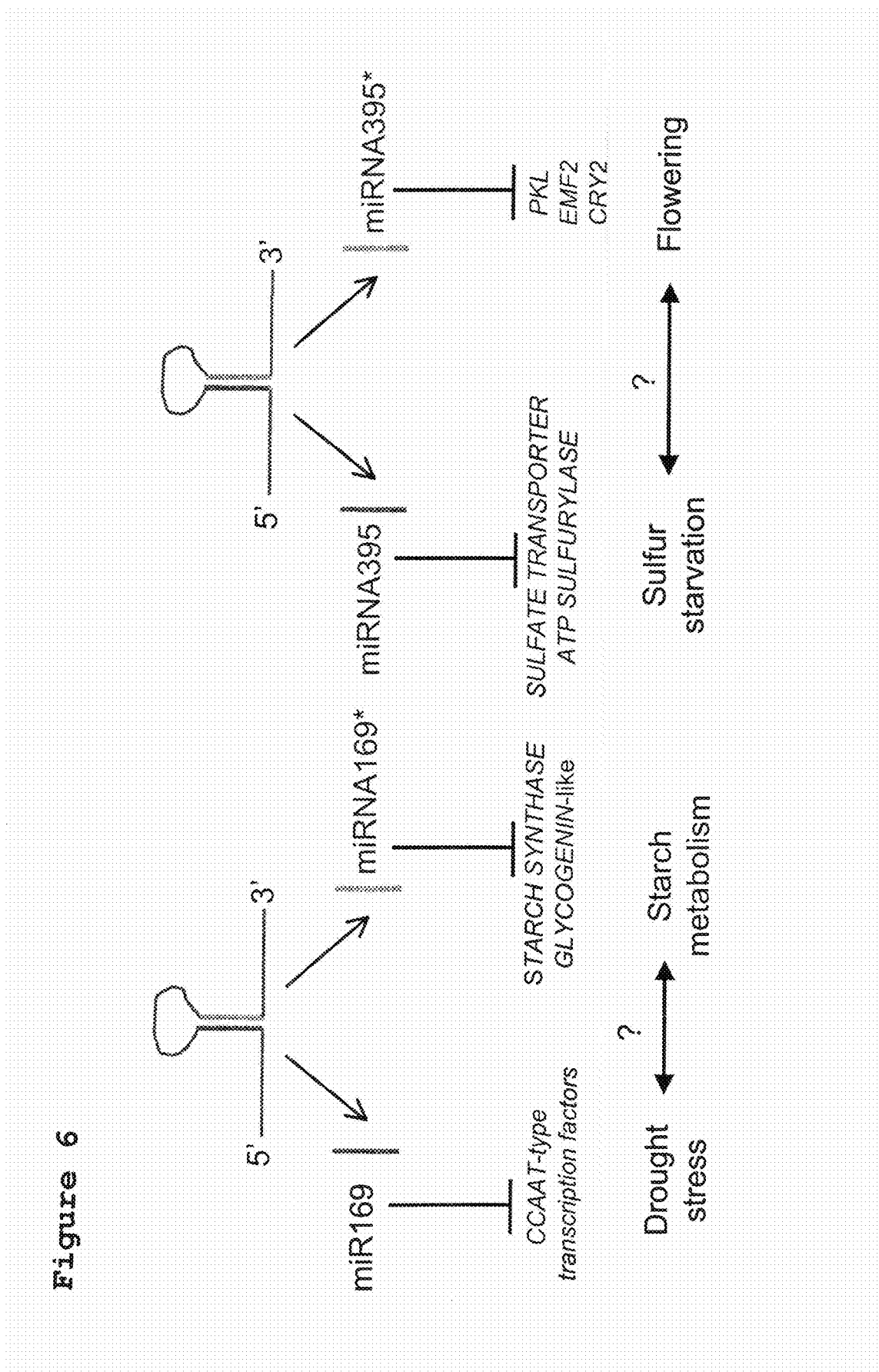
FIG. 6. Model describing the dual role of miR169 in drought stress and starch metabolism, and miR395 in sulfur starvation and flowering time. Through the selective production of miRNA/miRNA* species, a single miRNA could potentially regulate two different metabolic processes through the targeting of completely different classes of genes. The question marks symbolize the possibility of an interaction between drought and starch metabolism and sulfur and flowering respectively.

In summary, any given miRNA could potentially link two seemingly unrelated biological processes through the selective production of miRNA/miRNA* species (FIG. 6).

In the case of miR172, we detected cleavage products for the genes INDETERMINATE SPIKELET 1 (IDS1) and an AP2 transcription factor (Table 2 and FIG. 5). In addition, a FRIGIDA-like 2 (FRL2) and a TYPE A RESPONSE REGULATOR 3 (RR3) were predicted as novel targets of miR172 (Table 2), being the cleavage product of FRL2 experimentally validated, too. The FRIGIDA-related genes are a major determinant of natural variation in the winter-annual habit between *Arabidopsis* accessions (32, 33), whereas the TYPE A RESPONSE REGULATOR 3 (ARR3) has a function in the circadian clock (34). Although sorghum is a crop from semi-arid regions (5), the miR172-mediated post-transcriptional regulation of FRL2 could have a role in the adaptation of sorghum to temperate climates. Consistent with this, a role of miR172 in the regulation of flowering time by ambient temperature in *Arabidopsis* has been recently described (35).

New miRNAs Targeting Flowering and Sugar Related Genes

Figure 7:
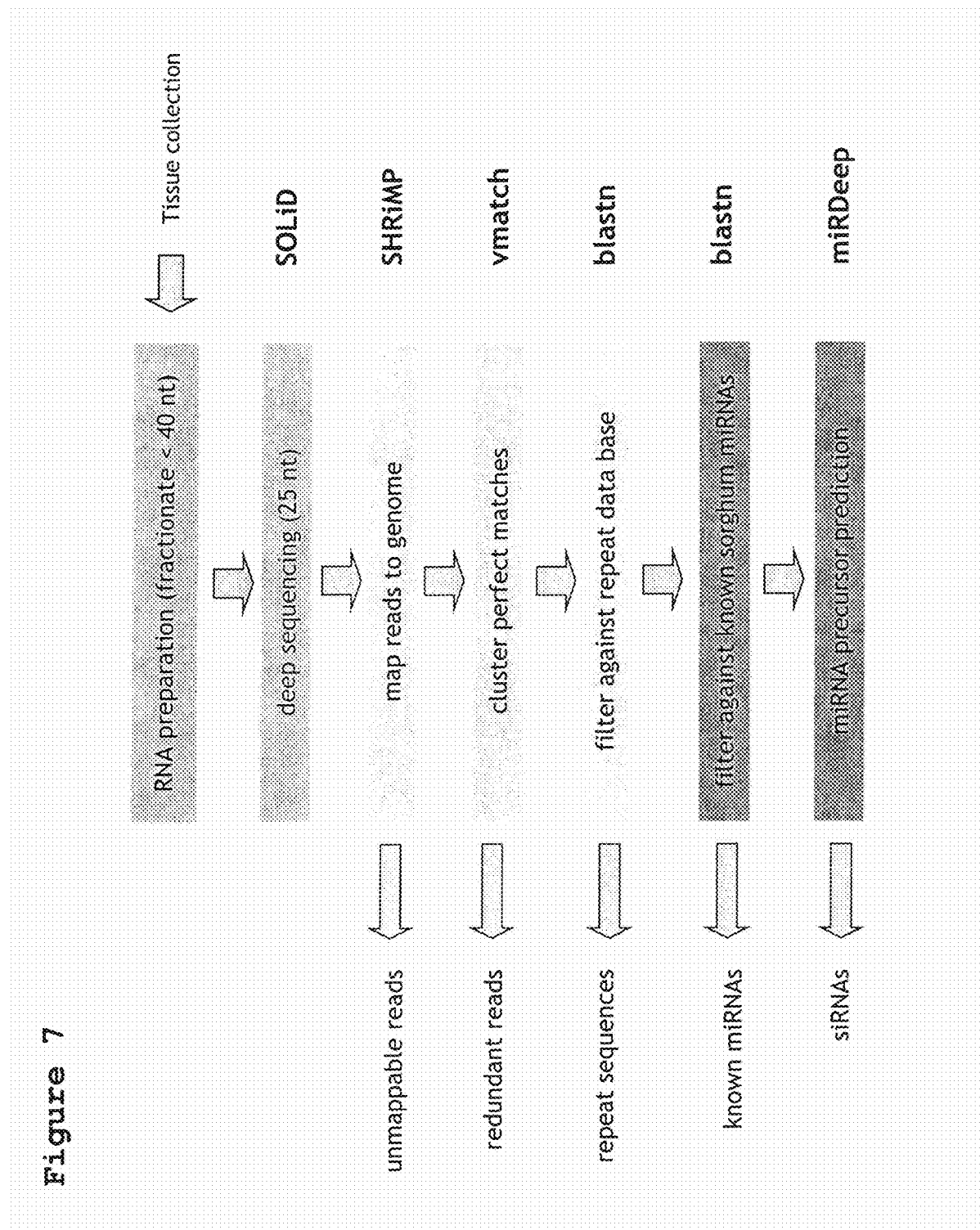
FIG. 7. Pipeline used for the de novo miRNA detection. All reads from SOLiD sequencing were mapped in color-space to the sorghum genome using SHRiMP. Perfect matching reads were clustered with Vmatch then filtered against the sorghum repeat sequences and compared with known sorghum miRNAs to classify them. The remaining sequences were taken for de novo miRNA prediction using miRDeep.

The miRDeep pipeline was adapted for de novo detection of miRNAs in sorghum (FIG. 7), and 223 new miRNA candidate genes were predicted (for a complete list of the new miRNAs refer to Tables C and G, and for their mature sequence and predicted gene targets refer to FIGS. 8-10). All predicted 223 miRNAs met the expression criteria used above for known miRNAs (Table D). Their expression abundance was very low, with the highest miRNA expression comprising only 0.08% of the BTx623 library. From all miRNAs that were expressed in sorghum stems, 19 of them were found to be within introns of protein coding genes (mirtrons), these included miR172c and miR437g, together with other 17 mirtrons from de novo predicted miRNAs (Table E).

Figure 4E:
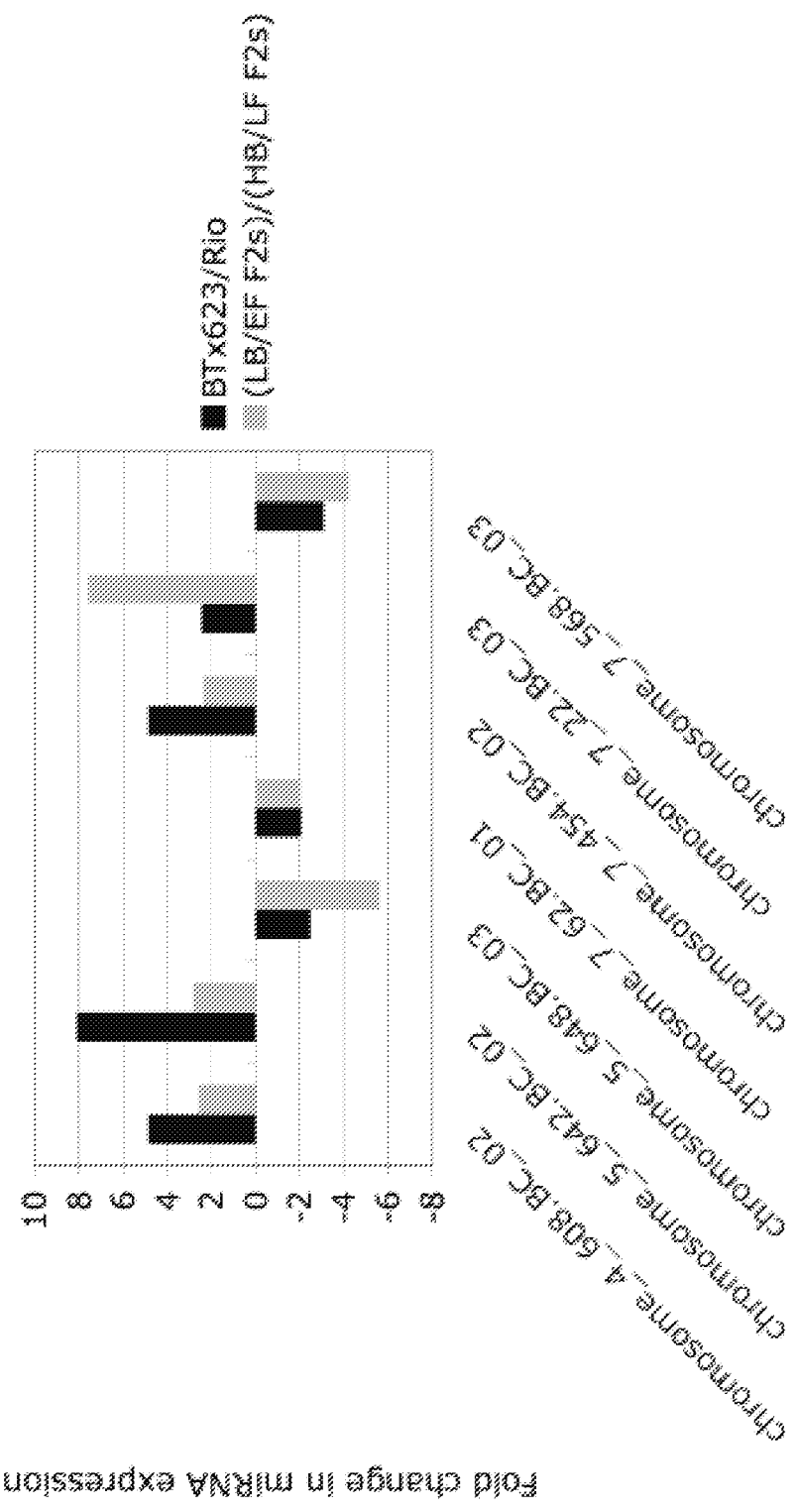
Figure 4F:
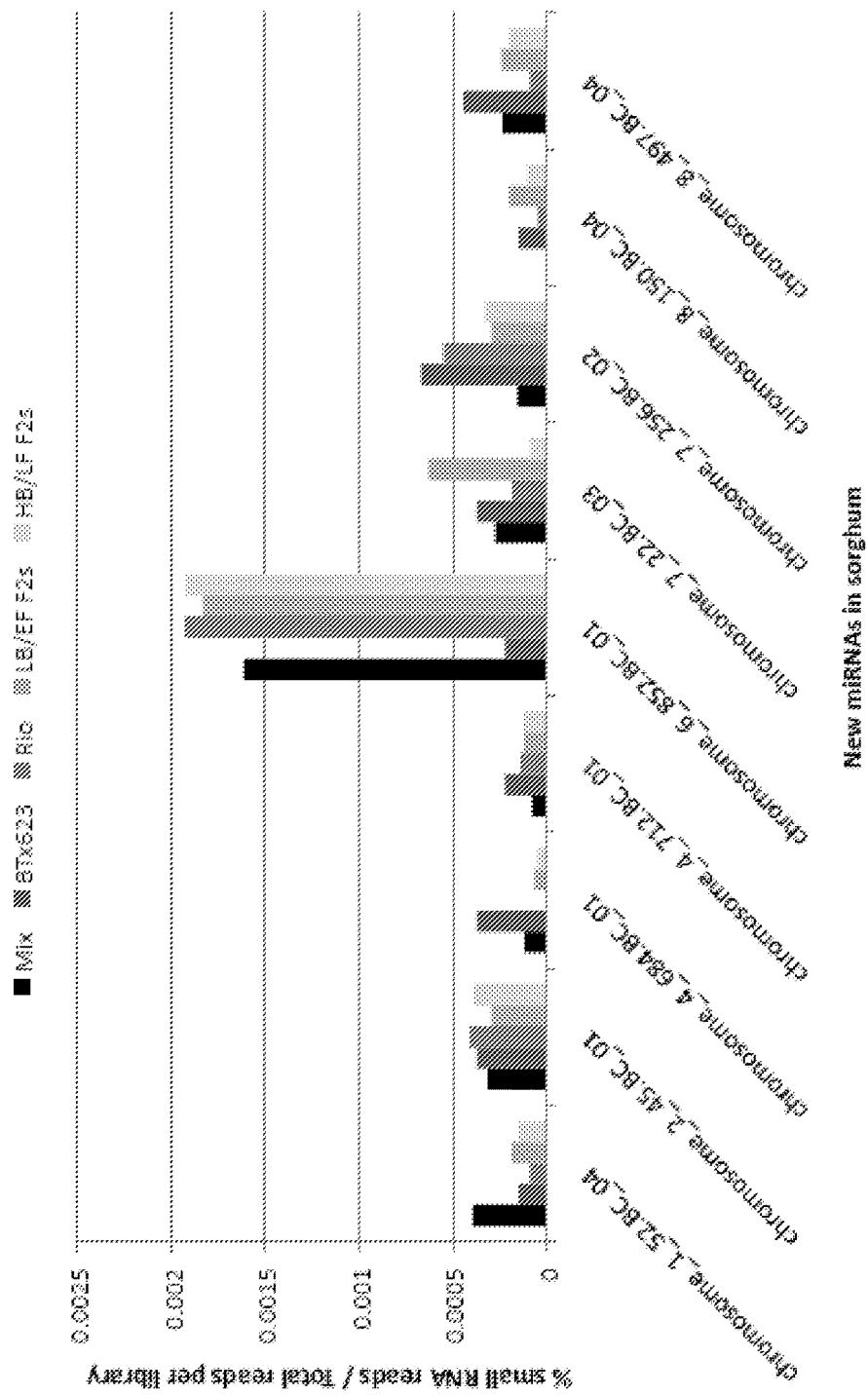
Figure 4G:
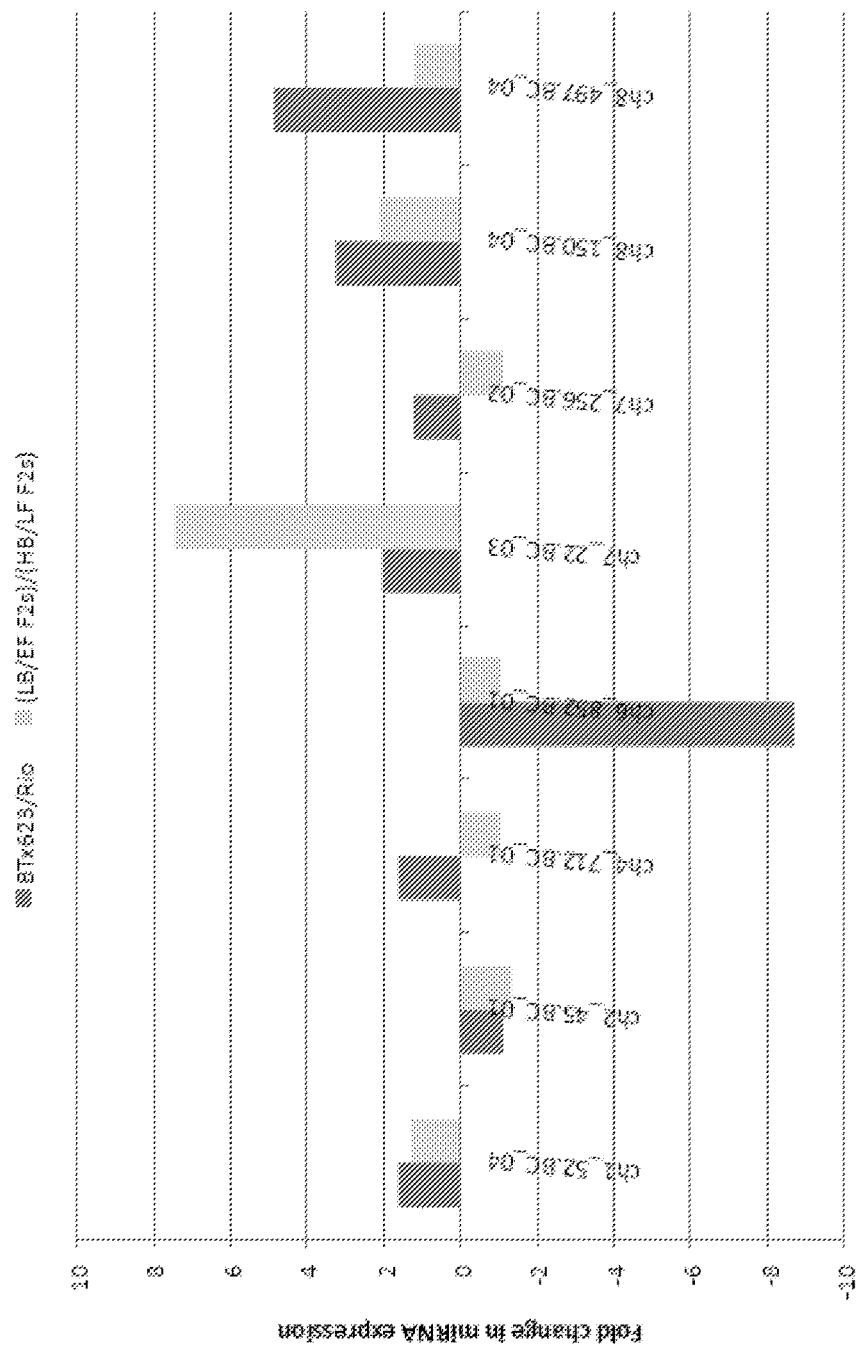

We were able to identify 7 miRNAs whose allelic variation in expression between BTx623 and Rio were inherited in the F2 offsprings (FIG. 4E and FIG. 3C). For three of them (chromosome_5_642. BC_02; chromosome_5_648. BC_03 and chromosome_7_568. BC_03), we could not find any putative target. For the remaining four miRNAs, their predicted target genes included an SNF2-type chromatin remodeling transcription factor (chromosome_4_608. BC_02), an arbutin synthase glycosyltransferase and a cellulose synthase gene (chromosome_7_22. BC_03). Regarding miRNAs, whose expression levels did not differ between BTx623 and Rio or differed but the expression pattern was not inherited in the F2 generation, we identified 9 miRNAs whose predicted targets were involved in the regulation of flowering time and 14 miRNAs whose predicted targets were involved in carbohydrate metabolism (Table 3). We also identified new miRNAs having as predicted targets sugar transporters and cell wall-related genes (Table F).

Overall, we identified 223 putative miRNAs in total, from which 7 of them displayed allelic differences in expression that were inherited in F2 progeny. Additionally, several miRNAs had as predicted targets, genes involved in traits highly relevant for biofuel applications such as flowering time, carbohydrate and cell wall metabolism.

Figure 5B:
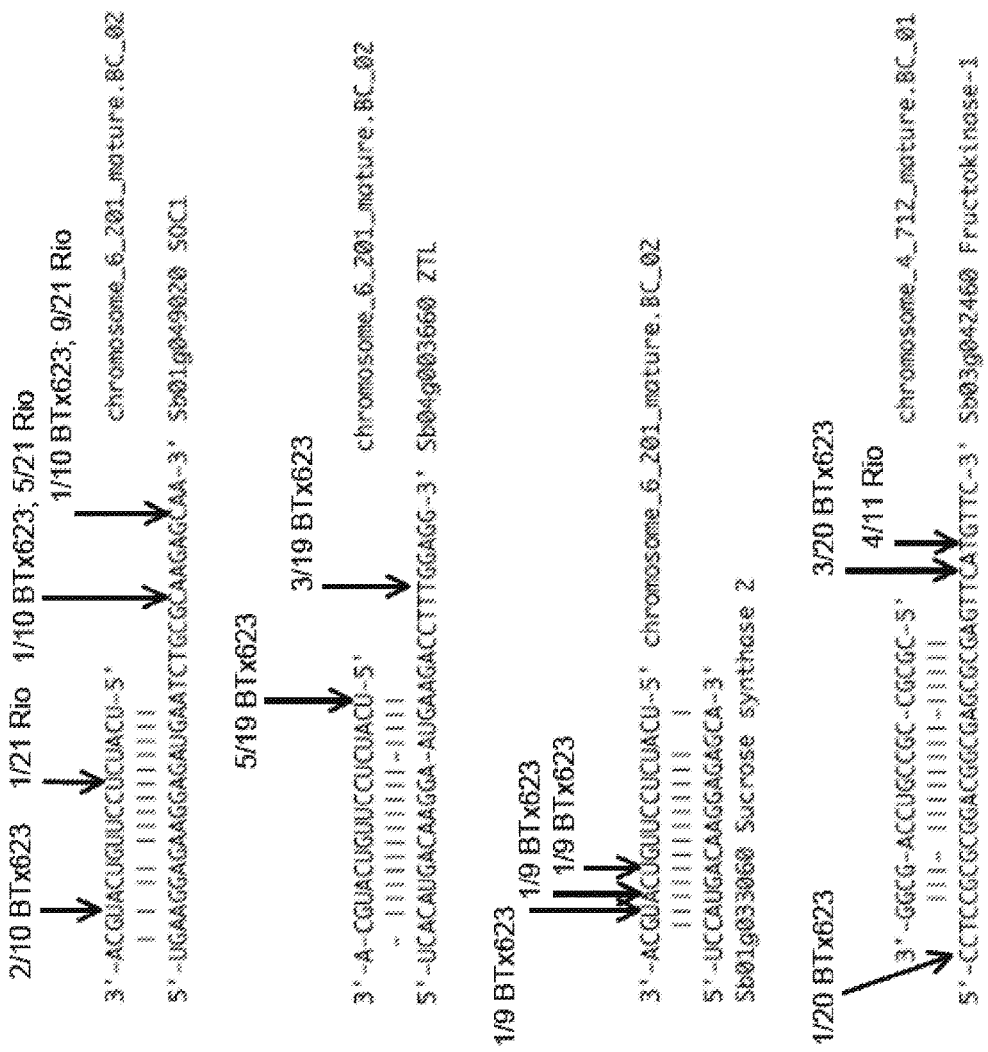

Several miRNAs and/or their Targets Co-Localized with Previously Reported QTLs for Brix and Flowering Time in Sorghum Several regions in the sorghum genome have recently been identified as QTLs for Brix and flowering time (7, 8, 36). For example, a recombinant inbred line (RIL) population derived from BTx623 and Rio, the same lines as in this study, was used to detect QTLs for Brix on chromosomes 3, 6, and 7, respectively (7). The QTL on chromosome 3 had the greatest effect on Brix, explaining 25% of the trait variance, whereas the QTL on chromosome 7 contributed 14%, respectively (7). Interestingly, several miRNAs and/or their targets genes identified in this study, co-localized with the nearest simple sequence repeat (SSR) markers of published Brix QTLs (FIG. S8A). For example, several targets predicted for miR169abi* co-localized with the Brix QTL on chromosome 3 (FIG. 11), together with a FRUCTOKINASE 1 (FRK1) gene as predicted target of the miRNA chromosome_4_712_mature.BC_01. Furthermore, the miRNA-mediated cleavage of FRK1 mRNA could also be experimentally demonstrated (FIG. 5B). In addition, the miR169 family members miR169cd and miR169lmn co-localized with the Brix QTLs on chromosomes 6, and 7, respectively.

Figure 11A:
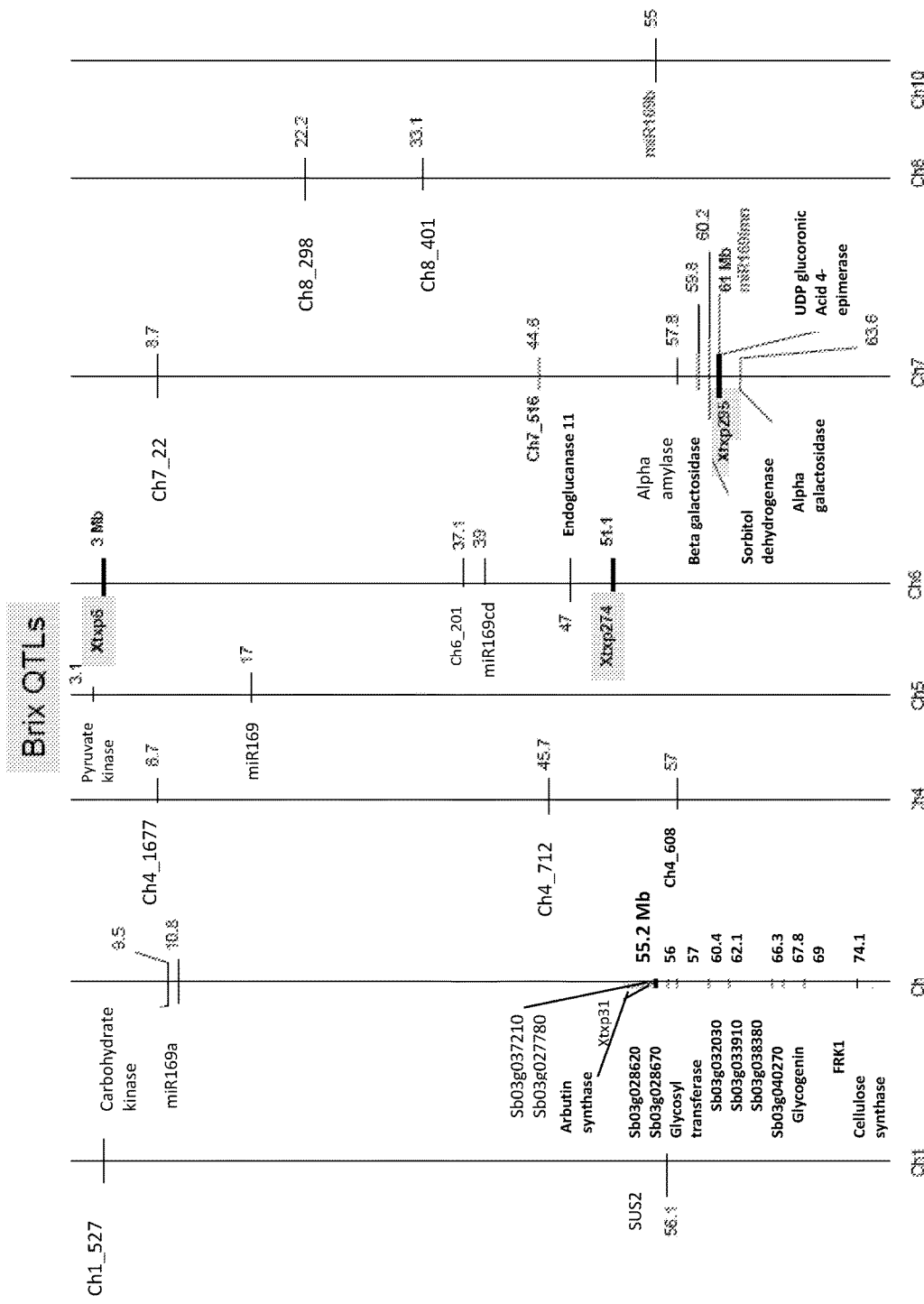
FIGS. 11A-11B. The miRNAs and/or their targets co-localize with previously reported QTLs for sugar content and flowering time. The simple sequence repeats (SSRs) markers (named Xtxp) nearest to the previously reported flowering and Brix QTLs derived from a BTx623×Rio RIL population (8), were placed in the BTx623 physical map and are shown in black and shaded yellow (Brix), and black and shaded orange (flowering), respectively. The markers Xtxp6 and Xtxp274 on chromosome 6 are flanking the QTL for Brix and flowering in the center. The miRNAs (in bold) and their target genes are shown in the same color. The genes targeted by two different miRNAs are shown in color font and shaded color.
Figure 11B:
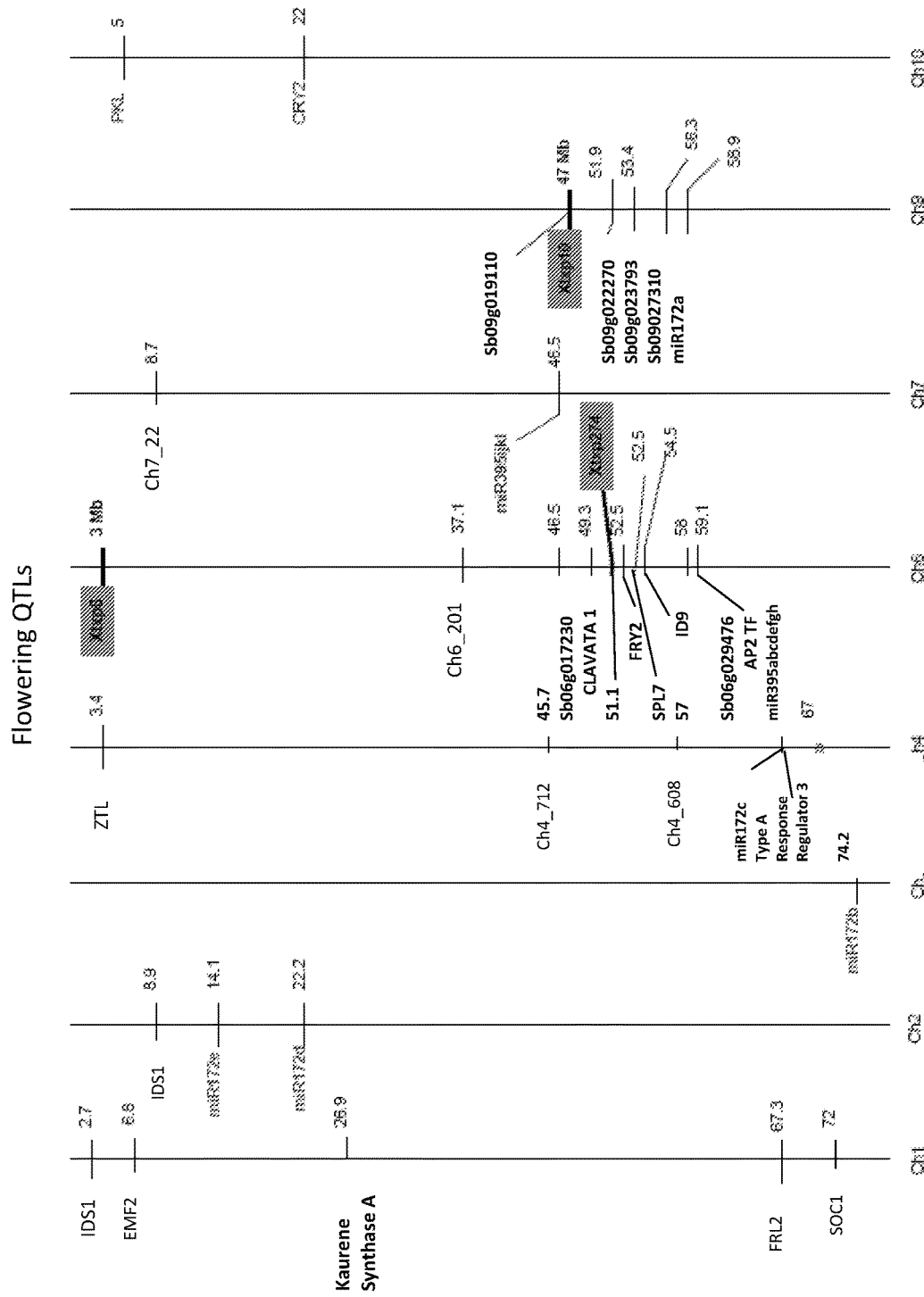

QTLs for flowering time in BTx623 and Rio, have been detected on chromosomes 6 and 9 (7). As with the Brix QTLs, several miRNAs and/or their predicted targets co-localized with SSR markers near these two QTLs (FIG. 11B). On chromosome 6, several miR172 targets as well as seven members of the MIR395 family including MIR395f are located near a QTL for flowering. In addition, MIR172a co-localized with the QTL for flowering on chromosome 9 (FIG. 11B).

Although a positive relationship between high sugar content and flowering time had been described in sorghum (8), the molecular mechanism remained unclear. In this work we could identify three miRNAs (ch4_712_mature.BC_01; ch6_201_mature.BC_02 and ch9_1189.mature.BC_09) that had predicted target genes involved in flowering and carbohydrate metabolism (Table 3). For example, ch6_201_mature.BC_02 had as predicted targets the clock gene ZEITLUPE (ZTL) and the flowering gene SUPPRESSOR OF CONSTANS 1 (SOC1), as well as the SUCROSE SYNTHASE 2 (SUR2) gene and we could experimentally validate their miRNA-mediated cleavage. Furthermore, this miRNA co-localized with a Brix and flowering QTL on chromosome 6 (FIGS. 11A and 11B).

In summary, the genomic location for several members of the MIR169, MIR172 and MIR395 gene families, and/or their predicted target genes co-localized with previously reported QTLs for Brix and flowering time, respectively. The same was true for many newly discovered miRNAs.

TABLE 2

Predicted targets of miR169, miR172 and miR395

| miRNA | Target gene | Gene function | Target site |
|---|---|---|---|
| sbi-miR169acdi | Sb08g021910 | CCAAT-binding transcription factor subunit B | 3' UTR |
| sbi-miR169cd | Sb05g026273 | GRAS family transcription factor | Exon |
| sbi-miR169bcdefgh | Sb01g045500 | CCAAT-binding transcription factor subunit B | 3' UTR |
| sbi-miR169efghi | Sb01g011220 | CCAAT-binding transcription factor subunit B | 3' UTR |
| sbi-miR169i | Sb02g003070 | TCP family transcription factor | 3' UTR |
| sbi-miR169a* | Sb03g038380 | Calcium/Calmodulin dependent protein kinase-related | Exon |
| sbi-miR169b* | Sb01g041700 | Glutamate decarboxylase | Exon |
| | Sb10g008200 | Starch synthase isoform | Exon |
| | Sb02g026670 | Calmodulin-like protein. Pfam EF-Hand domain | Exon |
| | Sb03g028620 | Cytochrome P450 | Exon |
| | Sb03g028670 | Cytochrome P450 | Exon |
| | Sb04g003200 | Putative cycloartenol synthase | 3' UTR |
| | Sb05g002790 | Microfibril-associated protein | Exon |
| sbi-miR169bfgh* | Sb01g036110 | Similar to Insulinase | Exon |
| sbi-miR169cd* | Sb05g024660 | BTB/POZ domain | Exon |
| sbi-miR169i* | Sb03g041660[1] | Similar Glycogenin-like protein | Exon |
| sbi-miR172abcde | Sb01g003400 | Indeterminate spikelet 1 | Exon |
| | Sb02g007000 | Indeterminate spikelet 1 | Exon |
| | Sb06g030670 | APETALA 2 transcription factor | Exon |
| | Sb09g002080 | APETALA 2 transcription factor | 3' UTR |
| sbi-miR172abcd | Sb10g025053 | Glossy 15 | Exon |
| sbi-miR172b | Sb06g023330 | Double-stranded RNA binding motif. Similar to AthFRY2/CPL1 | Exon |
| | Sb06g019750 | Protein kinase similar to CLAVATA 1 | Exon |
| sbi-miR172e | Sb01g044240 | FRIGIDA-like protein 2 | Exon |
| | Sb04g038320 | Type A response regulator 3 | 3' UTR |
| sbi-miR395abcdef | Sb01g044100 | Sulfate transporter | 5' UTR |
| | Sb01g008450 | ATP sulfurylase | Exon |
| sbi-miR395abcde* | Sb03g014780 | Chromating-remodeling complex ATPase chain | Exon |
| | Sb03g026410 | ATP synthase beta subunit/transcription terminator factor rho-like | Exon |
| sbi-miR395f* | Sb01g007878 | Embryonic flower 2 | Exon |
| | Sb10g005630[1] | Chromatin-remodeling factor CHD3 similar to PICKLE | Exon |
| | Sb10g013750 | Cryptochrome 2 | Exon |
| | Sb09g023793 | Similar to NOT2/NOT3/NOT5 family protein | Exon |
| | Sb10g012270 | Proton-dependent oligopeptide transport (POT) family protein | Exon |

[1]The target prediction was based on MicroPC web resource (Mhuantong and Wichadakul 2009)
In red: miRNA-mediated cleavage of target genes was experimentally validated

TABLE 3

List of new miRNAs that target genes involved in flowering and the starch and sucrose pathways

| miRNA | Target gene | Gene function | Target site |
|---|---|---|---|
| | | Flowering | |
| chromosome_1_970_mature.BC_03 | Sb03g035080 | Dof zinc finger similar to Ath CDF5 | Exon |
| chromosome_3_1462_mature.BC_04 | Sb04g024040 | F-box protein GID2 | Exon |
| chromosome_4_608_mature.BC_02 | Sb06g029476 | SWI/SNF helicase-like transcription factor | Exon |
| chromosome_4_712_mature.BC_01 | Sb01g021990 | Kaurene-synthase A | Exon |
| | Sb03g041900 | Gibberellin 20 oxidase 2 | Exon |
| | Sb03g043030 | Gibberellin response regulator like | Exon |
| | Sb03g047330 | Lux arrythmo | Exon |
| | Sb03g039060 | Similar to CONSTANS | 3' UTR |
| | Sb05g003660 | Similar Pseudo response regulator 9/5 | Exon |
| | Sb06g024630 | SBP7/SPL7 | Exon |

TABLE 3-continued

List of new miRNAs that target genes involved in flowering and the starch and sucrose pathways

| miRNA | Target gene | Gene function | Target site |
|---|---|---|---|
| chromosome_5_379_mature.BC_04 | Sb02g001110 | Casein kinase II subunit alpha | 5' UTR |
| chromosome_5_978_mature.BC_01 | Sb04g023680 | Cryptochrome 1a | 5' UTR |
| chromosome_6_201_mature.BC_02 | Sb01g021990 | Kaurene-synthase A | Exon |
|  | Sb04g003660 | ZTL | Exon |
|  | Sb01g049020 | SOC1 | Exon |
|  | Sb06g025550 | Indeterminate 9 | 5' UTR |
| chromosome_8_618_mature.BC_05 | Sb07g024550 | Indeterminate 1 | Exon |
| chromosome_9_1189_mature.BC_05 | Sb07g024550 | Indeterminate 1 | Exon |
|  |  | Starch and sucrose |  |
| chromosome_1_527_mature.BC_05 | Sb03g042460 | Fructokinase 1 | Exon |
| chromosome_1_1391_mature.BC_04 | Sb10g009270 | Endoglucanase 17 | Exon |
| chromosome_2_1061_mature.BC_05 | Sb01g035890 | Sucrose synthase 3 | Exon |
| chromosome_3_213_mature.BC_01 | Sb06g032760 | Endoglucanase 13 | Exon |
| chromosome_4_134_mature.BC_02 | Sb09g026080 | Hexokinase | 3' UTR |
| chromosome_4_557_mature.BC_02 | Sb10g006330 | Sucrose Synthase 1 | 5' UTR |
| chromosome_4_712_mature.BC_01 | Sb05g007310 | Sucrose phosphate synthase | Exon |
|  | Sb06g031910 | Beta-fructofuranosidase | Exon |
|  | Sb07g001140 | Beta-glucosidase | Exon |
|  | Sb03g042460 | Fructokinase 1 | Exon |
|  | Sb03g010640 | Alpha glucosidase | Exon |
|  | Sb09g019480 | Starch debranching enzyme | Exon |
|  | Sb10g009270 | Endoglucanase 17 | Exon |
|  | Sb10g030140 | Endoglucanase 18 | Exon |
| chromosome_4_1677_mature.BC_05 | Sb06g023760 | Beta-fructofuranosidase | Exon |
|  | Sb06g031910 | Beta-fructofuranosidase | Exon |
| chromosome_6_201_mature.BC_02 | Sb01g033060 | Sucrose synthase 2 | Exon |
|  | Sb03g008810 | Ribokinase, PfkB carbohydrate kinase | Exon |
|  | Sb05g002900 | Piruvate kinase | Exon |
| chromosome_7_516_mature.BC_03 | Sb06g017600 | Endoglucanase 11 | Exon |
| chromosome_7_1887_mature.BC_05 | Sb01g019850 | Beta amylase | Exon |
| chromosome_8_401_mature.BC_01 | Sb07g023020 | Alpha amylase isozyme | Exon |
| chromosome_9_1189_mature.BC_05 | Sb06g017600 | Endoglucanase 11 | Exon |
| chromosome_10_962_mature.BC_01 | Sb10g006330 | Sucrose Synthase 1 | Exon |

In red: miRNA-mediated cleavage of target genes was experimentally validated

CONCLUSION

Here we have described the first characterization of the small RNA component of the transcriptome from sorghum stems. The choice of stems as plant material is interesting not only because it is the tissue were fermentable sugars do accumulate, but it is also the venue for the movement of small RNA duplexes (siRNAs and miRNAs) from source to sink tissues, as have been recently demonstrated. Thus, one could expect the small RNA component of the stem to be quite diverse or heterogeneous. Indeed, the unexpected finding of a high abundance peak of RNAs with 25 nt or more in length lead us to the finding of rRNA and tRNA genes that have not been annotated yet in the sorghum genome. We have also shown that the abundance of the 22 nt small RNAs in sorghum stem tissue was greater than the 20 and 21 nt small RNAs respectively. Our results contrast the recently proposed notion that the 22 nt peak of small RNAs is exclusive of maize. Furthermore, we found that up to 15% of all the 22 nt small RNAs in the BTx623 library were derived from miR172c, which has been previously predicted to have a length of 20 nt (Paterson et al. 2009). Recently, 22 nt miRNAs have been described to trigger siRNA biogenesis from target transcripts in *Arabidopsis*. Thus, it would be interesting to test if miR172c can also trigger siRNA biogenesis in sorghum.

As expected, the specific genetic material, tissue sample and developmental stage used in our study, allowed us to capture a broad spectrum of the small RNA component of the sorghum transcriptome. On the other hand, the specificity of the material permitted us to gain new insights into how complex traits like sugar accumulation and flowering time are regulated at the post-transcriptional level. Such regulation of gene expression provide an opportunity to manipulate biofuel traits, where stem sugar rather than cellulose and increased biomass because of delayed flowering could be enhanced. By taking a genetic approach in conjunction with deep-sequencing of stem-derived small RNAs, we were able to correlate allelic variation in miRNA expression between grain and sweet sorghum, with the sugar and flowering phenotypes of selected F2 plants derived from their cross. In the case of miR395, it is interesting to note that there was genotypic variation in the miR395/miR395* ratio, with the Rio genotype expressing both strands at equal proportions in contrast to a clear predominance of miR395 abundance over miR395* in BTx623. This is reminiscent of the recently proposed "arm switching" model of miRNA evolution described for nematodes species, in which the mature miRNA is produced from the 5' arm of the miRNA hairpin in a particular species but in a different nematode species the 5' arm of the same MIR gene gives rise to the miRNA* instead. Interestingly, it has been shown recently that miRNA* species have physiological relevance in *Drosophila*, since a significant number of them are well conserved, can be loaded into the RISC complex through their preferential association with ARGONAUTE2 (AGO2) rather that AGO1, and can also regulate the expression of target genes. Furthermore, the regulatory potential of miRNA* species in vertebrates has been recently demonstrated as well.

Finally, several of the miRNAs described in this study as well as their predicted target genes, co-localized with previously described Brix and flowering QTLs, providing a set of candidate genes as the first step to map-based cloning of the quantitative differences in phenotype between grain and sweet sorghum lines.

REFERENCES FOR EXAMPLE I

1. K. Glasziou, R. Gayler, *Bot Rev* 38, 471 (1972).
2. G. Hoffman-Thoma, K. Hinkel, P. Nicolay, J. Willenbrink, *Physiologia Plantarum* 97, 277 (1996).
3. J. Goldemberg, *Science* 315, 808 (2007).
4. L. Grivet, P. Arruda, *Curr Opin Plant Biol* 5, 122 (2002).
5. A. H. Paterson et al., *Nature* 457, 551 (2009).
6. K. B. Ritter, C. L. McIntyre, I. D. Godwin, D. R. Jordan, S. C. Chapman, *Euphytica* 157, 161 (2007).
7. S. Murray et al., *Crop Science* 48, 2165 (2008).
8. K. Ritter et al., *Molecular Breeding* 22, 367 (2008).
9. M. Calviño, R. Bruggmann, J. Messing, *Rice* 1, 166 (2008).
10. Materials and Methods
11. K. Nobuta et al., *Proc Natl Acad Sci USA* 105, 14958 (2008).
12. R. Louro, A. S. Smirnova, S. Verjovski-Almeida, *Genomics* 93, 291 (2009).
13. K. Okamura, J. W. Hagen, H. Duan, D. M. Tyler, E. C. Lai, *Cell* 130, 89 (2007).
14. J. G. Ruby, C. H. Jan, D. P. Bartel, *Nature* 448, 83 (2007).
15. R. J. Taft et al., *Nat Genet* 41, 572 (2009).
16. R. J. Taft, C. D. Kaplan, C. Simons, J. S. Mattick, *Cell Cycle* 8, 2332 (2009).
17. G. Chuck, R. Meeley, E. Irish, H. Sakai, S. Hake, *Nat Genet* 39, 1517 (2007).
18. N. Lauter, A. Kampani, S. Carlson, M. Goebel, S. P. Moose, *Proc Natl Acad Sci USA* 102, 9412 (2005).
19. J. Mathieu, L. J. Yant, F. Miirdter, F. Kiittner, M. Schmid, *PLoS Biol* 7, e1000148 (2009).
20. G. Wu et al., *Cell* 138, 750 (2009).
21. Q. H. Zhu, N. M. Upadhyaya, F. Gubler, C. A. Helliwell, *BMC Plant Biol* 9, 149 (2009).
22. W. X. Li et al., *Plant Cell* 20, 2238 (2008).
23. C. G. Kawashima et al., *Plant J* 57, 313 (2009).
24. J. Lomako, W. M. Lomako, W. J. Whelan, *Biochim Biophys Acta* 1673, 45 (2004).
25. Y. Qi et al., *Planta* 221, 437 (2005).
26. J. Ogas, S. Kaufmann, J. Henderson, C. Somerville, *Proc Natl Acad Sci USA* 96, 13839 (1999).
27. S. El-Din El-Assal et al., *Plant Physiology* 133, 1504 (2003).
28. J. T. Henderson et al., *Plant Physiology* 134, 995 (2004).
29. M. Endo, N. Mochizuki, T. Suzuki, A. Nagatani, *Plant Cell* 19, 84 (2007).
30. D. Jiang, Y. Wang, Y. Wang, Y. He, *PLoS ONE* 3, e3404 (2008).
31. S. Y. Kim, T. Zhu, Z. R. Sung, *Plant Physiology* 152, 516 (2010).
32. S. D. Michaels, I. C. Bezerra, R. M. Amasino, *Proc Natl Acad Sci USA* 101, 3281 (2004).
33. M. R. Schläppi, *Plant Physiology* 142, 1728 (2006).
34. P. A. Salomé, J. P. To, J. J. Kieber, C. R. McClung, *Plant Cell* 18, 55 (2006).
35. H. Lee et al., *Nucleic Acids Res*, (2010).
36. S. C. Murray, W. L. Rooney, M. T. Hamblin, S. E. Mitchell, S. Kresovich, *The Plant Genome* 2, 48 (2009).
37. K. Swaminathan et al., *Genome Biol* 11, R12 (2010).
38. F. Torney, L. Moeller, A. Scarpa, K. Wang, *Current Opinion in Biotechnology* 18, 193 (2007).
39. M. Ghildiyal, J. Xu, H. Seitz, Z. Weng, P. D. Zamore, *RNA* 16, 43 (2010).

EXAMPLE II

Identification of miRNAs which influence flowering times, sugar metabolism, stress responses and sulfur storage provides the means to modulate these pathways via the introduction of nucleic molecules encoding or inhibiting the action of the same into recipient plants. Vectors useful for introducing heterologous nucleic acids into plants and methods of use of the same are known in the art. See for example, Segal et al., Genetics (2003) September; 165(1):387-97. Also see U.S. Pat. No. 6,849,779.

In one approach, vectors comprising miR172 or any other miRNA conferring beneficial properties to sorghum can be introduced into plants to increase expression thereof. As shown in Example I, alteration of miRNA172 levels in recipient plants should be effective to increase sugar content in stems thereby providing improved sorghum for the production of biofuels. Such plants also comprise an aspect of the invention.

EXAMPLE III

New MIR169 Gene Copies in the Rice, Sorghum and Maize Genomes

Here, we analyzed the process of tandem duplication that gave rise to MIR169 gene clusters in sorghum (*Sorghum bicolor* (L.) Moench) and traced its evolutionary path by aligning contiguous chromosomal segments of diploid *Brachypodium*, rice, foxtail millet, and the two homoeologous regions of allotetraploid maize. We have chosen miR169 as an example because of its possible role in stem-sugar accumulation in sorghum besides its previously described role in drought stress response in several plant species. We discovered allelic variation in miR169 expression between grain and sweet sorghum, suggesting that miR169 could also play a role in the sugar content of sorghum stems (See Example I). Although high sugar content in stems is a trait shared by sorghum and sugarcane (Calvino, et al. 2008; Calvino, et al. 2009), this trait seems to be silent in other grasses (Calvino and Messing 2011). This prompted us to investigate the evolution and dynamic amplification of miR169 gene copies in grass genomes. We found that synteny of chromosomal segments containing MIR169 gene copies was conserved between monocotyledoneous species such as *Brachypodium* and sorghum but surprisingly also across the monocot barrier in dicotyledoneous species such as grapevine, soybean, and cassava. Furthermore, linkage of MIR169 copies with a bHLH gene similar to *Arabidopsis* bHLH137 and with a CONSTANS-LIKE gene similar to *Arabidopsis* COL14 was conserved in all the grasses examined as well as in soybean and cassava (linkage between MIR169 and bHLH genes) and grapevine (linkage between MIR169 and COL14 genes). We discuss the importance of this finding for breeding crops with enhanced bioenergy traits.

Figure 12:
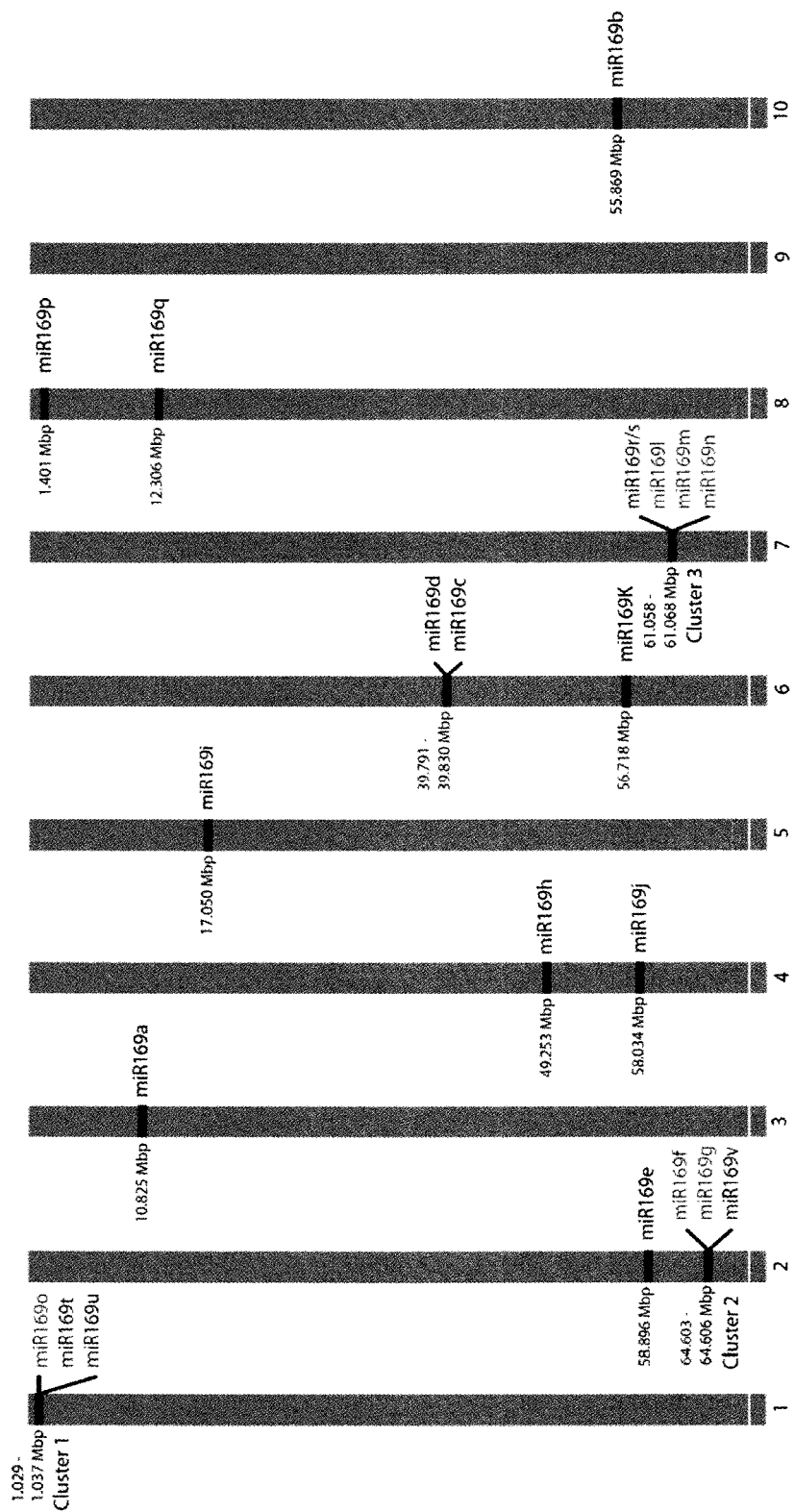
FIG. 12. Distribution of MIR169 gene copies in the genome of Sorghum bicolor cultivar BTx623. A total of 22 MIR169 gene copies are shown, with 17 copies previously annotated by the sorghum genome-sequencing consortium (shown in black and red color) (Paterson, et al. 2009), and with 5 additional MIR169 copies described in this study for the first time (shown in green color). The evolutionary trajectory of sorghum MIR169 gene copies arranged in clusters 1, 2 and 3 are described.

A miRNA cluster as defined in the miRBase database (release 19, August 2012) is composed of two or more miRNA gene copies that are located on the same chromosome and separated from each other by a distance of 10 Kbp or less. The distance set to define a miRNA cluster is arbitrary though, as evidenced by a cluster composed of sixteen copies of MIR2118 distributed over a 18 Kbp segment on rice chr4 (Sun, et al. 2012). The sequencing of the sorghum genome allowed the identification of seventeen MIR169 gene copies, from which five were arranged in two clusters, one located on chr2 (sbi-MIR169f and sbi-MIR169g) and the other located on chr7 (sbi-MIR169l, sbi-MIR169m and sbi-MIR169n, respectively (Paterson, et al. 2009) (FIG. 12; Table 1, Example III).

TABLE 1

Summary of MIR169 gene copies described in this study

| Chromosome | Gene ID[1] | Coordinates[2] | Strand | Distance between genes flanking the cluster[3] |
|---|---|---|---|---|
| *Brachypodium distachyon* | | | | |
| chr1 | bdi-MIR169k | 1,175,425 . . . 1,175,598 | + | |
| chr3 | bdi-MIR169e | 43,441,526 . . . 43,441,689 | + | Cluster 1: bdi-MIR169e to bdi-MIR169g = 2,960 bp |
|  | bdi-MIR169g | 43,444,486 . . . 43,444,666 | + | |
| *Oryza sativa* | | | | |
| chr3 | osa-MIR169r | 35,782,397 . . . 35,782,553 | + | |
| chr8 | osa-MIR169i | 26,891,154 . . . 26,891,261 | + | Cluster 1: osa-MIR169i to osa-MIR169q = 14,446 bp |
|  | osa-MIR169h | 26,895,354 . . . 26,895,475 | + | |
|  | osa-MIR169m | 26,901,902 . . . 26,902,039 | + | |
|  | osa-MIR169l | 26,905,493 . . . 26,905,600 | + | |
|  | osa-MIR169q | 26,905,600 . . . 26,905,493 | − | |
| chr9 | osa-MIR169j | 19,788,861 . . . 19,788,985 | + | Cluster 2: osa-MIR169j to osa-MIR169k = 3,272 bp |
|  | osa-MIR169k | 19,792,133 . . . 19,792,288 | + | |
| *Setaria italica* | | | | |
| chr9 | sit-MIR169o | 526,081 . . . 525,981 | − | |
| chr2 | sit-MIR169f | 36,921,078 . . . 36,921,205 | + | Cluster 1: sit-MIR169f to sit-MIR169h = 3,137 bp |
|  | sit-MIR169g | 36,923,991 . . . 36,924,143 | + | |
|  | sit-MIR169h | 36,924,215 . . . 36,924,361 | + | |
| chr6 | sit-MIR169i | 33,994,480 . . . 33,994,680 | + | Cluster 2: sit-MIR169i to sit-MIR169s = 8,922 bp |
|  | sit-MIR169j | 33,997,832 . . . 33,997,997 | + | |
|  | sit-MIR169k | 34,001,008 . . . 34,001,109 | + | |
|  | sit-MIR169r | 34,003,536 . . . 34,003,402 | − | |
|  | sit-MIR169s | 34,003,402 . . . 34,003,536 | + | |
| *Sorghum bicolor* | | | | |
| chr1 | sbi-MIR169o | 1,029,916 . . . 1,029,814 | − | Cluster 1: sbi-MIR169o to sbi-MIR169u = 7,321 bp |
|  | sbi-MIR169t | 1,030,265 . . . 1,030,155 | − | |
|  | sbi-MIR169u | 1,037,237 . . . 1,037,096 | − | |
| chr2 | sbi-MIR169f | 64,603,670 . . . 64,603,817 | + | Cluster 2: sbi-MIR169f to sbi-MIR169v = 3,049 bp |
|  | sbi-MIR169g | 64,606,503 . . . 64,606,654 | + | |
|  | sbi-MIR169v | 64,606,719 . . . 64,606,868 | + | |
| chr7 | sbi-MIR169r | 61,058,625 . . . 61,058,750 | + | Cluster 3: sbi-MIR169r to sbi-MIR169n = 12,648 bp |
|  | sbi-MIR169s | 61,058,750 . . . 61,058,625 | − | |
|  | sbi-MIR169l | 61,062,736 . . . 61,062,640 | − | |
|  | sbi-MIR169m | 61,068,118 . . . 61,068,027 | − | |
|  | sbi-MIR169n | 61,071,181 . . . 61,071,273 | + | |
| *Zea mays* | | | | |
| chr1 | zma-MIR169l | 298,277,019 . . . 298,277,107 | + | |
| chr2 | zma-MIR169j | 192,700,339 . . . 192,700,489 | + | Cluster 1: zma-MIR169j to zma-MIR169s = 277 bp |
|  | zma-MIR169s | 192,700,616 . . . 192,700,748 | + | |
| chr4 | zma-MIR169i | 47,241,963 . . . 47,242,153 | + | Cluster 2: zma-MIR169i to zma-MIR169e = 271,605 bp |
|  | zma-MIR169d | 47,454,177 . . . 47,454,304 | − | |
|  | zma-MIR169h | 47,513,567 . . . 47,513,694 | + | |
|  | zma-MIR169e | 47,513,695 . . . 47,513,568 | − | |
| chr7 | zma-MIR169k | 135,706,179 . . . 135,706,311 | − | |
| *Vitis vinifera* | | | | |
| chr1 | vvi-MIR169y | 22,233,573 . . . 22,233,820 | + | |
| chr14 | vvi-MIR169z | 25,082,612 . . . 25,082,498 | − | Cluster 1: vvi-MIR169z to vvi-MIR169e = 367 bp |
|  | vvi-MIR169e | 25,082,865 . . . 25,082,717 | − | |
| chr17 | vvi-MIR169x | 355,713 . . . 355,837 | − | |
| *Glycine max* | | | | |
| chr6 | gma-MIR169w | 13,783,352 . . . 13,783,225 | − | |
| chr8 | gma-MIR169x | 717,092 . . . 717226 | + | Cluster 1: gma-MIR169o to gma-MIR169p = 7,248 bp |
|  | gma-MIR169y | 724,205 . . . 724,340 | + | |
| *Manihot esculenta* | | | | |
| scaffold01701 | mes-MIR169w | 436,633 . . . 436,794 | + | |
| scaffold09876 | mes-MIR169y | 536,510 . . . 536,709 | − | |

Figure 13:
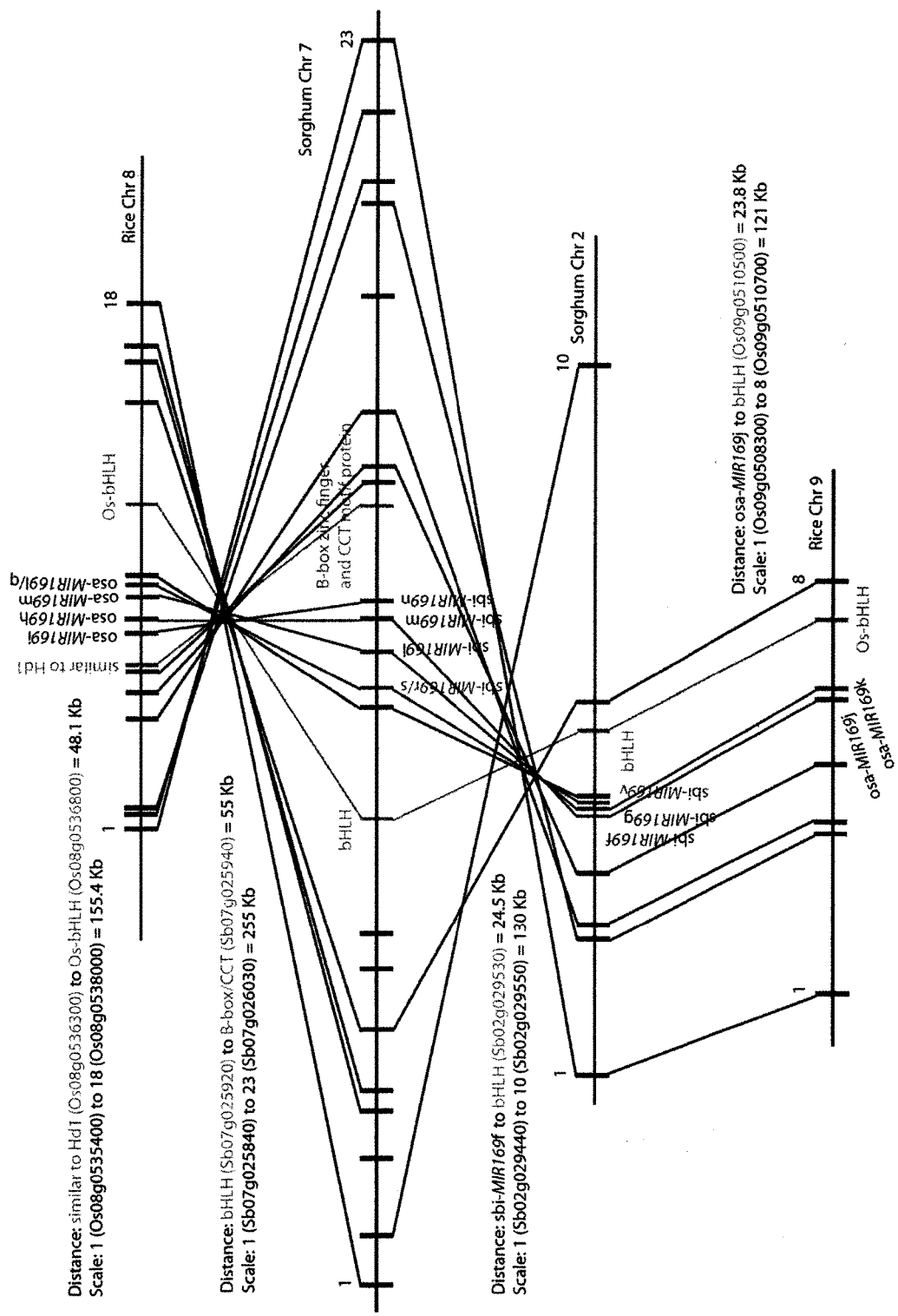
FIG. 13. Syntenic alignment of rice and sorghum chromosomal segments containing MIR169 gene clusters. Sorghum MIR169 gene clusters on chr2 and chr7 together with their flanking protein coding genes were aligned with rice via orthologous gene pair. Rice and sorghum chromosomes are represented as horizontal lines whereas genes along the chromosome are represented as rectangle bars. Known MIR169 gene copies are shown as red bars whereas new MIR169 gene copies described in this study are shown as green bars. The bHLH and B-box zinc finger and CCT motif (B-box/CCT) genes are represented as yellow bars. All other protein coding genes in the chromosomal regions under study are represented as black rectangle bars. Orthologous gene pairs are indicated as lines connecting bars, with red color indicating orthology between MIR169 gene pairs and yellow lines indicating orthology between bHLH and B-box/ CCT gene pairs respectively. All other orthology between rice and sorghum protein coding genes are indicated as black lines connecting black bars. The physical distance between bHLH and B-box/CCT genes and/or between bHLH or B-Box/CCT genes to the flanking MIR169 copy is indicated. In order to provide a scale of the chromosomal segments highlighted in the figure, the physical distance between the first and the last gene in the segment is indicated and thus serves as a reference to observe expansion and contraction of genomic regions. An inversion event on sorghum chr7 containing the MIR169 cluster occurred relative to the orthologous regions on sorghum chr2 and rice chr8 and chr9 respectively.
Figure 14A:
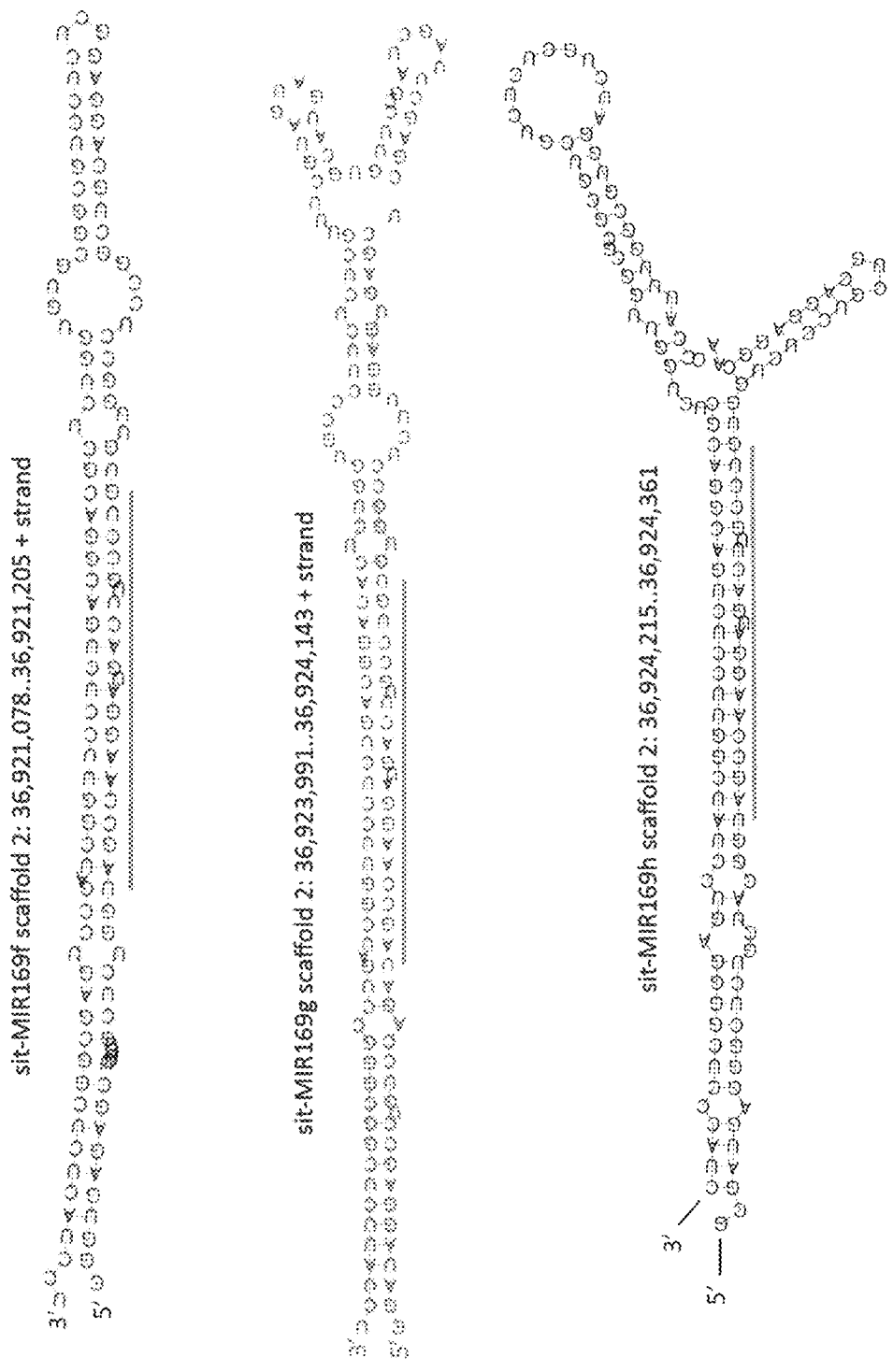
FIG. 14A-14F. Stem-loop precursor sequences of newly predicted MIR169 copies in rice, sorghum, foxtail millet and maize. The genomic location for each MIR169 stem-loop precursor is given. The predicted mature miR169 sequence is indicated with a red bar. SEQ ID NOs: 1-18 are provided, from top to bottom.
Figure 14B:
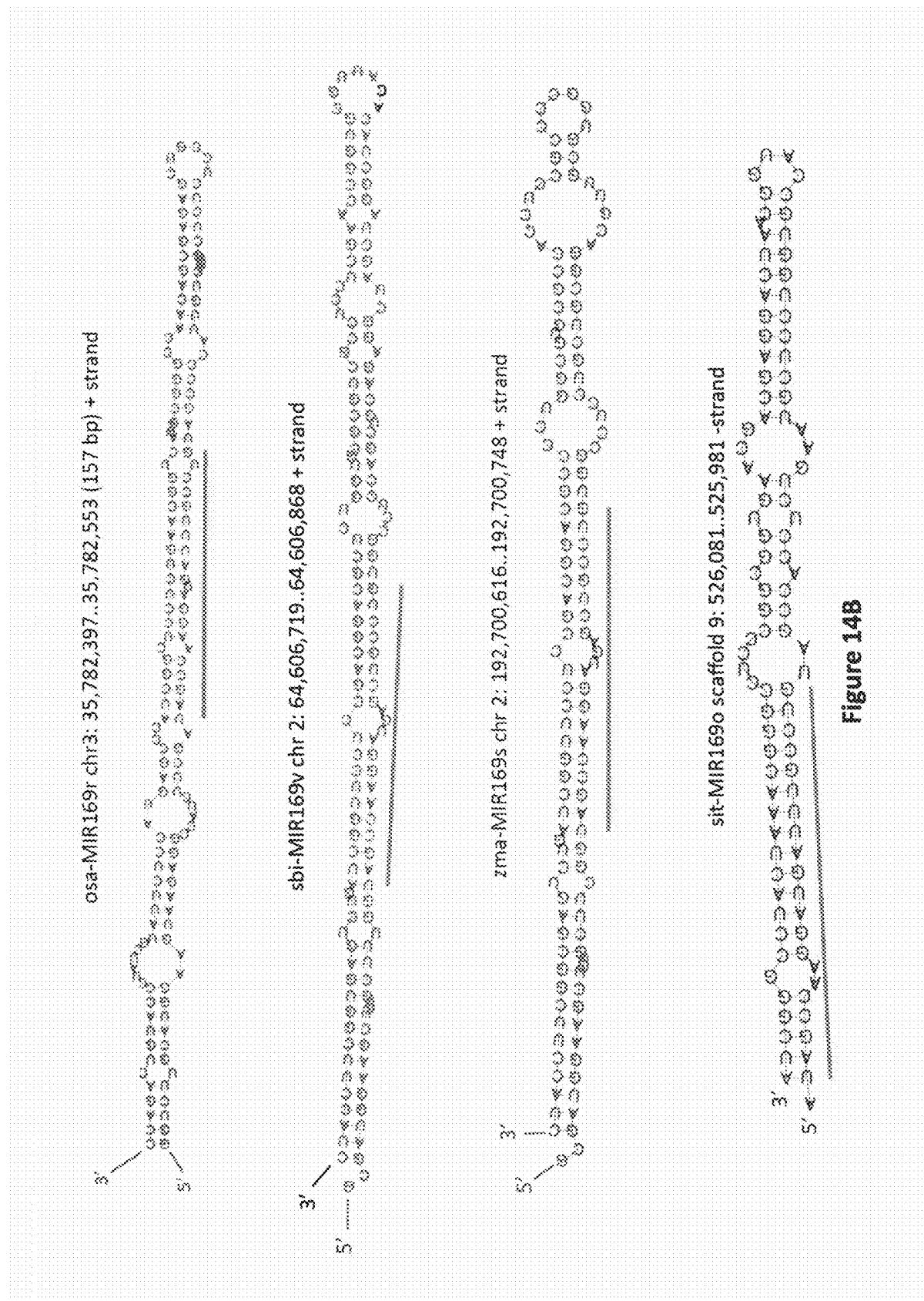
Figure 14C:
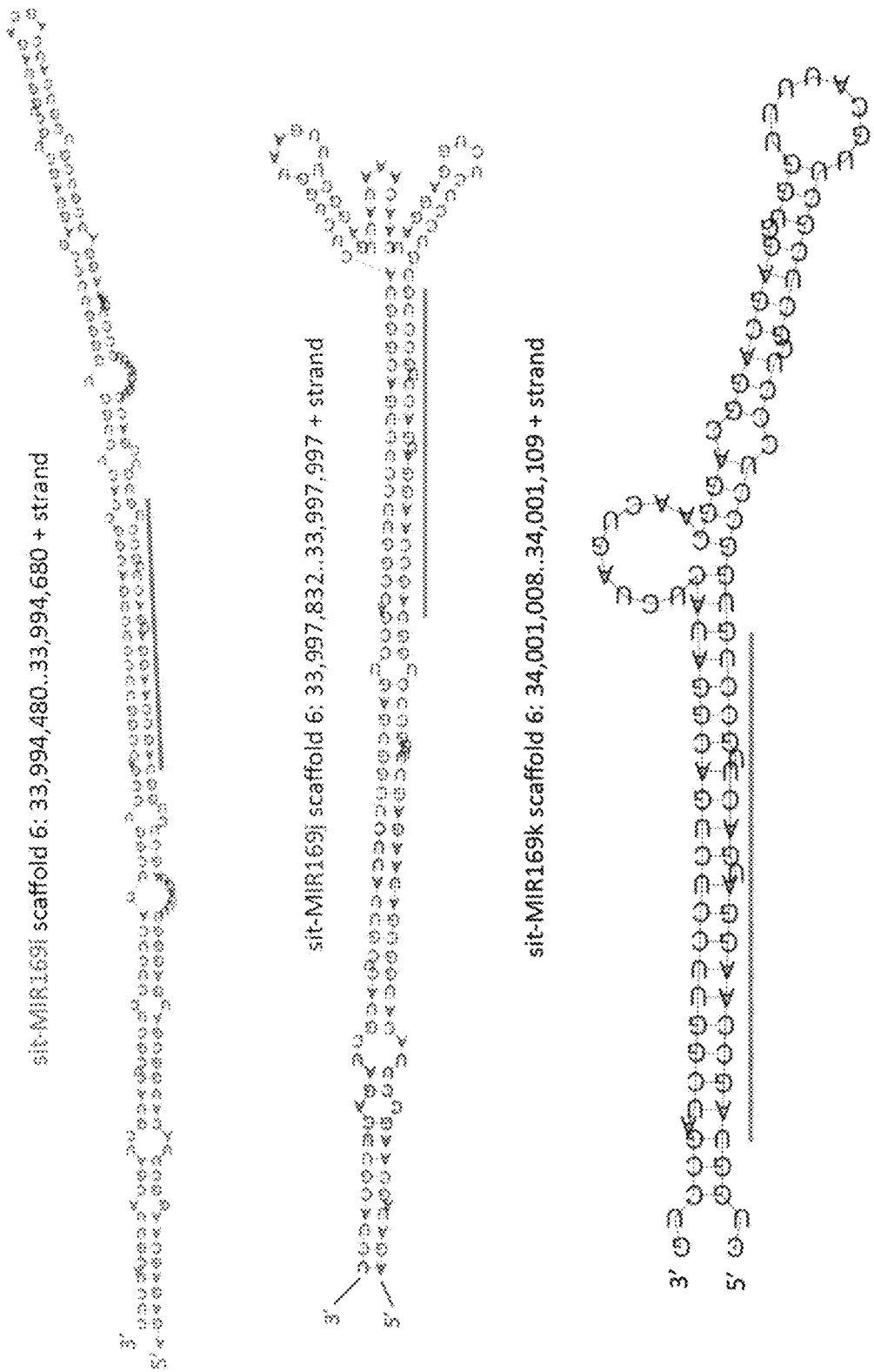
Figure 14D:
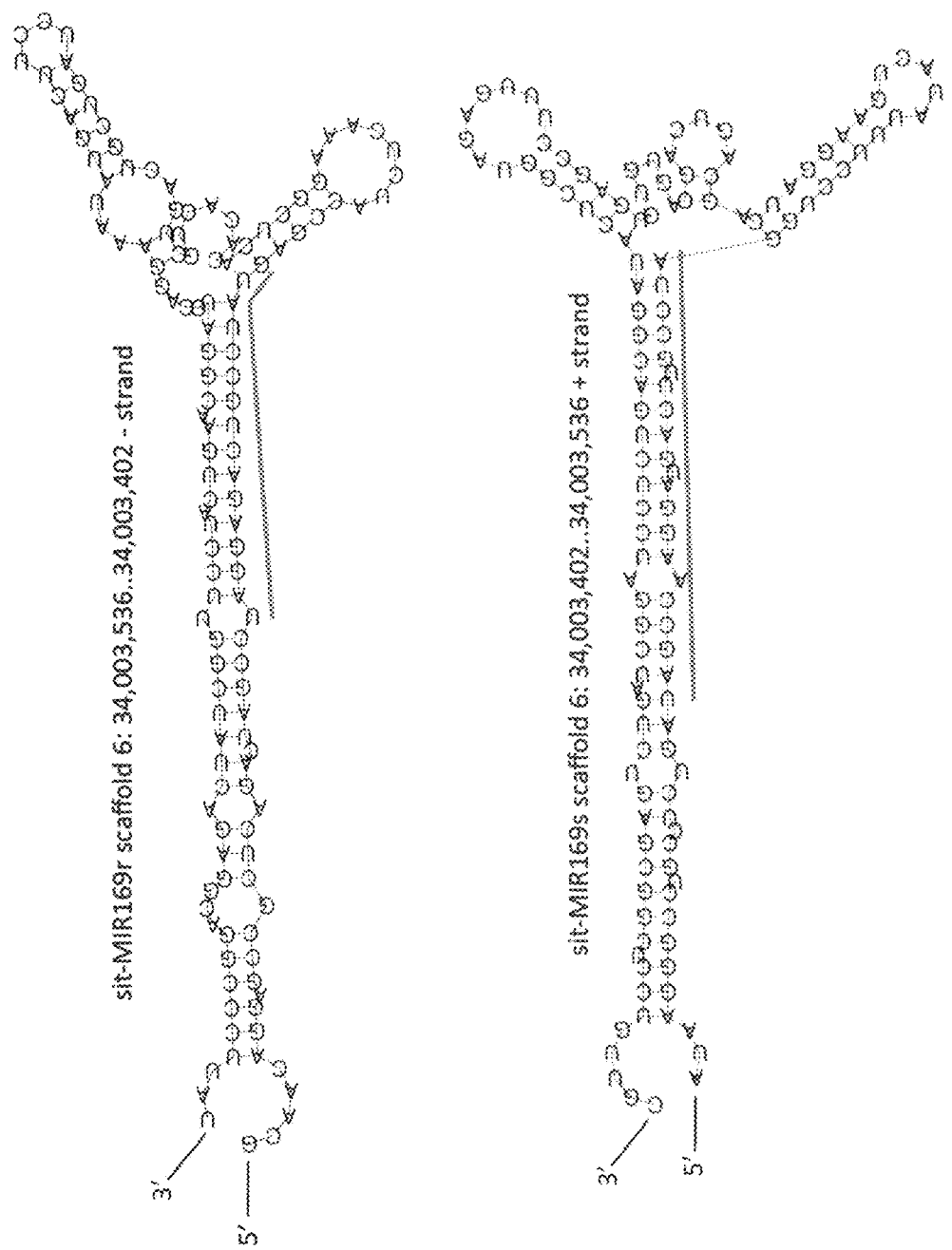
Figure 14E:
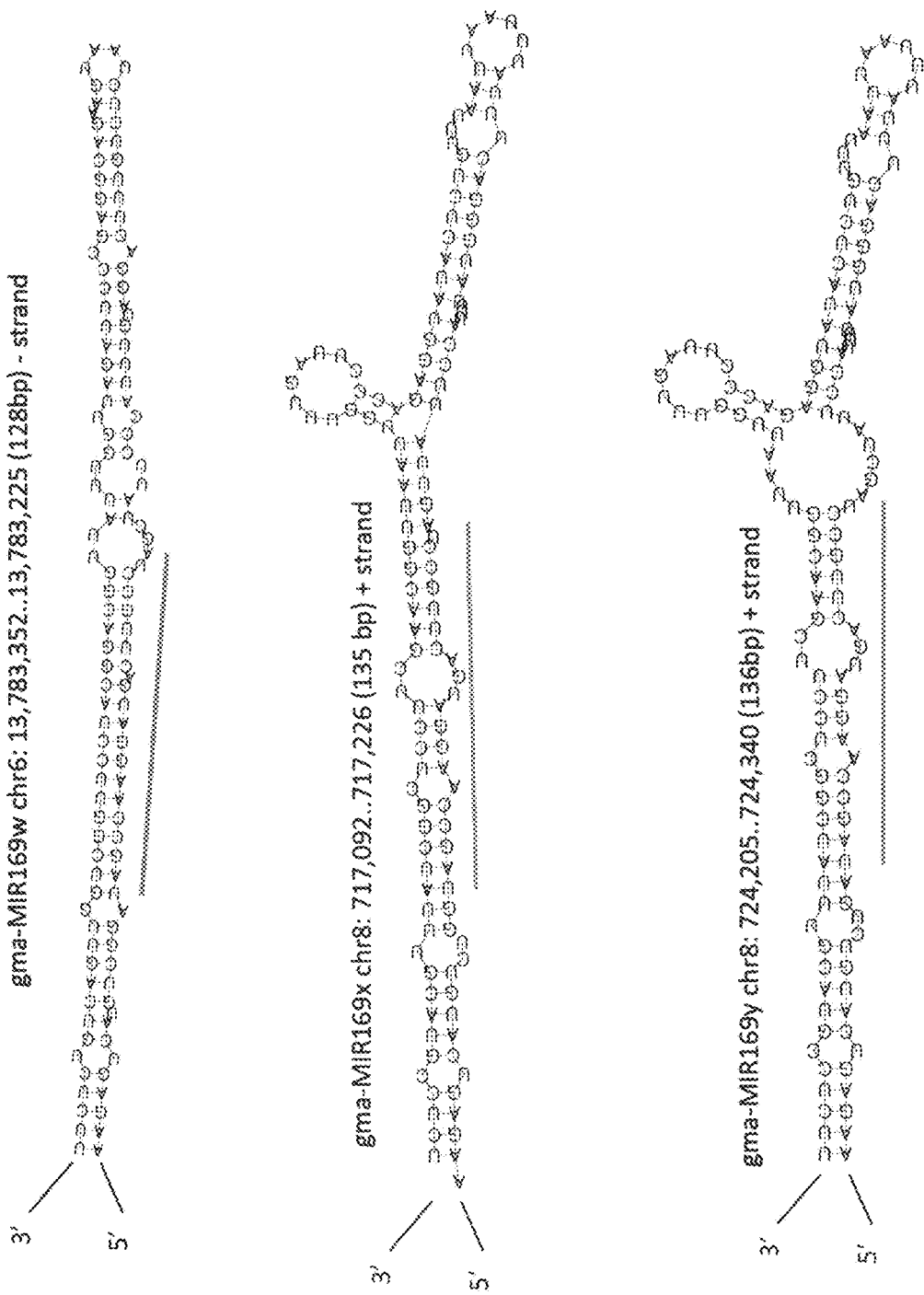
Figure 14F:
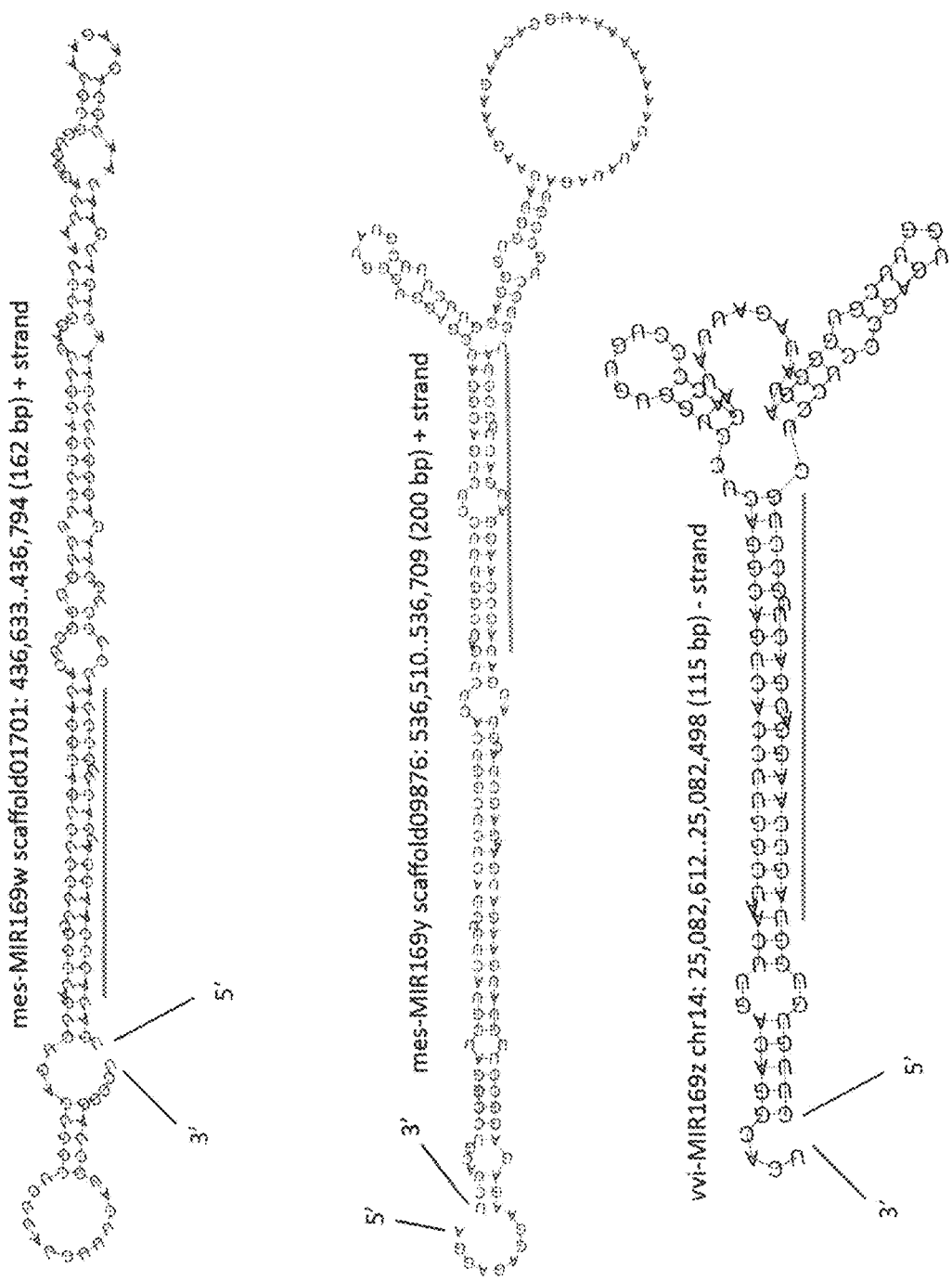
Figure 15:
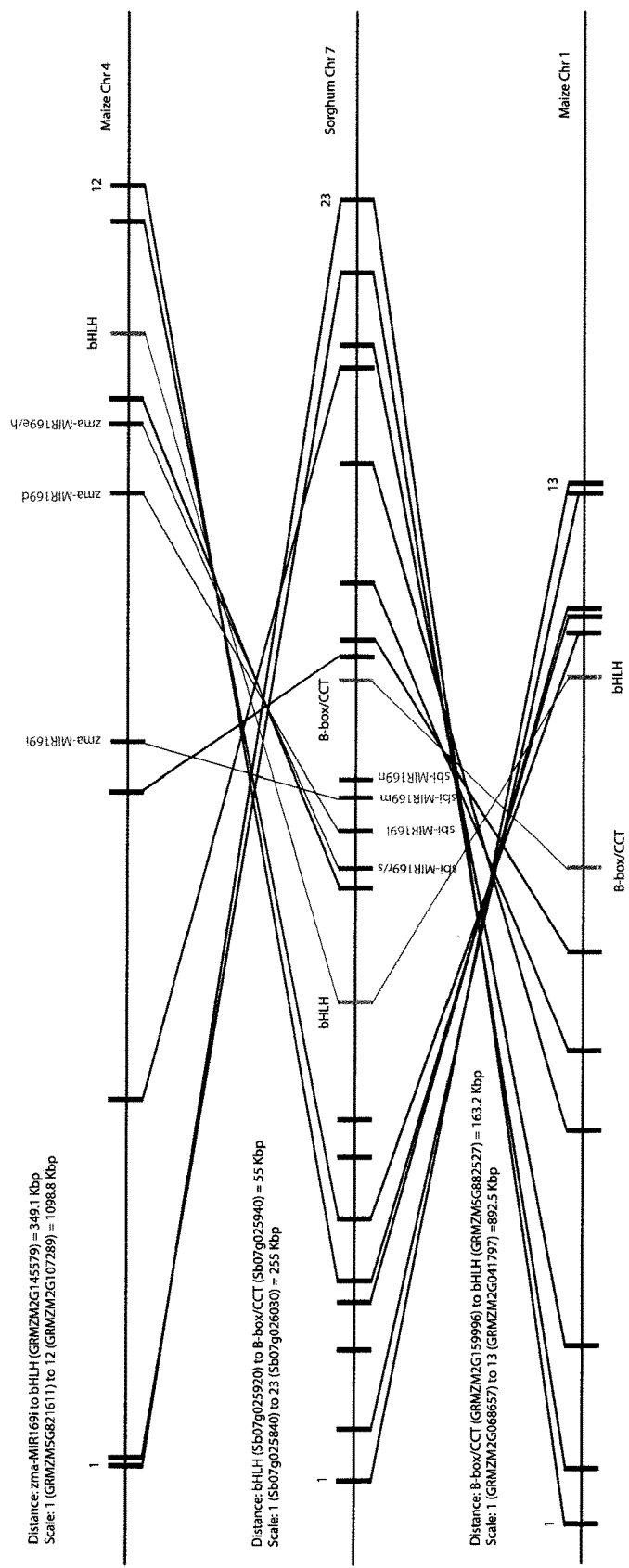
FIG. 15. Sequence alignment of sorghum chr7 segment containing MIR169 gene cluster to homoeologous chromosomal segments from maize. Sorghum sbi-MIR169r/s, sbi-MIR169l and sbi-MIR169m genes on chr7 are orthologous to maize zma-MIR169e/h; zma-MIR169d and zma-MIR169i respectively on chr4. Notice that the MIR169 cluster on the homoelogous region on maize chr1 was deleted although its flanking genes remained. The orthologous copy of sorghum B-box/CCT gene flanking the MIR169 gene cluster was lost on maize chr4 but retained on the homoelogous segment on chr1. Expansion in the maize genome relative to sorghum is clear when regions on maize chr1 and sorghum chr7 are compared. The region on sorghum chr7 is inverted relative to maize.

[1] In green color are microRNA genes identified in this study
[2] Chromosomal positions are based on Phytozome annotation for all the species except rice that is based on RAPDB annotation
[3] Distance within the cluster is calculated from the beginning of the first miRNA gene to the beginning of the last miRNA gene in the cluster We first analyzed the region containing the MIR169 cluster on sorghum chr7 because it had the highest number of gene copies. The alignment of sorghum genes flanking MIR169 copies to the rice genome permitted the identification of a collinear region on rice chr8 also containing a cluster of MIR169 gene copies (FIG. 13). Interestingly, the cluster on rice chr8 was composed of five MIR169 gene copies whereas the orthologous cluster on sorghum chr7 contained only three annotated MIR169 gene copies. Further investigation based on reciprocal Blastn analysis revealed that osa-MIR169l and osa-MIR169q are orthologous to a region on sorghum chr7, where there was no previous annotation of MIR169 genes. Indeed, by taking the sorghum DNA segment highly similar to osa-MIR169l and osa-MIR169q and subjecting it to an RNA folding program (RNAfold: available on the world wide web at rna.tbi.univie.ac.at/cgi-bin/RNAfold.cgi) in order to identify hairpin-like structures characteristic of microRNA precursors, we were able to discover two new MIR169 gene copies in sorghum that we named sbi-MIR169r and sbi-MIR169s, respectively (FIG. 13 and FIG. 14). Independent support for the new annotation of sbi-MIR169r and sbi-MIR169s was achieved through orthologous alignment of a third species, maize, through zma-MIR169e and zma-MIR169h gene copies (FIG. 15).

Figure 16:
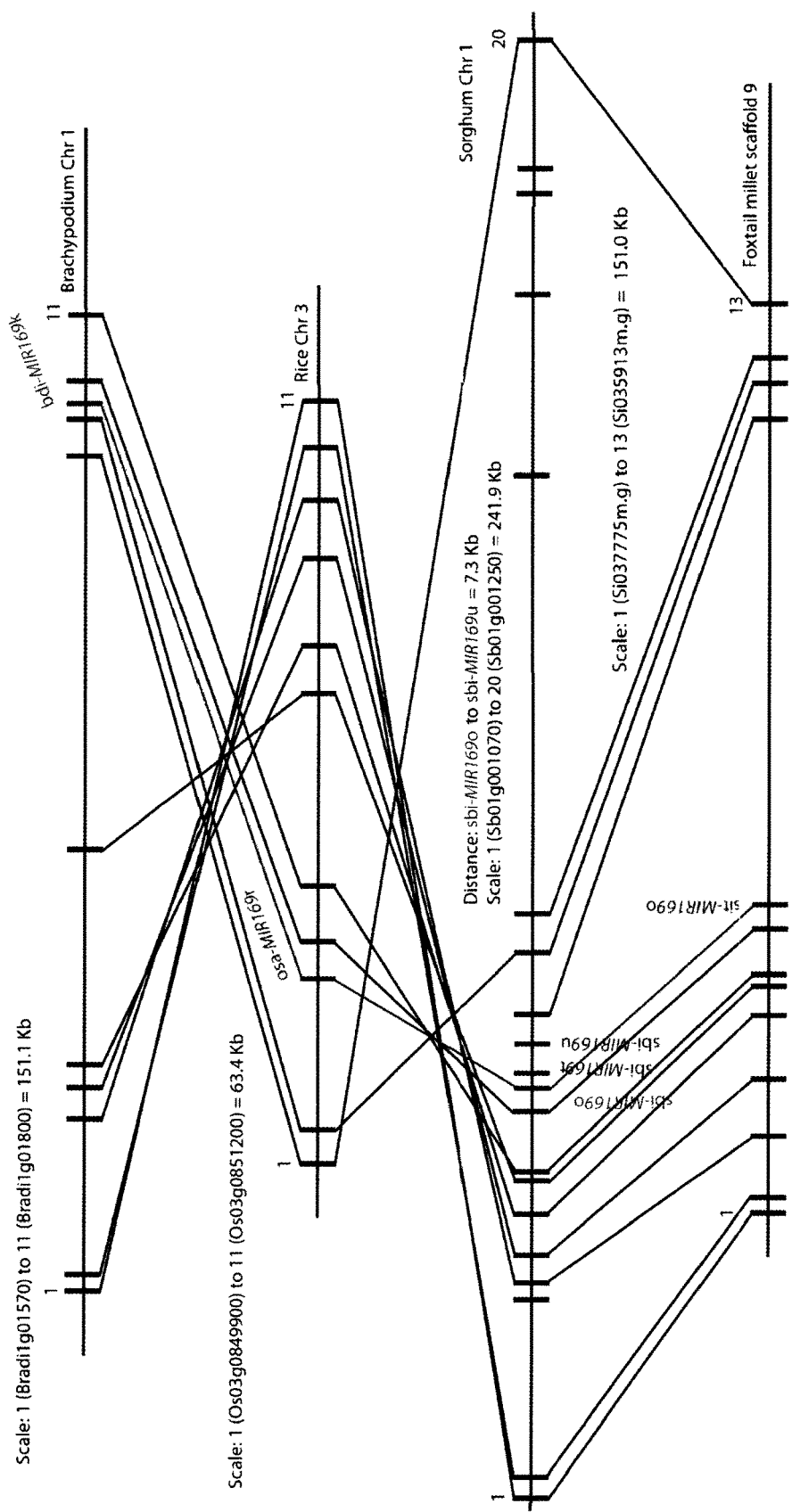
FIG. 16. Sequence alignment of sorghum MIR169 cluster on chr1 with orthologous regions from Brachypodium, rice and foxtail millet. The sbi-MIR169o copy in sorghum allowed the identification of the orthologous osa-MIR169r copy in rice and sit-MIR169o copy in foxtail millet respectively. For the region containing sbi-MIR169o/t/u on chr1, we could not find sufficient conservation of synteny to identify an orthologous region in sorghum, thus a synteny graph is only shown with sorghum chr1. An inversion event on rice chr3 occurred relative to Brachypodium, foxtail millet and sorghum.
Figure 17:
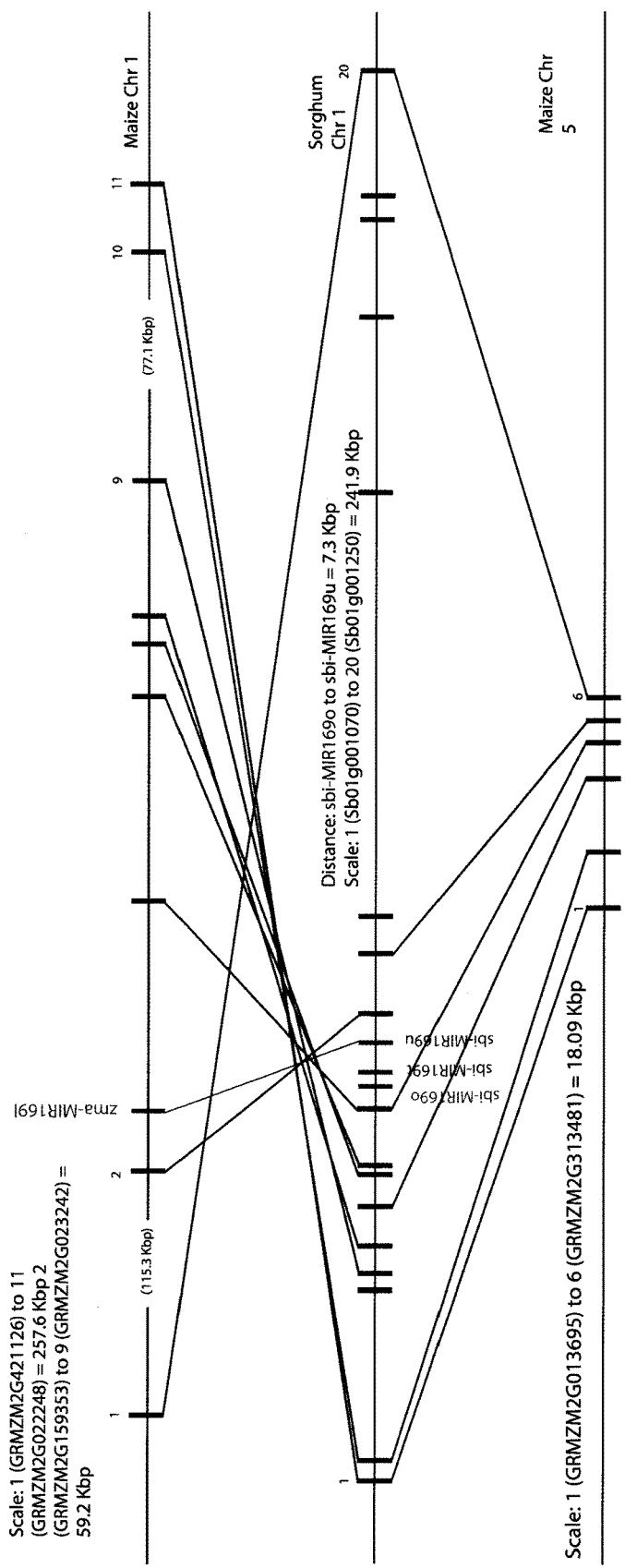
FIG. 17. Sequence alignment of sorghum MIR169 cluster on chr1 with orthologous regions from maize. Sorghum sbi-MIR169u and maize zma-MIR169l are orthologous copies. There isn't any orthologous MIR169 copy on maize homoeologous chr5. The region on maize chr1 is expanded (comprising a total of 257.6 Kbp) relative to the homoeologous region on chr5 (comprising 18.09 Kbp only). An inversion event occurred on maize homeologous region on chr1.

To identify additional MIR169 gene copies in sorghum that might have arisen by tandem duplication, we took each of the annotated MIR169 genes and performed Blastn analysis against the sorghum genome to search for new copies located in close proximity to any of the previously annotated ones. Such analysis identified two new MIR169 copies on sorghum chr1 when sbi-MIR169o was used as query that we named sbi-MIR169t and sbi-MIR169u, respectively (FIG. 14). Thus, sbi-MIR169o together with sbi-MIR169t and sbi-MIR169u constituted a new MIR169 cluster of the sorghum genome (Table 1, Example III). The segment containing the newly identified MIR169 cluster on sorghum chr1 was collinear with an orthologous segment of rice chr3 (FIG. 16), although no MIR169 gene had previously been found in this region. By performing reciprocal Blastn analysis with sbi-MIR169o against the rice genome we could identify the corresponding orthologous MIR169 copy on rice chr3 that we named osa-MIR169r (FIGS. 14 and 16). Furthermore, osa-MIR169r is contained within a segment that is collinear with an orthologous region of chr1 of a fourth species, *Brachypodium*, corresponding to bdi-MIR169k (FIG. 16). Comparison between sorghum and maize revealed that the MIR169 cluster on sorghum chr1 is collinear with a segment on maize chr1 that contains zma-MIR169l (FIG. 17). Indeed, sbi-MIR169u and zma-MIR169l are also orthologous gene copies. Finally, when the cluster on sorghum chr2 containing sbi-MIR169f and sbi-MIR169g was analyzed, collinearity with the segment on sorghum chr7 containing the sbi-MIR169r/s and sbi-MIR169l-n cluster revealed the existence of an additional MIR169 copy on sorghum chr2 that we named sbi-MIR169v (FIG. 13; FIG. 14; Table 1, Example III). Furthermore, the sbi-MIR169f/g/v cluster is syntenic with a region on maize chr7 containing zma-MIR169k and its homoeologous region on maize chr2 containing zma-MIR169j and the newly identified zma-MIR169s gene copy (FIG. 14 and FIG. 18; Table 1, Example III).

In summary, by aligning sorghum chromosomal segments containing MIR169 clusters with orthologous regions of *Brachypodium*, rice, and maize we were able to identify 5 additional MIR169 copies in sorghum and an additional copy in rice and maize, respectively.

New MIR169 Clusters in the Recently Sequenced Foxtail Millet Genome

The recent release of the complete reference genome sequence for foxtail millet (*Setaria italica*) (Bennetzen, et al. 2012; Zhang, et al. 2012) greatly enhances comparative genomics analysis within the Poaceae, with genome sequences available from five species. Foxtail millet provided us with additional information to study syntenic relationships with sorghum because they split from each other about 26 million years (myr) ago (Zhang, et al. 2012). Indeed, 19 collinear blocks were found between foxtail millet and sorghum, which comprised about 72% of the foxtail millet genome (Zhang, et al. 2012). Consequently, we could use sorghum to identify and predict MIR169 gene copies in the foxtail millet genome. We identified and predicted MIR169 copies in foxtail millet, collinear with sorghum MIR169 copies, arranged in clusters on chr1, chr2, and chr7, respectively. The sorghum MIR169 cluster on chr1 was collinear with a segment on chr9 of foxtail millet, from which sit-MIR169o was identified as the ortholog of sbi-MIR169o (FIG. 16; FIG. 14; Table 1, Example III). The sorghum MIR169 copies arranged in cluster on chr7 were collinear with a segment on chr6 from foxtail millet that harbored the newly identified orthologous MIR169 copies sit-MIR169i, sit-MIR169j, sit-MIR169k, sit-MIR169r, and sit-MIR169s (FIG. 19; FIG. 14; Table 1, Example III). Finally, tandem sorghum MIR169 copies on chr2 were collinear with a segment on foxtail millet chr2 that contained the three newly predicted MIR169 copies sit-MIR169f, sit-MIR169g and sit-MIR169h (FIG. 20; FIG. 14; Table 1, Example III).

In summary, we used sorghum as a reference genome to identify and predict nine MIR169 gene copies that were collinear with foxtail millet. The prediction of MIR169 genes in the foxtail millet will greatly facilitate their experimental validation through the sequencing of small RNAs from different tissues and developmental stages.

Gain and Losses of MIR169 Gene Copies During Grass Evolution

Figure 19:
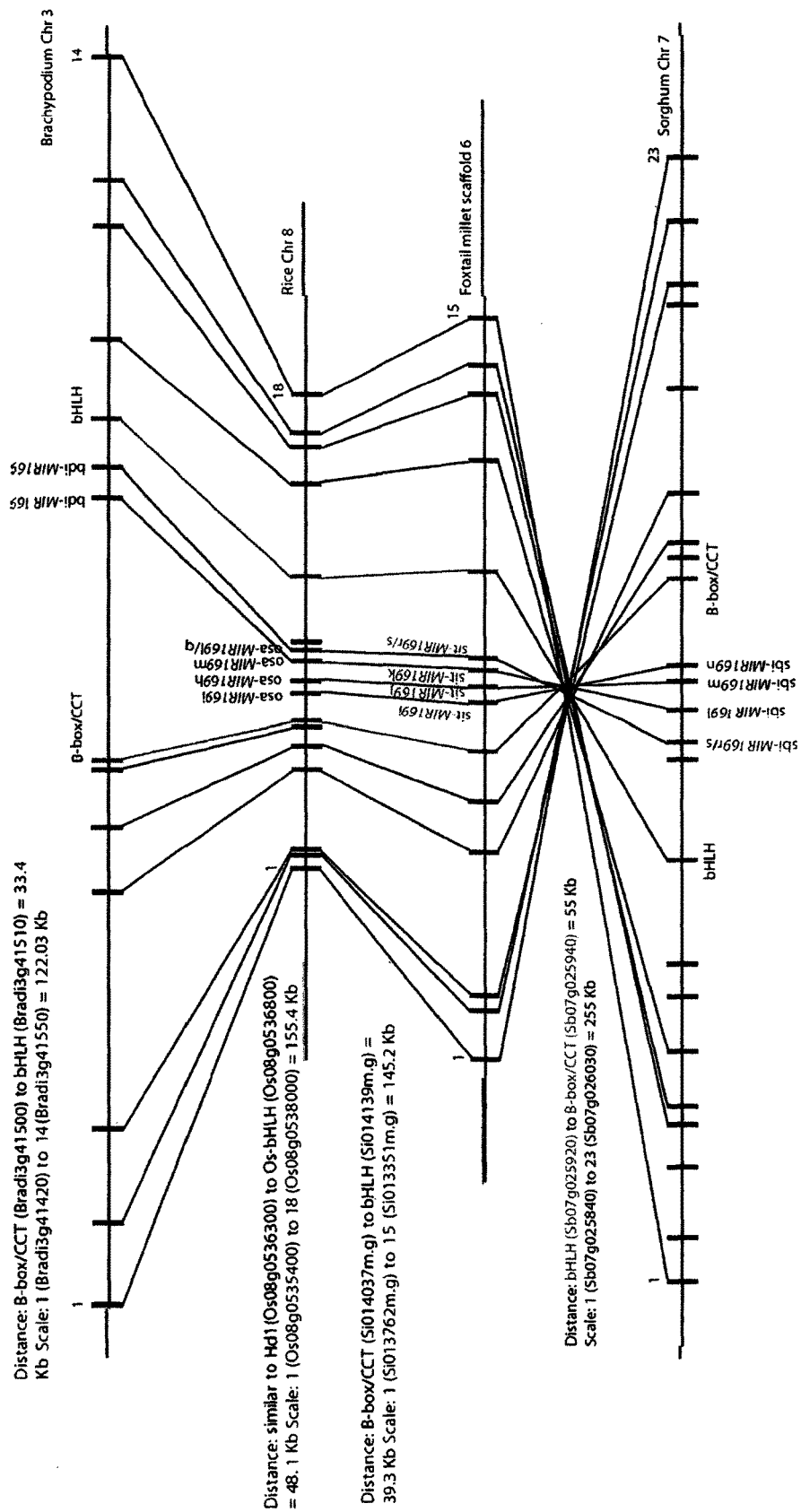
FIG. 19. Sequence alignment of sorghum MIR169 cluster on chr7 with orthologous regions from Brachypodium, rice and foxtail millet. Rice and sorghum MIR169 gene copies were used to identify and annotate five MIR169 genes in foxtail millet (shown in green). The bHLH and B-box/CCT genes were physically adjacent to MIR169 gene copies in the four species examined. The region examined on sorghum chr7 expanded relative to the orthologous region from the other three grasses and was inverted only in sorghum.
Figure 20:
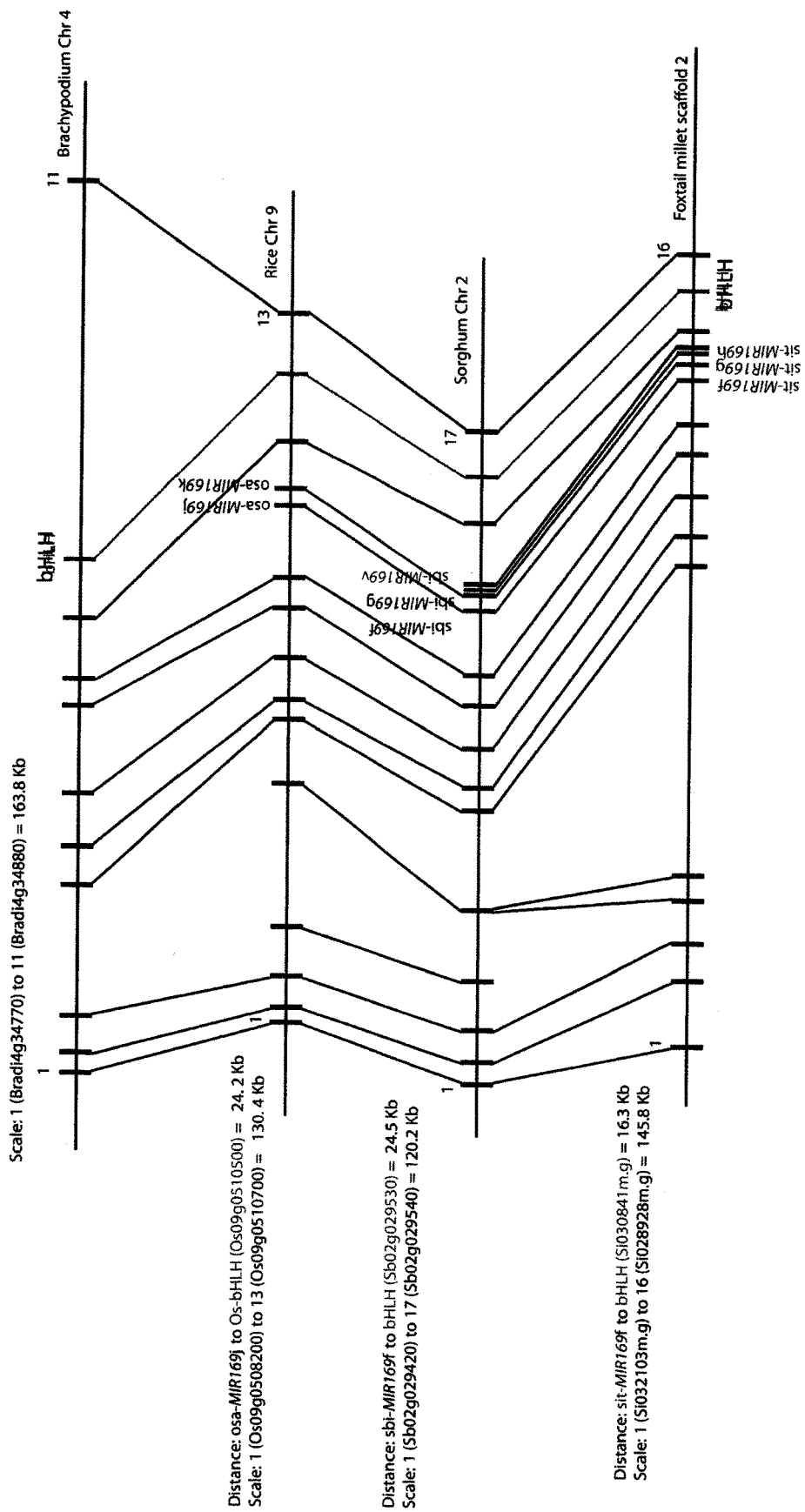
FIG. 20. Sequence alignment of sorghum MIR169 cluster on chr2 with orthologous regions from Brachypodium, rice and foxtail millet. MIR169 gene copies were deleted from Brachypodium chr4 but the flanking genes remained. The MIR169 gene cluster in rice was composed of two copies whereas in sorghum and foxtail millet the cluster comprised three copies. The bHLH gene was present in all four grasses and was physically adjacent to MIR169 gene copies in rice, sorghum and foxtail millet. Sorghum MIR169 gene copies were used to identify and annotate the orthologous copies on foxtail millet scaffold 2 (shown in green).
Figure 21A:
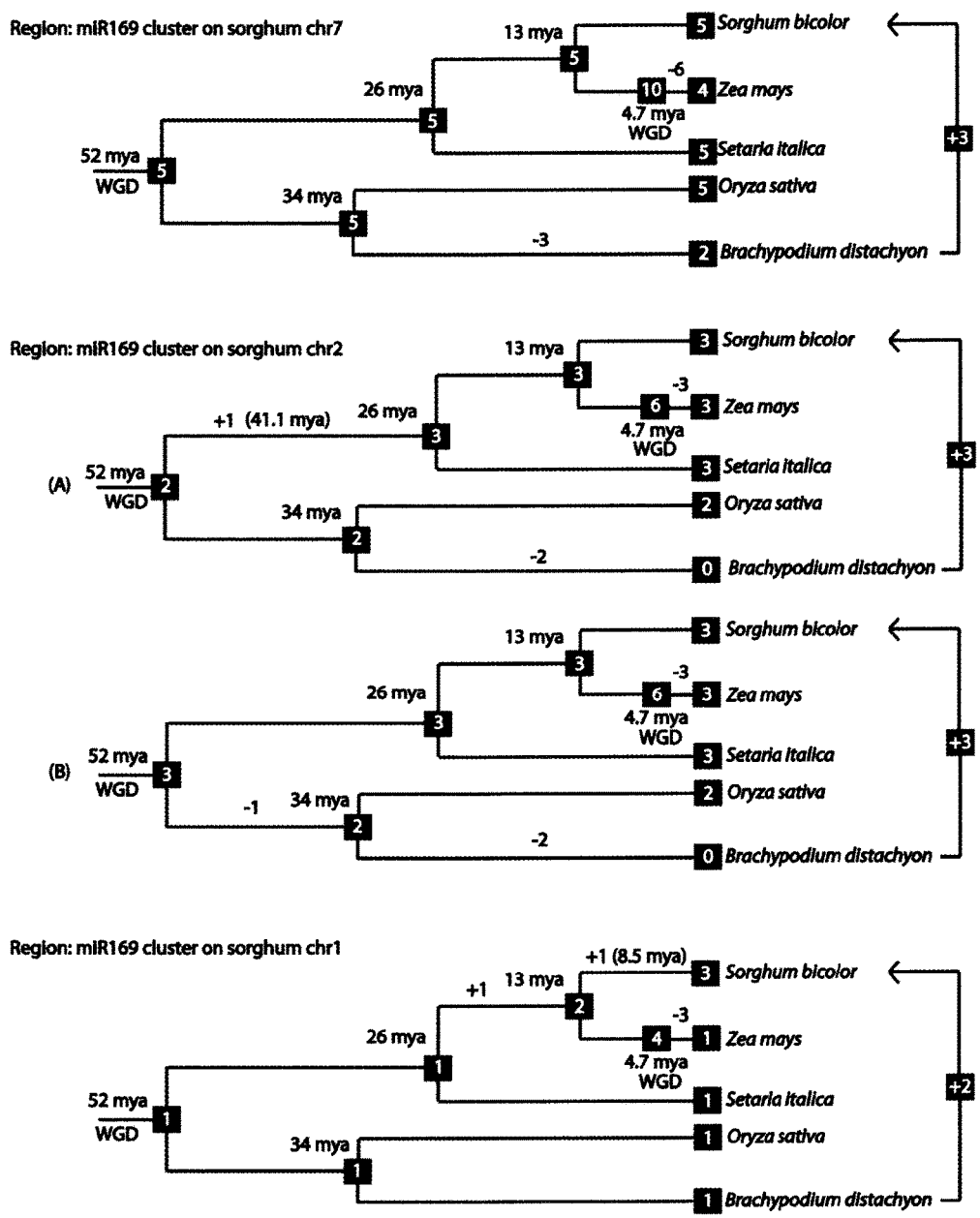
FIGS. 21A-21D. Gains and losses of MIR169 gene copies during grass evolution.
Figure 21B:
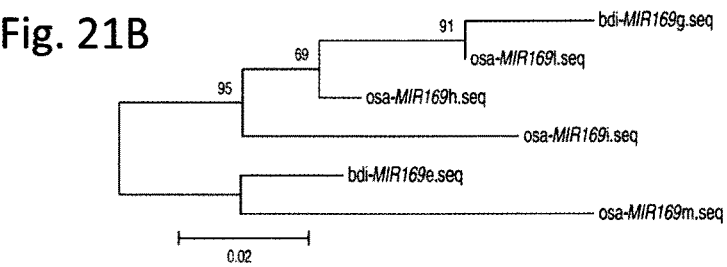

To determine expansion and contraction of the MIR169 gene clusters, we aligned collinear chromosomal segments of diploid *Brachypodium*, rice and foxtail millet, and the two homoeologous regions of allotetraploid maize. Based on nucleotide substitution rates, the cluster of MIR169 copies on sorghum chr7 was likely preserved from an ancestral grass chromosome and comprised five MIR169 gene copies, from which three of them were deleted in *Brachypodium* after the split of *Brachypodium* from the ancestor of rice, foxtail millet, and sorghum (FIGS. 19, and 21A and 21B). The number of MIR169 genes (five copies per cluster) was unchanged in rice, sorghum, and foxtail millet, whereas in maize four copies were retained on orthologous homoeologous region on chr4 but none on the homoeologous region on chr1 (FIG. 15 and FIG. 21A). Although the MIR169 copies were deleted from maize chr1, the flanking genes remained intact.

Figure 21C:
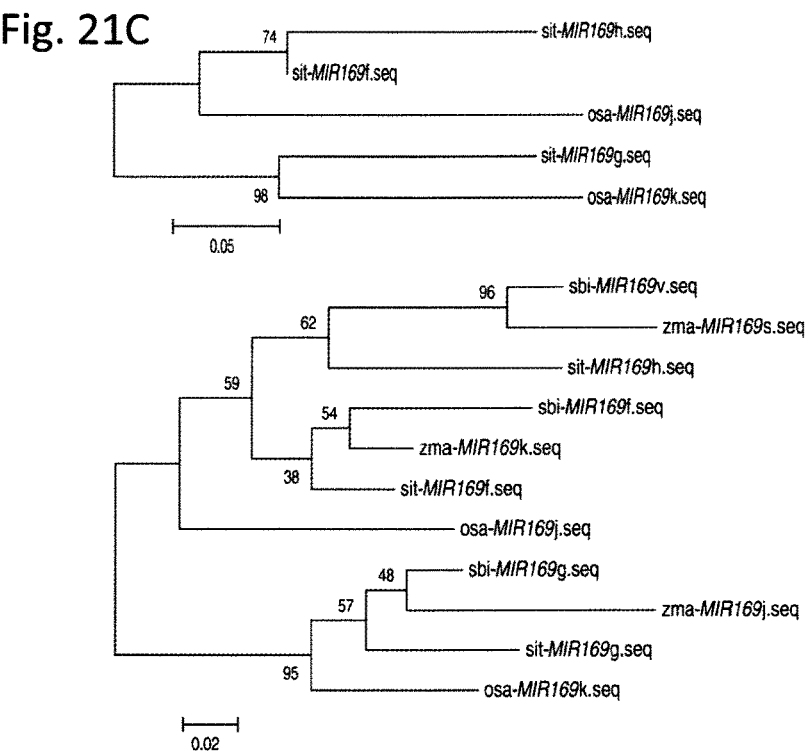

In the case of the MIR169 cluster on sorghum chr2, its evolution can be explained according to two models (FIG. 21A). In the first one, the ancestor of the grasses had two MIR169 copies and they were conserved before the split of *Brachypodium* and rice, with *Brachypodium* losing these two MIR169 copies were rice maintained them. An additional copy was gained in the common ancestor of foxtail millet, sorghum and maize, giving rise to a cluster with three MIR169 gene copies. Phylogenetic analysis suggested that the new copy in the ancestor of foxtail millet, sorghum, and maize was the ancestral copy that gave rise to sit-MIR169h, sbi-MIR169v and zma-MIR169s, respectively (FIG. 21C). We estimated that the time at which this copy arose in the progenitor of foxtail millet, sorghum and maize was about 41.1 mya (see methods section for estimation of time of duplication). Alternatively, the common ancestor of the grasses could have had three MIR169 gene copies and one copy was lost in the common ancestor of *Brachypodium* and rice, with a subsequent loss of two additional MIR169 gene copies in *Brachypodium* relative to rice (FIG. 21A).

Figure 21D:
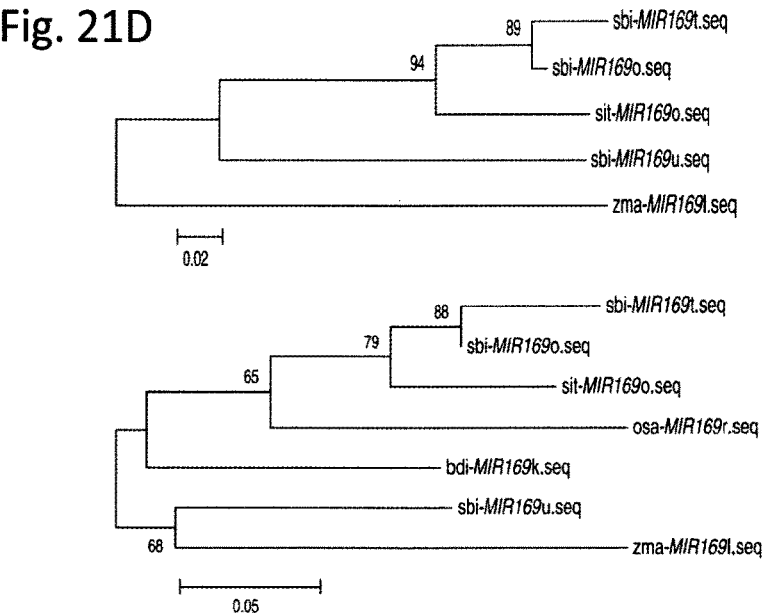

Regarding the cluster of MIR169 copies on sorghum chr1, we favor a model where the ancestor of the grasses had a single MIR169 copy because *Brachypodium*, rice and foxtail millet all have a single MIR169 copy (FIG. 21D). Thus, the additional two MIR169 copies present in the sorghum cluster could have arisen via duplication events. Phylogenetic analysis suggested that the ancestral copy in the cluster was sbi-MIR169o, from which sbi-MIR169t subsequently duplicated 8.5 mya (see methods) (FIG. 21D). Thus, sbi-MIR169t was acquired specifically in the sorghum lineage. Since sbi-MIR169u and zma-MIR169l are highly related but distantly related from sbi-MIR169o and sbi-MIR169t (FIG. 21D), we postulate that the ancestral copy of sbi-MIR169u and zma-MIR169l was inserted next to the other MIR169 gene copies in the progenitor of sorghum and maize. In the maize lineage, diploidization after allotetraploidization led to the deletion of the corresponding orthologous MIR169 copy from the homoeologous segment on chr5, whereas the flanking genes remained conserved (FIG. 17).

Figure 18:
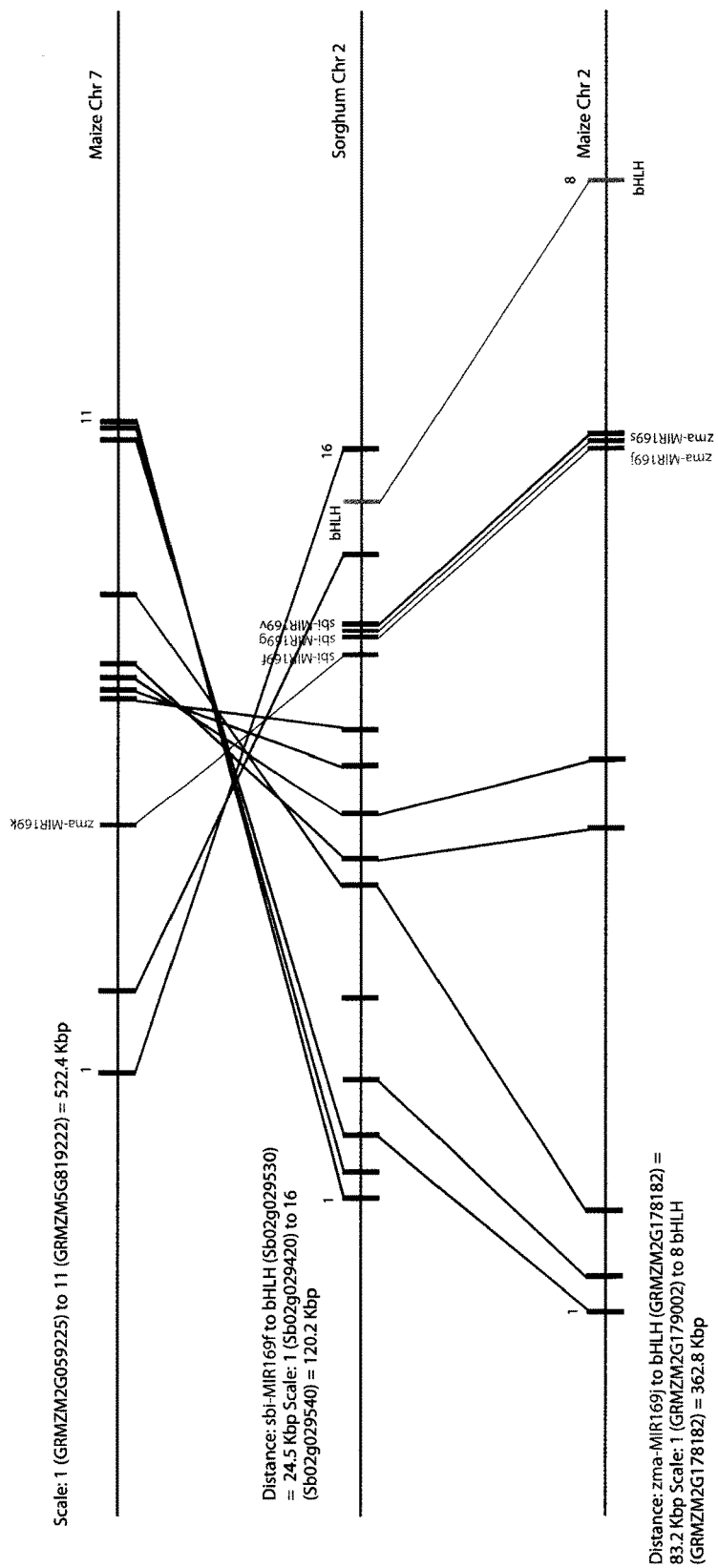
FIG. 18. Sequence alignment of sorghum MIR169 cluster on chr2 with orthologous regions from maize. Sorghum MIR169 gene cluster on chr2 is colinear with a region on maize chr7 that contains zma-MIR169k, and with the homeologous region on maize chr2 that contains the previously annotated zma-MIR169j and the new copy zma-MIR169s that is described in this study. Although the MIR169 gene cluster on maize chr2 is physically adjacent to the bHLH gene, similarly with the MIR169 gene cluster on sorghum chr2, the homeologous region containing zma-MIR169k lacked the bHLH gene copy. An inversion event on maize chr7 occurred relative to its homeologous region on chr2 and to sorghum chr2.

In summary, differences in MIR169 copy number between clusters from *Brachypodium*, rice, foxtail millet, sorghum and maize arose by duplication of ancestral MIR169 genes that were retained or lost during grass evolution. Overall, sorghum gained eight MIR169 copies relative to *Brachypodium*, three copies relative to rice, two copies relative to foxtail millet and three copies relative to maize. Polymorphisms in chromosomal inversions containing MIR169 clusters Through the analysis of three chromosomal regions in sorghum containing MIR169 clusters and their alignment with the genomes of *Brachypodium*, rice, foxtail millet, and maize we were able to identify four chromosomal inversions in total, one in rice chr3 containing osa-MIR169r (FIG. 16), a second on sorghum chr7 containing sbi-MIR169r, sbi-MIR169s, sbi-MIR169l, sbi-MIR169m and sbi-MIR169n (FIG. 13), a third on maize chr1 containing zma-MIR169l (FIG. 17) and the fourth on maize chr7 containing zma-MIR169k (FIG. 18), respectively. The inversion on rice chr3 was absent from the corresponding collinear regions on *Brachypodium* chr1, sorghum chr1 and foxtail millet chr9 (FIG. 16), indicating that the inversion happened after the split of rice from the common ancestor of sorghum and foxtail millet. The region on sorghum chr1 containing sbi-MIR169o, sbi-MIR169t and sbi-MIR169u that was collinear with the inverted segment on rice chr3 was also collinear with an inverted segment on the homoeologous region of maize chr1 containing zma-MIR169l (FIG. 16). However, the inversion did not occur on the homoeologous region on maize chr5, indicating that the inversion occurred after the allotetraploidization event that took place in maize. The inversion on sorghum chr7 containing sbi-MIR169r, sbi-MIR169s, sbi-MIR169l, sbi-MIR169m and sbi-MIR169n cluster only occurred in this species (FIG. 15 and FIG. 19), suggesting that it took place after the split of sorghum from the common ancestor of sorghum and maize. The MIR169 cluster on sorghum chr2 was collinear with an inverted region on maize chr7 containing zma-MIR169k (FIG. 18). The homologous region on chr2 did not exhibit the inversion, suggesting that it took place after the allotetraploidization event that occurred in maize.

In summary, four inversions containing MIR169 copies were found in total, one in rice, one in sorghum and two in maize. These inversions were lineage specific as none of them was present in a collinear region in the genome of a second grass species, indicating that these inversions happened after the species were formed.

Validation of Newly Identified MIR169 Gene Copies in Sorghum and Maize

In order to experimentally validate the new MIR169 gene copies found in sorghum through our syntenic analysis among grasses, we mapped previously sequenced small RNAs from sorghum stems to the newly predicted MIR169t/u/v/r/s hairpins. Similarly, to validate the newly described zma-MIR169s gene copy in maize, we constructed small RNA libraries from endosperm tissue belonging to cultivars B73, Mo17 and their reciprocal crosses (Table 2, Example III). Maize endosperm-derived small RNAs were then mapped to the new MIR169s hairpin annotated in this study. We could effectively map small RNA reads to the stem-loop sequences of all five predicted microRNA169 in sorghum (with respect of sbi-MIR169r/s see next section). In the case of sbi-MIR169t and sbi-MIR169u, the most abundant small RNA reads were derived from the miR169* sequence (FIG. 22) although small RNAs derived from the canonical miR169 sequence were also found but in less abundance. The experimental validation of sbi-MIR169v was supported with mapping of small RNAs to the corresponding predicted mature miR169v sequence (FIG. 22). Regarding the experimental validation of the predicted zma-MIR169s copy in maize, we were able to detect small RNA reads derived from miR169s although their abundance was very low.

TABLE 2, Ex. III

Deep sequencing statistics of maize endosperm-derived small RNAs

| Library | # Raw Sequences | # Sequences With Perfect Match to B73 Genome | % |
| --- | --- | --- | --- |
| B73 | 14,371,575 | 3,805,955 | 26.48 |
| Mo17 | 16,207,393 | 7,688,661 | 47.44 |
| B73 x Mo17 | 13,051,982 | 5,985,649 | 45.86 |
| Mo17 x B73 | 19,924,315 | 6,514,306 | 32.7 |

Antisense microRNA169 Gene Pairs Generate Small RNAs that Target Different Set of Genes In rice, osa-MIR169l and osa-MIR169q were annotated as antisense microRNAs and small RNA reads derived from both strands were identified (Xue, et al. 2009). In sorghum, sbi-MIR169r, and sbi-MIR169s are collinear with osa-MIR169l/q (FIGS. 2 and 8) and are antisense microRNAs as well (FIGS. 14 and 21A). Despite the lack of EST evidence for sbi-MIR169r and sbi-MIR169s annotation, our previously generated small RNA library from sorghum stem tissue (Calvino, et al. 2011) supported the transcription from both strands based on small RNA reads mapped to both sbi-MIR169r and sbi-MIR169s, respectively (FIG. 23A). Similarly, EST evidence supported the transcription from opposite strands in the microRNA antisense pair zma-MIR169e/h (ESTs ZM_BFb0354L14.r and ZM_BFb0294A24.f, respectively). Because small RNAs derived from zma-MIR169e/h had not been previously reported (miRBase database: release 19, August 2012), we used the SOLiD system to sequence small RNAs from endosperm tissue derived from B73 and Mo17 cultivars and their reciprocal crosses, however we could not detect small RNA reads derived from them, at least in endosperm tissue. Thus, antisense microRNAs from MIR169 gene copies are being actively produced in rice and sorghum, and possibly in maize.

With respect to sbi-MIR169r/s antisense gene pair, we found that the small RNA reads mapped to sbi-MIR169r were predominantly associated with the miR169r* sequence (FIG. 23A). The mature miRNA sequences for sbi-miR169r* and sbi-miR169s differed from each other in 7 nucleotides (FIG. 23B). Moreover, they would have different set of genes as targets based on their sequences (FIGS. 24 and 25). Moreover, the assumption that also microRNA* have functional roles was recently described (Meng, et al. 2011; Yang, et al. 2011).

Linkage of MIR169 Gene Copies with Flowering and Plant Height Genes

Figure 26:
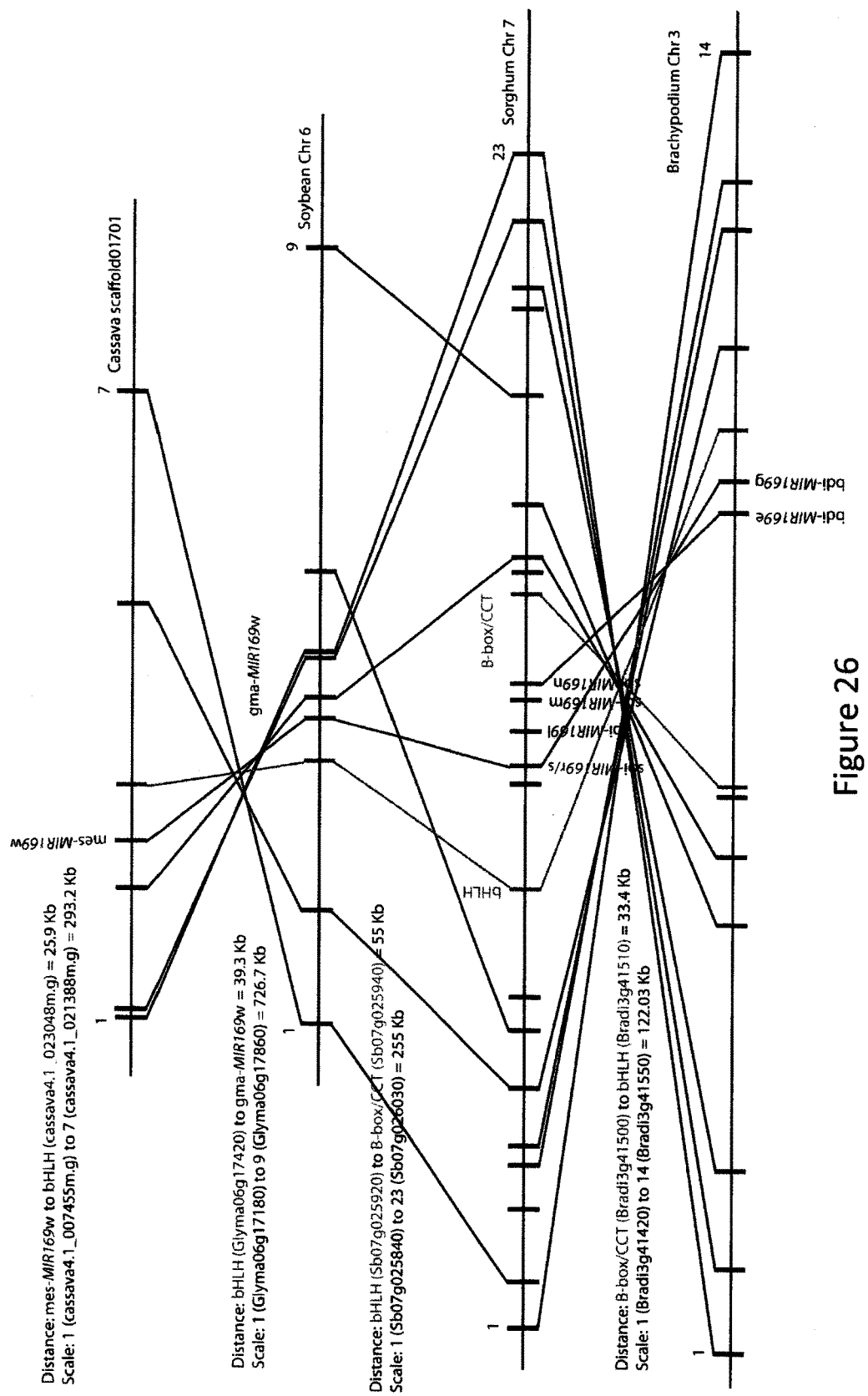
FIG. 26. Sequence alignment of sorghum MIR169 cluster on chr7 with orthologous regions from Brachypodium, soybean and cassava. There is conservation of synteny between monocot species Brachypodium and sorghum and dicot species soybean and cassava when chromosomal segments containing MIR169 gene copies and their flanking genes are aligned. Conservation of synteny allowed the identification of new MIR169 gene copies on soybean chromosome 6 (gma-MIR169w) and cassava scaffold 01701 (mes-MIR169w), respectively. Physical association on the chromosome between MIR169 and the flanking bHLH gene was retained in soybean and cassava as well. Notice the inversion on soybean chr6.
Figure 27:
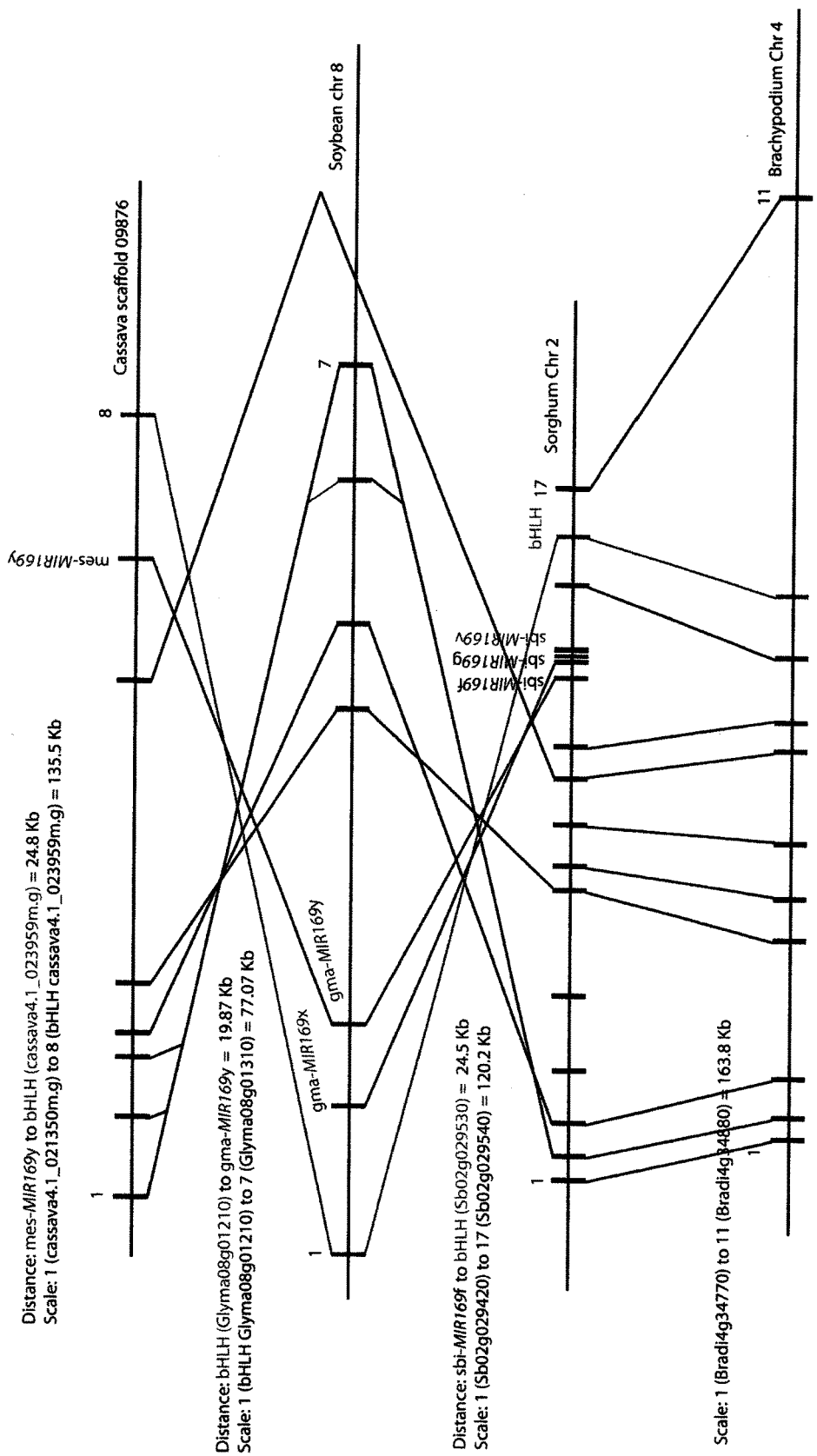
FIG. 27. Sequence alignment of sorghum MIR169 cluster on chr2 with orthologous regions from Brachypodium, soybean and cassava. The alignment of sorghum MIR169 cluster on chr2 with soybean chr8 and cassava scaffold 09876 allowed the identification of two new MIR169 gene copies in soybean (gma-MIR169x and gma-MIR169y) and one new copy in cassava (mes-MIR169y), respectively. The physical association of MIR169 gene copies with the bHLH was retained in soybean and cassava. An inversion occurred on soybean chr8.
Figure 28:
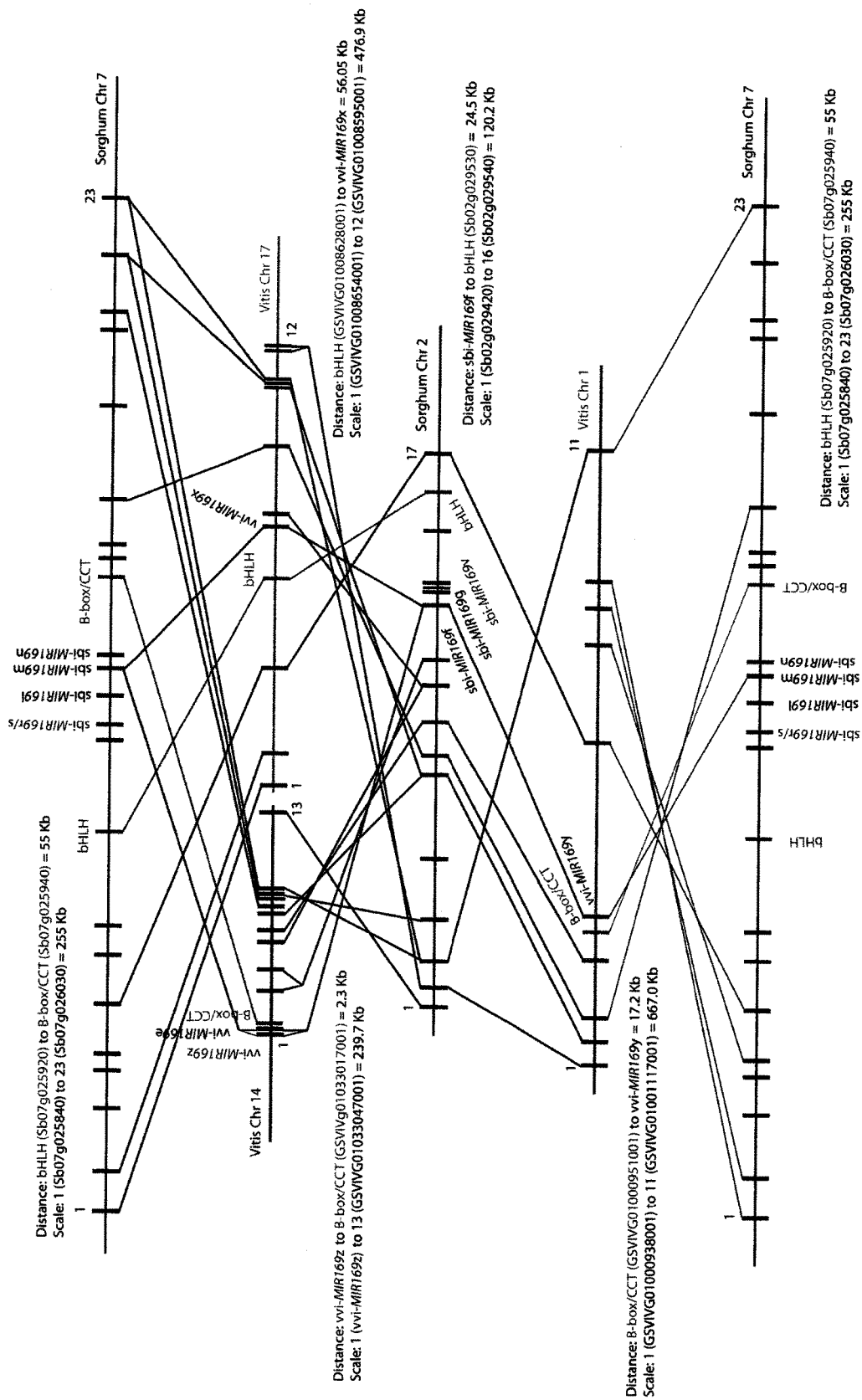
FIG. 28. Conservation of synteny between sorghum and grapevine chromosomal segments containing MIR169 gene copies. Sorghum segments containing MIR169 gene clusters from chr2 and chr7 were aligned to the grapevine genome based on orthologous gene pairs. Because grapevine is a hexopaleo-polyploid, we found a 2:3 chromosomal relationship between sorghum and grapevine. Colinearity allowed the identification of a new MIR169 copy (vvi-MIR169z) in grapevine chr14. Different grapevine chromosomes are represented in colors whereas sorghum chromosomes are in black. Relative to sorghum chr2, grapevine had in inversion event on chr14 and chr17. The association of MIR169 with its flanking COL gene was maintained on grapevine chr14 and chr1 whereas the association of MIR169 with the bHLH gene was maintained on chr1.

Based on the alignment of collinear regions containing MIR169 genes located on sorghum chr2 and chr7, we noticed a tight linkage of MIR169 copies with two genes encoding a bHLH protein, and a B-box zinc finger and CCT-motif protein that were similar to *Arabidopsis* bHLH137 and CONSTANS-LIKE 14 proteins (FIGS. 13, 19 and 20 and FIGS. 15 and 18). The *Arabidopsis* bHLH137 and COL14 genes were described to have a role in gibberellin signaling (mutations in genes involved in gibberellin signaling and/or perception affects plant height (Fernandez, et al. 2009)) and flowering time, respectively (Griffiths, et al. 2003; Wenkel, et al. 2006; Zentella, et al. 2007). The physical linkage of MIR169 gene copies to bHLH and COL genes (or any of the two) was present in all of the five grasses examined. We hypothesized that the physical association of MIR169 to either of these flowering and/or plant height genes could be of relevance because of previously reported trade-offs in sorghum between sugar content in stems and plant height and flowering time, respectively (Murray, et al. 2008). For breeding purposes, the introgression of a particular gene/phenotype from a specific cultivar into another would consequently also bring in the neighboring gene, a process known as linkage drag. Furthermore, linkage drag between MIR169 copies and the bHLH and COL genes could also be of ecological importance because a single chromosomal segment comprises genes involved in drought tolerance, sugar accumulation, and flowering. If this is case, linkage of MIR169 copies to either bHLH or COL genes could have been preserved even after the monocotyledoneous diversification. Indeed, we were able to find collinearity between chromosomal segments containing MIR169 and bHLH genes from *Brachypodium*, sorghum, soybean, and cassava (FIG. 26). Moreover, we found that the physical linkage between MIR169 and the bHLH gene on sorghum chr7 was retained in collinear regions of soybean chr6 and cassava scaffold 01701, respectively (FIG. 26). Similarly, the physical/genetic association of MIR169 with the bHLH gene from sorghum chr2 was retained in the corresponding collinear regions from soybean chr8 and cassava scaffold 09876 (FIG. 27). Interestingly, the linkage between MIR169 and the COL gene that was present in *Brachypodium* chr3 and sorghum chr7 was broken in the corresponding collinear regions of soybean chr6 and cassava scaffold 01701 (FIG. 26). We then compared the two MIR169 clusters from sorghum chr2 and chr7 to the grapevine genome because grapevine and sorghum are more closely related than sorghum to soybean and cassava, respectively. Our comparison revealed a two-to-three relationship between sorghum and grapevine (FIG. 28), and this is consistent with the palaeo-hexaploidy event that took place in the grapevine genome (Jaillon, et al. 2007). The physical/genetic linkage of MIR169 copies with the COL gene on sorghum chr7 was preserved in two out of the three homoeologous chromosomal segments in grapevine on chr1 and chr14, whereas the third homoeologous segment on chr17 retained the close association of MIR169 with the bHLH gene.

The finding of micro-synteny conservation between monocots and dicots species in chromosomal segments containing MIR169 gene copies together with bHLH and COL genes is remarkable because the estimated time of divergence between monocots and dicots is about 130-240 million years ago (mya) (Jaillon, et al. 2007; Wolfe, et al. 1989). Such micro-synteny conservation permitted the discovery of new MIR169 gene copies in soybean (gma-MIR169w, gma-MIR169x and gma-MIR169y), cassava (mes-MIR169w and mes-MIR169y) and grapevine (vvi-MIR169z).

Subfunctionalization of the bHLH Gene in the MIR169 Cluster of *Brachypodium*

Figure 29A:
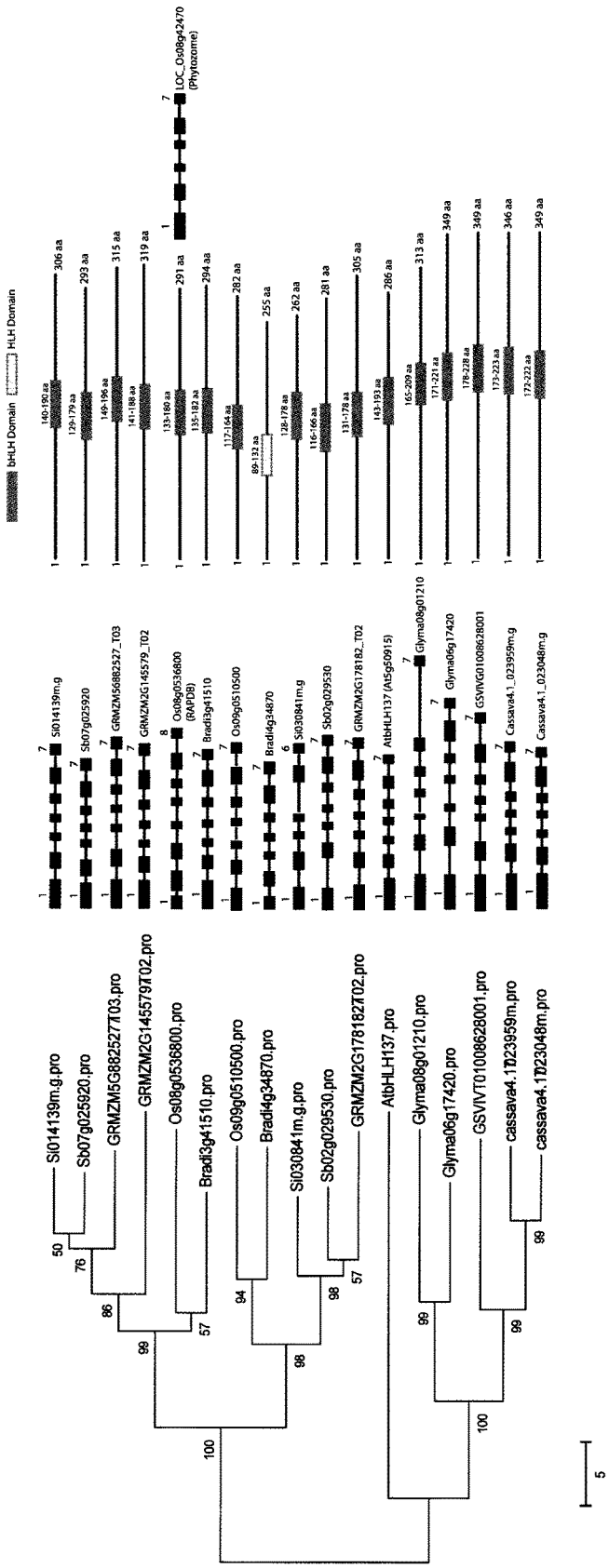
FIGS. 29A-29C. Sub-functionalization of *Brachypodium* bHLH gene copy.
Figure 29B:
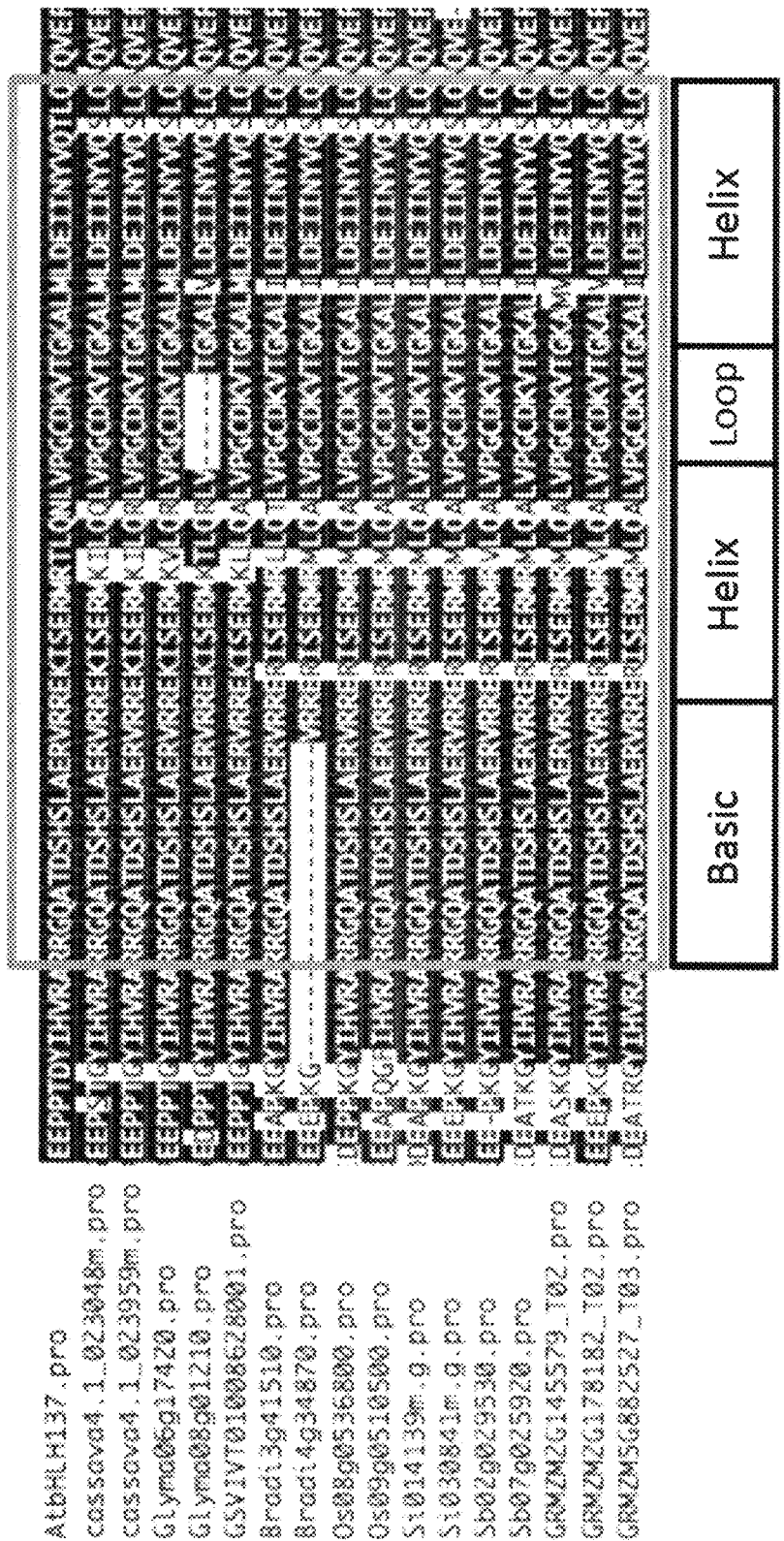
Figure 29C:
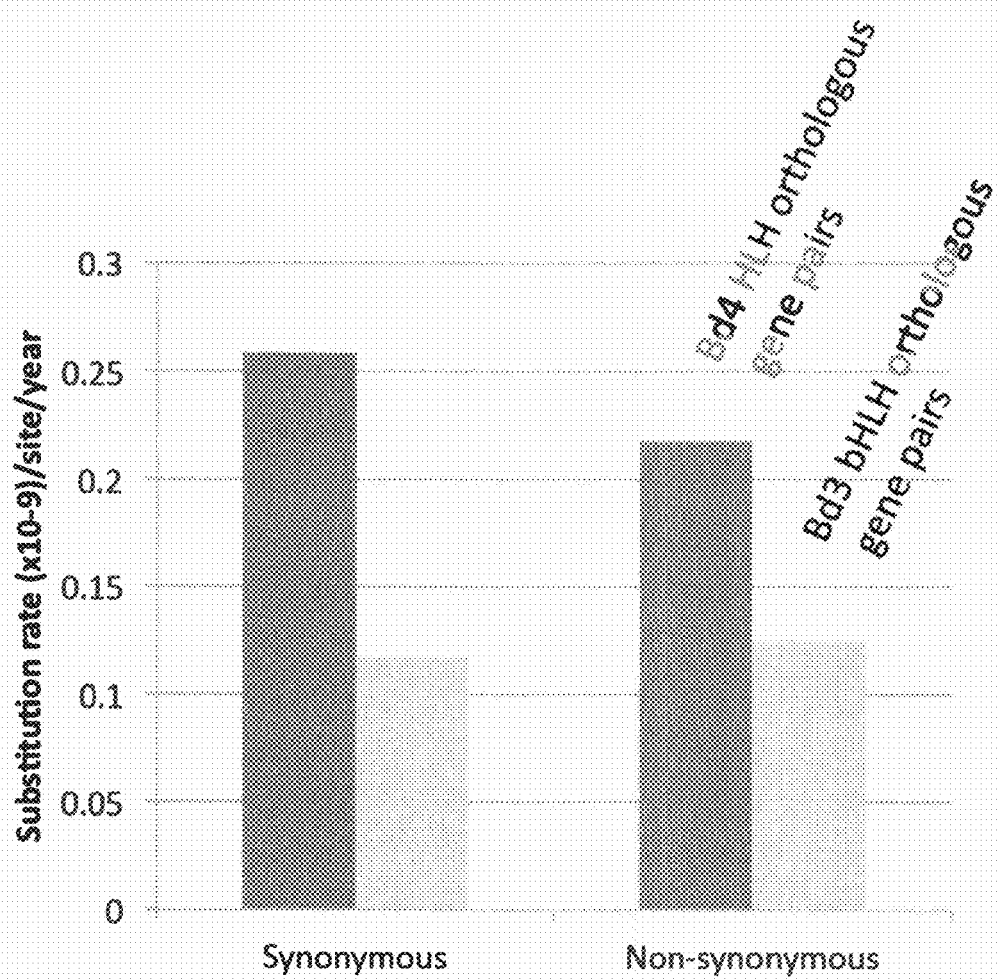

The microsynteny in chromosomal segments containing miR169 gene copies flanked by the bHLH gene among such distantly related species such as *Brachypodium* and cassava suggests that the linkage between miR169 and bHLH resulted from selection because of the divergence from a common ancestor about 130-240 mya. In support of this interpretation, the bHLH gene on *Brachypodium* chr4, where the miR169 cluster had been deleted, appeared to have undergone sub-functionalization. First, the bHLH copy on *Brachypodium* chr4 involved the loss of the basic domain, which is involved in DNA binding (Toledo-Ortiz 2003) and thus evolved into a HLH protein (FIGS. 29A and 29B). Because bHLH proteins act as homo- and/or heterodimers, where the basic domain of each bHLH protein bind DNA, HLH proteins homo- or heterodimerize and prevent the binding of the complex to DNA and thus becomes a negative regulator (Toledo-Ortiz 2003). Second, *Brachypodium* has a redundant intact orthologous copy on chr3, also a miR169 cluster next to it (FIG. 29). Third, the synonymous and non-synonymous substitution rate of the HLH orthologous gene pairs was higher than the synonymous and non-synonymous substitution rate in the bHLH orthologous gene pairs, respectively (FIG. 29C). Fourth, when we run a test for detecting adaptive evolution [calculated as the number of replacement mutations per replacement sites (dN) divided by the number of silent mutations per silent site (dS)] in the bHLH and HLH coding sequences, we found evidence on purifying selection on the HLH gene sequence (dN/dS ratio of −4.647).

Figure 30A:
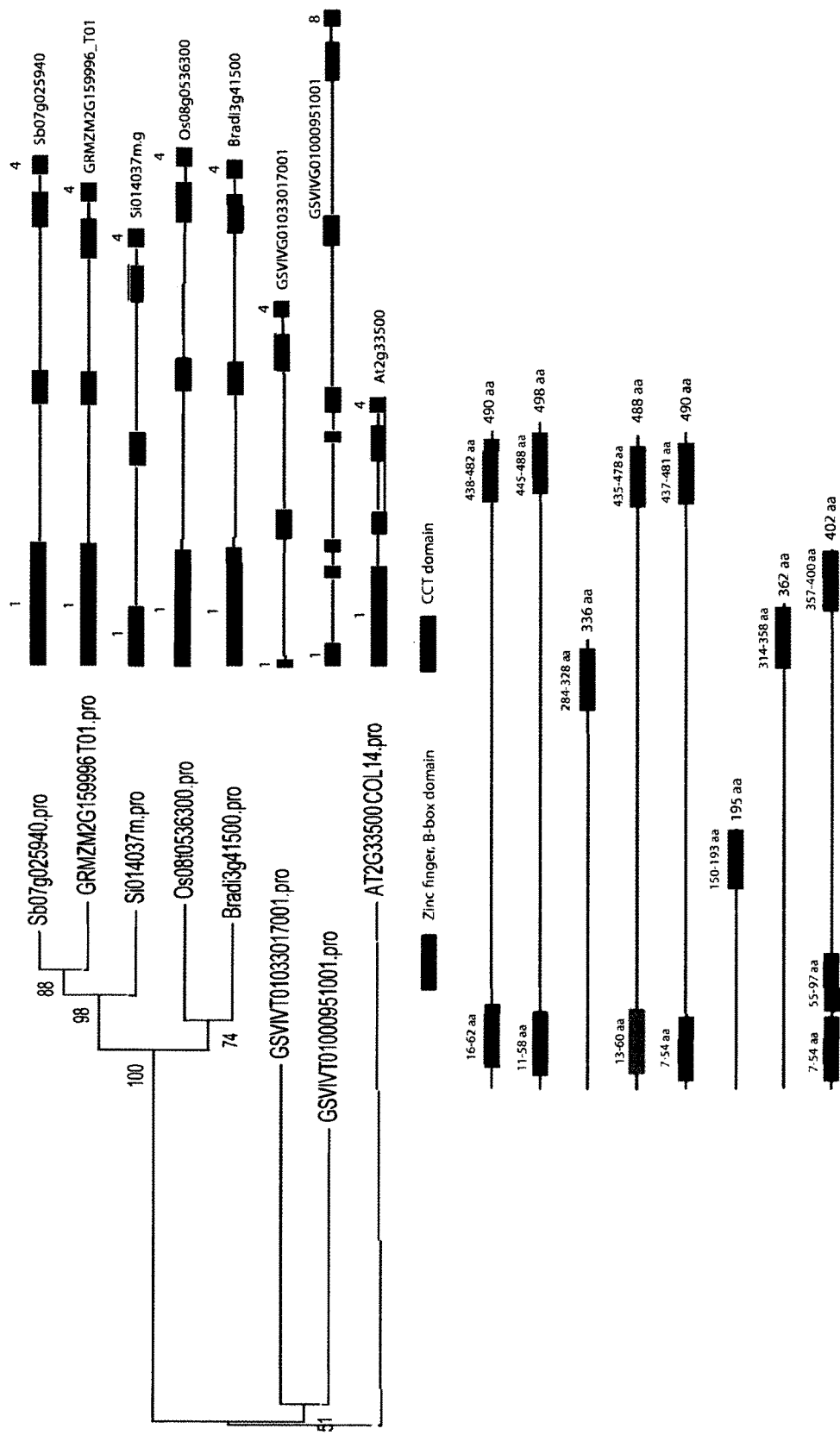
Figure 30B:
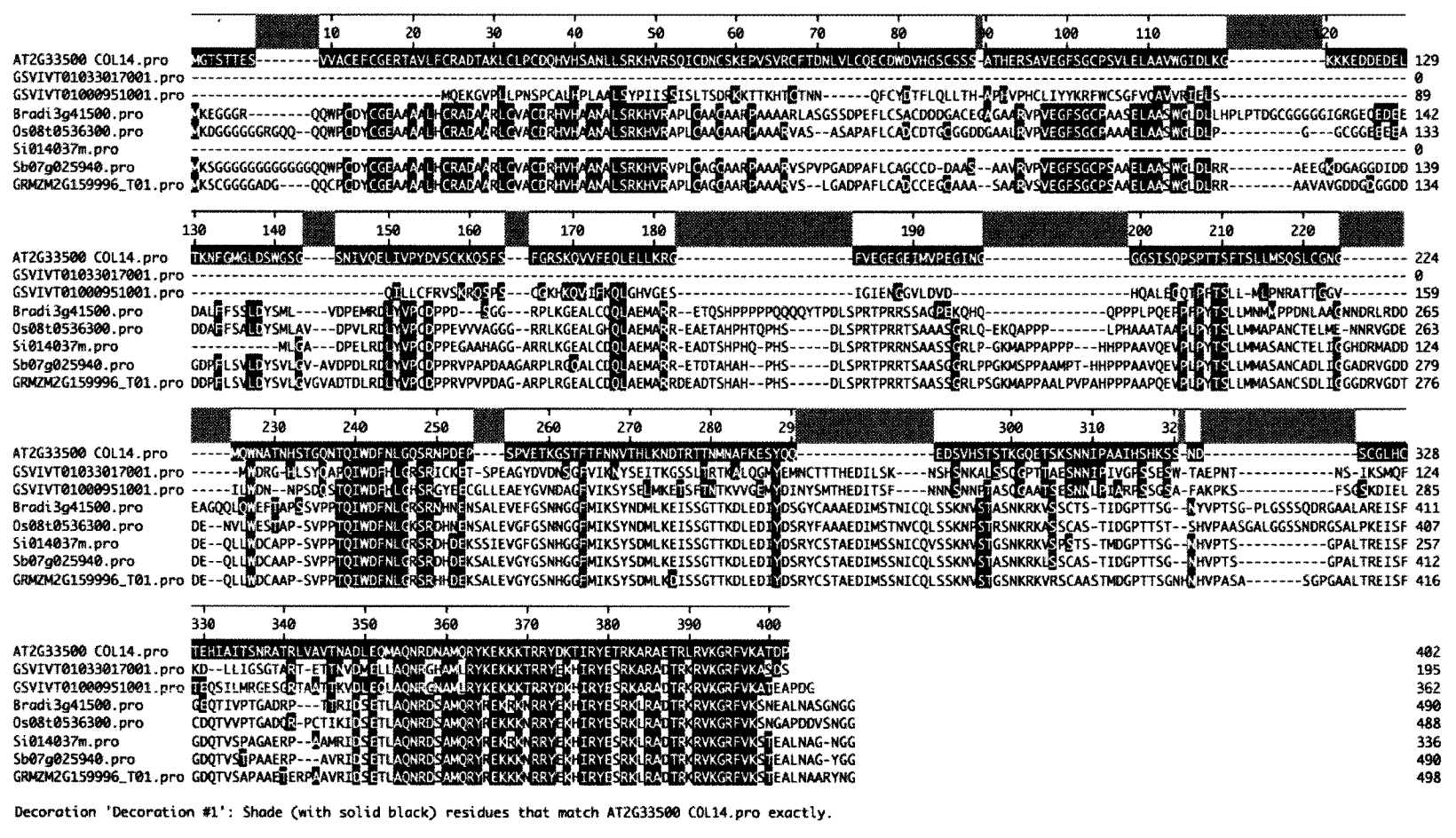

Conservation of synteny between sorghum and grapevine showed that the linkage between MIR169 gene copies and the COL gene was maintained in both species. Both COL genes in grapevine, on chr14 and on chr1, lost the B-box and zinc finger domain whereas the orthologous copy in sorghum retained it (FIGS. 30A and 30B). Similarly, foxtail millet COL protein lost the B-box and zinc finger domain whereas *Brachypodium*, rice, and maize retained it. The B-box and zinc finger domain are thought to mediate protein-protein interactions, whereas the CCT domain acts as a nuclear localization signal, with mutations in both domains causing flowering time phenotypes (Griffiths, et al. 2003; Valverde 2011; Wenkel, et al. 2006). Although the COL gene on grapevine chr14 has been recently identified as a candidate gene for a flowering QTL (Duchêne, et al. 2012), the function of its corresponding orthologous copy on sorghum chr7 remains to be elucidated.

Discussion

We describe the alignment of 25 chromosomal regions with orthologous gene pairs from eight different plant species. These regions contain a total of 48 MIR169 gene copies, from which 22 of them have been described and annotated here for the first time. The alignment of sorghum chromosomal regions containing MIR169 clusters to their corresponding orthologous regions from Brachypodium, rice, foxtail millet, and maize respectively, allows us not only to better understand the differential amplification of MIR169 gene copies during speciation, but also to identify new MIR169 gene copies not previously annotated in the rice, sorghum, and maize genomes. Our work highlights the usefulness of this approach in the discovery of microRNA gene copies in grass genomes and surprisingly also in dicotyledoneous genomes such as those from grapevine, soybean, and cassava. In addition, collinearity among grasses was used to predict and annotate MIR169 hairpin structures in the foxtail millet genome de-novo, from which no current microRNA annotation was available from the miRBase database (Release 19: August 2012). Our work suggests that synteny-based analysis should complement (whenever possible) homology-based searches of new microRNA gene copies in plant genomes.

Our analysis of MIR169 gene copies organized in clusters in the sorghum genome revealed that sorghum acquired eight MIR169 gene copies after Brachypodium split from a common ancestor, primarily due to gene losses (up to 5 MIR169 gene copies) in the Brachypodium lineage and new gene copies (up to 3) in the sorghum lineage (FIG. 17A). We propose that differences in MIR169 gene copy number between sorghum and Brachypodium is based on selective amplification in sorghum. Because diploidization of the maize genome resulted in the deletion of duplicated gene copies after allotetraploidization around 4.7 mya (Messing, et al. 2004; Swigonova, et al. 2004), also resulted in selective amplification in sorghum. Maize lost more than half, 9 out of 16 MIR169 gene copies, after allotetraploidization. Single gene losses in maize appear to be caused by short deletions that are predominantly in the 5 to 178 bp size range, with these deletions being about 2.3 times more frequent in one homoeologous chromosome than in the other (Woodhouse, et al. 2010). This observation is particularly relevant to maize microRNAs genes with average length distributions at the 5' regions of their primary microRNAs (pri-miRNAs) in the order of 100 to 300 nt (Zhang, et al. 2009). Although we detected chromosome breaks of the MIR169 neighboring gene COL14 on the maize homoeologous chr1-chr4 pair (FIG. 15) and the bHLH gene on maize homoeologous chr2-chr7 pair (FIG. 18), retention of the bHLH gene copy on both homoeologous regions from chr1 and chr4 was observed (FIG. 15). It has been observed that transcription factors are preferentially retained after whole genome duplication (WGD) (Murat, et al. 2010; Xu and Messing 2008), with a recent study showing that from 2,943 sorghum-maize syntenic shared genes, 43% of them were retained as homoeologous pairs in maize, from which transcription factors were 4.3 times more frequently among retained genes than other functions (Woodhouse, et al. 2010).

Alignment of sorghum regions containing MIR169 gene copies on chr2 and chr7 with their respective collinear regions from Brachypodium, rice, foxtail millet and maize revealed the close linkage of MIR169 gene copies with their flanking COL14 and Bhlh genes in all five grasses examined. Furthermore, collinearity of MIR169 gene copies with either the COL14 and/or the bHLH genes extended to dicot species such as grapevine, soybean, and cassava. Previously, it was suggested that conservation of collinearity between monocot and dicot species is rather rare because of the dynamic genomic rearrangements in genomes over 130-240 mya (Jaillon, et al. 2007; Wolfe, et al. 1989). Still, conservation of synteny between rice and grapevine was also previously observed (Tang, et al. 2010). Therefore, we hypothesized that preservation of collinearity in rare cases was subject to selection even after WGD events. In support of this hypothesis, the pseudo-functionalization and higher protein divergence rate of the HLH gene in Brachypodium chr4, where the MIR169 cluster was deleted, occurred in comparison to the orthologous bHLH copy on chr3 with the MIR169e and MIR169g copies next to it. Indeed, trade-offs between sugar content and flowering time/plant height were reported in sorghum (Murray, et al. 2008). When two genes controlling linked phenotypes are in close proximity on the chromosome for selection to act on both of them, the loss of one gene releases selection pressure on the other gene, allowing it to diverge. Based on its similarity to Arabidopsis bHLH137, which was postulated as putative DELLA target gene that functions in the GA response pathway (Zentella, et al. 2007), we hypothesize that the grass homolog may function either in flowering and/or plant height, which future research will have to confirm. On the other hand, the importance of COL family proteins in the regulation of flowering time is well known (Griffiths, et al. 2003; Wenkel, et al. 2006). Collinearity between sorghum and grapevine revealed the tight association of COL14 with vvi-MIR169z and vvi-MIR169e on grapevine chr14, with the three genes contained within a 2.3 Kbp interval. Furthermore, COL14 has been recently considered a candidate gene for a flowering QTL in grapevine (Duchêne, et al. 2012). With such a short physical distance between a flowering time gene and two MIR169 gene copies, it is tempting to propose that grapevine breeding for late or early flowering time could have brought different COL14 alleles together with its neighboring MIR169 genes, a process known as linkage drag. Interestingly, although we could not find extensive collinearity between sorghum and Arabidopsis thaliana as to draw a synteny graph, we did find a close association on chr5 between COL4 gene and ath-MIR169b, separated each other 61.7 Kbp (data not shown).

Based on these considerations, we can propose a hypothesis were the linkage of MIR169 gene copies with the neighboring COL gene could have co-evolved (FIG. 31). This hypothesis is based on the findings presented here, together with a previous report describing that CO and COL proteins can interact through their CCT domains with proteins belonging to the NF-Y (HAP) family of transcription factors (Wenkel, et al. 2006); specifically, it was described that CO together with COL15 interacted with NF-YB and NF-YC displacing NF-YA from the ternary complex. The mRNAs encoded by the NF-YA gene family are known targets of miR169 (Li, et al. 2008). Thus, the association on the chromosome of a COL gene with a MIR169 gene or gene cluster would ensure that miR169 would reduce the expression of the NF-YA mRNA and thus its protein levels so that the COL protein can replace NF-YA in the ternary complex and drive transcription of CCAAT box genes. Furthermore, this hypothesis could provide a genetic framework where to test the previously known drought and flowering trade-offs: when plants are exposed to drought stress during the growing season they flower earlier than control plants under well watered environments (Franks, et al. 2007), with the response being genetically inherited. For this reason, we decided to term our model the "Drought and Flowering Genetic Module Hypothesis".

We can envision a prominent role of linkage drag in breeding sorghum for enhanced biofuel traits such as high sugar content in stems and late flowering time for increased biomass. Under the MIR169-bHLH and/or MIR169-COL linkage drag model, any breeding scheme in sweet sorghum whose aim is to increase plant biomass through delayed flowering by crossing cultivars with different COL and/or bHLH alleles on either chr7 or chr2 respectively, should take into account the allelic variation at the neighboring MIR169 gene copies as they may affect sugar content in stems as well as drought tolerance. The same can be said in breeding sorghum for grain production where the norm is to increase germplasm diversity among grain sorghums through the introduction of dwarf and early flowering genes from a donor line into exotic tall and late flowering lines with African origins (Brown, et al. 2008).

Based on our results from comparative genomics analysis, we envision that any conservation in collinearity between closely associated genes (in this particular study between an microRNA and a protein-coding gene) controlling related phenotypes that is conserved among several plant species might be subject to linkage drag through breeding, opening a new area of research in genomics assisted breeding. In support of this notion, the early development of conserved ortholog set markers (referred as COS markers) among different plant species (Fulton, et al. 2002) highlighted the existence of a set of genes with synteny conservation because of the early radiation of dicotyledoneous plants that can be used in mapping through comparative genomics. In addition, conservation in linkage between candidate genes for seed glucosinolate content and SSR markers between *Arabidopsis* and oilseed rape (*Brassica napus* ssp. *napus*) were used in marker-assisted selection in breeding oilseed rape for total glucosinolate content (Hasan, et al. 2008).

REFERENCES FOR EXAMPLE III

Allen E, et al. 2004. Evolution of microRNA genes by inverted duplication of target gene sequences in *Arabidopsis thaliana*. Nature Genetics 36: 1282-1290. doi: 10.1038/ng1478

Axtell M J, Bowman J L 2008. Evolution of plant microRNAs and their targets. Trends in plant science 13: 343-349. doi: 10.1016/j.tplants.2008.03.009

Bennetzen J L, et al. 2012. Reference genome sequence of the model plant *Setaria*. Nature biotechnology. doi: 10.1038/nbt.2196

Brown P J, Rooney W L, Franks C, Kresovich S 2008. Efficient mapping of plant height quantitative trait loci in a sorghum association population with introgressed dwarfing genes. Genetics 180: 629-637. doi: 10.1534/genetics.108.092239

Calvino M, Bruggmann R, Messing J 2011. Characterization of the small RNA component of the transcriptome from grain and sweet sorghum stems. BMC genomics 12: 356. doi: 10.1186/1471-2164-12-356

Calvino M, Bruggmann R, Messing J 2008. Screen of Genes Linked to High-Sugar Content in Stems by Comparative Genomics. Rice 1: 166-176. doi: 10.1007/s12284-008-9012-9

Calvino M, Messing J 2011. Sweet sorghum as a model system for bioenergy crops. Current opinion in biotechnology 23: 1-7. doi: 10.1016/j.copbio.2011.12.002

Calvino M, Miclaus M, Bruggmann R, Messing J 2009. Molecular Markers for Sweet Sorghum Based on Microarray Expression Data. Rice 2: 129-142. doi: 10.1007/s12284-009-9029-8

Dai X, Zhao P X 2011. psRNATarget: a plant small RNA target analysis server. Nucleic Acids Research 39: W155-159. doi: 10.1093/nar/gkr319

Duchêne E, Butterlin G, Dumas V, Merdinoglu D 2012. Towards the adaptation of grapevine varieties to climate change: QTLs and candidate genes for developmental stages. Theoretical and Applied Genetics 124: 623-635. doi: 10.1007/s00122-011-1734-1

Fahlgren N, et al. 2007. High-throughput sequencing of *Arabidopsis* microRNAs: evidence for frequent birth and death of MIRNA genes. PloS one 2: e219-. doi: 10.1371/journal.pone.0000219

Fenselau de Felippes F, Schneeberger K, Dezulian T, Huson D H, Weigel D 2008. Evolution of *Arabidopsis thaliana* microRNAs from random sequences. RNA 14: 2455-2459. doi: 10.1261/rna.1149408

Fernandez M G S, Becraft P W, Yin Y, Luebberstedt T 2009. From dwarves to giants? Plant height manipulation for biomass yield. Trends in plant science 14: 454-461. doi: 10.1016/j.tplants.2009.06.005

Franks S J, Sim S, Weis A E 2007. Rapid evolution of flowering time by an annual plant in response to a climate fluctuation. Proceedings of the National Academy of Sciences of the United States of America 104: 1278-1282. doi: 10.1073/pnas.0608379104

Fulton T, Van der Hoeven R, Eannetta N, Tanksley S 2002. Identification, analysis, and utilization of conserved ortholog set markers for comparative genomics in higher plants. The Plant cell 14: 1457-1467. doi: 10.1105/tpc.010479

Griffiths S, Dunford R P, Coupland G, Laurie D A 2003. The Evolution of CONSTANS-Like Gene Families in Barley, Rice, and *Arabidopsis*. Plant Physiology 131: 1855-1867. doi: 10.1104/pp. 102.016188

Hasan M, et al. 2008. Association of gene-linked SSR markers to seed glucosinolate content in oilseed rape (*Brassica napus* ssp. *napus*). TAG. Theoretical and applied genetics. Theoretische und angewandte Genetik 116: 1035-1049. doi: 10.1007/s00122-008-0733-3

Initiative I B 2010. Genome sequencing and analysis of the model grass *Brachypodium* distachyon. Nature 463: 763-768. doi: 10.1038/nature08747

Jaillon O, et al. 2007. The grapevine genome sequence suggests ancestral hexaploidization in major angiosperm phyla. Nature 449: 463-U465. doi: 10.1038/nature06148

Jiang D, et al. 2006. Duplication and expression analysis of multicopy miRNA gene family members in *Arabidopsis* and rice. Cell Research 16: 507-518. doi: 10.1038/sj.cr.7310062

Li W X, et al. 2008. The *Arabidopsis* NFYA5 Transcription Factor Is Regulated Transcriptionally and Posttranscriptionally to Promote Drought Resistance. THE PLANT CELL ONLINE 20: 2238-2251. doi: 10.1105/tpc.108.059444

Ma Z, Coruh C, Axtell M J 2010. *Arabidopsis lyrata* small RNAs: transient MIRNA and small interfering RNA loci within the *Arabidopsis* genus. The Plant cell 22: 1090-1103. doi: 10.1105/tpc.110.073882

Maher C, Stein L, Ware D 2006. Evolution of *Arabidopsis* microRNA families through duplication events. Genome Research 16: 510-519. doi: 10.1101/gr.4680506

Meng Y, Shao C, Gou L, Jin Y, Chen M 2011. Construction of microRNA- and microRNA*-mediated regulatory networks in plants. RNA Biology 8: 1124-1148.

Messing J, et al. 2004. Sequence composition and genome organization of maize. Proceedings of the National Academy of Sciences of the United States of America 101: 14349-14354.

Meyers B C, et al. 2008. Criteria for annotation of plant MicroRNAs. The Plant cell 20: 3186-3190. doi: 10.1105/tpc.108.064311

Murat F, et al. 2010. Ancestral grass karyotype reconstruction unravels new mechanisms of genome shuffling as a source of plant evolution. Genome Res 20: 1545-1557. doi: gr.109744.110 [pii] 10.1101/gr.109744.110

Murray S C, et al. 2008. Genetic Improvement of Sorghum as a Biofuel Feedstock: I. QTL for Stem Sugar and Grain Nonstructural Carbohydrates. Crop science 48: 2165. doi: 10.2135/cropsci2008.01.0016

Nozawa M, Miura S, Nei M 2012. Origins and evolution of microRNA genes in plant species. Genome biology and evolution 4: 230-239. doi: 10.1093/gbe/evs002

Paterson A H, et al. 2009. The *Sorghum* bicolor genome and the diversification of grasses. Nature 457: 551-556. doi: 10.1038/nature07723

Piriyapongsa J, Jordan I K 2008. Dual coding of siRNAs and miRNAs by plant transposable elements. RNA 14: 814-821. doi: 10.1261/rna.916708

Sun J, Zhou M, Mao Z, Li C 2012. Characterization and Evolution of microRNA Genes Derived from Repetitive Elements and Duplication Events in Plants. PloS one 7: e34092. doi: 10.1371/journal.pone.0034092

Swigonova Z, et al. 2004. Close split of sorghum and maize genome progenitors. Genome research 14: 1916-1923.

Tamura K, et al. 2011. MEGA5: molecular evolutionary genetics analysis using maximum likelihood, evolutionary distance, and maximum parsimony methods. Molecular biology and evolution 28: 2731-2739. doi: 10.1093/molbev/msr121

Tang H, Bowers J E, Wang X, Paterson A H 2010. Angiosperm genome comparisons reveal early polyploidy in the monocot lineage. PNAS 107: 472-477. doi: 10.1073/pnas.0908007107

Toledo-Ortiz G 2003. The *Arabidopsis* Basic/Helix-Loop-Helix Transcription Factor Family. The Plant cell 15: 1749-1770. doi: 10.1105/tpc.013839

Valverde F 2011. CONSTANS and the evolutionary origin of photoperiodic timing of flowering. Journal of Experimental Botany 62: 2453-2463. doi: 10.1093/jxb/erq449

Wenkel S, et al. 2006. CONSTANS and the CCAAT Box Binding Complex Share a Functionally Important Domain and Interact to Regulate Flowering of *Arabidopsis*. The Plant cell 18: 2971-2984. doi: 10.1105/tpc.106.043299

Wolfe K H, Gouy M, Yang Y W, Sharp P M, Li W H 1989. Date of the monocot-dicot divergence estimated from chloroplast DNA sequence data. Proceedings of the National Academy of Sciences of the United States of America 86: 6201-6205. doi: 10.1073/pnas.86.16.6201

Woodhouse M R, et al. 2010. Following Tetraploidy in Maize, a Short Deletion Mechanism Removed Genes Preferentially from One of the Two Homeologs. PLoS biology 8: e1000409. doi: 10.1371/journal.pbio.1000409.t002

Xu J-H, Messing J 2008. Diverged Copies of the Seed Regulatory Opaque-2 Gene by a Segmental Duplication in the Progenitor Genome of Rice, Sorghum, and Maize. Mol Plant % R 10.1093/mp/ssn038 1: 760-769.

Xue L-J, Zhang J-J, Xue H-W 2009. Characterization and expression profiles of miRNAs in rice seeds. Nucleic Acids Research 37: 916-930. doi: 10.1093/nar/gkn998

Yang J S, et al. 2011. Widespread regulatory activity of vertebrate microRNA* species. RNA (New York, N.Y.) 17: 312-326. doi: 10.1261/rna.2537911

Zentella R, et al. 2007. Global Analysis of DELLA Direct Targets in Early Gibberellin Signaling in *Arabidopsis*. The Plant cell 19: 3037-3057. doi: 10.1105/tpc.107.054999

Zhang G, et al. 2012. Genome sequence of foxtail millet (*Setaria italica*) provides insights into grass evolution and biofuel potential. Nature biotechnology. doi: 10.1038/nbt.2195

Zhang L, et al. 2009. A genome-wide characterization of microRNA genes in maize. PLoS genetics 5: e1000716-. doi: 10.1371/journal.pgen.1000716

While certain of the preferred embodiments of the present invention have been described and specifically exemplified above, it is not intended that the invention be limited to such embodiments. Various modifications may be made thereto without departing from the scope and spirit of the present invention, as set forth in the following claims.

TABLE B

Frequency counts of small RNA reads for known miRNAs

| Chromosome | miRNA | Count of mapped reads to miRNA genes for each library | | | | |
|---|---|---|---|---|---|---|
| | | Mix | BTx623 | Rio | LB/EF F2s | HB/LF F2s |
| 4 | sbi-MIR156a | 336 | 136 | 464 | 1188 | 1830 |
| 3 | sbi-MIR156b | 655 | 416 | 867 | 3747 | 4123 |
| 3 | sbi-MIR156c | 635 | 321 | 796 | 3120 | 3617 |
| 2 | sbi-MIR156d | 3 | 1 | 2 | 12 | 10 |
| 10 | sbi-MIR156e | 26 | 26 | 21 | 151 | 101 |
| 2 | sbi-MIR156f | 345 | 82 | 349 | 857 | 1307 |
| 4 | sbi-MIR156g | 205 | 49 | 269 | 665 | 1050 |
| 6 | sbi-MIR156h | 218 | 49 | 276 | 704 | 1110 |
| 7 | sbi-MIR156i | 635 | 330 | 814 | 3213 | 3659 |
| 3 | sbi-MIR159 | 427 | 248 | 302 | 892 | 1496 |
| 3 | sbi-MIR159b | 55 | 19 | 4 | 24 | 48 |
| 4 | sbi-MIR160a | 90 | 45 | 45 | 296 | 249 |
| 10 | sbi-MIR160b | 106 | 88 | 58 | 331 | 272 |
| 7 | sbi-MIR160c | 92 | 45 | 43 | 312 | 253 |

TABLE B-continued

Frequency counts of small RNA reads for known miRNAs

Count of mapped reads to miRNA genes for each library

| Chromosome | miRNA | Mix | BTx623 | Rio | LB/EF F2s | HB/LF F2s |
|---|---|---|---|---|---|---|
| 1 | sbi-MIR160d | 90 | 45 | 44 | 312 | 253 |
| 2 | sbi-MIR160e | 90 | 45 | 44 | 312 | 255 |
| 4 | sbi-MIR162 | 2 | 1 | 4 | 11 | 10 |
| 9 | sbi-MIR164 | 222 | 141 | 231 | 1049 | 913 |
| 4 | sbi-MIR164b | 229 | 194 | 221 | 1224 | 817 |
| 1 | sbi-MIR164c | 1 | 1 | 0 | 7 | 2 |
| 2 | sbi-MIR164d | 137 | 91 | 111 | 617 | 506 |
| 9 | sbi-MIR164e | 125 | 134 | 93 | 790 | 482 |
| 1 | sbi-MIR166a | 703 | 615 | 492 | 2537 | 2076 |
| 1 | sbi-MIR166b | 254 | 142 | 135 | 762 | 881 |
| 1 | sbi-MIR166c | 245 | 177 | 161 | 764 | 705 |
| 4 | sbi-MIR166d | 289 | 279 | 239 | 1068 | 809 |
| 2 | sbi-MIR166e | 19 | 12 | 5 | 62 | 64 |
| 4 | sbi-MIR166f | 174 | 102 | 75 | 523 | 633 |
| 4 | sbi-MIR166g | 20 | 18 | 11 | 78 | 95 |
| 10 | sbi-MIR166h | 107 | 98 | 74 | 367 | 327 |
| 1 | sbi-MIR166i | 291 | 284 | 234 | 1072 | 804 |
| 1 | sbi-MIR166j | 702 | 612 | 492 | 2515 | 2059 |
| 8 | sbi-MIR166k | 755 | 655 | 511 | 2686 | 2328 |
| 1 | sbi-MIR167a | 120 | 39 | 102 | 359 | 551 |
| 1 | sbi-MIR167b | 524 | 232 | 463 | 1950 | 2688 |
| 10 | sbi-MIR167c | 1144 | 327 | 1098 | 5100 | 2828 |
| 2 | sbi-MIR167d | 979 | 255 | 1184 | 3363 | 4951 |
| 8 | sbi-MIR167e | 932 | 233 | 1130 | 3179 | 4714 |
| 1 | sbi-MIR167f | 1037 | 378 | 1222 | 3671 | 5144 |
| 3 | sbi-MIR167g | 941 | 237 | 1144 | 3248 | 4831 |
| 1 | sbi-MIR167h | 1403 | 557 | 1553 | 5094 | 7086 |
| 4 | sbi-MIR167.p2 | 1546 | 585 | 1672 | 5690 | 7524 |
| 8 | sbi-MIR167.p3 | 99 | 24 | 70 | 343 | 539 |
| 4 | sbi-MIR168 | 1397 | 459 | 1047 | 5736 | 3115 |
| 3 | sbi-MIR169a | 398 | 284 | 158 | 1551 | 1010 |
| 10 | sbi-MIR169b | 355 | 166 | 147 | 760 | 705 |
| 6 | sbi-MIR169c | 72 | 61 | 24 | 402 | 89 |
| 6 | sbi-MIR169d | 106 | 79 | 30 | 400 | 113 |
| 2 | sbi-MIR169f | 35 | 34 | 9 | 96 | 52 |
| 2 | sbi-MIR169g | 33 | 30 | 6 | 88 | 45 |
| 5 | sbi-MIR169i | 5 | 2 | 1 | 34 | 10 |
| 2 | sbi-MIR169e | 91 | 47 | 14 | 203 | 88 |
| 4 | sbi-MIR169h | 81 | 86 | 23 | 392 | 93 |
| 4 | sbi-MIR169j | 55 | 56 | 18 | 333 | 78 |
| 6 | sbi-MIR169k | 638 | 693 | 278 | 3319 | 1855 |
| 7 | sbi-MIR169l | 47 | 24 | 17 | 137 | 67 |
| 7 | sbi-MIR169m | 62 | 61 | 24 | 383 | 82 |
| 7 | sbi-MIR169n | 66 | 70 | 23 | 405 | 88 |
| 1 | sbi-MIR171a | 7 | 2 | 3 | 25 | 22 |
| 7 | sbi-MIR171b | 7 | 2 | 2 | 28 | 22 |
| 1 | sbi-MIR171d | 7 | 3 | 3 | 28 | 27 |
| 6 | sbi-MIR171e | 180 | 69 | 246 | 726 | 908 |
| 4 | sbi-MIR171f | 181 | 68 | 244 | 723 | 904 |
| 1 | sbi-MIR171h | 3 | 4 | 2 | 7 | 7 |
| 1 | sbi-MIR171i | 6 | 4 | 2 | 27 | 26 |
| 6 | sbi-MIR171k | 7 | 2 | 2 | 26 | 22 |
| 9 | sbi-MIR172a | 35138 | 37769 | 28459 | 124587 | 75185 |
| 3 | sbi-MIR172b | 647 | 503 | 96 | 978 | 515 |
| 4 | sbi-MIR172c | 34208 | 37173 | 28113 | 120975 | 72973 |
| 2 | sbi-MIR172e | 1167 | 567 | 555 | 4816 | 3725 |
| 2 | sbi-MIR172d | 3163 | 2178 | 2109 | 6411 | 4473 |
| 3 | sbi-MIR319 | 3935 | 4395 | 2673 | 13003 | 10606 |
| 3 | sbi-MIR319.p1 | 297 | 270 | 148 | 1164 | 735 |
| 1 | sbi-MIR390 | 3 | 1 | 0 | 6 | 5 |
| 6 | sbi-MIR393b | 151 | 73 | 104 | 610 | 949 |
| 3 | sbi-MIR393 | 3 | 7 | 2 | 12 | 13 |
| 2 | sbi-MIR394a | 171 | 191 | 74 | 569 | 489 |
| 4 | sbi-MIR394b | 175 | 198 | 82 | 579 | 519 |
| 6 | sbi-MIR395a | 7 | 8 | 14 | 23 | 39 |
| 6 | sbi-MIR395b | 10 | 24 | 26 | 50 | 76 |
| 6 | sbi-MIR395d | 20 | 13 | 21 | 26 | 56 |
| 6 | sbi-MIR395e | 21 | 26 | 33 | 46 | 82 |
| 6 | sbi-MIR395f | 40 | 17 | 74 | 52 | 144 |
| 6 | sbi-MIR395c | 21 | 14 | 20 | 31 | 75 |
| 6 | sbi-MIR395g | 19 | 14 | 30 | 31 | 70 |
| 6 | sbi-MIR395h | 83 | 21 | 151 | 87 | 263 |
| 7 | sbi-MIR395i | 8 | 2 | 12 | 12 | 33 |
| 7 | sbi-MIR395j | 21 | 3 | 34 | 26 | 78 |

TABLE B-continued

Frequency counts of small RNA reads for known miRNAs

Count of mapped reads to miRNA genes for each library

| Chromosome | miRNA | Mix | BTx623 | Rio | LB/EF F2s | HB/LF F2s |
|---|---|---|---|---|---|---|
| 7 | sbi-MIR395k | 18 | 1 | 28 | 12 | 51 |
| 7 | sbi-MIR395l | 65 | 10 | 140 | 69 | 214 |
| 4 | sbi-MIR396a | 193 | 38 | 102 | 473 | 572 |
| 10 | sbi-MIR396b | 191 | 38 | 97 | 472 | 575 |
| 4 | sbi-MIR396c | 705 | 621 | 337 | 2865 | 1988 |
| 4 | sbi-MIR396d | 5104 | 2553 | 2333 | 12123 | 19360 |
| 6 | sbi-MIR396e | 5222 | 2612 | 2428 | 12626 | 19719 |
| 4 | sbi-MIR397 | 1 | 0 | 2 | 8 | 6 |
| 3 | sbi-MIR399a | 5 | 3 | 9 | 32 | 24 |
| 4 | sbi-MIR399b | 5 | 12 | 7 | 58 | 24 |
| 9 | sbi-MIR399c | 6 | 3 | 10 | 33 | 23 |
| 10 | sbi-MIR399d | 86 | 76 | 94 | 308 | 233 |
| 10 | sbi-MIR399h | 6 | 4 | 12 | 40 | 30 |
| 6 | sbi-MIR399i | 15 | 10 | 12 | 46 | 29 |
| 4 | sbi-MIR399j | 6 | 4 | 12 | 40 | 30 |
| 3 | sbi-MIR408 | 41 | 5 | 43 | 364 | 75 |
| 4 | sbi-MIR444.p1 | 200 | 56 | 145 | 795 | 654 |
| 6 | sbi-MIR444.p3 | 113 | 49 | 93 | 359 | 408 |
| 1 | sbi-MIR437g | 1 | 1 | 0 | 6 | 5 |
| 1 | sbi-MIR528 | 259 | 26 | 171 | 2027 | 151 |
| 2 | sbi-MIR1432 | 48 | 26 | 68 | 280 | 243 |
| 9 | sbi-MIR1439.p1 | 2 | 0 | 3 | 12 | 12 |

TABLE C

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| Chromosome 1 | | | | | | | | | |
| chromosome_1_245.BC_01 | 7426502 | 7426720 | + | 21 | 7426572 | 7426701 | 21 | 7426523 | 7426652 |
| chromosome_1_827.BC_01 | 30266188 | 30266406 | + | 22 | 30266204 | 30266334 | 22 | 30266263 | 30266393 |
| chromosome_1_1396.BC_01 | 59548707 | 59548925 | + | 24 | 59548771 | 59548903 | 19 | 59548715 | 59548842 |
| chromosome_1_333.BC_01 | 10623817 | 10624035 | + | 25 | 10623839 | 10623972 | 25 | 10623878 | 10624011 |
| chromosome_1_686.BC_02 | 52670170 | 52670388 | + | 20 | 52670237 | 52670365 | 19 | 52670204 | 52670331 |
| chromosome_1_1088.BC_02 | 73137923 | 73138141 | + | 22 | 73137936 | 73138066 | 21 | 73138002 | 73138131 |
| chromosome_1_1016.BC_02 | 70200862 | 70201080 | + | 20 | 70200874 | 70201002 | 19 | 70200945 | 70201072 |
| chromosome_1_450.BC_02 | 26996128 | 26996346 | + | 20 | 26996202 | 26996330 | 20 | 26996131 | 26996259 |
| chromosome_1_862.BC_02 | 61161925 | 61162143 | + | 24 | 61161947 | 61162079 | 20 | 61161991 | 61162119 |
| chromosome_1_466.BC_02 | 28104732 | 28104950 | + | 19 | 28104783 | 28104910 | 18 | 28104746 | 28104872 |
| chromosome_1_398.BC_02 | 21449991 | 21450209 | + | 19 | 21450060 | 21450187 | 19 | 21450013 | 21450140 |
| chromosome_1_1560.BC_03 | 70027616 | 70027834 | + | 22 | 70027682 | 70027812 | 24 | 70027657 | 70027789 |
| chromosome_1_191.BC_03 | 7426502 | 7426726 | + | 23 | 7426531 | 7426665 | 21 | 7426564 | 7426696 |
| chromosome_1_40.BC_03 | 1791718 | 1791936 | + | 20 | 1791761 | 1791889 | 21 | 1791787 | 1791916 |
| chromosome_1_346.BC_03 | 12065225 | 12065443 | + | 23 | 12065266 | 12065397 | 24 | 12065297 | 12065429 |
| chromosome_1_1241.BC_03 | 58998763 | 58998981 | + | 21 | 58998783 | 58998912 | 18 | 58998820 | 58998946 |
| chromosome_1_350.BC_03 | 12127958 | 12128176 | + | 22 | 12128011 | 12128141 | 23 | 12127971 | 12128102 |
| chromosome_1_970.BC_03 | 49243733 | 49243951 | + | 19 | 49243796 | 49243923 | 19 | 49243822 | 49243949 |
| chromosome_1_375.BC_03 | 12875443 | 12875661 | + | 25 | 12875484 | 12875617 | 22 | 12875452 | 12875582 |
| chromosome_1_651.BC_03 | 22256944 | 22257162 | + | 24 | 22256993 | 22257125 | 23 | 22256953 | 22257084 |
| chromosome_1_345.BC_03 | 12065268 | 12065486 | + | 18 | 12065270 | 12065396 | 18 | 12065299 | 12065425 |
| chromosome_1_1337.BC_04 | 12088714 | 12088932 | + | 22 | 12088736 | 12088866 | 22 | 12088796 | 12088926 |
| chromosome_1_512.BC_04 | 5287266 | 5287484 | + | 23 | 5287350 | 5287481 | 23 | 5287287 | 5287418 |
| chromosome_1_882.BC_04 | 8457605 | 8457823 | + | 21 | 8457623 | 8457752 | 23 | 8457660 | 8457791 |
| chromosome_1_983.BC_04 | 9293698 | 9293916 | + | 18 | 9293757 | 9293883 | 18 | 9293730 | 9293856 |
| chromosome_1_754.BC_04 | 7395812 | 7396030 | + | 19 | 7395898 | 7396025 | 19 | 7395840 | 7395967 |
| chromosome_1_52.BC_04 | 574388 | 574606 | + | 19 | 574438 | 574565 | 19 | 574403 | 574530 |
| chromosome_1_1391.BC_04 | 12683183 | 12683401 | + | 18 | 12683211 | 12683337 | 18 | 12683248 | 12683374 |
| chromosome_1_2718.BC_05 | 17269612 | 17269830 | + | 23 | 17269667 | 17269798 | 21 | 17269645 | 17269774 |
| chromosome_1_527.BC_05 | 3707826 | 3708044 | + | 18 | 3707889 | 3708015 | 19 | 3707841 | 3707968 |
| chromosome_1_216.BC_05 | 1483152 | 1483370 | + | 19 | 1483216 | 1483343 | 22 | 1483191 | 1483321 |
| chromosome_1_595.BC_05 | 4260234 | 4260452 | + | 25 | 4260275 | 4260408 | 22 | 4260246 | 4260376 |
| Chromosome 2 | | | | | | | | | |
| chromosome_2_1473.BC_01 | 71061669 | 71061887 | + | 23 | 71061689 | 71061820 | 23 | 71061735 | 71061866 |
| chromosome_2_45.BC_01 | 1930828 | 1931046 | + | 18 | 1930837 | 1930963 | 18 | 1930911 | 1931037 |
| chromosome_2_902.BC_02 | 77661480 | 77661698 | + | 19 | 77661505 | 77661632 | 22 | 77661529 | 77661659 |
| chromosome_2_689.BC_03 | 48991679 | 48991897 | + | 21 | 48991714 | 48991843 | 22 | 48991741 | 48991871 |
| chromosome_2_3135.BC_04 | 54647513 | 54647731 | + | 20 | 54647548 | 54647676 | 23 | 54647577 | 54647708 |

TABLE C-continued

List of new miRNAs in sorghum

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| chromosome_2_790.BC_04 | 7717774 | 7717992 | + | 23 | 7717804 | 7717935 | 23 | 7717859 | 7717990 |
| chromosome_2_1490.BC_04 | 14065842 | 14066060 | + | 20 | 14065871 | 14065999 | 22 | 14065910 | 14066040 |
| chromosome_2_2159.BC_04 | 23325185 | 23325403 | + | 21 | 23325268 | 23325397 | 20 | 23325223 | 23325351 |
| chromosome_2_573.BC_04 | 5820867 | 5821085 | + | 25 | 5820949 | 5821082 | 25 | 5820884 | 5821017 |
| chromosome_2_721.BC_04 | 7147886 | 7148104 | + | 24 | 7147908 | 7148040 | 23 | 7147933 | 7148064 |
| chromosome_2_1464.BC_05 | 9193961 | 9194179 | + | 23 | 9194006 | 9194137 | 20 | 9194033 | 9194161 |
| chromosome_2_800.BC_05 | 4929446 | 4929664 | + | 23 | 4929468 | 4929599 | 23 | 4929523 | 4929654 |
| chromosome_2_3135.BC_05 | 26306294 | 26306512 | + | 21 | 26306334 | 26306463 | 21 | 26306311 | 26306440 |
| chromosome_2_1257.BC_05 | 7905274 | 7905492 | + | 21 | 7905330 | 7905459 | 23 | 7905296 | 7905427 |
| chromosome_2_2234.BC_05 | 14720976 | 14721194 | + | 24 | 14721021 | 14721153 | 24 | 14720996 | 14721128 |
| chromosome_2_1418.BC_05 | 8982285 | 8982503 | + | 24 | 8982308 | 8982440 | 22 | 8982343 | 8982473 |
| chromosome_2_1061.BC_05 | 6564443 | 6564661 | + | 18 | 6564508 | 6564634 | 18 | 6564477 | 6564603 |
| Chromosome 3 | | | | | | | | | |
| chromosome_3_1222.BC_01 | 64463912 | 64464130 | + | 21 | 64463932 | 64464061 | 21 | 64463980 | 64464109 |
| chromosome_3_397.BC_01 | 12450213 | 12450431 | + | 20 | 12450239 | 12450367 | 22 | 12450216 | 12450346 |
| chromosome_3_1128.BC_01 | 62015649 | 62015867 | + | 21 | 62015699 | 62015828 | 21 | 62015667 | 62015796 |
| chromosome_3_189.BC_01 | 6158157 | 6158375 | + | 23 | 6158179 | 6158310 | 23 | 6158225 | 6158356 |
| chromosome_3_1257.BC_01 | 65733952 | 65734170 | + | 18 | 65734042 | 65734168 | 18 | 65733982 | 65734108 |
| chromosome_3_1324.BC_01 | 68396564 | 68396782 | + | 24 | 68396622 | 68396754 | 24 | 68396595 | 68396727 |
| chromosome_3_1460.BC_01 | 74117994 | 74118212 | + | 18 | 74118001 | 74118127 | 18 | 74118043 | 74118169 |
| chromosome_3_47.BC_01 | 903355 | 903573 | + | 24 | 903407 | 903539 | 24 | 903366 | 903498 |
| chromosome_3_213.BC_01 | 7158612 | 7158830 | + | 19 | 7158680 | 7158807 | 20 | 7158646 | 7158774 |
| chromosome_3_39.BC_02 | 1528800 | 1529018 | + | 21 | 1528864 | 1528993 | 23 | 1528836 | 1528967 |
| chromosome_3_235.BC_02 | 11337364 | 11337582 | + | 20 | 11337451 | 11337579 | 20 | 11337430 | 11337558 |
| chromosome_3_562.BC_02 | 55328718 | 55328936 | + | 23 | 55328794 | 55328925 | 18 | 55328742 | 55328868 |
| chromosome_3_201.BC_02 | 9197165 | 9197383 | + | 21 | 9197218 | 9197347 | 25 | 9197176 | 9197309 |
| chromosome_3_514.BC_02 | 53307715 | 53307933 | + | 24 | 53307782 | 53307914 | 22 | 53307745 | 53307875 |
| chromosome_3_783.BC_02 | 67530313 | 67530531 | + | 25 | 67530345 | 67530478 | 23 | 67530374 | 67530505 |
| chromosome_3_107.BC_03 | 4540575 | 4540793 | + | 20 | 4540588 | 4540716 | 21 | 4540616 | 4540745 |
| chromosome_3_234.BC_03 | 9197788 | 9198006 | + | 23 | 9197844 | 9197975 | 21 | 9197875 | 9198004 |
| chromosome_3_1374.BC_04 | 12368774 | 12368992 | + | 20 | 12368802 | 12368930 | 20 | 12368837 | 12368965 |
| chromosome_3_954.BC_04 | 9321647 | 9321865 | + | 22 | 9321687 | 9321817 | 22 | 9321663 | 9321793 |
| chromosome_3_494.BC_04 | 5002679 | 5002897 | + | 22 | 5002717 | 5002847 | 19 | 5002749 | 5002876 |
| chromosome_3_215.BC_04 | 2081521 | 2081739 | + | 25 | 2081534 | 2081667 | 23 | 2081571 | 2081702 |
| chromosome_3_133.BC_04 | 1306612 | 1306830 | + | 19 | 1306634 | 1306761 | 21 | 1306678 | 1306807 |
| chromosome_3_1462.BC_04 | 13263113 | 13263331 | + | 18 | 13263122 | 13263248 | 18 | 13263154 | 13263280 |
| chromosome_3_1128.BC_04 | 10469325 | 10469543 | + | 24 | 10469392 | 10469524 | 24 | 10469359 | 10469491 |
| chromosome_3_821.BC_05 | 5098942 | 5099160 | + | 21 | 5098974 | 5099103 | 25 | 5098997 | 5099130 |
| chromosome_3_2132.BC_05 | 12834992 | 12835210 | + | 21 | 12835013 | 12835142 | 21 | 12835061 | 12835190 |
| chromosome_3_1435.BC_05 | 8752482 | 8752700 | + | 22 | 8752569 | 8752699 | 20 | 8752538 | 8752666 |
| chromosome_3_1223.BC_05 | 7696368 | 7696586 | + | 20 | 7696393 | 7696521 | 20 | 7696425 | 7696553 |
| chromosome_3_582.BC_05 | 3711612 | 3711830 | + | 24 | 3711637 | 3711769 | 23 | 3711665 | 3711796 |
| chromosome_3_851.BC_05 | 5462848 | 5463066 | + | 25 | 5462855 | 5462988 | 21 | 5462921 | 5463050 |
| chromosome_3_1127.BC_05 | 7158509 | 7158727 | + | 24 | 7158530 | 7158662 | 25 | 7158578 | 7158711 |
| chromosome_3_216.BC_05 | 1380827 | 1381045 | + | 19 | 1380849 | 1380976 | 20 | 1380880 | 1381008 |
| chromosome_3_468.BC_05 | 2844222 | 2844440 | + | 20 | 2844282 | 2844410 | 21 | 2844259 | 2844388 |
| Chromosome 4 | | | | | | | | | |
| chromosome_4_1028.BC_01 | 57083142 | 57083360 | + | 21 | 57083164 | 57083293 | 21 | 57083211 | 57083340 |
| chromosome_4_712.BC_01 | 45785396 | 45785614 | + | 18 | 45785462 | 45785588 | 19 | 45785428 | 45785555 |
| chromosome_4_684.BC_01 | 43242765 | 43242983 | + | 24 | 43242787 | 43242919 | 23 | 43242813 | 43242944 |
| chromosome_4_522.BC_01 | 18928653 | 18928871 | + | 24 | 18928734 | 18928866 | 24 | 18928661 | 18928793 |
| chromosome_4_83.BC_02 | 4139706 | 4139924 | + | 23 | 4139789 | 4139920 | 24 | 4139747 | 4139879 |
| chromosome_4_47.BC_02 | 2806728 | 2806956 | + | 23 | 2806731 | 2806867 | 22 | 2806818 | 2806953 |
| chromosome_4_608.BC_02 | 57049969 | 57050187 | + | 19 | 57049984 | 57050111 | 18 | 57050019 | 57050145 |
| chromosome_4_557.BC_02 | 54555310 | 54555528 | + | 19 | 54555314 | 54555441 | 23 | 54555345 | 54555476 |
| chromosome_4_134.BC_02 | 5979272 | 5979490 | + | 24 | 5979341 | 5979473 | 22 | 5979302 | 5979432 |
| chromosome_4_571.BC_03 | 41084010 | 41084228 | + | 20 | 41084063 | 41084191 | 23 | 41084031 | 41084162 |
| chromosome_4_2454.BC_04 | 41104168 | 41104386 | + | 22 | 41104251 | 41104381 | 22 | 41104224 | 41104354 |
| chromosome_4_1764.BC_04 | 13743465 | 13743683 | + | 23 | 13743538 | 13743669 | 24 | 13743467 | 13743599 |
| chromosome_4_831.BC_04 | 5805456 | 5805674 | + | 19 | 5805528 | 5805655 | 19 | 5805482 | 5805609 |
| chromosome_4_174.BC_05 | 1043442 | 1043660 | + | 23 | 1043464 | 1043595 | 24 | 1043512 | 1043644 |
| chromosome_4_785.BC_05 | 4139699 | 4139917 | + | 22 | 4139782 | 4139912 | 19 | 4139753 | 4139880 |
| chromosome_4_941.BC_05 | 4976389 | 4976607 | + | 24 | 4976455 | 4976587 | 20 | 4976407 | 4976535 |
| chromosome_4_626.BC_05 | 3152078 | 3152324 | + | 24 | 3152099 | 3152245 | 23 | 3152137 | 3152282 |
| chromosome_4_1911.BC_05 | 10424324 | 10424542 | + | 24 | 10424325 | 10424457 | 25 | 10424351 | 10424484 |
| chromosome_4_1912.BC_05 | 10424281 | 10424499 | + | 24 | 10424325 | 10424457 | 25 | 10424351 | 10424484 |
| chromosome_4_1677.BC_05 | 8737466 | 8737684 | + | 18 | 8737511 | 8737637 | 20 | 8737554 | 8737682 |
| Chromosome 5 | | | | | | | | | |
| chromosome_5_620.BC_01 | 35991780 | 35991998 | + | 23 | 35991798 | 35991929 | 20 | 35991832 | 35991960 |
| chromosome_5_1020.BC_01 | 57560746 | 57560964 | + | 22 | 57560813 | 57560943 | 22 | 57560770 | 57560900 |
| chromosome_5_70.BC_01 | 2390501 | 2390719 | + | 21 | 2390556 | 2390685 | 21 | 2390509 | 2390638 |
| chromosome_5_595.BC_01 | 35972458 | 35972676 | + | 24 | 35972500 | 35972632 | 24 | 35972527 | 35972659 |

TABLE C-continued

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| chromosome_5_737.BC_01 | 45964649 | 45964867 | + | 18 | 45964737 | 45964863 | 18 | 45964656 | 45964782 |
| chromosome_5_414.BC_01 | 14639628 | 14639846 | + | 24 | 14639697 | 14639829 | 24 | 14639660 | 14639792 |
| chromosome_5_978.BC_01 | 56200684 | 56200902 | + | 19 | 56200709 | 56200836 | 20 | 56200772 | 56200900 |
| chromosome_5_642.BC_02 | 56976805 | 56977023 | + | 22 | 56976823 | 56976953 | 22 | 56976865 | 56976995 |
| chromosome_5_468.BC_02 | 46744802 | 46745020 | + | 23 | 46744826 | 46744957 | 24 | 46744853 | 46744985 |
| chromosome_5_456.BC_02 | 46080609 | 46080827 | + | 22 | 46080635 | 46080765 | 22 | 46080675 | 46080805 |
| chromosome_5_455.BC_02 | 45878295 | 45878513 | + | 24 | 45878346 | 45878478 | 22 | 45878382 | 45878512 |
| chromosome_5_508.BC_02 | 49892025 | 49892243 | + | 24 | 49892035 | 49892167 | 24 | 49892073 | 49892205 |
| chromosome_5_612.BC_02 | 55180331 | 55180549 | + | 23 | 55180376 | 55180507 | 22 | 55180346 | 55180476 |
| chromosome_5_657.BC_02 | 58061752 | 58061970 | + | 25 | 58061830 | 58061963 | 22 | 58061807 | 58061937 |
| chromosome_5_509.BC_03 | 35939610 | 35939828 | + | 24 | 35939663 | 35939795 | 25 | 35939630 | 35939763 |
| chromosome_5_468.BC_03 | 30952732 | 30952950 | + | 23 | 30952756 | 30952887 | 24 | 30952813 | 30952945 |
| chromosome_5_148.BC_03 | 5711015 | 5711233 | + | 19 | 5711092 | 5711219 | 19 | 5711059 | 5711186 |
| chromosome_5_574.BC_03 | 36068848 | 36069066 | + | 24 | 36068869 | 36069001 | 21 | 36068896 | 36069025 |
| chromosome_5_737.BC_03 | 52069704 | 52069922 | + | 18 | 52069792 | 52069918 | 18 | 52069744 | 52069870 |
| chromosome_5_648.BC_03 | 47253576 | 47253794 | + | 25 | 47253637 | 47253770 | 21 | 47253664 | 47253793 |
| chromosome_5_609.BC_03 | 43098003 | 43098221 | + | 25 | 43098042 | 43098175 | 23 | 43098005 | 43098136 |
| chromosome_5_456.BC_04 | 3769844 | 3770062 | + | 22 | 3769870 | 3770000 | 23 | 3769908 | 3770039 |
| chromosome_5_74.BC_04 | 852222 | 852440 | + | 23 | 852291 | 852422 | 22 | 852266 | 852396 |
| chromosome_5_646.BC_04 | 5397961 | 5398179 | + | 23 | 5398016 | 5398147 | 22 | 5397977 | 5398107 |
| chromosome_5_631.BC_04 | 5062982 | 5063200 | + | 24 | 5063051 | 5063183 | 23 | 5063025 | 5063156 |
| chromosome_5_1387.BC_04 | 12954340 | 12954558 | + | 25 | 12954359 | 12954492 | 25 | 12954395 | 12954528 |
| chromosome_5_379.BC_04 | 3047742 | 3047960 | + | 18 | 3047758 | 3047884 | 19 | 3047819 | 3047946 |
| chromosome_5_661.BC_04 | 5454601 | 5454819 | + | 24 | 5454667 | 5454799 | 23 | 5454635 | 5454766 |
| chromosome_5_181.BC_05 | 1482116 | 1482334 | + | 18 | 1482198 | 1482324 | 18 | 1482138 | 1482264 |
| chromosome_5_1255.BC_05 | 8374317 | 8374535 | + | 25 | 8374380 | 8374513 | 20 | 8374338 | 8374466 |
| chromosome_5_139.BC_05 | 1149586 | 1149804 | + | 20 | 1149603 | 1149731 | 24 | 1149632 | 1149764 |
| Chromosome 6 | | | | | | | | | |
| chromosome_6_657.BC_01 | 49334150 | 49334368 | + | 20 | 49334212 | 49334340 | 19 | 49334162 | 49334289 |
| chromosome_6_146.BC_01 | 8616424 | 8616642 | + | 22 | 8616491 | 8616621 | 24 | 8616465 | 8616597 |
| chromosome_6_145.BC_01 | 8616466 | 8616684 | + | 22 | 8616491 | 8616621 | 22 | 8616548 | 8616678 |
| chromosome_6_166.BC_01 | 10062440 | 10062658 | + | 21 | 10062461 | 10062590 | 23 | 10062502 | 10062633 |
| chromosome_6_801.BC_01 | 54609029 | 54609247 | + | 23 | 54609115 | 54609246 | 24 | 54609049 | 54609181 |
| chromosome_6_852.BC_01 | 56307517 | 56307735 | + | 22 | 56307542 | 56307672 | 22 | 56307579 | 56307709 |
| chromosome_6_323.BC_01 | 36252403 | 36252621 | + | 24 | 36252456 | 36252588 | 24 | 36252415 | 36252547 |
| chromosome_6_235.BC_02 | 42197879 | 42198097 | + | 22 | 42197957 | 42198087 | 22 | 42197931 | 42198061 |
| chromosome_6_657.BC_02 | 62142098 | 62142316 | + | 21 | 62142146 | 62142275 | 18 | 62142168 | 62142294 |
| chromosome_6_555.BC_02 | 58149231 | 58149449 | + | 20 | 58149297 | 58149425 | 18 | 58149274 | 58149400 |
| chromosome_6_166.BC_02 | 31431683 | 31431901 | + | 21 | 31431704 | 31431833 | 25 | 31431736 | 31431869 |
| chromosome_6_357.BC_02 | 48274451 | 48274669 | + | 25 | 48274473 | 48274606 | 25 | 48274534 | 48274667 |
| chromosome_6_201.BC_02 | 37144624 | 37144842 | + | 18 | 37144642 | 37144768 | 18 | 37144670 | 37144795 |
| chromosome_6_313.BC_03 | 32230496 | 32230714 | + | 22 | 32230506 | 32230636 | 24 | 32230533 | 32230665 |
| chromosome_6_336.BC_03 | 35870213 | 35870431 | + | 22 | 35870254 | 35870384 | 21 | 35870288 | 35870417 |
| chromosome_6_337.BC_03 | 35870171 | 35870389 | + | 23 | 35870204 | 35870335 | 22 | 35870229 | 35870359 |
| chromosome_6_805.BC_03 | 56307471 | 56307689 | + | 21 | 56307473 | 56307602 | 21 | 56307528 | 56307657 |
| chromosome_6_632.BC_03 | 49334146 | 49334364 | + | 23 | 49334170 | 49334301 | 22 | 49334201 | 49334331 |
| chromosome_6_159.BC_03 | 8684276 | 8684494 | + | 24 | 8684340 | 8684472 | 20 | 8684318 | 8684446 |
| chromosome_6_888.BC_04 | 15123597 | 15123815 | + | 23 | 15123603 | 15123734 | 21 | 15123670 | 15123799 |
| chromosome_6_67.BC_04 | 554774 | 554992 | + | 22 | 554826 | 554956 | 24 | 554783 | 554915 |
| chromosome_6_889.BC_04 | 15123555 | 15123773 | + | 23 | 15123602 | 15123733 | 20 | 15123561 | 15123689 |
| chromosome_6_1475.BC_04 | 39647152 | 39647370 | + | 25 | 39647159 | 39647292 | 21 | 39647187 | 39647316 |
| chromosome_6_351.BC_05 | 2421512 | 2421730 | + | 22 | 2421574 | 2421704 | 22 | 2421551 | 2421681 |
| chromosome_6_200.BC_05 | 1379126 | 1379344 | + | 20 | 1379144 | 1379272 | 20 | 1379201 | 1379329 |
| chromosome_6_201.BC_05 | 1397640 | 1397858 | + | 20 | 1397702 | 1397830 | 20 | 1397675 | 1397803 |
| chromosome_6_202.BC_05 | 1397599 | 1397817 | + | 20 | 1397623 | 1397751 | 20 | 1397677 | 1397805 |
| chromosome_6_972.BC_05 | 9717365 | 9717583 | + | 25 | 9717405 | 9717538 | 25 | 9717442 | 9717575 |
| chromosome_6_1147.BC_05 | 15089799 | 15090017 | + | 24 | 15089804 | 15089936 | 23 | 15089834 | 15089965 |
| chromosome_6_180.BC_05 | 1207524 | 1207742 | + | 24 | 1207531 | 1207663 | 20 | 1207612 | 1207740 |
| Chromosome 7 | | | | | | | | | |
| chromosome_7_287.BC_01 | 8606527 | 8606745 | + | 22 | 8606565 | 8606695 | 24 | 8606606 | 8606738 |
| chromosome_7_243.BC_01 | 7722615 | 7722833 | + | 22 | 7722699 | 7722829 | 22 | 7722662 | 7722792 |
| chromosome_7_49.BC_01 | 1304239 | 1304457 | + | 24 | 1304246 | 1304378 | 24 | 1304277 | 1304409 |
| chromosome_7_294.BC_01 | 8897278 | 8897496 | + | 24 | 8897337 | 8897469 | 25 | 8897310 | 8897443 |
| chromosome_7_62.BC_01 | 1863068 | 1863286 | + | 25 | 1863146 | 1863279 | 25 | 1863074 | 1863207 |
| chromosome_7_395.BC_02 | 52628062 | 52628280 | + | 22 | 52628127 | 52628257 | 22 | 52628086 | 52628216 |
| chromosome_7_256.BC_02 | 15969322 | 15969540 | + | 25 | 15969325 | 15969458 | 25 | 15969389 | 15969522 |
| chromosome_7_454.BC_02 | 55721818 | 55722036 | + | 25 | 55721902 | 55722035 | 22 | 55721857 | 55721987 |
| chromosome_7_366.BC_03 | 14773724 | 14773942 | + | 18 | 14773807 | 14773933 | 18 | 14773766 | 14773892 |
| chromosome_7_516.BC_03 | 44603435 | 44603653 | + | 18 | 44603469 | 44603595 | 22 | 44603446 | 44603576 |
| chromosome_7_568.BC_03 | 51831832 | 51832050 | + | 24 | 51831842 | 51831974 | 25 | 51831913 | 51832046 |
| chromosome_7_454.BC_03 | 30877273 | 30877491 | + | 24 | 30877306 | 30877438 | 24 | 30877277 | 30877409 |
| chromosome_7_22.BC_03 | 877244 | 877462 | + | 20 | 877269 | 877397 | 23 | 877292 | 877423 |
| chromosome_7_287.BC_03 | 8855212 | 8855430 | + | 22 | 8855250 | 8855380 | 21 | 8855280 | 8855409 |

TABLE C-continued

List of new miRNAs in *sorghum*

| miRNA name | Precursor Start | Precursor Stop | Strand | miRNA size | miRNA start | miRNA stop | miRNA* size | miRNA* start | miRNA* stop |
|---|---|---|---|---|---|---|---|---|---|
| chromosome_7_483.BC_04 | 4175091 | 4175309 | + | 19 | 4175144 | 4175271 | 18 | 4175106 | 4175232 |
| chromosome_7_1053.BC_04 | 9092869 | 9093087 | + | 24 | 9092924 | 9093056 | 22 | 9092894 | 9093024 |
| chromosome_7_627.BC_05 | 4071783 | 4072001 | + | 21 | 4071785 | 4071914 | 23 | 4071856 | 4071987 |
| chromosome_7_159.BC_05 | 901857 | 902075 | + | 22 | 901929 | 902059 | 22 | 901863 | 901993 |
| chromosome_7_1887.BC_05 | 16365788 | 16366006 | + | 18 | 16365830 | 16365956 | 20 | 16365857 | 16365985 |
| chromosome_7_628.BC_05 | 4071740 | 4071958 | + | 24 | 4071788 | 4071920 | 20 | 4071820 | 4071948 |
| Chromosome 8 | | | | | | | | | |
| chromosome_8_401.BC_01 | 33145817 | 33146035 | + | 18 | 33145867 | 33145993 | 18 | 33145846 | 33145972 |
| chromosome_8_751.BC_01 | 53091509 | 53091727 | + | 18 | 53091531 | 53091657 | 18 | 53091588 | 53091714 |
| chromosome_8_208.BC_01 | 8468733 | 8468951 | + | 25 | 8468787 | 8468920 | 25 | 8468760 | 8468893 |
| chromosome_8_765.BC_02 | 53381583 | 53381801 | + | 19 | 53381628 | 53381755 | 19 | 53381654 | 53381781 |
| chromosome_8_533.BC_03 | 49871187 | 49871405 | + | 20 | 49871233 | 49871361 | 19 | 49871195 | 49871322 |
| chromosome_8_216.BC_03 | 11557635 | 11557853 | + | 19 | 11557647 | 11557774 | 19 | 11557668 | 11557795 |
| chromosome_8_497.BC_04 | 4848342 | 4848560 | + | 21 | 4848383 | 4848512 | 20 | 4848428 | 4848556 |
| chromosome_8_150.BC_04 | 1629110 | 1629328 | + | 22 | 1629180 | 1629310 | 23 | 1629138 | 1629269 |
| chromosome_8_216.BC_04 | 2247491 | 2247709 | + | 19 | 2247503 | 2247630 | 19 | 2247572 | 2247699 |
| chromosome_8_681.BC_04 | 7206216 | 7206434 | + | 24 | 7206280 | 7206412 | 23 | 7206254 | 7206385 |
| chromosome_8_190.BC_05 | 1557321 | 1557539 | + | 22 | 1557402 | 1557532 | 20 | 1557344 | 1557472 |
| chromosome_8_468.BC_05 | 3155112 | 3155330 | + | 20 | 3155180 | 3155308 | 22 | 3155139 | 3155269 |
| chromosome_8_618.BC_05 | 4378988 | 4379206 | + | 19 | 4379030 | 4379157 | 20 | 4379054 | 4379182 |
| chromosome_8_297.BC_05 | 2224286 | 2224504 | + | 19 | 2224291 | 2224418 | 19 | 2224336 | 2224463 |
| chromosome_8_298.BC_05 | 2224244 | 2224462 | + | 19 | 2224330 | 2224457 | 19 | 2224297 | 2224424 |
| Chromosome 9 | | | | | | | | | |
| chromosome_9_506.BC_01 | 44748115 | 44748333 | + | 24 | 44748177 | 44748309 | 21 | 44748137 | 44748266 |
| chromosome_9_544.BC_02 | 55105109 | 55105327 | + | 21 | 55105131 | 55105260 | 23 | 55105177 | 55105308 |
| chromosome_9_554.BC_02 | 55441635 | 55441853 | + | 20 | 55441708 | 55441836 | 20 | 55441661 | 55441789 |
| chromosome_9_19.BC_02 | 1285782 | 1286000 | + | 25 | 1285836 | 1285969 | 22 | 1285869 | 1285999 |
| chromosome_9_1410.BC_05 | 9601262 | 9601480 | + | 22 | 9601324 | 9601454 | 24 | 9601290 | 9601422 |
| chromosome_9_721.BC_05 | 4452093 | 4452311 | + | 24 | 4452115 | 4452247 | 19 | 4452160 | 4452287 |
| chromosome_9_1189.BC_05 | 7590118 | 7590336 | + | 21 | 7590169 | 7590298 | 21 | 7590119 | 7590248 |
| chromosome_9_1132.BC_05 | 7187470 | 7187688 | + | 22 | 7187471 | 7187601 | 22 | 7187556 | 7187686 |
| Chromosome 10 | | | | | | | | | |
| chromosome_10_93.BC_01 | 3709798 | 3710016 | + | 22 | 3709870 | 3710000 | 20 | 3709829 | 3709957 |
| chromosome_10_293.BC_01 | 9715817 | 9716035 | + | 25 | 9715901 | 9716034 | 25 | 9715823 | 9715956 |
| chromosome_10_962.BC_01 | 57054835 | 57055053 | + | 18 | 57054922 | 57055048 | 18 | 57054859 | 57054985 |
| chromosome_10_593.BC_02 | 58928507 | 58928725 | + | 22 | 58928587 | 58928717 | 22 | 58928554 | 58928684 |
| chromosome_10_295.BC_02 | 18366558 | 18366776 | + | 21 | 18366608 | 18366737 | 22 | 18366581 | 18366711 |
| chromosome_10_73.BC_03 | 2727316 | 2727534 | + | 24 | 2727382 | 2727514 | 25 | 2727343 | 2727476 |
| chromosome_10_792.BC_03 | 56170687 | 56170905 | + | 18 | 56170748 | 56170874 | 18 | 56170688 | 56170814 |
| chromosome_10_77.BC_03 | 2869845 | 2870063 | + | 20 | 2869846 | 2869974 | 20 | 2869877 | 2870005 |
| chromosome_10_1038.BC_04 | 8933922 | 8934140 | + | 18 | 8933981 | 8934107 | 22 | 8933926 | 8934056 |
| chromosome_10_766.BC_04 | 6613106 | 6613324 | + | 23 | 6613171 | 6613302 | 24 | 6613141 | 6613273 |
| chromosome_10_1088.BC_04 | 9544939 | 9545157 | + | 22 | 9544975 | 9545105 | 18 | 9545003 | 9545129 |
| chromosome_10_1564.BC_05 | 10350410 | 10350628 | + | 23 | 10350441 | 10350572 | 21 | 10350498 | 10350627 |
| chromosome_10_1885.BC_05 | 13819559 | 13819777 | + | 21 | 13819633 | 13819762 | 22 | 13819567 | 13819697 |
| chromosome_10_880.BC_05 | 5730338 | 5730556 | + | 22 | 5730360 | 5730490 | 19 | 5730404 | 5730531 |
| chromosome_10_216.BC_05 | 1572675 | 1572893 | + | 23 | 1572755 | 1572886 | 21 | 1572683 | 1572812 |
| chromosome_10_283.BC_05 | 2016636 | 2016854 | + | 21 | 2016699 | 2016828 | 25 | 2016657 | 2016790 |
| chromosome_10_73.BC_05 | 522969 | 523187 | + | 24 | 523035 | 523167 | 24 | 522996 | 523128 |

TABLE D

Frequency counts of small RNA reads for new miRNAs

| miRNA | Count of mapped reads to miRNA genes for each library | | | | |
|---|---|---|---|---|---|
| | Mix | BTx623 | Rio | LB/EF F2s | HB/LF F2s |
| chromosome_1_1396.BC_01 | 24 | 9 | 16 | 91 | 108 |
| chromosome_1_245.BC_01 | 254 | 142 | 135 | 762 | 882 |
| chromosome_1_333.BC_01 | 13 | 0 | 4 | 24 | 18 |
| chromosome_1_827.BC_01 | 5 | 5 | 8 | 10 | 14 |
| chromosome_1_1016.BC_02 | 4 | 7 | 3 | 12 | 19 |
| chromosome_1_1088.BC_02 | 8 | 12 | 2 | 12 | 21 |
| chromosome_1_398.BC_02 | 2 | 7 | 1 | 8 | 10 |
| chromosome_1_450.BC_02 | 2 | 3 | 5 | 11 | 15 |
| chromosome_1_466.BC_02 | 11 | 12 | 14 | 30 | 34 |
| chromosome_1_862.BC_02 | 26 | 15 | 16 | 63 | 96 |
| chromosome_1_686.BC_02 | 0 | 2 | 0 | 6 | 5 |
| chromosome_1_1241.BC_03 | 12 | 3 | 11 | 19 | 34 |
| chromosome_1_191.BC_03 | 254 | 142 | 135 | 762 | 882 |
| chromosome_1_345.BC_03 | 3 | 2 | 3 | 6 | 15 |
| chromosome_1_346.BC_03 | 3 | 2 | 3 | 7 | 14 |
| chromosome_1_350.BC_03 | 5 | 7 | 13 | 47 | 42 |
| chromosome_1_651.BC_03 | 5 | 4 | 4 | 17 | 21 |
| chromosome_1_40.BC_03 | 9 | 2 | 4 | 19 | 20 |

TABLE D-continued

Frequency counts of small RNA reads for new miRNAs

| miRNA | Mix | BTx623 | Rio | LB/EF F2s | HB/LF F2s |
|---|---|---|---|---|---|
| chromosome_1_970.BC_03 | 5 | 5 | 4 | 14 | 23 |
| chromosome_1_1560.BC_03 | 1 | 0 | 3 | 4 | 6 |
| chromosome_1_375.BC_03 | 1 | 1 | 2 | 7 | 5 |
| chromosome_1_1337.BC_04 | 4 | 1 | 5 | 5 | 10 |
| chromosome_1_1391.BC_04 | 28 | 14 | 30 | 95 | 136 |
| chromosome_1_52.BC_04 | 4 | 4 | 4 | 20 | 24 |
| chromosome_1_754.BC_04 | 14 | 7 | 6 | 49 | 53 |
| chromosome_1_882.BC_04 | 4 | 1 | 3 | 13 | 11 |
| chromosome_1_983.BC_04 | 0 | 2 | 4 | 16 | 29 |
| chromosome_1_512.BC_04 | 2 | 1 | 0 | 9 | 5 |
| chromosome_1_2718.BC_05 | 7 | 12 | 2 | 16 | 18 |
| chromosome_1_527.BC_05 | 64 | 34 | 52 | 217 | 282 |
| chromosome_1_216.BC_05 | 3 | 3 | 3 | 2 | 15 |
| chromosome_1_595.BC_05 | 11 | 2 | 2 | 7 | 37 |
| chromosome_2_1473.BC_01 | 35 | 6 | 27 | 70 | 120 |
| chromosome_2_45.BC_01 | 6 | 5 | 6 | 9 | 25 |
| chromosome_2_902.BC_02 | 15 | 13 | 22 | 53 | 67 |
| chromosome_2_689.BC_03 | 2 | 0 | 5 | 4 | 9 |
| chromosome_2_1490.BC_04 | 7 | 4 | 4 | 32 | 32 |
| chromosome_2_2159.BC_04 | 3 | 2 | 1 | 10 | 8 |
| chromosome_2_573.BC_04 | 21 | 10 | 15 | 80 | 123 |
| chromosome_2_3135.BC_04 | 5 | 1 | 3 | 4 | 5 |
| chromosome_2_721.BC_04 | 3 | 1 | 2 | 10 | 3 |
| chromosome_2_790.BC_04 | 7 | 1 | 2 | 4 | 6 |
| chromosome_2_1257.BC_05 | 1 | 1 | 2 | 5 | 18 |
| chromosome_2_1418.BC_05 | 0 | 0 | 2 | 5 | 15 |
| chromosome_2_2234.BC_05 | 0 | 0 | 4 | 4 | 10 |
| chromosome_2_3135.BC_05 | 7 | 4 | 10 | 13 | 29 |
| chromosome_2_800.BC_05 | 17 | 5 | 18 | 29 | 48 |
| chromosome_2_1061.BC_05 | 4 | 1 | 0 | 5 | 8 |
| chromosome_2_1464.BC_05 | 1 | 0 | 4 | 1 | 5 |
| chromosome_3_1128.BC_01 | 10 | 3 | 12 | 14 | 34 |
| chromosome_3_1222.BC_01 | 22 | 4 | 28 | 67 | 78 |
| chromosome_3_1257.BC_01 | 28 | 6 | 35 | 45 | 127 |
| chromosome_3_1324.BC_01 | 12 | 7 | 14 | 44 | 51 |
| chromosome_3_189.BC_01 | 13 | 3 | 9 | 37 | 56 |
| chromosome_3_213.BC_01 | 22 | 2 | 27 | 62 | 84 |
| chromosome_3_397.BC_01 | 9 | 3 | 11 | 18 | 27 |
| chromosome_3_47.BC51 | 13 | 13 | 16 | 51 | 79 |
| chromosome_3_1460.BC_01 | 6 | 2 | 2 | 6 | 7 |
| chromosome_3_235.BC_02 | 7 | 9 | 2 | 13 | 17 |
| chromosome_3_562.BC_02 | 4 | 5 | 4 | 10 | 9 |
| chromosome_3_201.BC_02 | 4 | 2 | 1 | 7 | 8 |
| chromosome_3_39.BC_02 | 6 | 9 | 0 | 5 | 6 |
| chromosome_3_514.BC_02 | 0 | 4 | 1 | 5 | 4 |
| chromosome_3_783.BC_02 | 0 | 2 | 1 | 2 | 8 |
| chromosome_3_234.BC_03 | 6 | 1 | 6 | 16 | 22 |
| chromosome_3_107.BC_03 | 0 | 1 | 4 | 6 | 7 |
| chromosome_3_1128.BC_04 | 7 | 5 | 3 | 13 | 27 |
| chromosome_3_133.BC_04 | 2 | 4 | 0 | 4 | 11 |
| chromosome_3_1374.BC_04 | 21 | 6 | 23 | 72 | 70 |
| chromosome_3_1462.BC_04 | 2 | 5 | 4 | 12 | 11 |
| chromosome_3_215.BC_04 | 1 | 4 | 11 | 17 | 17 |
| chromosome_3_494.BC_04 | 6 | 2 | 0 | 15 | 15 |
| chromosome_3_954.BC_04 | 9 | 3 | 1 | 17 | 15 |
| chromosome_3_1127.BC_05 | 3 | 1 | 7 | 16 | 28 |
| chromosome_3_1223.BC_05 | 14 | 3 | 22 | 47 | 54 |
| chromosome_3_2132.BC_05 | 27 | 22 | 39 | 95 | 128 |
| chromosome_3_216.BC_05 | 1 | 2 | 3 | 6 | 11 |
| chromosome_3_468.BC_05 | 5 | 2 | 3 | 14 | 16 |
| chromosome_3_582.BC_05 | 7 | 2 | 6 | 14 | 27 |
| chromosome_3_851.BC_05 | 6 | 0 | 16 | 26 | 26 |
| chromosome_3_1435.BC_05 | 0 | 0 | 1 | 9 | 8 |
| chromosome_3_821.BC_05 | 1 | 1 | 1 | 0 | 8 |
| chromosonne_4_684.BC_01 | 3 | 5 | 0 | 4 | 7 |
| chromosome_4_712.BC_01 | 2 | 2 | 1 | 3 | 8 |
| chromosome_4_1028.BC_01 | 9 | 0 | 2 | 24 | 28 |
| chromosome_4_522.BC_01 | 3 | 3 | 1 | 6 | 28 |
| chromosome_4_134.BC_02 | 4 | 5 | 6 | 3 | 12 |
| chromosome_4_83.BC_02 | 17 | 8 | 12 | 37 | 72 |
| chromosome_4_47.BC_02 | 10 | 6 | 6 | 26 | 46 |
| chromosome_4_557.BC_02 | 8 | 11 | 11 | 33 | 50 |
| chromosome_4_608.BC_02 | 2 | 6 | 2 | 18 | 10 |
| chromosonne_4_571.BC_03 | 7 | 1 | 7 | 27 | 30 |
| chromosome_4_831.BC_04 | 3 | 1 | 8 | 16 | 28 |
| chromosome_4_1764.BC_04 | 2 | 1 | 4 | 7 | 8 |
| chromosome_4_2454.BC_04 | 2 | 0 | 0 | 4 | 4 |
| chromosome_4_626.BC_05 | 7 | 10 | 4 | 35 | 33 |
| chromosome_4_785.BC_05 | 21 | 9 | 16 | 51 | 101 |
| chromosome_4_941.BC_05 | 9 | 2 | 2 | 9 | 16 |
| chromosome_4_1677.BC_05 | 0 | 1 | 2 | 3 | 9 |
| chromosome_4_174.BC_05 | 2 | 0 | 2 | 1 | 6 |
| chromosome_4_1911.BC_05 | 2 | 2 | 3 | 15 | 16 |
| chromosome_4_1912.BC_05 | 3 | 1 | 4 | 14 | 17 |
| chromosome_5_1020.BC_01 | 16 | 6 | 7 | 31 | 24 |
| chromosome_5_414.BC_01 | 6 | 14 | 8 | 34 | 40 |
| chromosome_5_595.BC_01 | 1806 | 1137 | 1293 | 5188 | 5759 |
| chromosome_5_620.BC_01 | 82 | 30 | 56 | 269 | 236 |
| chromosome_5_737.BC_01 | 2 | 0 | 0 | 4 | 8 |
| chromosome_5_978.BC_01 | 14 | 10 | 5 | 23 | 28 |
| chromosome_5_70.BC_01 | 16 | 10 | 5 | 28 | 50 |
| chromosome_5_456.BC_02 | 2 | 3 | 3 | 9 | 17 |
| chromosome_5_468.BC_02 | 567 | 272 | 483 | 1915 | 2410 |
| chromosome_5_508.BC_02 | 4 | 6 | 0 | 14 | 8 |
| chromosome_5_657.BC_02 | 14 | 7 | 9 | 35 | 35 |
| chromosome_5_455.BC_02 | 1 | 3 | 1 | 3 | 4 |
| chromosome_5_612.BC_02 | 0 | 4 | 1 | 4 | 6 |
| chromosome_5_642.BC_02 | 1 | 5 | 1 | 6 | 3 |
| chromosome_5_148.BC_03 | 9 | 3 | 10 | 21 | 42 |
| chromosome_5_468.BC_03 | 10 | 0 | 15 | 24 | 12 |
| chromosome_5_509.BC_03 | 187 | 80 | 165 | 508 | 621 |
| chromosome_5_574.BC_03 | 28 | 11 | 33 | 119 | 113 |
| chromosome_5_609.BC_03 | 0 | 0 | 3 | 4 | 3 |
| chromosome_5_648.BC_03 | 0 | 1 | 4 | 1 | 8 |
| chromosome_5_737.BC_03 | 0 | 1 | 3 | 2 | 6 |
| chromosome_5_631.BC_04 | 2 | 0 | 4 | 5 | 16 |
| chromosome_5_646.BC_04 | 6 | 6 | 0 | 17 | 12 |
| chromosome_5_661.BC_04 | 2 | 0 | 2 | 13 | 12 |
| chromosome_5_74.BC_04 | 3 | 2 | 6 | 7 | 15 |
| chromosome_5_1387.BC_04 | 1 | 0 | 0 | 3 | 6 |
| chromosome_5_379.BC_04 | 0 | 2 | 0 | 4 | 7 |
| chromosome_5_456.BC_04 | 0 | 0 | 2 | 7 | 7 |
| chromosome_5_181.BC_05 | 1 | 1 | 1 | 5 | 10 |
| chromosome_5_1255.BC_05 | 4 | 2 | 3 | 9 | 16 |
| chromosome_5_139.BC_05 | 2 | 2 | 1 | 18 | 13 |
| chromosome_6_145.BC_01 | 2 | 2 | 0 | 4 | 14 |
| chromosome_6_146.BC_01 | 2 | 2 | 1 | 4 | 15 |
| chromosome_6_166.BC_01 | 12 | 0 | 10 | 15 | 28 |
| chromosome_6_323.BC_01 | 8 | 8 | 12 | 32 | 51 |
| chromosome_6_657.BC_01 | 14 | 6 | 11 | 11 | 22 |
| chromosome_6_801.BC_01 | 180 | 69 | 246 | 726 | 908 |
| chromosome_6_852.BC_01 | 43 | 3 | 51 | 105 | 154 |
| chromosome_6_201.BC_02 | 3 | 4 | 1 | 2 | 0 |
| chromosome_6_235.BC_02 | 4 | 8 | 0 | 9 | 7 |
| chromosome_6_657.BC_02 | 1 | 3 | 2 | 4 | 0 |
| chromosome_6_166.BC_02 | 3 | 2 | 0 | 3 | 5 |
| chromosome_6_357.BC_02 | 5 | 2 | 3 | 13 | 14 |
| chromosome_6_555.BC_02 | 4 | 9 | 0 | 12 | 5 |
| chromosome_6_159.BC_03 | 1 | 2 | 3 | 5 | 11 |
| chromosome_6_313.BC_03 | 1 | 1 | 2 | 5 | 11 |
| chromosome_6_336.BC_03 | 2 | 5 | 3 | 16 | 16 |
| chromosome_6_337.BC_03 | 2 | 5 | 3 | 16 | 16 |
| chromosome_6_805.BC_03 | 43 | 3 | 51 | 105 | 154 |
| chromosome_6_632.BC_03 | 14 | 6 | 11 | 11 | 22 |
| chromosome_6_67.BC_04 | 3 | 2 | 3 | 7 | 11 |
| chromosome_6_888.BC_04 | 3 | 4 | 7 | 14 | 15 |
| chromosome_6_889.BC_04 | 2 | 4 | 5 | 13 | 13 |
| chromosome_6_1475.BC_04 | 5 | 5 | 1 | 7 | 9 |
| chromosome_6_351.BC_05 | 2 | 3 | 0 | 15 | 8 |
| chromosome_6_972.BC_05 | 5 | 1 | 4 | 16 | 21 |
| chromosome_6_200.BC_05 | 11 | 4 | 9 | 41 | 54 |
| chromosome_6_201.BC_05 | 4 | 1 | 3 | 9 | 14 |
| chromosome_6_202.BC_05 | 3 | 0 | 3 | 9 | 11 |
| chromosome_6_1147.BC_05 | 3 | 2 | 0 | 4 | 17 |

TABLE D-continued

Frequency counts of small RNA reads for new miRNAs

| miRNA | Count of mapped reads to miRNA genes for each library | | | | |
|---|---|---|---|---|---|
| | Mix | BTx623 | Rio | LB/EF F2s | HB/LF F2s |
| chromosome_6_180.BC_05 | 4 | 1 | 3 | 5 | 5 |
| chromosome_7_243.BC_01 | 12 | 2 | 6 | 18 | 37 |
| chromosome_7_294.BC_01 | 18 | 3 | 22 | 48 | 65 |
| chromosonne_7_49.BC_01 | 2 | 8 | 3 | 26 | 23 |
| chromosome_7_62.BC_01 | 7 | 3 | 10 | 13 | 38 |
| chromosome_7_287.BC_01 | 3 | 4 | 0 | 4 | 5 |
| chromosome_7_256.BC_02 | 0 | 3 | 4 | 5 | 6 |
| chromosome_7_395.BC_02 | 5 | 6 | 1 | 18 | 14 |
| chromosome_7_454.BC_02 | 1 | 3 | 1 | 10 | 6 |
| chromosome_7_22.BC_03 | 8 | 6 | 4 | 48 | 9 |
| chromosome_7_366.BC_03 | 12 | 3 | 8 | 28 | 17 |
| chromosome_7_454.BC_03 | 3 | 1 | 3 | 10 | 9 |
| chromosome_7_516.BC_03 | 3 | 2 | 4 | 3 | 9 |
| chromosome_7_568.BC_03 | 2 | 1 | 5 | 1 | 6 |
| chromosome_7_287.BC_03 | 2 | 0 | 4 | 9 | 9 |
| chromosome_7_1053.BC_04 | 2 | 3 | 5 | 12 | 17 |
| chromosome_7_483.BC_04 | 3 | 5 | 1 | 9 | 7 |
| chromosome_7_1887.BC_05 | 13 | 7 | 9 | 24 | 39 |
| chromosome_7_159.BC_05 | 0 | 0 | 2 | 5 | 8 |
| chromosome_7_627.BC_05 | 0 | 0 | 2 | 2 | 7 |
| chromosome_7_628.BC_05 | 0 | 0 | 2 | 1 | 7 |
| chromosome_8_765.BC_01 | 5 | 1 | 6 | 26 | 40 |
| chromosome_8_208.BC_01 | 3 | 2 | 0 | 4 | 4 |
| chromosome_8_401.BC_01 | 2 | 0 | 0 | 4 | 5 |
| chromosome_8_751.BC_01 | 5 | 2 | 2 | 5 | 4 |
| chromosome_8_533.BC_03 | 4 | 3 | 6 | 11 | 22 |
| chromosome_8_216.BC_03 | 3 | 7 | 2 | 9 | 8 |
| chromosome_8_150.BC_04 | 5 | 3 | 1 | 15 | 15 |
| chromosome_8_216.BC_04 | 11 | 3 | 9 | 23 | 24 |
| chromosome_8_681.BC_04 | 2 | 2 | 1 | 9 | 18 |
| chromosome_8_497.BC_04 | 2 | 4 | 3 | 7 | 6 |
| chromosome_8_190.BC_05 | 2 | 6 | 2 | 8 | 16 |
| chromosome_8_297.BC_05 | 13 | 8 | 14 | 51 | 67 |
| chromosome_8_298.BC_05 | 17 | 10 | 17 | 62 | 80 |
| chromosome_8_618.BC_05 | 2 | 3 | 1 | 3 | 10 |
| chromosome_8_468.BC_05 | 1 | 1 | 2 | 4 | 6 |
| chromosome_9_506.BC_01 | 5 | 0 | 1 | 7 | 4 |
| chromosome_9_19.BC_02 | 4 | 10 | 1 | 10 | 9 |
| chromosome_9_554.BC_02 | 4 | 10 | 3 | 22 | 20 |
| chromosome_9_544.BC_02 | 1 | 4 | 1 | 1 | 6 |
| chromosome_9_1189.BC_05 | 1 | 2 | 3 | 18 | 22 |
| chromosome_9_721.BC_05 | 6 | 3 | 4 | 7 | 19 |
| chromosome_9_1132.BC_05 | 6 | 1 | 2 | 5 | 6 |
| chromosome_9_1410.BC_05 | 2 | 2 | 2 | 4 | 5 |
| chromosome_10_293.BC_01 | 26 | 21 | 38 | 85 | 107 |
| chromosome_10_93.BC_01 | 34 | 17 | 23 | 109 | 99 |
| chromosome_10_962.BC_01 | 15 | 2 | 10 | 21 | 36 |
| chromosome_10_593.BC_02 | 8 | 7 | 6 | 25 | 35 |
| chromosome_10_295.BC_02 | 4 | 4 | 1 | 3 | 9 |
| chromosome_10_73.BC_03 | 6 | 3 | 9 | 6 | 24 |
| chromosome_10_77.BC_03 | 3 | 4 | 4 | 3 | 10 |
| chromosome_10_792.BC_03 | 574 | 103 | 594 | 3344 | 470 |
| chromosome_10_1088.BC_04 | 6 | 4 | 7 | 20 | 22 |
| chromosome_10_766.BC_04 | 1 | 2 | 4 | 8 | 11 |
| chromosome_10_1038.BC_04 | 0 | 1 | 0 | 4 | 5 |
| chromosonne_10_1564.BC_05 | 1 | 1 | 1 | 11 | 6 |
| chromosome_10_1885.BC_05 | 4 | 3 | 10 | 28 | 32 |
| chromosome_10_73.BC_05 | 3 | 3 | 1 | 3 | 11 |
| chromosome_10_880.BC_05 | 11 | 1 | 13 | 16 | 36 |
| chromosome_10_216.BC_05 | 2 | 1 | 1 | 1 | 6 |
| chromosome_10_283.BC_05 | 0 | 1 | 2 | 2 | 8 |

TABLE E

List of new miRNAs that are within introns of protein coding genes

| miRNA ID | start | stop | strand |
|---|---|---|---|
| chromosome_1_333.BC_01 | 10623817 | 10624035 | + |
| chromosome_1_1241.BC_03 | 58998763 | 58998981 | + |
| chromosome_2_1490.BC_04 | 14065842 | 14066060 | + |
| chromosome_2_689.BC_03 | 48991679 | 48991897 | + |
| chromosome_2_3135.BC_05 | 26306294 | 26306512 | + |
| chromosome_2_3135.BC_04 | 54647513 | 54647731 | + |
| chromosome_3_1462.BC_04 | 13263113 | 13263331 | + |
| chromosome_4_2454.BC_04 | 41104168 | 41104386 | + |
| chromosome_4_571.BC_03 | 41084010 | 41084228 | + |
| chromosome_5_737.BC_03 | 52069704 | 52069922 | + |
| chromosome_5_1020.BC_01 | 57560746 | 57560964 | + |
| chromosome_6_337.BC_03 | 35870171 | 35870389 | + |
| chromosome_6_1147.BC_05 | 15089799 | 15090017 | + |
| chromosome_6_336.BC_03 | 35870213 | 35870431 | + |
| chromosome_7_454.BC_02 | 55721818 | 55722036 | + |
| chromosome_8_468.BC_05 | 3155112 | 3155330 | + |
| chromosome_9_721.BC_05 | 4452093 | 4452311 | + |

TABLE F

List of new miRNAs that target genes encoding sugar transporters and cell wall related proteins

| miRNA | Target gene | Gene function | Target site |
|---|---|---|---|
| | | Sugar transport | |
| chromosome_4_712_mature.BC_01 | Sb04g036140 | Monosaccharide transporter 6 | Exon |
| chromosome_4_1677_mature.BC_05 | Sb01g016730 | Monosaccharide transporter 2 | Exon |
| | Sb08g016530 | Sugar transporter | Exon |
| chromosome_7_516_mature.BC_03 | Sb10g031000 | Hexose transporter | Exon |
| | | Cell wall metabolism | |
| chromosome_1_882_mature.BC_04 | Sb10g003090 | Pectate lyase homolog | Exon |
| chromosome_1_970_mature.BC_03 | Sb09g020980 | Class III peroxidase 124 precursor | Exon |
| | Sb09g021000 | Class III peroxidase 124 precursor | Exon |
| | Sb03g035080 | Cinnamoyl CoA reductase | Exon |
| chromosome_1_983_mature.BC_04 | Sb04g037050 | Alcohol dehydrogenase class-3 (EC 1.1.1.1) | Exon |
| chromosome_2_45_mature.BC_01 | Sb01g027960 | Xyloglucan endotransglucosylase/hydrolase protein 28 precursor | 3' UTR |
| chromosome_2_1061_mature.BC_05 | Sb01g048630 | Callose synthase 1 catalytic subunit | Exon |
| chromosome_2_1490_mature.BC_04 | Sb05g019040 | O-methyltransferase ZRP4 | Exon |
| chromosome_3_133_mature.BC_04 | Sb09g000430 | Polygalacturonase inhibiting protein 2 precursor | Exon |
| chromosome_3_216_mature.BC_05 | Sb06g000490 | Class III peroxidase 52 precursor | Exon |

TABLE F-continued

List of new miRNAs that target genes encoding sugar transporters and cell wall related proteins

| miRNA | Target gene | Gene function | Target site |
|---|---|---|---|
| chromosome_4_712_mature.BC_01 | Sb07g024870 | Beta-galactosidase 11 precursor | Exon |
| | Sb10g022620 | Beta-galactosidase 9 precursor | Exon |
| | Sb10g024490 | Cinnamoyl CoA reductase | Exon |
| | Sb10g024500 | Cinnamoyl CoA reductase | Exon |
| | Sb049010000 | Expansin-A24 precursor | Exon |
| | Sb04g010160 | Expansin-A23 precursor | Exon |
| | Sb04g010170 | Expansin-A23 precursor | Exon |
| | Sb04g028090 | Expansin-A5 precursor | Exon |
| | Sb04g032830 | Expansin-B11 precursor | Exon |
| | Sb06g023380 | Expansin-B17 precursor | Exon |
| | Sb02g041050 | Esterase | Exon |
| | Sb03g001870 | Esterase | Exon |
| | Sb02g037310 | Fasciclin-like arabinogalactan-protein | Exon |
| | Sb05g026710 | O-methyltransferase | Exon |
| | Sb05g026730 | O-methyltransferase | Exon |
| | Sb03g013070 | Pectinacetylesterase | Exon |
| | Sb02g001130 | Peroxidase | Exon |
| | Sb10g010040 | Peroxidase 49 | Exon |
| | Sb10g005820 | Glutathione peroxidase | Exon |
| | Sb01g028610 | Class III peroxidase 120 precursor | Exon |
| | Sb02g029340 | Class III peroxidase 123 precursor | Exon |
| | Sb049026510 | Phenylalanine ammonia-lyase | Exon |
| | Sb02g022220 | Polygalacturonase isoenzyme 1 beta subunit-like | Exon |
| | Sb03g013310 | Polygalacturonase PG2 | Exon |
| | Sb07g025220 | Sorbitol dehydrogenase | Exon |
| chromosome_4_1677_mature.BC_05 | Sb02g039600 | Alcohol dehydrogenase | Exon |
| | Sb03g029770 | Glycosyl transferase family 1 protein-like | Exon |
| | Sb02g001045 | 4-coumarate-CoA ligase 1 | Exon |
| | Sb02g001050 | 4-coumarate-CoA ligase 1 | Exon |
| | Sb07g007810 | 4-coumarate-CoA ligase 1 | Exon |
| | Sb01g037900 | Pectinesterase family protein | Exon |
| | Sb02g042780 | Pectinesterase | Exon |
| | Sb03g016510 | Peroxidase family protein | Exon |
| | Sb07g026520 | UDP-glucuronic acid 4-epimerase isoform 3 | Exon |
| | Sb01g020070 | Xyloglucan galactosyltransferase KATAMARI 1 | Exon |
| chromosome_5_181_mature.BC_05 | Sb06g033440 | Glutathione peroxidase-like protein GPX15Hv | Exon |
| | Sb08g000990 | Class III peroxidase 135 precursor | 3' UTR |
| chromosome_5_379_mature.BC_04 | Sb07g021680 | Cinnamoyl CoA reductase | Exon |
| | Sb02g010110 | Cellulose synthase-7 | Exon |
| | Sb03g004320 | Cellulose synthase-1 | Exon |
| | Sb04g008640 | Cationic peroxidase 1 precursor | Exon |
| | Sb01g049890 | LysM domain containing protein | Exon |
| chromosome_5_737_mature.BC_03 | Sb06g026010 | Xyloglucan galactosyltransferase | Exon |
| chromosome_7_22_mature.BC_03 | Sb03g028190 | Arbutin synthase-like | Exon |
| | Sb03g047220 | Cellulose synthase | Exon |
| | Sb09g018400 | Esterase | Exon |
| | Sb09g018440 | Esterase | Exon |
| chromosome_7_366_mature.BC_03 | Sb06g024650 | Expansin-B15 precursor | Exon |
| | Sb10g028460 | Class III peroxidase 93 precursor | Exon |
| chromosome_7_627_mature.BC_05 | Sb03g013170 | S-adenosylmethionine synthetase 1 | Exon |
| chromosome_7_1887_mature.BC_05 | Sb02g033070 | Expansin-like A3 precursor | Exon |
| | Sb02g035070 | Brittle stalk-2-like protein 5 | Exon |
| chromosome_8_297_mature.BC_05 | Sb03g011930 | S-adenosylmethionine synthetase 1 | Exon |
| chromosome_8_298_mature.BC_05 | Sb07g028620 | Alkaline alpha galactosidase 3 | Exon |
| chromosome_8_618_mature.BC_05 | Sb09g025540 | O-methyltransferase ZRP4 | Exon |
| | Sb09g025560 | O-methyltransferase ZRP4 | Exon |
| | Sb05g025950 | Extensin-like protein precursor | Exon |
| chromosome_8_751_mature.BC_01 | Sb01g016630 | 4-coumarate-CoA ligase 1 | Exon |
| chromosome_9_1189_mature.BC_05 | Sb01g045200 | Glycosyl transferase, group 1 family protein | 5' UTR |
| | Sb10g008060 | Glycosyl transferase protein A-like | Exon |
| | Sb10g006230 | Pectin methylesterase | Exon |
| | Sb10g028480 | Peroxidase ATP8a | Exon |
| chromosome_10_792_mature.BC_03 | Sb02g000470 | Class III peroxidase 97 precursor | Exon |
| chromosome_10_962_mature.BC_01 | Sb03g047440 | Pectinacetylesterase | Exon |

TABLE G

List of new predicted MIR genes in sorghum

| MIR gene ID | Position | Strand | miRNA size | miRNA sequence 5'-3' | miRNA* sequence 5'-3' | miRNA* size |
|---|---|---|---|---|---|---|
| chromosome_1_52.BC_04 | Ch1: 574388 ... 574497 | + | 19 | AAGATCTGTGGCGCCGAGC | TCGGCGCTAAGATCTCTGG | 19 |

TABLE G-continued

List of new predicted MIR genes in sorghum

| MIR gene ID | Position | Strand | miRNA size | miRNA sequence 5'-3' | miRNA* sequence 5'-3' | miRNA* size |
|---|---|---|---|---|---|---|
| chromosome_2_45.BC_01 | Ch2: 1930828 . . . 1930937 | + | 18 | CCAATCTAAACAGGCCCT | GACCTGTTTAGATTGGGA | 18 |
| chromosome_4_684.BC_01 | Ch4: 43242765 . . . 43242874 | + | 24 | ATGACAGAGCTCCGGCAGAGATAT | TTCTCCGCCGAGCTTATCTGTGG | 23 |
| chromosome_4_712.BC_01 | Ch4: 45785396 . . . 45785505 | + | 18 | CGCGCCGCCGTCCAGCGG | CTTGGCCGGTGCACGCGTC | 19 |
| chromosome_6_852.BC_01 | Ch6: 56307517 . . . 56307626 | + | 22 | ACCACCAACCCCACCGCTTCTC | GAAGCGGTGGTGTTGGTGGTGA | 22 |
| chromosome_7_22.BC_03* | Ch7: 877244 . . . 877353 | + | 20 | CGTCGCTGTCGCGCGCGCTG | GGTCAGGGCAGAGCACGCA | 19 |
| chromosome_7_256.BC_02 | Ch7: 15969322 . . . 15969431 | + | 25 | TAACACGAACCGGTGCTAAAGGATC | CCCTTTAGCACCGGTTCGTGTTACA | 25 |
| chromosome_8_150.BC_04 | Ch8: 1629110 . . . 1629219 | + | 22 | ATCTTTGCCGGGTGTCTCTGAC | CAGCAAACATTCGGCAAAGAAAA | 23 |
| chromosome_8_497.BC_04 | Ch8: 4848342 . . . 4848451 | + | 21 | GCTTGAGTTTATCAGCCGAGT | ATGGCTTATCAGCCAAGTGA | 20 |

*All the small RNA reads mapped to "chromosome_7_22.BC_03" were derived from the predicted miRNA* strand
miRNA sequences from top to bottom are SEQ ID NOs: 28-36 and miRNA* sequences from top to bottom are SEQ ID NOs: 37-45

What is claimed is:

1. A composition comprising at least one miR169 in a biologically compatible carrier, for modulating expression of a sorghum plant target gene, said gene encoding a protein which regulates sugar metabolism, wherein said at least one miR169 is selected from
sbi-miR169b*
sbi-miR169i*
sbi-miR169s and
sbi-miR169r*.

2. The composition of claim 1, wherein said at least one miR169 is cloned into an expression vector, wherein expression of said miRNA from said vector in a sorghum plant decreases sugar content in said sorghum plant, wherein said miR169 is miR169b* and/or miR169i*.

3. The composition of claim 2, wherein said target gene is starch synthase (Sb10g008200) and/or glycogenin-like (sb03g041660).

4. A method for modulating sugar content in a sorghum plant or plant cell comprising contacting said plant or plant cell with an effective amount of the composition as claimed in claim 1, cloned within an expression vector or the vector of claim 2.

5. A sorghum plant comprising an expression vector which expresses the miRNA169 composition of claim 1 or the expression vector of claim 2.

6. The composition of claim 1, wherein said miR169 is sbi-miR169s.

7. The composition of claim 1, wherein said miR169 is sbi-miR169r*.

* * * * *

SEQUENCE LISTING

<160> NUMBER OF SEQ ID NOS: 873

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
tgcagccttg tctttgtttg                                                    20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
cctggaacct gtggtgaaat                                                    20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
gcccatatgg acggaagata                                                    20

<210> SEQ ID NO 4
<211> LENGTH: 20
<212> TYPE: DNA

<213> ORGANISM: Artificial Sequence
<220> FEATURE:
<223> OTHER INFORMATION: Primer

<400> SEQUENCE: 4
ctggtagccg gagaacaact                                                   20

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
ttgacaatgt ctgcctggtc                                                   20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cgctggtcag caatctgata                                                   20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gcactcaagt ccagcacaaa                                                   20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tttcatcagt gcttgccaat                                                   20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
tggctggatc taccacttcc                                                   20

<210> SEQ ID NO 10
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 10
ggcaggucuu cuuggcuagc                                                   20

```
<210> SEQ ID NO 11
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 11
gaaagccaag aagacucguu uguuu                                              25

<210> SEQ ID NO 12
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 12
ugaaucuuga ugaugcugca c                                                  21

<210> SEQ ID NO 13
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 13
gcgcaggcau caucaagauc a                                                  21

<210> SEQ ID NO 14
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 14
ggaucuugau gaugcugca                                                     19

<210> SEQ ID NO 15
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 15
ugcagcauca ucaggauucu c                                                  21

<210> SEQ ID NO 16
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 16
guucccuuca agcacuucac a                                                  21

<210> SEQ ID NO 17
<211> LENGTH: 21
<212> TYPE: DNA
<213> ORGANISM: Artificial Sequence
<220> FEATURE:
```

<223> OTHER INFORMATION: Synthetic Sequence

<400> SEQUENCE: 17
tgtggagtgc ttgaagagag t                                                     21

<210> SEQ ID NO 18
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 18
ggaaucuuga ugaugcugca                                                       20

<210> SEQ ID NO 19
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 19
ugcagcauca ucacgauucc                                                       20

<210> SEQ ID NO 20
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 20
ucaucuccuu gucaugca                                                         18

<210> SEQ ID NO 21
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 21
ugaaggagaa ggagaugaat ctgcgcaaga gcaa                                       34

<210> SEQ ID NO 22
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 22
ucaucuccuu gucaugca                                                         18

<210> SEQ ID NO 23
<211> LENGTH: 31
<212> TYPE: DNA
<213> ORGANISM: Artificial Sequence
<220> FEATURE:
<223> OTHER INFORMATION: Synthetic Sequence

<400> SEQUENCE: 23
ucacaugaca aggaaugaag acctttggag g                                          31

```
<210> SEQ ID NO 24
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 24
ucaucuccuu gucaugca                                                       18

<210> SEQ ID NO 25
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 25
uccaugacaa ggagagca                                                       18

<210> SEQ ID NO 26
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 26
cgcgccgccg uccagcgg                                                       18

<210> SEQ ID NO 27
<211> LENGTH: 34
<212> TYPE: DNA
<213> ORGANISM: Artificial Sequence
<220> FEATURE:
<223> OTHER INFORMATION: Synthetic Sequence

<400> SEQUENCE: 27
cctccgcgcg gacggcgagc gcgagttcat gttc                                     34

<210> SEQ ID NO 28
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 28
aagatctgtg gcgccgagc                                                      19

<210> SEQ ID NO 29
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 29
ccaatctaaa caggccct                                                       18

<210> SEQ ID NO 30
<211> LENGTH: 24
<212> TYPE: DNA
<213> ORGANISM: Artificial Sequence
<220> FEATURE:
<223> OTHER INFORMATION: Synthetic Sequence
```

-continued

<400> SEQUENCE: 30
atgacagagc tccggcagag atat                                        24

<210> SEQ ID NO 31
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 31
cgcgccgccg tccagcgg                                               18

<210> SEQ ID NO 32
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 32
accaccaacc ccaccgcttc tc                                          22

<210> SEQ ID NO 33
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 33
cgtcgctgtc gcgcgcgctg                                             20

<210> SEQ ID NO 34
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 34
taacacgaac cggtgctaaa ggatc                                       25

<210> SEQ ID NO 35
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 35
atctttgccg ggtgtctctg ac                                          22

<210> SEQ ID NO 36
<211> LENGTH: 21
<212> TYPE: DNA
<213> ORGANISM: Artificial Sequence
<220> FEATURE:
<223> OTHER INFORMATION: Synthetic Sequence

<400> SEQUENCE: 36
gcttgagttt atcagccgag t                                           21

<210> SEQ ID NO 37
<211> LENGTH: 19

<212> TYPE: DNA
<213> ORGANISM: Artificial Sequence
<220> FEATURE:
<223> OTHER INFORMATION: Synthetic Sequence

<400> SEQUENCE: 37
tcggcgctaa gatctctgg                                          19

<210> SEQ ID NO 38
<211> LENGTH: 18
<212> TYPE: DNA
<213> ORGANISM: Artificial Sequence
<220> FEATURE:
<223> OTHER INFORMATION: Synthetic Sequence

<400> SEQUENCE: 38
gacctgttta gattggga                                           18

<210> SEQ ID NO 39
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 39
ttctccgccg agcttatctg tgg                                     23

<210> SEQ ID NO 40
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 40
cttggccggt gcacgcgtc                                          19

<210> SEQ ID NO 41
<211> LENGTH: 22
<212> TYPE: DNA
<213> ORGANISM: Artificial Sequence
<220> FEATURE:
<223> OTHER INFORMATION: Synthetic Sequence

<400> SEQUENCE: 41
gaagcggtgg tgttggtggt ga                                      22

<210> SEQ ID NO 42
<211> LENGTH: 19
<212> TYPE: DNA
<213> ORGANISM: Artificial Sequence
<220> FEATURE:
<223> OTHER INFORMATION: Synthetic Sequence

<400> SEQUENCE: 42
ggtcagggca gagcacgca                                          19

<210> SEQ ID NO 43
<211> LENGTH: 25
<212> TYPE: DNA
<213> ORGANISM: Artificial Sequence
<220> FEATURE:
<223> OTHER INFORMATION: Synthetic Sequence

<400> SEQUENCE: 43 cccttttagca ccggttcgtg ttaca                                          25

<210> SEQ ID NO 44
<211> LENGTH: 23
<212> TYPE: DNA
<213> ORGANISM: Artificial Sequence
<220> FEATURE:
<223> OTHER INFORMATION: Synthetic Sequence

<400> SEQUENCE: 44
cagcaaacat tcggcaaaga aaa                                             23

<210> SEQ ID NO 45
<211> LENGTH: 20
<212> TYPE: DNA
<213> ORGANISM: Artificial Sequence
<220> FEATURE:
<223> OTHER INFORMATION: Synthetic Sequence

<400> SEQUENCE: 45
atggcttatc agccaagtga                                                 20

<210> SEQ ID NO 46
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 46
uagccaagga ugacuugccu a                                               21

<210> SEQ ID NO 47
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 47
uaggcaaggc cuacuuggcu a                                               21

<210> SEQ ID NO 48
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 48
uagccaagaa ugacuugccu a                                               21

<210> SEQ ID NO 49
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 49
uaggcaaggc cuacuuggcu a                                               21

<210> SEQ ID NO 50
<211> LENGTH: 21
<212> TYPE: RNA
<213> ORGANISM: Artificial Sequence

```
<220> FEATURE:
<223> OTHER INFORMATION: Synthetic Sequence

<400> SEQUENCE: 50
gugaaguguu uggggggaacu c                                              21

<210> SEQ ID NO 51
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 51
gaguuuuccc aaacacuuca u                                               21

<210> SEQ ID NO 52
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 52
augaaguguu uggggggaacu c                                              21

<210> SEQ ID NO 53
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 53
gaguuuuccc aaacacuuca u                                               21

<210> SEQ ID NO 54
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 54
gggaagaggu gcgaggau                                                   18

<210> SEQ ID NO 55
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 55
auccucgcac gcucccuccc                                                 20

<210> SEQ ID NO 56
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 56
uucuuugccg agagccugc                                                  19
```

<210> SEQ ID NO 57
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 57
gcagucucuc ggaagagaa                                                19

<210> SEQ ID NO 58
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 58
uucuuugccg agagccugc                                                19

<210> SEQ ID NO 59
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 59
gcagucucuc ggaagagaa                                                19

<210> SEQ ID NO 60
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 60
ucaucuccuu gucaugca                                                 18

<210> SEQ ID NO 61
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 61
aguaugacaa ggaaauga                                                 18

<210> SEQ ID NO 62
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 62
ugcauuguga gugcccuua                                                19

<210> SEQ ID NO 63
<211> LENGTH: 19
<212> TYPE: RNA
<213> ORGANISM: Artificial Sequence
<220> FEATURE:
<223> OTHER INFORMATION: Synthetic Sequence

```
<400> SEQUENCE: 63
uaagggcacu cacaauaca                                            19

<210> SEQ ID NO 64
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 64
cgcacggcgg cggcgcgacg g                                         21

<210> SEQ ID NO 65
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 65
ccgucgccgc cgccgccgcc g                                         21

<210> SEQ ID NO 66
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 66
cgcacggcgg cggcgcgacg g                                         21

<210> SEQ ID NO 67
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 67
ccgccgccgc cgccgcccug cg                                        22

<210> SEQ ID NO 68
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 68
caauccacau gcguuggggu gg                                        22

<210> SEQ ID NO 69
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 69
ccaccucaac acaugcggau ug                                        22

<210> SEQ ID NO 70
```

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 70
caauccacau gcguuggggu gg                                              22

<210> SEQ ID NO 71
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 71
ccacaccaac acauguggau ug                                              22

<210> SEQ ID NO 72
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 72
caauccacau gcguuggggu gg                                              22

<210> SEQ ID NO 73
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 73
ccacuucaac acauguggau ug                                              22

<210> SEQ ID NO 74
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 74
caauccacau gcguuggggu gg                                              22

<210> SEQ ID NO 75
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 75
ccacuccaac acauguggau ug                                              22

<210> SEQ ID NO 76
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 76
```
acauguguug gaguggauug ggg                              23

<210> SEQ ID NO 77
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 77
cuccaaucca caccaacaca ugu                              23

<210> SEQ ID NO 78
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 78
acauguguug gaguggauug ggg                              23

<210> SEQ ID NO 79
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 79
ccccaaucca cuucaacaca ugu                              23

<210> SEQ ID NO 80
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 80
acauguguug gaguggauug ggg                              23

<210> SEQ ID NO 81
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 81
ccccaaucca cuccaacaca ugu                              23

<210> SEQ ID NO 82
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 82
acauguguug agguggauug ggg                              23

<210> SEQ ID NO 83
<211> LENGTH: 23
<212> TYPE: RNA

```
<213> ORGANISM: Artificial Sequence
<220> FEATURE:
<223> OTHER INFORMATION: Synthetic Sequence

<400> SEQUENCE: 83
ccccaaucca cuccaacaca ugu                                            23

<210> SEQ ID NO 84
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 84
acauguguug agguggauug ggg                                            23

<210> SEQ ID NO 85
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 85
cuccaaucua ccucaacacg ugu                                            23

<210> SEQ ID NO 86
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 86
aaauuccacc cuaauccacu ccaa                                           24

<210> SEQ ID NO 87
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 87
uuggaguaga uuggggugga auuu                                           24

<210> SEQ ID NO 88
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 88
aaauuccacc cuaauccacu ccaa                                           24

<210> SEQ ID NO 89
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 89
uuggagugga uuggggugga auuu                                           24
```

<210> SEQ ID NO 90
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 90
aucccaaucc acaccaacac acau                                              24

<210> SEQ ID NO 91
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 91
auguguguug guguggguug gagu                                              24

<210> SEQ ID NO 92
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 92
uagccaagga ugacuugccu a                                                 21

<210> SEQ ID NO 93
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 93
uagagcaagu cguccuugga ua                                                22

<210> SEQ ID NO 94
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 94
cagccaagga ugacuugccg g                                                 21

<210> SEQ ID NO 95
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 95
ccggcaacuc aucaguggcu g                                                 21

<210> SEQ ID NO 96
<211> LENGTH: 21
<212> TYPE: RNA
<213> ORGANISM: Artificial Sequence
<220> FEATURE:

<223> OTHER INFORMATION: Synthetic Sequence

<400> SEQUENCE: 96
cagccaagga ugacuugccg a                                      21

<210> SEQ ID NO 97
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 97
uccggcaaau cauccuuggc g                                      21

<210> SEQ ID NO 98
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 98
cagccaagga ugacuugccg g                                      21

<210> SEQ ID NO 99
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 99
uccggcaaau cauccuuggc g                                      21

<210> SEQ ID NO 100
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 100
uaggcaaguc auccuuggcu a                                      21

<210> SEQ ID NO 101
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 101
uagccaagga ugcagccua                                         19

<210> SEQ ID NO 102
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 102
ucggcaaguc auccuuggcu g                                      21

```
<210> SEQ ID NO 103
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 103
cugccggagg augacuugcc ga                                              22

<210> SEQ ID NO 104
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 104
ccggcaaguc auccuuggcu g                                               21

<210> SEQ ID NO 105
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 105
cuaguccaag gaugacuuac cgg                                             23

<210> SEQ ID NO 106
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 106
caggcaaguc auccuuggcu a                                               21

<210> SEQ ID NO 107
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 107
uaguccaagg augacuuacc gg                                              22

<210> SEQ ID NO 108
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 108
ccggcaaguc auccuuggcu g                                               21

<210> SEQ ID NO 109
<211> LENGTH: 20
<212> TYPE: RNA
<213> ORGANISM: Artificial Sequence
<220> FEATURE:
<223> OTHER INFORMATION: Synthetic Sequence
```

```
<400> SEQUENCE: 109
cagcaaggag gaccugccgg                                              20

<210> SEQ ID NO 110
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 110
uaggcaaguc auucuuggcu a                                            21

<210> SEQ ID NO 111
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 111
uaaccaagaa ugaguugccu c                                            21

<210> SEQ ID NO 112
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 112
ccggcaaguc auccuuggcu g                                            21

<210> SEQ ID NO 113
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 113
cagccuggau gacugccgg                                               19

<210> SEQ ID NO 114
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 114
ucggcaaguc auccuuggcu g                                            21

<210> SEQ ID NO 115
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 115
cagccaggau aguugccga                                               19

<210> SEQ ID NO 116
<211> LENGTH: 21
```

```
<212> TYPE: RNA
<213> ORGANISM: Artificial Sequence
<220> FEATURE:
<223> OTHER INFORMATION: Synthetic Sequence

<400> SEQUENCE: 116
ccggcaaguc auccuuggcu g                                              21

<210> SEQ ID NO 117
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 117
cgccaaagau gacuugcugg                                                20

<210> SEQ ID NO 118
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 118
ccggcaaguc auccuuggcu g                                              21

<210> SEQ ID NO 119
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 119
caccaaagau gacuugcugg                                                20

<210> SEQ ID NO 120
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 120
uaggcaaguc auccuuggcu a                                              21

<210> SEQ ID NO 121
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 121
uagccaagga ugcagccua                                                 19

<210> SEQ ID NO 122
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 122
```
ucggcaaguc auccuuggcu g                                            21

<210> SEQ ID NO 123
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 123
cagccacagg augaguugcg a                                            21

<210> SEQ ID NO 124
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 124
ucggcaaguc auccuuggcu g                                            21

<210> SEQ ID NO 125
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 125
cgccaaggag cuugccga                                                18

<210> SEQ ID NO 126
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 126
ccggcaaguc auccuuggcu g                                            21

<210> SEQ ID NO 127
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 127
ccgccaagga ugaccgccgg                                              20

<210> SEQ ID NO 128
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 128
ccggcaaguc auccuuggcu g                                            21

<210> SEQ ID NO 129
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 129
ccgccaagga ugaccgccgg                                             20

<210> SEQ ID NO 130
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 130
uaggcaaguc auccuuggcu a                                           21

<210> SEQ ID NO 131
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 131
uagccaagga ugcugcua                                               18

<210> SEQ ID NO 132
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 132
ccggcaaguc auccuuggcu g                                           21

<210> SEQ ID NO 133
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 133
aagccaagga ugauuccgg                                              19

<210> SEQ ID NO 134
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 134
agaaucuuga ugaugcugca                                             20

<210> SEQ ID NO 135
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 135
ugcagcauca ucaggauucu                                             20

<210> SEQ ID NO 136
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 136
ggaaucuuga ugaugcugca                                               20

<210> SEQ ID NO 137
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 137
ugcagcauca ucaggauucu c                                             21

<210> SEQ ID NO 138
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 138
ggaaucuuga ugaugcugca                                               20

<210> SEQ ID NO 139
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 139
uggagcacca ucaagauucu                                               20

<210> SEQ ID NO 140
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 140
agaaucuuga ugaugcugca                                               20

<210> SEQ ID NO 141
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 141
uggagcacca ucaagauucu                                               20

<210> SEQ ID NO 142
<211> LENGTH: 20
<212> TYPE: RNA
<213> ORGANISM: Artificial Sequence
<220> FEATURE:
<223> OTHER INFORMATION: Synthetic Sequence

```
<400> SEQUENCE: 142
agaaucuuga ugaugcugca                                              20

<210> SEQ ID NO 143
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 143
ucagcaugau caagcauucu                                              20

<210> SEQ ID NO 144
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 144
ggaaucuuga ugaugcugca                                              20

<210> SEQ ID NO 145
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 145
uugcugcauc auaagauucc                                              20

<210> SEQ ID NO 146
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 146
ggaaucuuga ugaugcugca                                              20

<210> SEQ ID NO 147
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 147
cgcagcauca ucaggauucc                                              20

<210> SEQ ID NO 148
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 148
agaaucuuga ugaugcugca                                              20

<210> SEQ ID NO 149
```

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 149
cgcagcauca ucaggauucc                                                    20

<210> SEQ ID NO 150
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 150
agaaucuuga ugaugcugca                                                    20

<210> SEQ ID NO 151
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 151
ugcaagcauc aucaaggcuc u                                                  21

<210> SEQ ID NO 152
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 152
agaaucuuga ugaugcugca                                                    20

<210> SEQ ID NO 153
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 153
ugagcaucau caaaauucau                                                    20

<210> SEQ ID NO 154
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 154
ugaaucuuga ugaugcugca c                                                  21

<210> SEQ ID NO 155
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 155
```
gcgcaggcau caucaagauc a                                             21

<210> SEQ ID NO 156
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 156
ugaaucuuga ugaugcugca c                                             21

<210> SEQ ID NO 157
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 157
cugcagcauc aucaggauuc u                                             21

<210> SEQ ID NO 158
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 158
ugaaucuuga ugaugcugca c                                             21

<210> SEQ ID NO 159
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 159
gugacagcau aucaacauuc a                                             21

<210> SEQ ID NO 160
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 160
ugaaucuuga ugaugcugca c                                             21

<210> SEQ ID NO 161
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 161
guacagcaca cucaagauuc a                                             21

<210> SEQ ID NO 162
<211> LENGTH: 21
<212> TYPE: RNA

```
<213> ORGANISM: Artificial Sequence
<220> FEATURE:
<223> OTHER INFORMATION: Synthetic Sequence

<400> SEQUENCE: 162
ugaaucuuga ugaugcugca c                                              21

<210> SEQ ID NO 163
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 163
gcugcagauc augaagauuc a                                              21

<210> SEQ ID NO 164
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 164
ugaaucuuga ugaugcugca c                                              21

<210> SEQ ID NO 165
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 165
gcugcagcau caucacgauu cc                                             22

<210> SEQ ID NO 166
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 166
agaaucuuga ugaugcugca                                                20

<210> SEQ ID NO 167
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 167
ugcagcauca ucacgauucc                                                20

<210> SEQ ID NO 168
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 168
ggaaucuuga ugaugcugca                                                20
```

<210> SEQ ID NO 169
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 169
ugcagcauca ucacgauucc                                                    20

<210> SEQ ID NO 170
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 170
gugaaguguu uggggaacu c                                                   21

<210> SEQ ID NO 171
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 171
gaguuccucc aagcacuuca u                                                  21

<210> SEQ ID NO 172
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 172
augaaguguu uggggaacu c                                                   21

<210> SEQ ID NO 173
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 173
gaguuccucc aagcacuuca u                                                  21

<210> SEQ ID NO 174
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 174
gaguuccccc aaacacuuca c                                                  21

<210> SEQ ID NO 175
<211> LENGTH: 19
<212> TYPE: RNA
<213> ORGANISM: Artificial Sequence
<220> FEATURE:

<223> OTHER INFORMATION: Synthetic Sequence

<400> SEQUENCE: 175
gugaaguuuu ugggaauc                                                          19

<210> SEQ ID NO 176
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 176
gaguuccccc aaacacuuca c                                                      21

<210> SEQ ID NO 177
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 177
gugauguguu ugggaauc                                                          19

<210> SEQ ID NO 178
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 178
gaguuccccc aaacacuuca u                                                      21

<210> SEQ ID NO 179
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 179
augaauguug ggggaaauc                                                         19

<210> SEQ ID NO 180
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 180
gaguuccccc aaacacuuca u                                                      21

<210> SEQ ID NO 181
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 181
augaaguguu uugggagcuc                                                        20

```
<210> SEQ ID NO 182
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 182
gaguuccccc aaacacuuca u                                              21

<210> SEQ ID NO 183
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 183
augaagguug ggggaacuac                                                20

<210> SEQ ID NO 184
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 184
uuaaugugaa uccaauga                                                  18

<210> SEQ ID NO 185
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 185 ucauggaug cacaguag                                                   18

<210> SEQ ID NO 186
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 186
uuaaugugaa uccaauga                                                  18

<210> SEQ ID NO 187
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 187 ucauggcau ugacauuga                                                  19

<210> SEQ ID NO 188
<211> LENGTH: 19
<212> TYPE: RNA
<213> ORGANISM: Artificial Sequence
<220> FEATURE:
<223> OTHER INFORMATION: Synthetic Sequence
```

<400> SEQUENCE: 188
agaucugugg ugccgagcu					19

<210> SEQ ID NO 189
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 189
cugcucggca ccaagaucu					19

<210> SEQ ID NO 190
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 190
cgugccugau agugccgug					19

<210> SEQ ID NO 191
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 191
cucggcacca gcaggcacg					19

<210> SEQ ID NO 192
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 192
cugagggugc aaguggga					18

<210> SEQ ID NO 193
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 193
cucccacugc accuucag					18

<210> SEQ ID NO 194
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 194
guccgcgaca accacgaag					19

<210> SEQ ID NO 195
<211> LENGTH: 19

```
<212> TYPE: RNA
<213> ORGANISM: Artificial Sequence
<220> FEATURE:
<223> OTHER INFORMATION: Synthetic Sequence

<400> SEQUENCE: 195
cuucguggau guucgcgac                                                       19

<210> SEQ ID NO 196
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 196
guccgcgaca accacgaag                                                       19

<210> SEQ ID NO 197
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 197
cuucgagguu gucgaugac                                                       19

<210> SEQ ID NO 198
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 198
guccgcgaca accacgaag                                                       19

<210> SEQ ID NO 199
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 199
cuucgagguu gucgaugac                                                       19

<210> SEQ ID NO 200
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 200
guccgcgaca accacgaag                                                       19

<210> SEQ ID NO 201
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 201
```
cuucgucguc gucgcggac                                                19

<210> SEQ ID NO 202
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 202
acaaagcuca acuucacu                                                 18

<210> SEQ ID NO 203
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 203
agugaaguug cuauuugu                                                 18

<210> SEQ ID NO 204
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 204
acaaagcuca acuucacu                                                 18

<210> SEQ ID NO 205
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 205
agugaagucg agcuugagu                                                19

<210> SEQ ID NO 206
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 206
aagaucugug gcgccgagc                                                19

<210> SEQ ID NO 207
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 207
gcucguucgc caagaucuu                                                19

<210> SEQ ID NO 208
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 208
cuucccaugg uucgacggg                                               19

<210> SEQ ID NO 209
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 209
cccgacgaaa caugggacag                                              20

<210> SEQ ID NO 210
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 210
agccgcccuu acugugagca                                              20

<210> SEQ ID NO 211
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 211
ugaucacagu caagggcgcc u                                            21

<210> SEQ ID NO 212
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 212
ccucaacaca cuggauug                                                19

<210> SEQ ID NO 213
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 213
aaauccaaau cuguugagg                                               19

<210> SEQ ID NO 214
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 214
guuggagaaa cugcaauagg uu                                           22

<210> SEQ ID NO 215
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 215
aaccuauugc ugauucaucc aac                                    23

<210> SEQ ID NO 216
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 216
ucggaccagg cuucauuccc c                                      21

<210> SEQ ID NO 217
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 217
ugggaaugaa gccucguccg c                                      21

<210> SEQ ID NO 218
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 218
uugagguaga uuggagug                                          18

<210> SEQ ID NO 219
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 219
cgcuccaacu cuaccuuaa                                         19

<210> SEQ ID NO 220
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 220
uugagguaga uuggagug                                          18

<210> SEQ ID NO 221
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 221
cuacuccaac uaccucag                                                    18

<210> SEQ ID NO 222
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 222
ccucgacucc gcgugcgcau c                                                21

<210> SEQ ID NO 223
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 223
gaugcgcacg cggagcgacg g                                                21

<210> SEQ ID NO 224
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 224
ugcaaucgga ccgguaaaaa                                                  20

<210> SEQ ID NO 225
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 225
uuuauaccac uccgauugca                                                  20

<210> SEQ ID NO 226
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 226
gcgggagcuc cuccuuagcc uggu                                             24

<210> SEQ ID NO 227
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 227
accaggcuaa ggaggaacuc ccgg                                             24

<210> SEQ ID NO 228

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 228
acgccugagg gugcaagugg gag                                          23

<210> SEQ ID NO 229
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 229 gucccuugc acccucaggc cgu                                           23

<210> SEQ ID NO 230
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 230
ggugggccgg ucauggcggg g                                            21

<210> SEQ ID NO 231
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 231
ccccguccau gacccggccc ucc                                          23

<210> SEQ ID NO 232
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 232
ugaagucgcc cgccauggcc gcga                                         24

<210> SEQ ID NO 233
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 233
ucgcggucau ggcgggcggc uuca                                         24

<210> SEQ ID NO 234
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 234
```
uggcgacggc ggucucggcc guac                                          24

<210> SEQ ID NO 235
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 235
guacggccga daccgccgca gccg                                          24

<210> SEQ ID NO 236
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 236
acgaagggcg ugagugcggg g                                             21

<210> SEQ ID NO 237
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 237
ccccgacauc acgcgcuucg u                                             21

<210> SEQ ID NO 238
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 238
uugcucuuag aaguugugc                                                19

<210> SEQ ID NO 239
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 239
gcacagcaac uaagagcaa                                                19

<210> SEQ ID NO 240
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 240
cgucguggug ggggacgugg                                               20

<210> SEQ ID NO 241
<211> LENGTH: 20
<212> TYPE: RNA

<213> ORGANISM: Artificial Sequence
<220> FEATURE:
<223> OTHER INFORMATION: Synthetic Sequence

<400> SEQUENCE: 241
ccagucccac cacuacgacg                                               20

<210> SEQ ID NO 242
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 242
cgucguggug ggggacgugg                                               20

<210> SEQ ID NO 243
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 243
caacgucucc cuccacgacg                                               20

<210> SEQ ID NO 244
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 244
ccagauccca ccagcgggcg u                                             21

<210> SEQ ID NO 245
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 245
acgccugcug gugggaccug g                                             21

<210> SEQ ID NO 246
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 246
ccaaucuaaa caggcccu                                                 18

<210> SEQ ID NO 247
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 247
agggccuguu uccaaugg                                                 18

```
<210> SEQ ID NO 248
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 248
ccguacaagc uguagcuagg                                                     20

<210> SEQ ID NO 249
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 249
ccuagccaga gcuuguccgg                                                     20

<210> SEQ ID NO 250
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 250
uggccuuugu cgugugug                                                       18

<210> SEQ ID NO 251
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 251
gcaccacggc aaaggcca                                                       18

<210> SEQ ID NO 252
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 252
uggccuuugu cgugugug                                                       18

<210> SEQ ID NO 253
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 253
cacauaccga aaaggcca                                                       18

<210> SEQ ID NO 254
<211> LENGTH: 18
<212> TYPE: RNA
<213> ORGANISM: Artificial Sequence
<220> FEATURE:
```

<223> OTHER INFORMATION: Synthetic Sequence

<400> SEQUENCE: 254
uggccuuugu cgugugug    18

<210> SEQ ID NO 255
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 255
ucacacacga caaaagca    18

<210> SEQ ID NO 256
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 256
cacacuucuc aaugcgaa    18

<210> SEQ ID NO 257
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 257
uuuacauuga gcagugug    18

<210> SEQ ID NO 258
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 258
caaguuccac ucuaauccac    20

<210> SEQ ID NO 259
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 259
guggauucag aauggaauug    20

<210> SEQ ID NO 260
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 260
cucaccuuca guucggauug ua    22

```
<210> SEQ ID NO 261
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 261
uacaauccca acuggaggug ac                                          22

<210> SEQ ID NO 262
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 262
ccucgggaug ccccuggcgg c                                           21

<210> SEQ ID NO 263
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 263
cgccgccggg gcagcccgag g                                           21

<210> SEQ ID NO 264
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 264
aguucgagcc ggagguggcg                                             20

<210> SEQ ID NO 265
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 265
cuccaccucc ggcuccaacc                                             20

<210> SEQ ID NO 266
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 266
guguuggagu ggauuggg                                               18

<210> SEQ ID NO 267
<211> LENGTH: 18
<212> TYPE: RNA
<213> ORGANISM: Artificial Sequence
<220> FEATURE:
<223> OTHER INFORMATION: Synthetic Sequence
```

```
<400> SEQUENCE: 267
cccaucacac ugcaacac                                                 18

<210> SEQ ID NO 268
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 268
uugaggugga uuggagugga                                               20

<210> SEQ ID NO 269
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 269
uccaauccaa uccaacacaa                                               20

<210> SEQ ID NO 270
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 270
auuugccccg ccaagcaugg                                               20

<210> SEQ ID NO 271
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 271
ccgaugcuug gggggcaauu                                               20

<210> SEQ ID NO 272
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 272
gaagucggag ccguuucgg                                                19

<210> SEQ ID NO 273
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 273
ccgaaccgga cuccgacucc                                               20

<210> SEQ ID NO 274
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 274
gaagucggag ccguuucgg                                                  19

<210> SEQ ID NO 275
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 275
ccgcaacggc uucgccuuc                                                  19

<210> SEQ ID NO 276
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 276
gcucggacgg gccagugu                                                   18

<210> SEQ ID NO 277
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 277
accucuggcc cgucgagc                                                   18

<210> SEQ ID NO 278
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 278
gcucggacgg gccagugu                                                   18

<210> SEQ ID NO 279
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 279
acacuggguc cuccgagc                                                   18

<210> SEQ ID NO 280
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 280
```
aacuccagca gagccccua                                      19

<210> SEQ ID NO 281
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 281 uggggggcugc ugcugcaguu                                    20

<210> SEQ ID NO 282
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 282
aacuccagca gagccccua                                      19

<210> SEQ ID NO 283
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 283
aaggggucuc cgcuggaguu                                     20

<210> SEQ ID NO 284
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 284
gcugagcugc uagcuuccau a                                   21

<210> SEQ ID NO 285
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 285
uaugggaagu aggagcucag c                                   21

<210> SEQ ID NO 286
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 286
ccagcggcuc cuucacccac accg                                24

<210> SEQ ID NO 287
<211> LENGTH: 24
<212> TYPE: RNA
<213> ORGANISM: Artificial Sequence

```
<220> FEATURE:
<223> OTHER INFORMATION: Synthetic Sequence

<400> SEQUENCE: 287 cgguguggu gaaggagcug cugg                                        24

<210> SEQ ID NO 288
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 288
uggagcaccc gucagcggcc cu                                         22

<210> SEQ ID NO 289
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 289
agguccgcga cggcgugcuc ca                                         22

<210> SEQ ID NO 290
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 290
uccacuccaa uccacuccaa c                                          21

<210> SEQ ID NO 291
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 291
gguggagugg auuguacugg a                                          21

<210> SEQ ID NO 292
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 292
gaacaacggc cgggacguc                                             19

<210> SEQ ID NO 293
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 293
gacguccggc cggguguuc                                             19
```

<210> SEQ ID NO 294
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 294
gaacaacggc cgggacguc                                                    19

<210> SEQ ID NO 295
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 295
gaccgacccg gccguguuc                                                    19

<210> SEQ ID NO 296
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 296
cgcggccaga gcagcggcgg cgcu                                              24

<210> SEQ ID NO 297
<211> LENGTH: 26
<212> TYPE: RNA
<213> ORGANISM: Artificial Sequence
<220> FEATURE:
<223> OTHER INFORMATION: Synthetic Sequence

<400> SEQUENCE: 297
agcucacgcc gcugcaucug gccgcg                                            26

<210> SEQ ID NO 298
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 298
ugcauuguga gugcccuua                                                    19

<210> SEQ ID NO 299
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 299
uaagggcaau cacaaggaa                                                    19

<210> SEQ ID NO 300
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 300
gaggcgcugc uguccuccac ac                                             22

<210> SEQ ID NO 301
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 301
ggugcaggac agcagccgcc uc                                             22

<210> SEQ ID NO 302
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 302
aaucaauuuc aacacaugu                                                 19

<210> SEQ ID NO 303
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 303
acauuugaug aaauugaug                                                 19

<210> SEQ ID NO 304
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 304
cgcgccgccg uccagcgg                                                  18

<210> SEQ ID NO 305
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 305
ccguggaggg cggcgucg                                                  18

<210> SEQ ID NO 306
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 306
cgcgccgccg uccagcgg                                                  18

<210> SEQ ID NO 307

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 307
aagcuggacg gcggcggg                                                 18

<210> SEQ ID NO 308
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 308
cgcgccgccg uccagcgg                                                 18

<210> SEQ ID NO 309
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 309
cgcgcuggac ggcgccagcg                                               20

<210> SEQ ID NO 310
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 310
cgcgccgccg uccagcgg                                                 18

<210> SEQ ID NO 311
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 311
ccgcuggcgg uggcgccg                                                 18

<210> SEQ ID NO 312
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 312
cgcgccgccg uccagcgg                                                 18

<210> SEQ ID NO 313
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 313
```
cgcgcuggac gcggcgcu                                                      18

<210> SEQ ID NO 314
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 314
cgcgccgccg uccagcgg                                                      18

<210> SEQ ID NO 315
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 315
ccgcaggcgg cggcggcg                                                      18

<210> SEQ ID NO 316
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 316
cgcgccgccg uccagcgg                                                      18

<210> SEQ ID NO 317
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 317
ccgcguggcg gcggucgcg                                                     19

<210> SEQ ID NO 318
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 318
cgcgccgccg uccagcgg                                                      18

<210> SEQ ID NO 319
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 319
gcgcuggcgg cggcagcg                                                      18

<210> SEQ ID NO 320
<211> LENGTH: 18
<212> TYPE: RNA

```
<213> ORGANISM: Artificial Sequence
<220> FEATURE:
<223> OTHER INFORMATION: Synthetic Sequence

<400> SEQUENCE: 320
cgcgccgccg uccagcgg                                                  18

<210> SEQ ID NO 321
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 321
ccgccgacgg cggcggcg                                                  18

<210> SEQ ID NO 322
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 322
cgcgccgccg uccagcgg                                                  18

<210> SEQ ID NO 323
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 323
uggcuggacg gcggcggg                                                  18

<210> SEQ ID NO 324
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 324
cgcgccgccg uccagcgg                                                  18

<210> SEQ ID NO 325
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 325
gcgcuggagg cggcggcg                                                  18

<210> SEQ ID NO 326
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 326
cgcgccgccg uccagcgg                                                  18
```

<210> SEQ ID NO 327
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 327
ccgcgcggac ggcgagcgcg                                               20

<210> SEQ ID NO 328
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 328
cgcgccgccg uccagcgg                                                 18

<210> SEQ ID NO 329
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 329
ccgcggagac ggcggcgg                                                 18

<210> SEQ ID NO 330
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 330
cgcgccgccg uccagcgg                                                 18

<210> SEQ ID NO 331
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 331
cccauggacg gcggagcg                                                 18

<210> SEQ ID NO 332
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 332
cgcgccgccg uccagcgg                                                 18

<210> SEQ ID NO 333
<211> LENGTH: 20
<212> TYPE: RNA
<213> ORGANISM: Artificial Sequence
<220> FEATURE:

<223> OTHER INFORMATION: Synthetic Sequence

<400> SEQUENCE: 333
ccgccgagac ggcggcggcg                                              20

<210> SEQ ID NO 334
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 334
cgcgccgccg uccagcgg                                                18

<210> SEQ ID NO 335
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 335
ccgcggagac ggcggcgg                                                18

<210> SEQ ID NO 336
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 336
cgcgccgccg uccagcgg                                                18

<210> SEQ ID NO 337
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 337
ccgcuggagg ugcggccg                                                18

<210> SEQ ID NO 338
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 338
cgcgccgccg uccagcgg                                                18

<210> SEQ ID NO 339
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 339
cgcgcuggcg gcggcgcu                                                18

```
<210> SEQ ID NO 340
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 340
cgcgccgccg uccagcgg                                                 18

<210> SEQ ID NO 341
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 341
ccugcuggcg gcggcggcg                                                19

<210> SEQ ID NO 342
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 342
cgcgccgccg uccagcgg                                                 18

<210> SEQ ID NO 343
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 343
gcgauggacg gcgccgcg                                                 18

<210> SEQ ID NO 344
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 344
cgcgccgccg uccagcgg                                                 18

<210> SEQ ID NO 345
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 345
gcgcuggacg gcgccgcg                                                 18

<210> SEQ ID NO 346
<211> LENGTH: 18
<212> TYPE: RNA
<213> ORGANISM: Artificial Sequence
<220> FEATURE:
<223> OTHER INFORMATION: Synthetic Sequence
```

```
<400> SEQUENCE: 346
cgcgccgccg uccagcgg                                               18

<210> SEQ ID NO 347
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 347
cacgcggacg gcggcgcug                                              19

<210> SEQ ID NO 348
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 348
cgcgccgccg uccagcgg                                               18

<210> SEQ ID NO 349
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 349
acgcggacgg cggcgcug                                               18

<210> SEQ ID NO 350
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 350
cgcgccgccg uccagcgg                                               18

<210> SEQ ID NO 351
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 351
cacgcggacg gcggcgcug                                              19

<210> SEQ ID NO 352
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 352
cgcgccgccg uccagcgg                                               18

<210> SEQ ID NO 353
<211> LENGTH: 18
```

```
<212> TYPE: RNA
<213> ORGANISM: Artificial Sequence
<220> FEATURE:
<223> OTHER INFORMATION: Synthetic Sequence

<400> SEQUENCE: 353
ccgcucggag guggcgcg                                                 18

<210> SEQ ID NO 354
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 354
cgcgccgccg uccagcgg                                                 18

<210> SEQ ID NO 355
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 355
cggcagugac ggcggcgcg                                                19

<210> SEQ ID NO 356
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 356
cgcgccgccg uccagcgg                                                 18

<210> SEQ ID NO 357
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 357
cggcagcgac ggcggcgcg                                                19

<210> SEQ ID NO 358
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 358
cgcgccgccg uccagcgg                                                 18

<210> SEQ ID NO 359
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 359
```
gcgcuggagg gcgucgcg                                    18

<210> SEQ ID NO 360
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 360
cgcgccgccg uccagcgg                                    18

<210> SEQ ID NO 361
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 361
ccgcgggcgg cggcggcg                                    18

<210> SEQ ID NO 362
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 362
cgcgccgccg uccagcgg                                    18

<210> SEQ ID NO 363
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 363
ccgcaggcgg cggcgucg                                    18

<210> SEQ ID NO 364
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 364
cgcgccgccg uccagcgg                                    18

<210> SEQ ID NO 365
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 365
gccgcggacg gcggcgag                                    18

<210> SEQ ID NO 366
<211> LENGTH: 18
<212> TYPE: RNA
<213> ORGANISM: Artificial Sequence

```
<220> FEATURE:
<223> OTHER INFORMATION: Synthetic Sequence

<400> SEQUENCE: 366
cgcgccgccg uccagcgg                                                 18

<210> SEQ ID NO 367
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 367
gccgcggacg gcggcgag                                                 18

<210> SEQ ID NO 368
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 368
cgcgccgccg uccagcgg                                                 18

<210> SEQ ID NO 369
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 369
ccgcugccac ggcggccg                                                 18

<210> SEQ ID NO 370
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 370
cgcgccgccg uccagcgg                                                 18

<210> SEQ ID NO 371
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 371
cgcgcuggcc ggcggcccg                                                19

<210> SEQ ID NO 372
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 372
cgcgccgccg uccagcgg                                                 18
```

```
<210> SEQ ID NO 373
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 373
ccgcgggacg acggcgacg                                                   19

<210> SEQ ID NO 374
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 374
cgcgccgccg uccagcgg                                                    18

<210> SEQ ID NO 375
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 375
ccgcguacgg cggcggcg                                                    18

<210> SEQ ID NO 376
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 376
cgcgccgccg uccagcgg                                                    18

<210> SEQ ID NO 377
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 377
cgcgcuggcc ggcggggcg                                                   19

<210> SEQ ID NO 378
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 378
cgcgccgccg uccagcgg                                                    18

<210> SEQ ID NO 379
<211> LENGTH: 18
<212> TYPE: RNA
<213> ORGANISM: Artificial Sequence
<220> FEATURE:
<223> OTHER INFORMATION: Synthetic Sequence
```

<400> SEQUENCE: 379
ccgccggacg ucggcgcg                                              18

<210> SEQ ID NO 380
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 380
cgcgccgccg uccagcgg                                              18

<210> SEQ ID NO 381
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 381
ccgcugaacu ggggcgcg                                              18

<210> SEQ ID NO 382
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 382
cgcgccgccg uccagcgg                                              18

<210> SEQ ID NO 383
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 383
uccguggacg guggcgcg                                              18

<210> SEQ ID NO 384
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 384
cgcgccgccg uccagcgg                                              18

<210> SEQ ID NO 385
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 385
ccgcaggccg ccggcgcg                                              18

<210> SEQ ID NO 386

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 386
cgcgccgccg uccagcgg                                                       18

<210> SEQ ID NO 387
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 387
ccugcuggcg gcgcgcgcg                                                      19

<210> SEQ ID NO 388
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 388
cgcggccaga gcagcggcgg cgcu                                                24

<210> SEQ ID NO 389
<211> LENGTH: 26
<212> TYPE: RNA
<213> ORGANISM: Artificial Sequence
<220> FEATURE:
<223> OTHER INFORMATION: Synthetic Sequence

<400> SEQUENCE: 389
agcucacgcc gcugcaucug gccgcg                                              26

<210> SEQ ID NO 390
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 390
gcggcccggg cgcagggcga ggu                                                 23

<210> SEQ ID NO 391
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 391
accucgcccu gcgcccgcgc cgc                                                 23

<210> SEQ ID NO 392
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 392
```
ccgccuccac ggccaaugc                                             19

<210> SEQ ID NO 393
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 393
gcacuggccg cggcggcgg                                             19

<210> SEQ ID NO 394
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 394
ccgccuccac ggccaaugc                                             19

<210> SEQ ID NO 395
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 395
gcacugccca uggaggcgg                                             19

<210> SEQ ID NO 396
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 396
ccgccuccac ggccaaugc                                             19

<210> SEQ ID NO 397
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 397
gcaguggccu uggaggagg                                             19

<210> SEQ ID NO 398
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 398
ccgccuccac ggccaaugc                                             19

<210> SEQ ID NO 399
<211> LENGTH: 20
<212> TYPE: RNA

<213> ORGANISM: Artificial Sequence
<220> FEATURE:
<223> OTHER INFORMATION: Synthetic Sequence

<400> SEQUENCE: 399
gcauuggccu uggcggcgug                                                   20

<210> SEQ ID NO 400
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 400
uccauccacg gcggccgc                                                     18

<210> SEQ ID NO 401
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 401
gcagccggcg uggcugga                                                     18

<210> SEQ ID NO 402
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 402
uccauccacg gcggccgc                                                     18

<210> SEQ ID NO 403
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 403
gcggcggccg uggagggc                                                     18

<210> SEQ ID NO 404
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 404
uccauccacg gcggccgc                                                     18

<210> SEQ ID NO 405
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 405
gcgggcgcug uggcugga                                                     18

<210> SEQ ID NO 406
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 406
uccauccacg gcggccgc                                                 18

<210> SEQ ID NO 407
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 407
gcgcccgccg ugggugga                                                 18

<210> SEQ ID NO 408
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 408
uccauccacg gcggccgc                                                 18

<210> SEQ ID NO 409
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 409
gcggcggcgc guggaagga                                                19

<210> SEQ ID NO 410
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 410
uccauccacg gcggccgc                                                 18

<210> SEQ ID NO 411
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 411
gcggccgcug gagaugga                                                 18

<210> SEQ ID NO 412
<211> LENGTH: 18
<212> TYPE: RNA
<213> ORGANISM: Artificial Sequence
<220> FEATURE:

<223> OTHER INFORMATION: Synthetic Sequence

<400> SEQUENCE: 412
uccauccacg gcggccgc                                                 18

<210> SEQ ID NO 413
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 413
gcggccgcag gggcugga                                                 18

<210> SEQ ID NO 414
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 414
uccauccacg gcggccgc                                                 18

<210> SEQ ID NO 415
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 415
gcgggccgcc gaggagga                                                 18

<210> SEQ ID NO 416
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 416
uccauccacg gcggccgc                                                 18

<210> SEQ ID NO 417
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 417
gcgcgccgcc gaggagga                                                 18

<210> SEQ ID NO 418
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 418
uccauccacg gcggccgc                                                 18

```
<210> SEQ ID NO 419
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 419
ggcugccgcc guggagga                                                 18

<210> SEQ ID NO 420
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 420
uccauccacg gcggccgc                                                 18

<210> SEQ ID NO 421
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 421
ggggcggccg uggaagga                                                 18

<210> SEQ ID NO 422
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 422
uccauccacg gcggccgc                                                 18

<210> SEQ ID NO 423
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 423
gcggccgccg uggagcggca                                               20

<210> SEQ ID NO 424
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 424
uccauccacg gcggccgc                                                 18

<210> SEQ ID NO 425
<211> LENGTH: 18
<212> TYPE: RNA
<213> ORGANISM: Artificial Sequence
<220> FEATURE:
<223> OTHER INFORMATION: Synthetic Sequence
```

<400> SEQUENCE: 425
gcaggccggc uggaugga                                                 18

<210> SEQ ID NO 426
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 426
uccauccacg gcggccgc                                                 18

<210> SEQ ID NO 427
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 427
gccggccggc guggugga                                                 18

<210> SEQ ID NO 428
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 428
uccauccacg gcggccgc                                                 18

<210> SEQ ID NO 429
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 429 gcgucgccg uggacgga                                                  18

<210> SEQ ID NO 430
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 430
acccgggcuu cggcguugcc                                               20

<210> SEQ ID NO 431
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 431
ggcaacgccg aagcccgggc u                                             21

<210> SEQ ID NO 432
<211> LENGTH: 18

<212> TYPE: RNA
<213> ORGANISM: Artificial Sequence
<220> FEATURE:
<223> OTHER INFORMATION: Synthetic Sequence

<400> SEQUENCE: 432
ccuuugucga gugcccgc                                                      18

<210> SEQ ID NO 433
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 433
gcgcgcaucg acaacagg                                                      18

<210> SEQ ID NO 434
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 434
ccuuugucga gugcccgc                                                      18

<210> SEQ ID NO 435
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 435
gcggugcacc gacaacgg                                                      18

<210> SEQ ID NO 436
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 436
ggacucgguc gcucgagggu ag                                                 22

<210> SEQ ID NO 437
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 437
cuacgccucg gcgaccgagu uc                                                 22

<210> SEQ ID NO 438
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 438
gagaugugug uuuacacac 19

<210> SEQ ID NO 439
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 439
gggugaaaca ccacaucuc 19

<210> SEQ ID NO 440
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 440
cacgugucag ccacgucagc a 21

<210> SEQ ID NO 441
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 441
ugcugacguu ggcuggacac gg 22

<210> SEQ ID NO 442
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 442
ucggcuuacc cauguucaag ugcc 24

<210> SEQ ID NO 443
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 443
ggcacuugca cauggguaag ccga 24

<210> SEQ ID NO 444
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 444
uucuuugccg agagccugc 19

<210> SEQ ID NO 445
<211> LENGTH: 20
<212> TYPE: RNA
<213> ORGANISM: Artificial Sequence

```
<220> FEATURE:
<223> OTHER INFORMATION: Synthetic Sequence

<400> SEQUENCE: 445
gaagccucuc uggcaaagaa                                                    20

<210> SEQ ID NO 446
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 446
cccaacacau auagauug                                                      18

<210> SEQ ID NO 447
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 447
caagcuauau gcuguuggc                                                     19

<210> SEQ ID NO 448
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 448
cccaacacau auagauug                                                      18

<210> SEQ ID NO 449
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 449
caacuauacu gaguuggg                                                      18

<210> SEQ ID NO 450
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 450 gagguccca ccugcaugcg                                                     20

<210> SEQ ID NO 451
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 451
cgcagcagga ggaggaccuc                                                    20
```

```
<210> SEQ ID NO 452
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 452
uugcuugaga uaugauggag ccg                                              23

<210> SEQ ID NO 453
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 453
uggcuccauc auaucuacaa caa                                              23

<210> SEQ ID NO 454
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 454
gggaagaggu gcgaggau                                                    18

<210> SEQ ID NO 455
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 455
cucgucgccc cucuuccc                                                    18

<210> SEQ ID NO 456
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 456
gggaagaggu gcgaggau                                                    18

<210> SEQ ID NO 457
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 457
auccucgcca agcucuuccc                                                  20

<210> SEQ ID NO 458
<211> LENGTH: 18
<212> TYPE: RNA
<213> ORGANISM: Artificial Sequence
<220> FEATURE:
<223> OTHER INFORMATION: Synthetic Sequence
```

-continued

<400> SEQUENCE: 458
gggaagaggu gcgaggau                                          18

<210> SEQ ID NO 459
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 459
guccucgcac cucuuugc                                          18

<210> SEQ ID NO 460
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 460
gggaagaggu gcgaggau                                          18

<210> SEQ ID NO 461
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 461
gauccuccac cucuaccc                                          18

<210> SEQ ID NO 462
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 462
gggaagaggu gcgaggau                                          18

<210> SEQ ID NO 463
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 463
auccucgccc ucguuacc                                          18

<210> SEQ ID NO 464
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 464
gggaagaggu gcgaggau                                          18

<210> SEQ ID NO 465

```
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 465
cuccucccuc cucuuccc                                                        18

<210> SEQ ID NO 466
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 466
auccacaugu guuaaggugg                                                      20

<210> SEQ ID NO 467
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 467
ucaccuugac agauguggau                                                      20

<210> SEQ ID NO 468
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 468
ugguggagcc ggcggcgcuc cug                                                  23

<210> SEQ ID NO 469
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 469
cagcagcgcc gccggcccag cca                                                  23

<210> SEQ ID NO 470
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 470
agcugggacu ugggccgugc                                                      20

<210> SEQ ID NO 471
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 471
```
gcgacggucc aaguaccagc u                    21

<210> SEQ ID NO 472
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 472
agaggccagu gccggucuug aaggu                25

<210> SEQ ID NO 473
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 473
accuucaaga ccggcaccgg ccugu                25

<210> SEQ ID NO 474
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 474
ugagccgaac caauaucacu cau                  23

<210> SEQ ID NO 475
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 475
ccgggugaua uugguucggc uca                  23

<210> SEQ ID NO 476
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 476
aggccaagga agaggagauu cg                   22

<210> SEQ ID NO 477
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 477
cgcaucuccu ccuccucggc cu                   22

<210> SEQ ID NO 478
<211> LENGTH: 22
<212> TYPE: RNA

```
<213> ORGANISM: Artificial Sequence
<220> FEATURE:
<223> OTHER INFORMATION: Synthetic Sequence

<400> SEQUENCE: 478
gcuggcuccu cuggccaccc ag                                          22

<210> SEQ ID NO 479
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 479
cucgauggcc agaggagcga gc                                          22

<210> SEQ ID NO 480
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 480
gcgaaucuaa uggaugggag                                             20

<210> SEQ ID NO 481
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 481
cuccaaucuc auuggauucg c                                           21

<210> SEQ ID NO 482
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 482
ucaucuccuu gucaugca                                               18

<210> SEQ ID NO 483
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 483
agcauuacaa gagagauga                                              19

<210> SEQ ID NO 484
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 484
ucaucuccuu gucaugca                                               18
```

<210> SEQ ID NO 485
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 485
ugcauugaca aggaaaucga                                              20

<210> SEQ ID NO 486
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 486
ucaucuccuu gucaugca                                                18

<210> SEQ ID NO 487
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 487
ucacaugaca aggaauga                                                18

<210> SEQ ID NO 488
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 488
ucaucuccuu gucaugca                                                18

<210> SEQ ID NO 489
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 489
ugaaggagaa ggagauga                                                18

<210> SEQ ID NO 490
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 490
ucaucuccuu gucaugca                                                18

<210> SEQ ID NO 491
<211> LENGTH: 18
<212> TYPE: RNA
<213> ORGANISM: Artificial Sequence
<220> FEATURE:

```
<223> OTHER INFORMATION: Synthetic Sequence

<400> SEQUENCE: 491
uccaugacaa ggagagca                                                 18

<210> SEQ ID NO 492
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 492
ucaucuccuu gucaugca                                                 18

<210> SEQ ID NO 493
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 493
uggauguaca agcagauga                                                19

<210> SEQ ID NO 494
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 494
ucaucuccuu gucaugca                                                 18

<210> SEQ ID NO 495
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 495
ugaagugaaa ggagauga                                                 18

<210> SEQ ID NO 496
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 496
ccgggccaaa uugccgugcu                                               20

<210> SEQ ID NO 497
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 497
agcacgagca auuuggccag c                                             21
```

```
<210> SEQ ID NO 498
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 498
ucccgguguc caaccacugc u                                              21

<210> SEQ ID NO 499
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 499
agcauguggu uggacagggg ga                                             22

<210> SEQ ID NO 500
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 500
gaucaguuga agaugacgga g                                              21

<210> SEQ ID NO 501
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 501
cucgucaucu ucaaccgcau c                                              21

<210> SEQ ID NO 502
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 502
ggcaaagcau ccggcacucg gc                                             22

<210> SEQ ID NO 503
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 503
gccggagugc cgaugcuuug cu                                             22

<210> SEQ ID NO 504
<211> LENGTH: 22
<212> TYPE: RNA
<213> ORGANISM: Artificial Sequence
<220> FEATURE:
<223> OTHER INFORMATION: Synthetic Sequence
```

<400> SEQUENCE: 504
gacgggucga gggagagcac gg                                          22

<210> SEQ ID NO 505
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 505
ccgugcuuuc ccucgacacc gac                                         23

<210> SEQ ID NO 506
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 506
ggcccucccc gaccggug                                               18

<210> SEQ ID NO 507
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 507
cagccggccg aggagggcc                                              19

<210> SEQ ID NO 508
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 508
ggcccucccc gaccggug                                               18

<210> SEQ ID NO 509
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 509
caccggugcu gggagcggcc                                             20

<210> SEQ ID NO 510
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 510
ggcccucccc gaccggug                                               18

<210> SEQ ID NO 511
<211> LENGTH: 19

```
<212> TYPE: RNA
<213> ORGANISM: Artificial Sequence
<220> FEATURE:
<223> OTHER INFORMATION: Synthetic Sequence

<400> SEQUENCE: 511
cagccggccg uggagggcc                                                    19

<210> SEQ ID NO 512
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 512
ggggaagcgc gaccgccgug g                                                 21

<210> SEQ ID NO 513
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 513
ccucggcggu ggcgccuccc c                                                 21

<210> SEQ ID NO 514
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 514
ggggaagcgc gaccgccgug g                                                 21

<210> SEQ ID NO 515
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 515
ccacggcggu ggcgccuucu cc                                                22

<210> SEQ ID NO 516
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 516
gaggucccga ugcggacg                                                     18

<210> SEQ ID NO 517
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 517
```
cgccagcacc gggaccuc                                         18

<210> SEQ ID NO 518
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 518
gaggucccga ugcggacg                                         18

<210> SEQ ID NO 519
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 519
cgccccaucg cggaccuc                                         18

<210> SEQ ID NO 520
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 520
gaggucccga ugcggacg                                         18

<210> SEQ ID NO 521
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 521
cguccgcauc gccgacguc                                        19

<210> SEQ ID NO 522
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 522
gaggucccga ugcggacg                                         18

<210> SEQ ID NO 523
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 523 cguccguca ucguggaccu c                                      21

<210> SEQ ID NO 524
<211> LENGTH: 18
<212> TYPE: RNA
<213> ORGANISM: Artificial Sequence

```
<220> FEATURE:
<223> OTHER INFORMATION: Synthetic Sequence

<400> SEQUENCE: 524
ggcacacggu auaccugg                                                   18

<210> SEQ ID NO 525
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 525
ccagggauuc cguguucc                                                   18

<210> SEQ ID NO 526
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 526
ggcacacggu auaccugg                                                   18

<210> SEQ ID NO 527
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 527
ccaguacacc cgugugcc                                                   18

<210> SEQ ID NO 528
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 528
gcgcgcagcc gcucgcgauu cgcc                                            24

<210> SEQ ID NO 529
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 529
ggagaacccc gagcggcugc gcgc                                            24

<210> SEQ ID NO 530
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 530
gcguuucuuu gccgggacc                                                  19
```

<210> SEQ ID NO 531
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 531
ugcccggcaa agaacacgc                                                    19

<210> SEQ ID NO 532
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 532
gcugggugca caacggcggc ggcg                                              24

<210> SEQ ID NO 533
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 533
gcgccgccgc cgcuggcacc cagc                                              24

<210> SEQ ID NO 534
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 534
caggaggcug gcuggcgcgc uc                                                22

<210> SEQ ID NO 535
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 535
gaagggcgcc ugccagccuc cug                                               23

<210> SEQ ID NO 536
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 536
aagggcagca ccggcucggg aa                                                22

<210> SEQ ID NO 537
<211> LENGTH: 23
<212> TYPE: RNA
<213> ORGANISM: Artificial Sequence
<220> FEATURE:
<223> OTHER INFORMATION: Synthetic Sequence

```
<400> SEQUENCE: 537
uucccgcgcc ggugcugccg cgu                                          23

<210> SEQ ID NO 538
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 538
gcgcgcgcug caggccaugu                                              20

<210> SEQ ID NO 539
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 539
acauggccuc cggcgcgccc                                              20

<210> SEQ ID NO 540
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 540
gcgcgcgcug caggccaugu                                              20

<210> SEQ ID NO 541
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 541
accuggcgcu gcagugcgcg c                                            21

<210> SEQ ID NO 542
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 542
gcgcgcgcug caggccaugu                                              20

<210> SEQ ID NO 543
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 543
acauggucgu gcagcgcgcc                                              20

<210> SEQ ID NO 544
```

```
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 544
gcgcgcgcug caggccaugu                                                    20

<210> SEQ ID NO 545
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 545
acaaggacug cagcgcgagc                                                    20

<210> SEQ ID NO 546
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 546
gcgcgcgcug caggccaugu                                                    20

<210> SEQ ID NO 547
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 547
acauggccug caacagccgc gc                                                 22

<210> SEQ ID NO 548
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 548
gcgcgcgcug caggccaugu                                                    20

<210> SEQ ID NO 549
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 549
acauggccgg cugcggcgcg c                                                  21

<210> SEQ ID NO 550
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 550
```
gcgcgcgcug caggccaugu    20

<210> SEQ ID NO 551
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 551
acauggccgg cugcggcgcg c    21

<210> SEQ ID NO 552
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 552
cacuccaauc caccccaaca ca    22

<210> SEQ ID NO 553
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 553
ugugcugugg guggauagga gug    23

<210> SEQ ID NO 554
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 554
uggaagucca ccaaugaca    19

<210> SEQ ID NO 555
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 555
uguccauggu ggacuucaa    19

<210> SEQ ID NO 556
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 556
uggaagucca ccaaugaca    19

<210> SEQ ID NO 557
<211> LENGTH: 19
<212> TYPE: RNA

```
<213> ORGANISM: Artificial Sequence
<220> FEATURE:
<223> OTHER INFORMATION: Synthetic Sequence

<400> SEQUENCE: 557
uugucauugg uggaccuca                                                      19

<210> SEQ ID NO 558
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 558
gcuugaguuu aucagccgag u                                                   21

<210> SEQ ID NO 559
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 559
aguaggcuga caaacucaag c                                                   21

<210> SEQ ID NO 560
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 560
cggcgcagag aagcgagugu                                                     20

<210> SEQ ID NO 561
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 561
acagcucggu uccugcgccg                                                     20

<210> SEQ ID NO 562
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 562
gccucuuggu aguagucg                                                       18

<210> SEQ ID NO 563
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 563
cgacgacuac gaggaggc                                                       18
```

<210> SEQ ID NO 564
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 564
gccucuuggu aguagucg                                                 18

<210> SEQ ID NO 565
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 565
cgacuucacu accaagggc                                                19

<210> SEQ ID NO 566
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 566
ccgaccaugg ugguggugg                                                19

<210> SEQ ID NO 567
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 567
ccaccacgac cacguucgg                                                19

<210> SEQ ID NO 568
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 568
ccgaccaugg ugguggugg                                                19

<210> SEQ ID NO 569
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 569
ccaccaccac caucggcag                                                19

<210> SEQ ID NO 570
<211> LENGTH: 19
<212> TYPE: RNA
<213> ORGANISM: Artificial Sequence
<220> FEATURE:

<223> OTHER INFORMATION: Synthetic Sequence

<400> SEQUENCE: 570
ccgaccaugg ugguggugg                                                      19

<210> SEQ ID NO 571
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 571
ccauccacca gcauggcgg                                                      19

<210> SEQ ID NO 572
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 572
ccgaccaugg ugguggugg                                                      19

<210> SEQ ID NO 573
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 573
ccauccacca gcauggcgg                                                      19

<210> SEQ ID NO 574
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 574
ccgaccaugg ugguggugg                                                      19

<210> SEQ ID NO 575
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 575
ccaccaccac cagcuccgg                                                      19

<210> SEQ ID NO 576
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 576
gucgacucga agcuggugua                                                     20

```
<210> SEQ ID NO 577
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 577
uucgccagcu ucgagacgac                                                   20

<210> SEQ ID NO 578
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 578
guggauugga guggaacuu                                                    19

<210> SEQ ID NO 579
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 579 aaguccacu ccuuccauc                                                     19

<210> SEQ ID NO 580
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 580
aaccgguguu aaaggguc                                                     18

<210> SEQ ID NO 581
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 581
gacccuuuug caccaguu                                                     18

<210> SEQ ID NO 582
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 582
aaccgguguu aaaggguc                                                     18

<210> SEQ ID NO 583
<211> LENGTH: 18
<212> TYPE: RNA
<213> ORGANISM: Artificial Sequence
<220> FEATURE:
<223> OTHER INFORMATION: Synthetic Sequence
```

<400> SEQUENCE: 583
gacgcuuaac agccgguu 18

<210> SEQ ID NO 584
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 584
aaguugucau uggugggcu 19

<210> SEQ ID NO 585
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 585
agccacaaca cugacaacuu 20

<210> SEQ ID NO 586
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 586
gcaucaaucc acaaguguu 19

<210> SEQ ID NO 587
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 587
agcacuugug cauucaugc 19

<210> SEQ ID NO 588
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 588
uauuugccga gcgcuauuu 19

<210> SEQ ID NO 589
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 589
aagauaucga ucggcaaaua 20

<210> SEQ ID NO 590
<211> LENGTH: 21

```
<212> TYPE: RNA
<213> ORGANISM: Artificial Sequence
<220> FEATURE:
<223> OTHER INFORMATION: Synthetic Sequence

<400> SEQUENCE: 590
gccugcuccc uugggucgug c                                              21

<210> SEQ ID NO 591
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 591
gcucgacgca agggugcagg c                                              21

<210> SEQ ID NO 592
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 592
cgcacggcgg cggcgcgacg g                                              21

<210> SEQ ID NO 593
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 593
ccgcucgcgc cgccgccgcg gg                                             22

<210> SEQ ID NO 594
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 594
cgcacggcgg cggcgcgacg g                                              21

<210> SEQ ID NO 595
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 595
ccgucgcgcc gccgcagaug ucg                                            23

<210> SEQ ID NO 596
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 596
```
cgcacggcgg cggcgcgacg g                                           21

<210> SEQ ID NO 597
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 597
cacgacgcgc gcgccgccgu gcg                                         23

<210> SEQ ID NO 598
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 598
cgcacggcgg cggcgcgacg g                                           21

<210> SEQ ID NO 599
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 599
ccguccgcgc cgcgccgcgc g                                           21

<210> SEQ ID NO 600
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 600
cgcacggcgg cggcgcgacg g                                           21

<210> SEQ ID NO 601
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 601
ccgucgucuc cgccgccggc g                                           21

<210> SEQ ID NO 602
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 602
cgcacggcgg cggcgcgacg g                                           21

<210> SEQ ID NO 603
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 603
ccgccgcccg ccgccgucgc g                                              21

<210> SEQ ID NO 604
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 604
gggcuuugua gucaggucac                                                20

<210> SEQ ID NO 605
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 605
gugccugagu acaaagcucc                                                20

<210> SEQ ID NO 606
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 606
cccaauccac accaacacac au                                             22

<210> SEQ ID NO 607
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 607
aagugugcug guguggauuc gg                                             22

<210> SEQ ID NO 608
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 608
cucgggaaag cuuucuccga                                                20

<210> SEQ ID NO 609
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 609
ugggagaaag uuuucccuga g                                              21

<210> SEQ ID NO 610
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 610
caacacaugu ggauugag                                                     18

<210> SEQ ID NO 611
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 611
cucaagccua cuguguug                                                     18

<210> SEQ ID NO 612
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 612
caacacaugu ggauugag                                                     18

<210> SEQ ID NO 613
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 613
cccaauccaa ugugcuug                                                     18

<210> SEQ ID NO 614
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 614
caacacaugu ggauugag                                                     18

<210> SEQ ID NO 615
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 615
cucaauccag cauaugaug                                                    19

<210> SEQ ID NO 616
<211> LENGTH: 18
<212> TYPE: RNA
<213> ORGANISM: Artificial Sequence
<220> FEATURE:
<223> OTHER INFORMATION: Synthetic Sequence

```
<400> SEQUENCE: 616
ucgccagauc auguugca                                                    18

<210> SEQ ID NO 617
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 617
ugcaccauga ucucgguga                                                   19

<210> SEQ ID NO 618
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 618
ucgccagauc auguugca                                                    18

<210> SEQ ID NO 619
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 619
ugcaccauga ucauggcga                                                   19

<210> SEQ ID NO 620
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 620
cguucgcugg ggaugacgac g                                                21

<210> SEQ ID NO 621
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 621
cgucgucauc cccggcggcc g                                                21

<210> SEQ ID NO 622
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 622
ugcucggacg acaugcagag accu                                             24

<210> SEQ ID NO 623
```

```
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 623
aggugcucug caugucgguc cagca                                             25

<210> SEQ ID NO 624
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 624
cagccaagga ugacuugccg a                                                 21

<210> SEQ ID NO 625
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 625
uaggcaaauc auucuuggcu g                                                 21

<210> SEQ ID NO 626
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 626
cagccaagga ugacuugccg g                                                 21

<210> SEQ ID NO 627
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 627
cuggcaacuc auccuuggcu u                                                 21

<210> SEQ ID NO 628
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 628
uagccaagga ugacuugccu g                                                 21

<210> SEQ ID NO 629
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 629
```
caggcaauuc auucuuggcu u          21

<210> SEQ ID NO 630
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 630
uagccaagga ugacuugccu g          21

<210> SEQ ID NO 631
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 631
cuggcaacuc auccuuggcu ua         22

<210> SEQ ID NO 632
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 632
uagccaagga ugacuugccu a          21

<210> SEQ ID NO 633
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 633
uggcaacuca uccuuggcuu a          21

<210> SEQ ID NO 634
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 634
uagccaagga ugacuugccu a          21

<210> SEQ ID NO 635
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 635
uaggcaaauc auucuuggcu ga         22

<210> SEQ ID NO 636
<211> LENGTH: 21
<212> TYPE: RNA

<213> ORGANISM: Artificial Sequence
<220> FEATURE:
<223> OTHER INFORMATION: Synthetic Sequence

<400> SEQUENCE: 636
uagccaagaa ugacuugccu a    21

<210> SEQ ID NO 637
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 637
ucaggcaauu cauucuuggc uu    22

<210> SEQ ID NO 638
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 638
uagccaagaa ugacuugccu a    21

<210> SEQ ID NO 639
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 639
gagucaaguc acucuuggcu a    21

<210> SEQ ID NO 640
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 640
ugaaucuuga ugaugcugca c    21

<210> SEQ ID NO 641
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 641
gcugcagcau caucaggauu cu    22

<210> SEQ ID NO 642
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 642
ugaaucuuga ugaugcugca c    21

<210> SEQ ID NO 643
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 643
gaugcagauc aucaggauuc a        21

<210> SEQ ID NO 644
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 644
ggaaucuuga ugaugcugca        20

<210> SEQ ID NO 645
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 645
ugcaacauaa ucaagacuuc c        21

<210> SEQ ID NO 646
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 646
ggaaucuuga ugaugcugca        20

<210> SEQ ID NO 647
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 647
ugcagcauca ucaggauucu c        21

<210> SEQ ID NO 648
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 648
agaaucuuga ugaugcugca        20

<210> SEQ ID NO 649
<211> LENGTH: 20
<212> TYPE: RNA
<213> ORGANISM: Artificial Sequence
<220> FEATURE:

<223> OTHER INFORMATION: Synthetic Sequence

<400> SEQUENCE: 649
ugcagcauca ucaggauucu                                                    20

<210> SEQ ID NO 650
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 650
uuaaugugaa uccaauga                                                      18

<210> SEQ ID NO 651
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 651
ucauugaauu cgcauuag                                                      18

<210> SEQ ID NO 652
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 652
agaucugugg ugccgagcu                                                     19

<210> SEQ ID NO 653
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 653
agcccggcac cacagauuu                                                     19

<210> SEQ ID NO 654
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 654
guccgcgaca accacgaag                                                     19

<210> SEQ ID NO 655
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 655
cuucuuguug ucgcuggac                                                     19

```
<210> SEQ ID NO 656
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 656
cgugccugau agugccgug                                                   19

<210> SEQ ID NO 657
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 657
cacggcacca ugcacgcacg                                                  20

<210> SEQ ID NO 658
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 658
caauccacau gcguuggggu gg                                               22

<210> SEQ ID NO 659
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 659
ccacccaaca cauguggaug ug                                               22

<210> SEQ ID NO 660
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 660
cuucccaugg uucgacggg                                                   19

<210> SEQ ID NO 661
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 661
ccuguucaac caugggaag                                                   19

<210> SEQ ID NO 662
<211> LENGTH: 19
<212> TYPE: RNA
<213> ORGANISM: Artificial Sequence
<220> FEATURE:
<223> OTHER INFORMATION: Synthetic Sequence
```

```
<400> SEQUENCE: 662
ccucaacaca uuggauug                                              19

<210> SEQ ID NO 663
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 663
caauucacau guguuggg                                              19

<210> SEQ ID NO 664
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 664
uugagguaga uuggagug                                              18

<210> SEQ ID NO 665
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 665
cuacuccaau ccaccucaa                                             19

<210> SEQ ID NO 666
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 666
acaaagcuca acuucacu                                              18

<210> SEQ ID NO 667
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 667
auugaaggug agcauuugu                                             19

<210> SEQ ID NO 668
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 668
uugcucuuag aaguguge                                              19

<210> SEQ ID NO 669
<211> LENGTH: 19
```

```
<212> TYPE: RNA
<213> ORGANISM: Artificial Sequence
<220> FEATURE:
<223> OTHER INFORMATION: Synthetic Sequence

<400> SEQUENCE: 669
gcacaacuua uaagacaua                                                    19

<210> SEQ ID NO 670
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 670
acauguguug gaguggauug ggg                                               23

<210> SEQ ID NO 671
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 671
cacccuaauc cacccaacac augu                                              24

<210> SEQ ID NO 672
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 672
gcacacuucu caaagcaaau ucaau                                             25

<210> SEQ ID NO 673
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 673
auuguauucg cuuugagaag ugugc                                             25

<210> SEQ ID NO 674
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 674
ccaaucuaaa caggcccu                                                     18

<210> SEQ ID NO 675
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 675
```
aaggccuguu uggauugu                                                 18

<210> SEQ ID NO 676
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 676
ccaaucuaaa caggcccu                                                 18

<210> SEQ ID NO 677
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 677
agggccuguu uggaucgu                                                 18

<210> SEQ ID NO 678
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 678
uggccuuugu cgugugug                                                 18

<210> SEQ ID NO 679
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 679
caccacacga aauggcca                                                 18

<210> SEQ ID NO 680
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 680
caaguuccac ucuaauccac                                               20

<210> SEQ ID NO 681
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 681
guggauugaa guggaacuug                                               20

<210> SEQ ID NO 682
<211> LENGTH: 21
<212> TYPE: RNA
<213> ORGANISM: Artificial Sequence

```
<220> FEATURE:
<223> OTHER INFORMATION: Synthetic Sequence

<400> SEQUENCE: 682
acauguguug ggguagauug g                                              21

<210> SEQ ID NO 683
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 683
ccuaauccac ccaacacaug u                                              21

<210> SEQ ID NO 684
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 684
cacacuucuc aaugcgaa                                                  18

<210> SEQ ID NO 685
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 685
uucgauugag gaauugug                                                  18

<210> SEQ ID NO 686
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 686
guguuggagu ggauuggg                                                  18

<210> SEQ ID NO 687
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 687
cccuaaucca cccaacac                                                  18

<210> SEQ ID NO 688
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 688
uugaggugga uuggagugga                                                20
```

```
<210> SEQ ID NO 689
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 689
ucuacuccaa uccaccucaa                                              20

<210> SEQ ID NO 690
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 690
aaauuccacc cuaauccacu ccaa                                         24

<210> SEQ ID NO 691
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 691
uuggagugga uuaagguaga aauu                                         24

<210> SEQ ID NO 692
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 692
aucccaaucc acaccaacac acau                                         24

<210> SEQ ID NO 693
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 693
auauguguug gaguggauug gggu                                         24

<210> SEQ ID NO 694
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 694
aacuccagca gagccccua                                               19

<210> SEQ ID NO 695
<211> LENGTH: 19
<212> TYPE: RNA
<213> ORGANISM: Artificial Sequence
<220> FEATURE:
<223> OTHER INFORMATION: Synthetic Sequence
```

```
<400> SEQUENCE: 695
uagaggcacu gcuggagcu                                               19

<210> SEQ ID NO 696
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 696
uuaggaugcc cgccucgguu                                              20

<210> SEQ ID NO 697
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 697
aaccguggcg ggcauuguaa                                              20

<210> SEQ ID NO 698
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 698
uccacuccaa uccacuccaa c                                            21

<210> SEQ ID NO 699
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 699
auuggugugg guuggagugg a                                            21

<210> SEQ ID NO 700
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 700
ugcauuguga gugcccuua                                               19

<210> SEQ ID NO 701
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 701
uuagggcacu cacaaugca                                               19

<210> SEQ ID NO 702
```

```
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 702
gaggcgcugc uguccuccac ac                                              22

<210> SEQ ID NO 703
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 703
gugcggaggg cagcagcgcc ac                                              22

<210> SEQ ID NO 704
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 704
aaucaauuuc aacacaugu                                                  19

<210> SEQ ID NO 705
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 705
acauguguug gaguggauu                                                  19

<210> SEQ ID NO 706
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 706
cgcgccgccg uccagcgg                                                   18

<210> SEQ ID NO 707
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 707
ccgcugcaag gccggcgcg                                                  19

<210> SEQ ID NO 708
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 708
```
cgcgccgccg uccagcgg                                                      18

<210> SEQ ID NO 709
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 709
ccgcucgauc ggggcgcg                                                      18

<210> SEQ ID NO 710
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 710
acaauguuga auagcuagca gauu                                               24

<210> SEQ ID NO 711
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 711
aaucugcuag ccauuuaaca gugu                                               24

<210> SEQ ID NO 712
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 712
acacaugugg auugagguga aucc                                               24

<210> SEQ ID NO 713
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 713
ggauucacau caaucuacau augu                                               24

<210> SEQ ID NO 714
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 714
ccgccuccac ggccaaugc                                                     19

<210> SEQ ID NO 715
<211> LENGTH: 19
<212> TYPE: RNA

-continued

<213> ORGANISM: Artificial Sequence
<220> FEATURE:
<223> OTHER INFORMATION: Synthetic Sequence

<400> SEQUENCE: 715
gcauaggccg uguaggcag					19

<210> SEQ ID NO 716
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 716
acauguauug gaguggauug g					21

<210> SEQ ID NO 717
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 717
ccuaauccac ccaacacaug u					21

<210> SEQ ID NO 718
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 718
uccauccacg gcggccgc					18

<210> SEQ ID NO 719
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 719
gcggcgaucg uggaugga					18

<210> SEQ ID NO 720
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 720
uccauccacg gcggccgc					18

<210> SEQ ID NO 721
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 721
gcggccgcgc gugguggu					18

<210> SEQ ID NO 722
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 722
ccaaccggug uuaaaggg                                                   18

<210> SEQ ID NO 723
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 723
ccauuuaaca gcguuugg                                                   18

<210> SEQ ID NO 724
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 724
ccuuugucga gugcccgc                                                   18

<210> SEQ ID NO 725
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 725
ucgggcacuc ggcaaagag                                                  19

<210> SEQ ID NO 726
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 726
gagaugugug uuuacacac                                                  19

<210> SEQ ID NO 727
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 727
gugugcaaac acacaucuc                                                  19

<210> SEQ ID NO 728
<211> LENGTH: 24
<212> TYPE: RNA
<213> ORGANISM: Artificial Sequence
<220> FEATURE:

<223> OTHER INFORMATION: Synthetic Sequence

<400> SEQUENCE: 728
ucggcuuacc cauguucaag ugcc 24

<210> SEQ ID NO 729
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 729
ggcacuugca caugguaag ccga 24

<210> SEQ ID NO 730
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 730
cccaacacau auagauug 18

<210> SEQ ID NO 731
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 731
caaucuacau auguuggg 18

<210> SEQ ID NO 732
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 732
cccaacacau auagauug 18

<210> SEQ ID NO 733
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 733
cuaucuauau cuguugagg 19

<210> SEQ ID NO 734
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 734
cccaauccac aacaacacac au 22

```
<210> SEQ ID NO 735
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 735
auauguguug gaguggauug gg                                              22

<210> SEQ ID NO 736
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 736
gggaagaggu gcgaggau                                                   18

<210> SEQ ID NO 737
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 737
agccugcauc cucuuccc                                                   18

<210> SEQ ID NO 738
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 738
auccacaugu guuaaggugg                                                 20

<210> SEQ ID NO 739
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 739
uccacccaac acauguggau                                                 20

<210> SEQ ID NO 740
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 740
gcgaaucuaa uggaugggag                                                 20

<210> SEQ ID NO 741
<211> LENGTH: 21
<212> TYPE: RNA
<213> ORGANISM: Artificial Sequence
<220> FEATURE:
<223> OTHER INFORMATION: Synthetic Sequence
```

<400> SEQUENCE: 741
cugcccaucc aacagauucg c					21

<210> SEQ ID NO 742
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 742
ucaucuccuu gucaugca					18

<210> SEQ ID NO 743
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 743
ugcugacaag gaagagga					18

<210> SEQ ID NO 744
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 744
aucccaaucc acaccaacac acau					24

<210> SEQ ID NO 745
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 745
auauguguug gaguggauug gggu					24

<210> SEQ ID NO 746
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 746
ggcaaagcau ccggcacucg gc					22

<210> SEQ ID NO 747
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 747
gccgaguguc auaugcuuug cc					22

<210> SEQ ID NO 748
<211> LENGTH: 18

```
<212> TYPE: RNA
<213> ORGANISM: Artificial Sequence
<220> FEATURE:
<223> OTHER INFORMATION: Synthetic Sequence

<400> SEQUENCE: 748
ggcccucccc gaccggug                                                    18

<210> SEQ ID NO 749
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 749
cgcucggauc ggggagggcc                                                  20

<210> SEQ ID NO 750
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 750 gagguccega ugcggacg                                                    18

<210> SEQ ID NO 751
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 751
cuucagcauc cggaccuc                                                    18

<210> SEQ ID NO 752
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 752
ggcacacggu auaccugg                                                    18

<210> SEQ ID NO 753
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 753
acagguauac cggugugac                                                   19

<210> SEQ ID NO 754
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 754
```
aacacacaug gauugaagug aauac                                        25

<210> SEQ ID NO 755
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 755
agauucacuu caauccaugu guauu                                        25

<210> SEQ ID NO 756
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 756
caggaggcug gcuggcgcgc uc                                           22

<210> SEQ ID NO 757
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 757
cacgcgccag ccagccugcc ug                                           22

<210> SEQ ID NO 758
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 758
uuggggugga uuggagugga acuu                                         24

<210> SEQ ID NO 759
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 759
aaguucuacu ccaauccacc ucaa                                         24

<210> SEQ ID NO 760
<211> LENGTH: 24
<212> TYPE: RNA
<213> ORGANISM: Artificial Sequence
<220> FEATURE:
<223> OTHER INFORMATION: Synthetic Sequence

<400> SEQUENCE: 760
aaauuccacc ccaauccacu ccaa                                         24

<210> SEQ ID NO 761
<211> LENGTH: 24
<212> TYPE: RNA
<213> ORGANISM: Artificial Sequence

```
<220> FEATURE:
<223> OTHER INFORMATION: Synthetic Sequence

<400> SEQUENCE: 761 uuggugugggg uuggagugga auuu                                            24

<210> SEQ ID NO 762
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 762
cacuccaauc caccccaaca ca                                               22

<210> SEQ ID NO 763
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 763
uguauuggug uggguuggag ug                                               22

<210> SEQ ID NO 764
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 764
uggaagucca ccaaugaca                                                   19

<210> SEQ ID NO 765
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 765
ugucauuugu gguguucca                                                   19

<210> SEQ ID NO 766
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 766
gcuugaguuu aucagccgag u                                                21

<210> SEQ ID NO 767
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 767
auucgccuga uaagcucaag c                                                21
```

```
<210> SEQ ID NO 768
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 768
gccucuuggu aguagucg                                                 18

<210> SEQ ID NO 769
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 769
cuacuacuac caaggaagc                                                19

<210> SEQ ID NO 770
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 770
ccgaccaugg ugguggugg                                                19

<210> SEQ ID NO 771
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 771
ccaccacuac cuggucugg                                                19

<210> SEQ ID NO 772
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 772
guggauugga guggaacuu                                                19

<210> SEQ ID NO 773
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 773
aaguucuacu ccaauccac                                                19

<210> SEQ ID NO 774
<211> LENGTH: 19
<212> TYPE: RNA
<213> ORGANISM: Artificial Sequence
<220> FEATURE:
<223> OTHER INFORMATION: Synthetic Sequence
```

```
<400> SEQUENCE: 774
aaguugucau uggugggcu                                              19

<210> SEQ ID NO 775
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 775
agcccaccac ugacuacuu                                              19

<210> SEQ ID NO 776
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 776
gcaucaaucc acaaguguu                                              19

<210> SEQ ID NO 777
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 777
aacauaugug gauugaugu                                              19

<210> SEQ ID NO 778
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 778
uauuugccga gcgcuauuu                                              19

<210> SEQ ID NO 779
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 779
aaauagcugc uagcaaaua                                              19

<210> SEQ ID NO 780
<211> LENGTH: 21
<212> TYPE: RNA
<213> ORGANISM: Artificial Sequence
<220> FEATURE:
<223> OTHER INFORMATION: Synthetic Sequence

<400> SEQUENCE: 780
cgcacggcgg cggcgcgacg g                                           21

<210> SEQ ID NO 781
```

```
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 781
ccgccgccgc cgccgcccgu gcg                                              23

<210> SEQ ID NO 782
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 782
cccgguuggu gagaccaacc gg                                               22

<210> SEQ ID NO 783
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 783
ccgguugguc ucaugaaccg gg                                               22

<210> SEQ ID NO 784
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 784
acugcucagc gucucacggc ac                                               22

<210> SEQ ID NO 785
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 785
gugcugugag aggcugaaca gu                                               22

<210> SEQ ID NO 786
<211> LENGTH: 22
<212> TYPE: RNA
<213> ORGANISM: Artificial Sequence
<220> FEATURE:
<223> OTHER INFORMATION: Synthetic Sequence

<400> SEQUENCE: 786
cccaauccac accaacacac au                                               22

<210> SEQ ID NO 787
<211> LENGTH: 23
<212> TYPE: RNA
<213> ORGANISM: Artificial Sequence
<220> FEATURE:
<223> OTHER INFORMATION: Synthetic Sequence

<400> SEQUENCE: 787
```
auguguauug gugugguug gag 23

<210> SEQ ID NO 788
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 788
acauguggau ugaugcgaau ccgac 25

<210> SEQ ID NO 789
<211> LENGTH: 25
<212> TYPE: RNA
<213> ORGANISM: Artificial Sequence
<220> FEATURE:
<223> OTHER INFORMATION: Synthetic Sequence

<400> SEQUENCE: 789
gucggauuca caucaaucua cauau 25

<210> SEQ ID NO 790
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 790
caacacaugu ggauugag 18

<210> SEQ ID NO 791
<211> LENGTH: 19
<212> TYPE: RNA
<213> ORGANISM: Artificial Sequence
<220> FEATURE:
<223> OTHER INFORMATION: Synthetic Sequence

<400> SEQUENCE: 791
caucaaucua cauauguug 19

<210> SEQ ID NO 792
<211> LENGTH: 18
<212> TYPE: RNA
<213> ORGANISM: Artificial Sequence
<220> FEATURE:
<223> OTHER INFORMATION: Synthetic Sequence

<400> SEQUENCE: 792
ucgccagauc auguugca 18

<210> SEQ ID NO 793
<211> LENGTH: 20
<212> TYPE: RNA
<213> ORGANISM: Artificial Sequence
<220> FEATURE:
<223> OTHER INFORMATION: Synthetic Sequence

<400> SEQUENCE: 793
uggcaacaug augcuggcaa 20

<210> SEQ ID NO 794
<211> LENGTH: 128
<212> TYPE: RNA

<213> ORGANISM: Setaria italica

<400> SEQUENCE: 794

| | | |
|---|---|---|
| cggugagagc ucucugcucu gguagccaag gaugacuugc cuguguuggc cuccggcugc | 60 |
| aggaggcucu ccugcggcgu guggcucucgc aggcagucuc cuuggcuagc cugagcggcu | 120 |
| cucauccu | 128 |

<210> SEQ ID NO 795
<211> LENGTH: 153
<212> TYPE: RNA
<213> ORGANISM: Setaria italica

<400> SEQUENCE: 795

| | | |
|---|---|---|
| cgauaggagc cuguccagau agccaaggau gacuugccug guggccucu uggagugagc | 60 |
| ucgagcuuag cuagccuugu gcaugaugau gcuuugcucu cuucccgugg ucucacaggc | 120 |
| agucuccuug gcuaguccgg gcggcucuua ucu | 153 |

<210> SEQ ID NO 796
<211> LENGTH: 147
<212> TYPE: RNA
<213> ORGANISM: Setaria italica

<400> SEQUENCE: 796

| | | |
|---|---|---|
| gcgaugaggg cucugcuacg guagccaagg augacuugcc ugggucucc ugcugcagga | 60 |
| ggcaacccau uggcgugga ucugcucucu gcugcgcgcg guuggucucg caggcagucu | 120 |
| ccuuggcuau ccugaggggc ucccauc | 147 |

<210> SEQ ID NO 797
<211> LENGTH: 157
<212> TYPE: RNA
<213> ORGANISM: Oryza sativa

<400> SEQUENCE: 797

| | | |
|---|---|---|
| ggucuugcau ggaaguaaga ggccaucuuc gauagccaag gaugauuugc cuguagcccc | 60 |
| auugucauca gcucucuccg ucgagagcga caaccgggcu cuacuggcaa gucuccucgg | 120 |
| cuacccgagu accucuuaug cuaucccaug ucagacc | 157 |

<210> SEQ ID NO 798
<211> LENGTH: 150
<212> TYPE: RNA
<213> ORGANISM: Sorghum bicolor

<400> SEQUENCE: 798

| | | |
|---|---|---|
| gcgauggaag cucugcuuug guagccaagg augagcugcc uguggccucc agcugcagag | 60 |
| gcuagcuagg cuacacauug cguggccaag cuccuccgcu gcgcgggguc ucgcaggcag | 120 |
| ccuccuuggc uagucugagu ggcuuccauc | 150 |

<210> SEQ ID NO 799
<211> LENGTH: 133
<212> TYPE: RNA
<213> ORGANISM: Zea mays

<400> SEQUENCE: 799

| | | |
|---|---|---|
| gcgauggaag cucugcuucg guagccaagg augagcugcc uguggccucc ugcugcggac | 60 |
| guugcgguggc cccgccucca ccgcgugcgg uccccgcagg cagccuccuu ggcuagucug | 120 |
| agcggcuucc auc | 133 |

<210> SEQ ID NO 800
<211> LENGTH: 101
<212> TYPE: RNA
<213> ORGANISM: Setaria italica

<400> SEQUENCE: 800
auagccaagg augauugcc uguagccacc ucugaaugcu ccuggugcca uggcaaucag      60
gagcagcaag uggcggcccu ccgggcaaau cauccgggcu a                       101

<210> SEQ ID NO 801
<211> LENGTH: 201
<212> TYPE: RNA
<213> ORGANISM: Setaria italica

<400> SEQUENCE: 801
agagagcaag gcuuacaugg cgaugagggu uuuaguagcu cugguagcca aggaugacuu      60 gccugucg accugaucuu ucccugaaag gaucgucguc gucacagca gauggucguc       120 gaugagccuu ggguggucu caccggcagu cuccuuggcu agccuggcuc acucccucg      180 cucaugcuag cauugcaucu c                                              201

<210> SEQ ID NO 802
<211> LENGTH: 166
<212> TYPE: RNA
<213> ORGANISM: Setaria italica

<400> SEQUENCE: 802
agauagcaag ccuuacaugg cgauaagagu uggcucugg uagccaagga ugacuugccu      60
guguccucuc uggaggauca acaaauauug aggcuuugaa uggucucaug ggcagucucc    120
uuggcuagcc ugaguggcuc uuauugcuca ugcuagacuu gcaucu                   166

<210> SEQ ID NO 803
<211> LENGTH: 102
<212> TYPE: RNA
<213> ORGANISM: Setaria italica

<400> SEQUENCE: 803
cugguagcca aggaugacuu gccuguggcc ucccucgcuc gcuugcauuu uggugagca      60 ggcaggcaac ugaucucaua ggcagucucc uuggcuagcc ug                       102

<210> SEQ ID NO 804
<211> LENGTH: 135
<212> TYPE: RNA
<213> ORGANISM: Setaria italica

<400> SEQUENCE: 804
gcaacaggag ccgcucagac uagccuagga gacugccuau gagccaucuc aaaggcucac      60
acacugcuga cugcugaucc uucaguauaa aggaccuagg caagucaucc uuggcuauca    120
gaggcaggcc cuuau                                                     135

<210> SEQ ID NO 805
<211> LENGTH: 135
<212> TYPE: RNA
<213> ORGANISM: Setaria italica

<400> SEQUENCE: 805
auaagggccu gccucugaua gccaaggaug acuugccuag guccuuuaua cugaaggauc      60

```
agcagucagc agugugugag ccuugagau ggcucauagg cagucccua ggcuagucug    120 agcggcuccu guugc                                                   135

<210> SEQ ID NO 806
<211> LENGTH: 128
<212> TYPE: RNA
<213> ORGANISM: Glycine max

<400> SEQUENCE: 806
aagagacagu caaccagcca aggaugccug ccaauaaacc aaucuaaggg cuccgucuuc    60
auuagagaca aaguccuaca aaugggaaua gcuaggcaag ucauccuugg cuauccgaca   120
ugacucuu                                                           128

<210> SEQ ID NO 807
<211> LENGTH: 135
<212> TYPE: RNA
<213> ORGANISM: Glycine max

<400> SEQUENCE: 807
aagagucaug ucgguagcc aaggaugacu gccuaguua uuccauuuua ugggacuuua     60
uuuaauuaau uugucucaua uggagacccu aguuugguu aauggcaag cuuccucggc   120 uauuugcaug ccucu                                                   135

<210> SEQ ID NO 808
<211> LENGTH: 136
<212> TYPE: RNA
<213> ORGANISM: Glycine max

<400> SEQUENCE: 808
aagagucaug ucugauagcc aaggaugacu gccuagcua uuccauuuua ugggacuuua    60
uuuaauuaau uugucucaua uggagacccu aguuugguu aauggcaag cuuccucggc   120 uauuugcaug ccucuu                                                  136

<210> SEQ ID NO 809
<211> LENGTH: 162
<212> TYPE: RNA
<213> ORGANISM: Manihot esculenta

<400> SEQUENCE: 809
ugauagccaa ggaugacuug ccuaucuccu ccaacagggu uucaaacaga ugaauaaugc    60
agaagaaugc ggugggauua aucuggauuu ggagcucuuu uguggucau aggcagucuc   120 cuucggcuag ucugacuggc ucuuaucuuu caugcuaggc cu                      162

<210> SEQ ID NO 810
<211> LENGTH: 200
<212> TYPE: RNA
<213> ORGANISM: Manihot esculenta

<400> SEQUENCE: 810
aggagaggaa gagaggccuu guaugaagau gaagagcuac guaugauagc caaggaugac    60
uugccuaucu ccugccguag auauauaaaa aaaaaugcac aagaaagaau auggugggag   120
guucuuucgu augguggag cuaggcaguc uccuuuggcu agucucacug gcucucaucu   180
uucaugcuag gccugcaucu                                               200

<210> SEQ ID NO 811
<211> LENGTH: 115
```

-continued

<212> TYPE: RNA
<213> ORGANISM: Vitis vinifera

<400> SEQUENCE: 811
cugugugguu agccaaggau gacuugccug cuccucccga gugguucgug gggauauaga    60
uuauagaccc cugugugguc cucaggcagu caccuuggcu aacuugacag gcacu        115

<210> SEQ ID NO 812
<211> LENGTH: 111
<212> TYPE: DNA
<213> ORGANISM: Sorghum bicolor

<400> SEQUENCE: 812
tagccaagga tgatttgcct gtagctagca acctctgagc gctcctgctg ccatggcatg    60
gcagtcaggg gcgcgtagtg ggtgcttctc cgggcaaatc atctgggcta g             111

<210> SEQ ID NO 813
<211> LENGTH: 142
<212> TYPE: DNA
<213> ORGANISM: Sorghum bicolor

<400> SEQUENCE: 813
aagaggcatc tttgatagcc aggatgatt tgccctgtag caccatgcat gcatgcaacc    60
tctcgcgtta gctcctgctg actgcatgct gccatgacaa gttccacggg caaatcattc   120
ctggctaatc tgagtgcctc tt                                             142

<210> SEQ ID NO 814
<211> LENGTH: 149
<212> TYPE: DNA
<213> ORGANISM: Setaria italica

<400> SEQUENCE: 814
gcgatggaag ctctgctttg gtagccaagg atgagctgcc tgtggcctcc agctgcagag    60
gctagctagg ctacacattg cgtggccaag ctcctccgct gcgcgtggtc tcgcaggcag   120
cctccttgct agtctgagtg gcttccatc                                      149

<210> SEQ ID NO 815
<211> LENGTH: 132
<212> TYPE: DNA
<213> ORGANISM: Zea mays

<400> SEQUENCE: 815
gcgatggaag ctctgcttcg gtagccaagg atgagctgcc tgtggcctcc tgctgcggac    60
gttgcgtggc cccgcctcca ccgcgtgcgg tccccgcagg cagcctcctt ggctagtctg   120
agcggctcca tc                                                        132

<210> SEQ ID NO 816
<211> LENGTH: 126
<212> TYPE: RNA
<213> ORGANISM: Sorghum bicolor

<400> SEQUENCE: 816
gcaauagggg ccacucaggc uagccaagga gacugccuau gaaccaacuc aaagguucac    60
auucugaucc uuugggacaa aggacauagg caagucaucc uuggcuauca gaggcagacc   120
cuuauu                                                               126

<210> SEQ ID NO 817

-continued

```
<211> LENGTH: 126
<212> TYPE: RNA
<213> ORGANISM: Sorghum bicolor

<400> SEQUENCE: 817
aauaaggguc ugccucugau agccaaggau gacuugccua uguccuuugu cccaaaggau      60
cagaauguga accuuugagu ugguucauag gcagucuccu uggcuagccu gaguggcccc    120
uauugc                                                                126

<210> SEQ ID NO 818
<211> LENGTH: 21
<212> TYPE: DNA
<213> ORGANISM: Sorghum bicolor

<400> SEQUENCE: 818
taggcaagtc atccttggct a                                                21

<210> SEQ ID NO 819
<211> LENGTH: 21
<212> TYPE: DNA
<213> ORGANISM: Sorghum bicolor

<400> SEQUENCE: 819
tagccaagga tgacttgcct a                                                21

<210> SEQ ID NO 820
<211> LENGTH: 20
<212> TYPE: RNA
<213> ORGANISM: Sorghum bicolor

<400> SEQUENCE: 820
ucgguuccua cugaacggau                                                  20

<210> SEQ ID NO 821
<211> LENGTH: 21
<212> TYPE: RNA
<213> ORGANISM: Sorghum bicolor

<400> SEQUENCE: 821
aucgguuccu acugaacgga u                                                21

<210> SEQ ID NO 822
<211> LENGTH: 19
<212> TYPE: RNA
<213> ORGANISM: Sorghum bicolor

<400> SEQUENCE: 822
aucgguuccu acugaacgg                                                   19

<210> SEQ ID NO 823
<211> LENGTH: 18
<212> TYPE: RNA
<213> ORGANISM: Sorghum bicolor

<400> SEQUENCE: 823
ucgguuccua cugaacgg                                                    18

<210> SEQ ID NO 824
<211> LENGTH: 20
<212> TYPE: RNA
<213> ORGANISM: Sorghum bicolor

<400> SEQUENCE: 824
```

-continued

```
agccaagaau gauuugccua                                              20

<210> SEQ ID NO 825
<211> LENGTH: 20
<212> TYPE: RNA
<213> ORGANISM: Sorghum bicolor

<400> SEQUENCE: 825
agccaagaau gaauugccug                                              20

<210> SEQ ID NO 826
<211> LENGTH: 20
<212> TYPE: RNA
<213> ORGANISM: Sorghum bicolor

<400> SEQUENCE: 826
agccaaggga uacuuguuua                                              20

<210> SEQ ID NO 827
<211> LENGTH: 21
<212> TYPE: RNA
<213> ORGANISM: Sorghum bicolor

<400> SEQUENCE: 827
ugcccaagca uggcuugccu g                                            21

<210> SEQ ID NO 828
<211> LENGTH: 19
<212> TYPE: RNA
<213> ORGANISM: Sorghum bicolor

<400> SEQUENCE: 828
ugcccaagca uggcuugcc                                               19

<210> SEQ ID NO 829
<211> LENGTH: 21
<212> TYPE: RNA
<213> ORGANISM: Sorghum bicolor

<400> SEQUENCE: 829
uugauaagga uggcuugccu g                                            21

<210> SEQ ID NO 830
<211> LENGTH: 20
<212> TYPE: RNA
<213> ORGANISM: Sorghum bicolor

<400> SEQUENCE: 830
agccaaggag aacuugucuu                                              20

<210> SEQ ID NO 831
<211> LENGTH: 18
<212> TYPE: RNA
<213> ORGANISM: Sorghum bicolor

<400> SEQUENCE: 831
ggccaaugau gauuugcc                                                18

<210> SEQ ID NO 832
<211> LENGTH: 18
<212> TYPE: RNA
<213> ORGANISM: Sorghum bicolor
```

-continued

<400> SEQUENCE: 832
agcaaaggau gauuugca                                                    18

<210> SEQ ID NO 833
<211> LENGTH: 18
<212> TYPE: RNA
<213> ORGANISM: Sorghum bicolor

<400> SEQUENCE: 833
agccgaugau gauuugcu                                                    18

<210> SEQ ID NO 834
<211> LENGTH: 18
<212> TYPE: RNA
<213> ORGANISM: Sorghum bicolor

<400> SEQUENCE: 834
cgccaaagau gacuugcu                                                    18

<210> SEQ ID NO 835
<211> LENGTH: 18
<212> TYPE: RNA
<213> ORGANISM: Sorghum bicolor

<400> SEQUENCE: 835
ugccaaugau gacuugca                                                    18

<210> SEQ ID NO 836
<211> LENGTH: 19
<212> TYPE: RNA
<213> ORGANISM: Sorghum bicolor

<400> SEQUENCE: 836
uagccaagga agauuuggc                                                   19

<210> SEQ ID NO 837
<211> LENGTH: 19
<212> TYPE: RNA
<213> ORGANISM: Sorghum bicolor

<400> SEQUENCE: 837
ugccggagga ugacuugcc                                                   19

<210> SEQ ID NO 838
<211> LENGTH: 19
<212> TYPE: RNA
<213> ORGANISM: Sorghum bicolor

<400> SEQUENCE: 838
uggccaagga ugauuucuc                                                   19

<210> SEQ ID NO 839
<211> LENGTH: 19
<212> TYPE: RNA
<213> ORGANISM: Sorghum bicolor

<400> SEQUENCE: 839
uagcgaggga uggcuuccc                                                   19

<210> SEQ ID NO 840
<211> LENGTH: 18
<212> TYPE: RNA
<213> ORGANISM: Sorghum bicolor -continued

<400> SEQUENCE: 840
agccaagaau gauuugcc                                                   18

<210> SEQ ID NO 841
<211> LENGTH: 18
<212> TYPE: RNA
<213> ORGANISM: Sorghum bicolor

<400> SEQUENCE: 841
guccaaggau gacuuacc                                                   18

<210> SEQ ID NO 842
<211> LENGTH: 20
<212> TYPE: RNA
<213> ORGANISM: Sorghum bicolor

<400> SEQUENCE: 842
uccguucagu aggaaccgau                                                 20

<210> SEQ ID NO 843
<211> LENGTH: 21
<212> TYPE: RNA
<213> ORGANISM: Sorghum bicolor

<400> SEQUENCE: 843
auccguucag uaggaaccga u                                               21

<210> SEQ ID NO 844
<211> LENGTH: 20
<212> TYPE: RNA
<213> ORGANISM: Sorghum bicolor

<400> SEQUENCE: 844
uggcaacuca uccuuggcuu                                                 20

<210> SEQ ID NO 845
<211> LENGTH: 20
<212> TYPE: RNA
<213> ORGANISM: Sorghum bicolor

<400> SEQUENCE: 845
aggcagcuug uacuuggcua                                                 20

<210> SEQ ID NO 846
<211> LENGTH: 21
<212> TYPE: RNA
<213> ORGANISM: Sorghum bicolor

<400> SEQUENCE: 846
uaaucaaauc auucuuggcu g                                               21

<210> SEQ ID NO 847
<211> LENGTH: 21
<212> TYPE: RNA
<213> ORGANISM: Sorghum bicolor

<400> SEQUENCE: 847
uaggcaaauc auucuuggcu g                                               21

<210> SEQ ID NO 848
<211> LENGTH: 20
<212> TYPE: RNA

<213> ORGANISM: Sorghum bicolor

<400> SEQUENCE: 848
aggcaauuca uucuuggcuu                                                        20

<210> SEQ ID NO 849
<211> LENGTH: 72
<212> TYPE: PRT
<213> ORGANISM: Arabidopsis thaliana

<400> SEQUENCE: 849

Glu Glu Pro Pro Thr Asp Tyr Ile His Val Arg Ala Arg Arg Gly Gln
 1               5                  10                  15

Ala Thr Asp Ser His Ser Leu Ala Glu Arg Val Arg Arg Glu Lys Ile
            20                  25                  30

Ser Glu Arg Met Arg Thr Leu Gln Asn Leu Val Pro Gly Cys Asp Lys
        35                  40                  45

Val Thr Gly Lys Ala Leu Met Leu Asp Glu Ile Ile Asn Tyr Val Gln
    50                  55                  60

Thr Leu Gln Thr Gln Val Glu Phe
65                  70

<210> SEQ ID NO 850
<211> LENGTH: 72
<212> TYPE: PRT
<213> ORGANISM: Manihot esculenta

<400> SEQUENCE: 850

Glu Glu Pro Ser Thr Gly Tyr Ile His Val Arg Ala Arg Arg Gly Gln
 1               5                  10                  15

Ala Thr Asp Ser His Ser Leu Ala Glu Arg Val Arg Arg Glu Lys Ile
            20                  25                  30

Ser Glu Arg Met Lys Ile Leu Gln Gln Leu Val Pro Gly Cys Asp Lys
        35                  40                  45

Val Thr Gly Lys Ala Leu Met Leu Asp Glu Ile Ile Asn Tyr Val Gln
    50                  55                  60

Ser Leu Gln Asn Gln Val Glu Phe
65                  70

<210> SEQ ID NO 851
<211> LENGTH: 72
<212> TYPE: PRT
<213> ORGANISM: Manihot esculenta

<400> SEQUENCE: 851

Glu Glu Pro Pro Thr Gly Tyr Ile His Val Arg Ala Arg Arg Gly Gln
 1               5                  10                  15

Ala Thr Asp Ser His Ser Leu Ala Glu Arg Val Arg Arg Glu Lys Ile
            20                  25                  30

Ser Glu Arg Met Lys Ile Leu Gln Arg Leu Val Pro Gly Cys Asp Lys
        35                  40                  45

Val Thr Gly Lys Ala Leu Met Leu Asp Glu Ile Ile Asn Tyr Val Gln
    50                  55                  60

Ser Leu Gln Asn Gln Val Glu Phe
65                  70

<210> SEQ ID NO 852
<211> LENGTH: 72
<212> TYPE: PRT

<213> ORGANISM: Glycine max

<400> SEQUENCE: 852

Glu Glu Pro Pro Thr Gly Tyr Ile His Val Arg Ala Arg Arg Gly Gln
1               5                   10                  15

Ala Thr Asp Ser His Ser Leu Ala Glu Arg Val Arg Arg Glu Lys Ile
            20                  25                  30

Ser Glu Arg Met Lys Val Leu Gln Arg Leu Val Pro Gly Cys Asp Lys
        35                  40                  45

Val Thr Gly Lys Ala Leu Met Leu Asp Glu Ile Ile Asn Tyr Val Gln
    50                  55                  60

Ser Leu Gln Asn Gln Val Glu Phe
65                  70

<210> SEQ ID NO 853
<211> LENGTH: 66
<212> TYPE: PRT
<213> ORGANISM: Glycine max

<400> SEQUENCE: 853

Glu Asp Pro Pro Thr Gly Tyr Ile His Val Arg Ala Arg Arg Gly Gln
1               5                   10                  15

Ala Thr Asp Ser His Ser Leu Ala Glu Arg Val Arg Arg Glu Lys Ile
            20                  25                  30

Ser Glu Arg Met Lys Thr Leu Gln Arg Leu Val Thr Gly Lys Ala Leu
        35                  40                  45

Val Leu Asp Glu Ile Ile Asn Tyr Val Gln Ser Leu Gln Asn Gln Val
    50                  55                  60

Glu Phe
65

<210> SEQ ID NO 854
<211> LENGTH: 72
<212> TYPE: PRT
<213> ORGANISM: Vitis vinifera

<400> SEQUENCE: 854

Glu Glu Pro Pro Thr Gly Tyr Ile His Val Arg Ala Arg Arg Gly Gln
1               5                   10                  15

Ala Thr Asp Ser His Ser Leu Ala Glu Arg Val Arg Arg Glu Lys Ile
            20                  25                  30

Ser Glu Arg Met Lys Leu Leu Gln Ala Leu Val Pro Gly Cys Asp Lys
        35                  40                  45

Val Thr Gly Lys Ala Leu Met Leu Asp Glu Ile Ile Asn Tyr Val Gln
    50                  55                  60

Ser Leu Gln Asn Gln Val Glu Phe
65                  70

<210> SEQ ID NO 855
<211> LENGTH: 72
<212> TYPE: PRT
<213> ORGANISM: Brachypodium distachyon

<400> SEQUENCE: 855

Glu Glu Ala Pro Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

```
Ser Glu Arg Met Arg Leu Leu Gln Thr Leu Val Pro Gly Cys Asp Lys
         35                  40                  45

Val Thr Gly Lys Ala Leu Ile Leu Asp Glu Ile Ile Asn Tyr Val Gln
 50                  55                  60

Ser Leu Gln Asn Gln Val Glu Phe
 65                  70
```

<210> SEQ ID NO 856
<211> LENGTH: 52
<212> TYPE: PRT
<213> ORGANISM: Brachypodium distachyon

<400> SEQUENCE: 856

```
Glu Glu Glu Pro Lys Gly Val Arg Arg Glu Arg Ile Ser Glu Arg Met
 1               5                  10                  15

Arg Met Leu Gln Ala Leu Val Pro Gly Cys Asp Lys Val Thr Gly Lys
             20                  25                  30

Ala Leu Ile Leu Asp Glu Ile Ile Asn Tyr Val Gln Ser Leu Gln Asn
         35                  40                  45

Gln Val Glu Phe
     50
```

<210> SEQ ID NO 857
<211> LENGTH: 72
<212> TYPE: PRT
<213> ORGANISM: Oryza sativa

<400> SEQUENCE: 857

```
Asp Glu Pro Pro Lys Gly Tyr Ile His Val Arg Ala Arg Arg Gly Gln
 1               5                  10                  15

Ala Thr Asp Ser His Ser Leu Ala Glu Arg Val Arg Arg Glu Arg Ile
             20                  25                  30

Ser Glu Arg Met Arg Met Leu Gln Ala Leu Val Pro Gly Cys Asp Lys
         35                  40                  45

Val Thr Gly Lys Ala Leu Ile Leu Asp Glu Ile Ile Asn Tyr Val Gln
 50                  55                  60

Ser Leu Gln Asn Gln Val Glu Phe
 65                  70
```

<210> SEQ ID NO 858
<211> LENGTH: 72
<212> TYPE: PRT
<213> ORGANISM: Oryza sativa

<400> SEQUENCE: 858

```
Glu Glu Ala Pro Gln Gly Phe Ile His Val Arg Ala Arg Arg Gly Gln
 1               5                  10                  15

Ala Thr Asp Ser His Ser Leu Ala Glu Arg Val Arg Arg Glu Arg Ile
             20                  25                  30

Ser Glu Arg Met Arg Met Leu Gln Ala Leu Val Pro Gly Cys Asp Lys
         35                  40                  45

Val Thr Gly Lys Ala Leu Ile Leu Asp Glu Ile Ile Asn Tyr Val Gln
 50                  55                  60

Ser Leu Gln Asn Gln Val Glu Phe
 65                  70
```

<210> SEQ ID NO 859
<211> LENGTH: 72
<212> TYPE: PRT

<213> ORGANISM: Setaria italica

<400> SEQUENCE: 859

Asp Glu Ala Pro Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

Ser Glu Arg Met Arg Met Leu Gln Ala Leu Val Pro Gly Cys Asp Lys
        35                  40                  45

Val Thr Gly Lys Ala Leu Ile Leu Asp Glu Ile Ile Asn Tyr Val Gln
    50                  55                  60

Ser Leu Gln Asn Gln Val Glu Phe
65                  70

<210> SEQ ID NO 860
<211> LENGTH: 71
<212> TYPE: PRT
<213> ORGANISM: Setaria italica

<400> SEQUENCE: 860

Glu Glu Glu Pro Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

Ser Glu Arg Met Arg Met Leu Gln Ala Leu Val Pro Gly Cys Asp Lys
        35                  40                  45

Val Thr Gly Lys Ala Leu Ile Leu Asp Glu Ile Ile Asn Tyr Val Gln
    50                  55                  60

Ser Leu Gln Asn Gln Val Glu
65                  70

<210> SEQ ID NO 861
<211> LENGTH: 71
<212> TYPE: PRT
<213> ORGANISM: Sorghum bicolor

<400> SEQUENCE: 861

Glu Glu Pro Lys Gly Tyr Ile His Val Arg Ala Arg Arg Gly Gln Ala
1               5                   10                  15

Thr Asp Ser His Ser Leu Ala Arg Val Arg Arg Glu Arg Ile Ser
            20                  25                  30

Glu Arg Met Arg Val Leu Gln Ala Leu Val Pro Gly Cys Asp Lys Val
        35                  40                  45

Thr Gly Lys Ala Leu Ile Leu Asp Glu Ile Ile Asn Tyr Val Gln Ser
    50                  55                  60

Leu Gln Asn Gln Val Glu Phe
65                  70

<210> SEQ ID NO 862
<211> LENGTH: 72
<212> TYPE: PRT
<213> ORGANISM: Sorghum bicolor

<400> SEQUENCE: 862

Asp Glu Ala Thr Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

```
Ser Glu Arg Met Arg Met Leu Gln Ala Leu Val Pro Gly Cys Asp Lys
            35                  40                  45

Val Thr Gly Lys Ala Leu Ile Leu Asp Glu Ile Ile Asn Tyr Val Gln
        50                  55                  60

Ser Leu Gln Asn Gln Val Glu Phe
65                  70

<210> SEQ ID NO 863
<211> LENGTH: 72
<212> TYPE: PRT
<213> ORGANISM: Zea mays

<400> SEQUENCE: 863

Asp Glu Ala Ser Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

Ser Glu Arg Met Arg Met Leu Gln Ala Leu Val Pro Gly Cys Asp Lys
            35                  40                  45

Val Thr Gly Lys Ala Met Val Leu Asp Glu Ile Ile Asn Tyr Val Gln
        50                  55                  60

Ser Leu Gln Asn Gln Val Glu Phe
65                  70

<210> SEQ ID NO 864
<211> LENGTH: 72
<212> TYPE: PRT
<213> ORGANISM: Zea mays

<400> SEQUENCE: 864

Glu Glu Glu Pro Lys Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

Ser Glu Arg Met Arg Val Leu Gln Ala Leu Val Pro Gly Cys Asp Lys
            35                  40                  45

Val Thr Gly Lys Ala Leu Val Leu Asp Glu Ile Ile Asn Tyr Val Gln
        50                  55                  60

Ser Leu Gln Asn Gln Val Glu Phe
65                  70

<210> SEQ ID NO 865
<211> LENGTH: 72
<212> TYPE: PRT
<213> ORGANISM: Zea mays

<400> SEQUENCE: 865

Asp Glu Ala Thr Arg Gly Tyr Ile His Val Arg Ala Arg Arg Gly Gln
1               5                   10                  15

Ala Thr Asp Ser His Ser Leu Ala Glu Arg Val Arg Arg Glu Arg Ile
            20                  25                  30

Ser Glu Arg Met Arg Met Leu Gln Ala Leu Val Pro Gly Cys Asp Lys
            35                  40                  45

Val Thr Gly Lys Ala Leu Ile Leu Asp Glu Ile Ile Asn Tyr Val Gln
        50                  55                  60

Ser Leu Gln Asn Gln Val Glu Phe
65                  70
```

<210> SEQ ID NO 866
<211> LENGTH: 402
<212> TYPE: PRT
<213> ORGANISM: Arabidopsis thaliana

<400> SEQUENCE: 866

| Met | Gly | Thr | Ser | Thr | Thr | Glu | Ser | Val | Val | Ala | Cys | Glu | Phe | Cys | Gly |
|---|---|---|---|---|---|---|---|---|---|---|---|---|---|---|---|
| 1 | | | | 5 | | | | | 10 | | | | | 15 | |

| Glu | Arg | Thr | Ala | Val | Leu | Phe | Cys | Arg | Ala | Asp | Thr | Ala | Lys | Leu | Cys |
|---|---|---|---|---|---|---|---|---|---|---|---|---|---|---|---|
| | | | 20 | | | | | 25 | | | | | 30 | | |

| Leu | Pro | Cys | Asp | Gln | His | Val | His | Ser | Ala | Asn | Leu | Leu | Ser | Arg | Lys |
| | | 35 | | | | | 40 | | | | | 45 | | | |

| His | Val | Arg | Ser | Gln | Ile | Cys | Asp | Asn | Cys | Ser | Lys | Glu | Pro | Val | Ser |
| 50 | | | | | 55 | | | | | 60 | | | | | |

| Val | Arg | Cys | Phe | Thr | Asp | Asn | Leu | Val | Leu | Cys | Gln | Glu | Cys | Asp | Trp |
| 65 | | | | | 70 | | | | | 75 | | | | | 80 |

| Asp | Val | His | Gly | Ser | Cys | Ser | Ser | Ala | Thr | His | Glu | Arg | Ser | Ala |
| | | | | 85 | | | | | 90 | | | | | 95 | |

| Val | Glu | Gly | Phe | Ser | Gly | Cys | Pro | Ser | Val | Leu | Glu | Leu | Ala | Ala | Val |
| | | | | 100 | | | | | 105 | | | | | 110 | |

| Trp | Gly | Ile | Asp | Leu | Lys | Gly | Lys | Lys | Lys | Glu | Asp | Asp | Glu | Asp | Glu |
| | | | | 115 | | | | | 120 | | | | | 125 | |

| Leu | Thr | Lys | Asn | Phe | Gly | Met | Gly | Leu | Asp | Ser | Trp | Gly | Ser | Gly | Ser |
| | 130 | | | | | 135 | | | | | 140 | | | | |

| Asn | Ile | Val | Gln | Glu | Leu | Ile | Val | Pro | Tyr | Asp | Val | Ser | Cys | Lys | Lys |
| 145 | | | | | 150 | | | | | 155 | | | | | 160 |

| Gln | Ser | Phe | Ser | Phe | Gly | Arg | Ser | Lys | Gln | Val | Val | Phe | Glu | Gln | Leu |
| | | | | 165 | | | | | 170 | | | | | 175 | |

| Glu | Leu | Leu | Lys | Arg | Gly | Phe | Val | Glu | Gly | Glu | Gly | Glu | Ile | Met | Val |
| | | | 180 | | | | | 185 | | | | | 190 | | |

| Pro | Glu | Gly | Ile | Asn | Gly | Gly | Gly | Ser | Ile | Ser | Gln | Pro | Ser | Pro | Thr |
| | | | 195 | | | | | 200 | | | | | 205 | | |

| Thr | Ser | Phe | Thr | Ser | Leu | Leu | Met | Ser | Gln | Ser | Leu | Cys | Gly | Asn | Gly |
| | 210 | | | | | 215 | | | | | 220 | | | | |

| Met | Gln | Trp | Asn | Ala | Thr | Asn | His | Ser | Thr | Gly | Gln | Asn | Thr | Gln | Ile |
| 225 | | | | | 230 | | | | | 235 | | | | | 240 |

| Trp | Asp | Phe | Asn | Leu | Gly | Gln | Ser | Arg | Asn | Pro | Asp | Glu | Pro | Ser | Pro |
| | | | | 245 | | | | | 250 | | | | | 255 | |

| Val | Glu | Thr | Lys | Gly | Ser | Thr | Phe | Thr | Phe | Asn | Asn | Val | Thr | His | Leu |
| | | | 260 | | | | | 265 | | | | | 270 | | |

| Lys | Asn | Asp | Thr | Arg | Thr | Thr | Asn | Met | Asn | Ala | Phe | Lys | Glu | Ser | Tyr |
| | | | 275 | | | | | 280 | | | | | 285 | | |

| Gln | Gln | Glu | Asp | Ser | Val | His | Ser | Thr | Ser | Lys | Gly | Gln | Glu | Thr |
| | 290 | | | | | 295 | | | | | 300 | | | | |

| Ser | Lys | Ser | Asn | Asn | Ile | Pro | Ala | Ala | Ile | His | Ser | His | Lys | Ser | Ser |
| 305 | | | | | 310 | | | | | 315 | | | | | 320 |

| Asn | Asp | Ser | Cys | Gly | Leu | His | Cys | Thr | Glu | His | Ile | Ala | Ile | Thr | Ser |
| | | | | 325 | | | | | 330 | | | | | 335 | |

| Asn | Arg | Ala | Thr | Arg | Leu | Val | Ala | Val | Thr | Asn | Ala | Asp | Leu | Glu | Gln |
| | | | 340 | | | | | 345 | | | | | 350 | | |

| Met | Ala | Gln | Asn | Arg | Asp | Asn | Ala | Met | Gln | Arg | Tyr | Lys | Glu | Lys | Lys |
| | | | 355 | | | | | 360 | | | | | 365 | | |

| Lys | Thr | Arg | Arg | Tyr | Asp | Lys | Thr | Ile | Arg | Tyr | Glu | Thr | Arg | Lys | Ala |
| | 370 | | | | | 375 | | | | | 380 | | | | |

```
Arg Ala Glu Thr Arg Leu Arg Val Lys Gly Arg Phe Val Lys Ala Thr
385                 390                 395                 400

Asp Pro

<210> SEQ ID NO 867
<211> LENGTH: 195
<212> TYPE: PRT
<213> ORGANISM: Vitis vinifera

<400> SEQUENCE: 867

Met Trp Asp Arg Gly His Leu Ser Tyr Gln Ala Pro Gln Ile Trp Asp
1               5                   10                  15

Phe His Leu Gly Arg Ser Arg Ile Cys Lys Glu Thr Ser Pro Glu Ala
            20                  25                  30

Gly Tyr Asp Val Asp Asn Ser Gly Phe Val Ile Lys Asn Tyr Ser Glu
        35                  40                  45

Ile Thr Lys Gly Ser Ser Leu Thr Arg Thr Lys Ala Leu Gln Gly Met
    50                  55                  60

Tyr Glu Met Asn Cys Thr Thr Thr His Glu Asp Ile Leu Ser Lys Asn
65                  70                  75                  80

Ser His Ser Asn Lys Ala Leu Ser Gln Gly Pro Thr Thr Ala Glu
                85                  90                  95

Ser Asn Asn Ile Pro Ile Val Gly Pro Ser Ser Glu Ser Trp Thr Ala
            100                 105                 110

Glu Pro Asn Thr Asn Ser Ile Lys Ser Met Gln Phe Lys Asp Leu Leu
        115                 120                 125

Ile Gly Ser Gly Thr Ala Arg Thr Glu Thr Thr Asn Val Asp Met Glu
    130                 135                 140

Leu Leu Ala Gln Asn Arg Gly His Ala Met Leu Arg Tyr Lys Glu Lys
145                 150                 155                 160

Lys Lys Thr Arg Arg Tyr Glu Lys His Ile Arg Tyr Glu Ser Arg Lys
                165                 170                 175

Ala Arg Ala Asp Thr Arg Lys Arg Val Lys Gly Arg Phe Val Lys Ala
            180                 185                 190

Ser Asp Ser
        195

<210> SEQ ID NO 868
<211> LENGTH: 362
<212> TYPE: PRT
<213> ORGANISM: Vitis vinifera

<400> SEQUENCE: 868

Met Gln Glu Lys Gly Val Pro Leu Leu Pro Asn Ser Pro Cys Ala Leu
1               5                   10                  15

His Pro Leu Ala Ala Leu Ser Tyr Pro Ile Ile Ser Ser Ile Ser Leu
            20                  25                  30

Thr Ser Asp Arg Lys Lys Thr Thr Lys His Thr Cys Thr Asn Asn Gln
        35                  40                  45

Phe Cys Tyr Asp Thr Phe Leu Gln Leu Thr His Ala Pro His Val
    50                  55                  60

Pro His Cys Leu Ile Tyr Tyr Lys Arg Phe Trp Cys Ser Gly Phe Val
65                  70                  75                  80

Gln Ala Val Val Arg Ile Glu Leu Ser Gln Ile Leu Leu Cys Phe Arg
                85                  90                  95

Val Ser Lys Arg Gln Ser Pro Ser Cys Gly Lys His Lys Gln Val Ile
```

```
            100                 105                 110
Phe Lys Gln Leu Gly His Val Gly Glu Ser Ile Gly Ile Glu Asn Gly
        115                 120                 125

Gly Val Leu Asp Val Asp His Gln Ala Leu Glu Gln Gln Thr Pro Phe
    130                 135                 140

Thr Ser Leu Leu Met Leu Pro Asn Arg Ala Thr Gly Gly Val Ile
145                 150                 155                 160

Leu Trp Asp Asn Asn Pro Ser Asp Gln Ser Thr Gln Ile Trp Asp Phe
                165                 170                 175

His Leu Gly His Ser Arg Gly Tyr Glu Glu Cys Gly Leu Leu Glu Ala
            180                 185                 190

Glu Tyr Gly Val Asn Asp Ala Gly Phe Val Ile Lys Ser Tyr Ser Glu
        195                 200                 205

Leu Met Lys Glu Thr Ser Phe Thr Asn Thr Lys Val Val Gly Glu Met
    210                 215                 220

Tyr Asp Ile Asn Tyr Ser Met Thr His Glu Asp Ile Thr Ser Phe Asn
225                 230                 235                 240

Asn Asn Ser Asn Asn Pro Thr Ala Ser Gln Gly Ala Ala Thr Ser Glu
                245                 250                 255

Ser Asn Asn Leu Pro Ile Ala Arg Pro Ser Ser Gly Ser Ala Phe Ala
            260                 265                 270

Lys Pro Lys Ser Phe Ser Gly Ser Lys Asp Ile Glu Leu Thr Glu Gln
        275                 280                 285

Ser Ile Leu Met Arg Gly Glu Ser Gly Arg Thr Ala Ala Thr Thr Lys
    290                 295                 300

Val Asp Leu Glu Gln Leu Ala Gln Asn Arg Gly Asn Ala Met Leu Arg
305                 310                 315                 320

Tyr Lys Glu Lys Lys Thr Arg Arg Tyr Asp Lys His Ile Arg Tyr
                325                 330                 335

Glu Ser Arg Lys Ala Arg Ala Asp Thr Arg Lys Arg Val Lys Gly Arg
            340                 345                 350

Phe Val Lys Ala Thr Glu Ala Pro Asp Gly
        355                 360

<210> SEQ ID NO 869
<211> LENGTH: 490
<212> TYPE: PRT
<213> ORGANISM: Brachypodium distachyon

<400> SEQUENCE: 869

Met Lys Glu Gly Gly Gly Arg Gln Gln Trp Pro Cys Asp Tyr Cys Gly
1               5                   10                  15

Glu Ala Ala Ala Leu His Cys Arg Ala Asp Ala Ala Arg Leu Cys
            20                  25                  30

Val Ala Cys Asp Arg His Val His Ala Ala Asn Ala Leu Ser Arg Lys
    35                  40                  45

His Val Arg Ala Pro Leu Cys Ala Ala Cys Ala Ala Arg Pro Ala Ala
    50                  55                  60

Ala Ala Arg Leu Ala Ser Gly Ser Ser Asp Pro Glu Phe Leu Cys Ser
65                  70                  75                  80

Ala Cys Asp Asp Asp Gly Ala Cys Glu Gly Ala Gly Ala Ala Arg Val
                85                  90                  95

Pro Val Glu Gly Phe Ser Gly Cys Pro Ala Ala Ser Glu Leu Ala Ala
            100                 105                 110
```

Ser Trp Gly Leu Asp Leu Leu His Pro Leu Pro Thr Asp Gly Cys Gly
115                 120                 125

Gly Gly Gly Gly Ile Gly Arg Gly Glu Gln Glu Asp Glu Glu Asp Ala
    130                 135                 140

Leu Phe Phe Ser Ser Leu Asp Tyr Ser Met Leu Val Asp Pro Glu Met
145                 150                 155                 160

Arg Asp Leu Tyr Val Pro Cys Asp Pro Pro Asp Ser Gly Gly Arg Pro
                165                 170                 175

Leu Lys Gly Glu Ala Leu Cys Gln Gln Leu Ala Glu Met Ala Arg Arg
            180                 185                 190

Glu Thr Gln Ser His Pro Pro Pro Pro Gln Gln Gln Gln Tyr Thr
        195                 200                 205

Pro Asp Leu Ser Pro Arg Thr Pro Arg Arg Ser Ser Ala Gly Pro Glu
    210                 215                 220

Lys Gln His Gln Gln Pro Pro Pro Leu Pro Gln Glu Pro Pro Phe Pro
225                 230                 235                 240

Tyr Thr Ser Leu Leu Met Asn Met Met Pro Pro Asp Asn Leu Ala Ala
                245                 250                 255

Gly Asn Asn Asp Arg Leu Arg Asp Asp Glu Ala Gly Gln Gln Leu Gln
            260                 265                 270

Trp Glu Phe Thr Ala Pro Ser Ser Val Pro Pro Thr Gln Ile Trp Asp
        275                 280                 285

Phe Asn Leu Gly Arg Ser Arg Asn His Asn Glu Asn Ser Ala Leu Glu
    290                 295                 300

Val Glu Phe Gly Ser Asn Asn Gly Gly Phe Met Ile Lys Ser Tyr Asn
305                 310                 315                 320

Asp Met Leu Lys Glu Ile Ser Ser Gly Thr Thr Lys Asp Leu Glu Asp
                325                 330                 335

Ile Tyr Asp Ser Gly Tyr Cys Ala Ala Ala Glu Asp Ile Met Ser Thr
            340                 345                 350

Asn Ile Cys Gln Leu Ser Ser Lys Asn Val Ser Thr Ala Ser Asn Lys
        355                 360                 365

Arg Lys Val Ser Ser Cys Thr Ser Thr Ile Asp Gly Pro Thr Thr Ser
    370                 375                 380

Gly Asn Tyr Val Pro Thr Ser Gly Pro Leu Gly Ser Ser Ser Gln Asp
385                 390                 395                 400

Arg Gly Ala Ala Leu Ala Arg Glu Ile Ser Phe Gly Glu Gln Thr Ile
                405                 410                 415

Val Pro Thr Gly Ala Asp Arg Pro Thr Thr Arg Ile Asp Ser Glu Thr
            420                 425                 430

Leu Ala Gln Asn Arg Asp Ser Ala Met Gln Arg Tyr Arg Glu Lys Arg
        435                 440                 445

Lys Asn Arg Arg Tyr Glu Lys His Ile Arg Tyr Glu Ser Arg Lys Leu
    450                 455                 460

Arg Ala Asp Thr Arg Lys Arg Val Lys Gly Arg Phe Val Lys Ser Asn
465                 470                 475                 480

Glu Ala Leu Asn Ala Ser Gly Asn Gly Gly
                485                 490

<210> SEQ ID NO 870
<211> LENGTH: 488
<212> TYPE: PRT
<213> ORGANISM: Oryza sativa

<400> SEQUENCE: 870

-continued

```
Met Lys Asp Gly Gly Gly Gly Arg Gly Gln Gln Gln Gln Trp
  1               5                  10                 15

Pro Cys Asp Tyr Cys Gly Glu Ala Ala Ala Leu His Cys Arg Ala
             20                  25              30

Asp Ala Ala Arg Leu Cys Val Ala Cys Asp Arg His Val His Ala Ala
         35                  40                  45

Asn Ala Leu Ser Arg Lys His Val Arg Ala Pro Leu Cys Ala Ala Cys
     50                  55                  60

Ala Ala Arg Pro Ala Ala Arg Val Ala Ser Ala Ser Ala Pro Ala
 65              70                  75              80

Phe Leu Cys Ala Asp Cys Asp Thr Gly Cys Gly Gly Asp Asp Gly Ala
                 85                  90                  95

Ala Leu Arg Val Pro Val Glu Gly Phe Ser Gly Cys Pro Ala Ala Ala
                100                 105                 110

Glu Leu Ala Ala Ser Trp Gly Leu Asp Leu Pro Gly Gly Cys Gly Gly
                115                 120                 125

Glu Glu Glu Glu Ala Asp Asp Ala Phe Phe Ser Ala Leu Asp Tyr Ser
130                 135                 140

Met Leu Ala Val Asp Pro Val Leu Arg Asp Leu Tyr Val Pro Cys Asp
145                 150                 155                 160

Pro Pro Glu Val Val Ala Gly Gly Arg Arg Leu Lys Gly Glu
                165                 170                 175

Ala Leu Gly His Gln Leu Ala Glu Met Ala Arg Arg Glu Ala Glu Thr
                180                 185                 190

Ala His Pro His Thr Gln Pro His Ser Asp Leu Ser Pro Arg Thr Pro
        195                 200                 205

Arg Arg Thr Ser Ala Ala Ala Ser Gly Arg Leu Gln Glu Lys Gln Ala
        210                 215                 220

Pro Pro Pro Leu Pro His Ala Ala Ala Thr Ala Ala Pro Leu Pro Tyr
225                 230                 235                 240

Thr Ser Leu Leu Met Met Ala Pro Ala Asn Cys Thr Glu Leu Met Glu
                245                 250                 255

Asn Asn Arg Val Gly Asp Glu Asp Glu Asn Val Leu Trp Glu Ser Thr
                260                 265                 270

Ala Pro Ser Val Pro Pro Thr Gln Ile Trp Asp Phe Asn Leu Gly Lys
        275                 280                 285

Ser Arg Asp His Asn Glu Asn Ser Ala Leu Glu Val Gly Phe Gly Ser
        290                 295                 300

Asn Asn Gly Gly Phe Met Ile Lys Ser Tyr Asn Asp Met Leu Lys Glu
305                 310                 315                 320

Ile Ser Ser Gly Thr Thr Lys Asp Leu Glu Asp Ile Tyr Asp Ser Arg
                325                 330                 335

Tyr Phe Ala Ala Ala Glu Asp Ile Met Ser Thr Asn Val Cys Gln Leu
                340                 345                 350

Ser Ser Lys Asn Pro Ser Thr Arg Ser Asn Lys Arg Lys Ala Ser Ser
        355                 360                 365

Cys Ala Ser Thr Ile Asp Gly Pro Thr Thr Ser Thr Ser His Val Pro
370                 375                 380

Ala Ala Ser Gly Ala Leu Gly Gly Ser Ser Asn Asp Arg Gly Ser Ala
385                 390                 395                 400

Leu Pro Lys Glu Ile Ser Phe Cys Asp Gln Thr Val Val Pro Thr Gly
                405                 410                 415
```

```
Ala Asp Gln Arg Pro Cys Thr Ile Lys Ile Asp Ser Glu Thr Leu Ala
            420                 425                 430

Gln Asn Arg Asp Ser Ala Met Gln Arg Tyr Arg Glu Lys Lys Lys Asn
        435                 440                 445

Arg Arg Tyr Glu Lys His Ile Arg Tyr Glu Ser Arg Lys Leu Arg Ala
    450                 455                 460

Asp Thr Arg Lys Arg Val Lys Gly Arg Phe Val Lys Ser Asn Gly Ala
465                 470                 475                 480

Pro Asp Asp Val Ser Asn Gly Gly
                485

<210> SEQ ID NO 871
<211> LENGTH: 336
<212> TYPE: PRT
<213> ORGANISM: Setaria italica

<400> SEQUENCE: 871

Met Leu Gly Ala Asp Pro Glu Leu Arg Asp Leu Tyr Val Pro Cys Asp
  1               5                  10                  15

Pro Pro Glu Gly Ala Ala His Ala Gly Gly Ala Arg Arg Leu Lys Gly
             20                  25                  30

Glu Ala Leu Cys Asp Gln Leu Ala Glu Met Ala Arg Arg Glu Ala Asp
         35                  40                  45

Thr Ser His Pro His Gln Pro Ser Asp Leu Ser Pro Arg Thr Pro
     50                  55                  60

Arg Arg Asn Ser Ala Ala Ser Ser Gly Arg Leu Pro Gly Lys Met Ala
 65                  70                  75                  80

Pro Pro Ala Pro Pro His His Pro Pro Ala Ala Val Gln Glu Val
                 85                  90                  95

Pro Leu Pro Tyr Thr Ser Leu Leu Met Met Ala Ser Ala Asn Cys Thr
            100                 105                 110

Glu Leu Ile Gly Gly His Asp Arg Met Ala Asp Asp Glu Gln Leu
        115                 120                 125

Leu Trp Asp Cys Ala Pro Pro Ser Val Pro Pro Thr Gln Ile Trp Asp
130                 135                 140

Phe Asn Leu Gly Arg Ser Arg Asp His Asp Glu Lys Ser Ser Ile Glu
145                 150                 155                 160

Val Gly Phe Gly Ser Asn His Gly Gly Phe Met Ile Lys Ser Tyr Ser
                165                 170                 175

Asp Met Leu Lys Glu Ile Ser Ser Gly Thr Thr Lys Asp Leu Glu Asp
            180                 185                 190

Ile Tyr Asp Ser Arg Tyr Cys Ser Thr Ala Glu Asp Ile Met Ser Ser
        195                 200                 205

Asn Ile Cys Gln Val Ser Ser Lys Asn Val Ser Thr Gly Ser Asn Lys
    210                 215                 220

Arg Lys Val Ser Pro Ser Thr Ser Thr Met Asp Gly Pro Thr Ser
225                 230                 235                 240

Gly Asn His Val Pro Thr Ser Gly Pro Ala Leu Thr Arg Glu Ile Ser
                245                 250                 255

Phe Gly Asp Gln Thr Val Ser Pro Ala Gly Ala Glu Arg Pro Ala Ala
            260                 265                 270

Met Arg Ile Asp Ser Glu Thr Leu Ala Gln Asn Arg Asp Ser Ala Met
        275                 280                 285

Gln Arg Tyr Arg Glu Lys Arg Lys Asn Arg Arg Tyr Glu Lys His Ile
    290                 295                 300
```

```
Arg Tyr Glu Ser Arg Lys Leu Arg Ala Asp Thr Arg Lys Arg Val Lys
305                 310                 315                 320

Gly Arg Phe Val Lys Ser Thr Glu Ala Leu Asn Ala Gly Asn Gly Gly
                325                 330                 335

<210> SEQ ID NO 872
<211> LENGTH: 490
<212> TYPE: PRT
<213> ORGANISM: Sorghum bicolor

<400> SEQUENCE: 872

Met Lys Ser Gly Gly Gly Gly Gly Gly Gly Gly Gly Gly Gly Gln
1               5                   10                  15

Gln Trp Pro Cys Asp Tyr Cys Gly Glu Ala Ala Ala Ala Leu His Cys
                20                  25                  30

Arg Ala Asp Ala Ala Arg Leu Cys Val Ala Cys Asp Arg His Val His
            35                  40                  45

Ala Ala Asn Ala Leu Ser Arg Lys His Val Arg Val Pro Leu Cys Ala
        50                  55                  60

Gly Cys Ala Ala Arg Pro Ala Ala Arg Val Ser Pro Val Pro Gly
65                  70                  75                  80

Ala Asp Pro Ala Phe Leu Cys Ala Gly Cys Asp Ala Ala Ser
                85                  90                  95

Ala Ala Val Arg Val Pro Val Glu Gly Phe Ser Gly Cys Pro Ser Ala
            100                 105                 110

Ala Glu Leu Ala Ala Ser Trp Gly Leu Asp Leu Arg Arg Ala Glu Glu
        115                 120                 125

Gly Lys Asp Gly Ala Gly Gly Asp Ile Asp Asp Gly Asp Pro Phe Leu
    130                 135                 140

Ser Val Leu Asp Tyr Ser Val Leu Gly Val Ala Val Asp Pro Asp Leu
145                 150                 155                 160

Arg Asp Leu Tyr Val Pro Cys Asp Pro Pro Arg Val Pro Ala Pro Asp
                165                 170                 175

Ala Ala Gly Ala Arg Pro Leu Arg Gly Gln Ala Leu Cys Asp Gln Leu
            180                 185                 190

Ala Glu Met Ala Arg Arg Glu Thr Asp Thr Ala His Ala His Pro His
        195                 200                 205

Ser Asp Leu Ser Pro Arg Thr Pro Arg Arg Thr Ser Ala Ala Ser Gly
    210                 215                 220

Gly Arg Leu Pro Pro Gly Lys Met Ser Pro Ala Ala Met Pro Thr
225                 230                 235                 240

His His Pro Pro Pro Ala Ala Val Gln Glu Val Pro Leu Pro Tyr Thr
                245                 250                 255

Ser Leu Leu Met Met Ala Ser Ala Asn Cys Ala Asp Leu Ile Gly Gly
            260                 265                 270

Ala Asp Arg Val Gly Asp Asp Glu Gln Leu Leu Trp Asp Cys Ala
        275                 280                 285

Ala Pro Ser Val Pro Pro Thr Gln Ile Trp Asp Phe Asn Leu Gly Arg
    290                 295                 300

Ser Arg Asp His Asp Glu Lys Ser Ala Leu Glu Val Gly Tyr Gly Ser
305                 310                 315                 320

Asn His Gly Gly Phe Met Ile Lys Ser Tyr Ser Asp Met Leu Lys Glu
                325                 330                 335

Ile Ser Ser Gly Thr Thr Lys Asp Leu Glu Asp Ile Tyr Asp Ser Arg
            340                 345                 350
```

Tyr Cys Ser Thr Ala Glu Asp Ile Met Ser Ser Asn Ile Cys Gln Leu
        355                 360                 365

Ser Ser Lys Asn Val Ser Thr Ala Ser Asn Lys Arg Lys Leu Ser Ser
    370                 375                 380

Cys Ala Ser Thr Ile Asp Gly Pro Thr Thr Ser Gly Asn His Val Pro
385                 390                 395                 400

Thr Ser Gly Pro Ala Leu Thr Arg Glu Ile Ser Phe Gly Asp Gln Thr
                405                 410                 415

Val Ser Thr Pro Ala Ala Glu Arg Pro Ala Val Arg Ile Asp Ser Glu
            420                 425                 430

Thr Leu Ala Gln Asn Arg Asp Ser Ala Met Gln Arg Tyr Arg Glu Lys
        435                 440                 445

Lys Lys Asn Arg Arg Tyr Glu Lys His Ile Arg Tyr Glu Ser Arg Lys
    450                 455                 460

Leu Arg Ala Asp Thr Arg Lys Arg Val Lys Gly Arg Phe Val Lys Ser
465                 470                 475                 480

Thr Glu Ala Leu Asn Ala Gly Tyr Gly Gly
                485                 490

<210> SEQ ID NO 873
<211> LENGTH: 498
<212> TYPE: PRT
<213> ORGANISM: Zea mays

<400> SEQUENCE: 873

Met Lys Ser Cys Gly Gly Gly Ala Asp Gly Gln Gln Cys Pro Cys
 1               5                  10                  15

Asp Tyr Cys Gly Glu Ala Ala Ala Leu His Cys Arg Ala Asp Ala
                20                  25                  30

Ala Arg Leu Cys Val Ala Cys Asp Arg His Val His Ala Ala Asn Ala
        35                  40                  45

Leu Ser Arg Lys His Val Arg Ala Pro Leu Cys Ala Gly Cys Ala Ala
    50                  55                  60

Arg Pro Ala Ala Ala Arg Val Ser Leu Gly Ala Asp Pro Ala Phe Leu
65                  70                  75                  80

Cys Ala Asp Cys Cys Glu Gly Cys Ala Ala Ser Ala Ala Arg Val
                85                  90                  95

Ser Val Glu Gly Phe Ser Gly Cys Pro Ser Ala Ala Glu Leu Ala Ala
                100                 105                 110

Ser Trp Gly Leu Asp Leu Arg Arg Ala Ala Val Ala Val Gly Asp Asp
        115                 120                 125

Gly Asp Gly Gly Asp Asp Asp Pro Phe Leu Ser Val Leu Asp Tyr
130                 135                 140

Ser Val Leu Gly Val Gly Val Ala Asp Thr Asp Leu Arg Asp Leu Tyr
145                 150                 155                 160

Val Pro Cys Asp Pro Arg Val Pro Val Pro Asp Ala Gly Ala Arg
                165                 170                 175

Pro Leu Arg Gly Glu Ala Leu Cys Asp Gln Leu Ala Glu Met Ala Arg
            180                 185                 190

Arg Asp Glu Ala Asp Thr Ser His Ala His Pro His Ser Asp Leu Ser
        195                 200                 205

Pro Arg Thr Pro Arg Arg Thr Ser Ala Ala Ser Ser Gly Arg Leu Pro
    210                 215                 220

Ser Gly Lys Met Ala Pro Pro Ala Ala Leu Pro Val Pro Ala His Pro
225                 230                 235                 240

```
Pro Pro Ala Ala Pro Gln Glu Val Pro Leu Pro Tyr Thr Ser Leu Leu
            245                 250                 255
Met Met Ala Ser Ala Asn Cys Ser Asp Leu Ile Gly Gly Gly Asp Arg
            260                 265                 270
Val Gly Asp Thr Asp Glu Gln Leu Leu Trp Asp Cys Ala Ala Pro Ser
            275                 280                 285
Val Pro Pro Thr Gln Ile Trp Asp Phe Asn Leu Gly Arg Ser Arg His
            290                 295                 300
His Asp Glu Lys Ser Ala Leu Glu Val Gly Tyr Gly Ser Asn His Gly
305                 310                 315                 320
Gly Phe Met Ile Lys Ser Tyr Ser Asp Met Leu Lys Asp Ile Ser Ser
            325                 330                 335
Gly Thr Thr Lys Asp Leu Glu Asp Ile Tyr Asp Ser Arg Tyr Cys Ser
            340                 345                 350
Thr Ala Glu Asp Ile Met Ser Ser Asn Ile Cys Gln Leu Ser Ser Lys
            355                 360                 365
Asn Val Ser Thr Gly Ser Asn Lys Arg Lys Val Arg Ser Cys Ala Ala
            370                 375                 380
Ser Thr Met Asp Gly Pro Thr Thr Ser Gly Asn His Asn His Val Pro
385                 390                 395                 400
Ala Ser Ala Ser Gly Pro Gly Ala Ala Leu Thr Arg Glu Ile Ser Phe
            405                 410                 415
Gly Asp Gln Thr Val Ser Ala Pro Ala Ala Glu Thr Glu Arg Pro Ala
            420                 425                 430
Ala Val Arg Ile Asp Ser Glu Thr Leu Ala Gln Asn Arg Asp Ser Ala
            435                 440                 445
Met Gln Arg Tyr Arg Glu Lys Lys Lys Asn Arg Arg Tyr Glu Lys His
            450                 455                 460
Ile Arg Tyr Glu Ser Arg Lys Leu Arg Ala Asp Thr Arg Lys Arg Val
465                 470                 475                 480
Lys Gly Arg Phe Val Lys Ser Thr Glu Ala Leu Asn Ala Ala Arg Tyr
            485                 490                 495
Asn Gly
```